(12) United States Patent
Cavaco Paulo et al.

(10) Patent No.: US 12,383,484 B2
(45) Date of Patent: *Aug. 12, 2025

(54) PEPTIDE COMPOSITION AND RESPECTIVE USES

(71) Applicant: Universidade do Minho, Braga (PT)

(72) Inventors: Artur Manuel Cavaco Paulo, Braga (PT); Celia Freitas Da Cruz, Guimaraes (PT); Margarida Maria Macedo Francesko Fernandes, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,900

(22) Filed: Oct. 30, 2023

(65) Prior Publication Data

US 2024/0082135 A1 Mar. 14, 2024

Related U.S. Application Data

(60) Division of application No. 18/334,287, filed on Jun. 13, 2023, now Pat. No. 12,115,242, which is a continuation of application No. 18/194,372, filed on Mar. 31, 2023, now Pat. No. 12,102,706, which is a continuation of application No. 16/439,889, filed on Jun. 13, 2019, now Pat. No. 11,642,298, which is a continuation of application No. 15/030,313, filed as application No. PCT/IB2014/065375 on Oct. 16, 2014, now Pat. No. 10,709,655.

(30) Foreign Application Priority Data

Oct. 18, 2013 (PT) .......................... 107244

(51) Int. Cl.
| | |
|---|---|
| A61K 8/64 | (2006.01) |
| A61Q 5/00 | (2006.01) |
| A61Q 5/04 | (2006.01) |
| A61Q 5/06 | (2006.01) |

(52) U.S. Cl.
CPC ............... *A61K 8/64* (2013.01); *A61K 8/645* (2013.01); *A61Q 5/002* (2013.01); *A61Q 5/04* (2013.01); *A61Q 5/06* (2013.01); *A61Q 5/065* (2013.01); *A61K 2800/30* (2013.01)

(58) Field of Classification Search
CPC ...... A61K 8/64; A61K 8/645; A61K 2800/30; A61Q 5/002; A61Q 5/04; A61Q 5/06; A61Q 5/065
See application file for complete search history.

(56) References Cited

U.S. PATENT DOCUMENTS

| | | |
|---|---|---|
| 5,028,419 A | 7/1991 | Pigiet |
| 5,635,170 A | 6/1997 | Lang et al. |
| 6,020,163 A | 2/2000 | Conklin |
| 7,622,273 B2 | 11/2009 | Gibbs |
| 7,919,456 B2 | 4/2011 | Ghosh |
| 8,034,338 B2 | 10/2011 | Loibner et al. |
| 8,383,580 B2 | 2/2013 | Rui et al. |
| 9,713,604 B2 | 7/2017 | Dreher |
| 10,709,655 B2 | 7/2020 | Cavaco et al. |
| 11,642,298 B2 | 5/2023 | Cavaco Paulo et al. |
| 11,712,410 B2 | 8/2023 | Sahib et al. |
| 12,102,706 B2 | 10/2024 | Cavaco Paulo et al. |
| 12,115,242 B2 | 10/2024 | Cavaco Paulo et al. |
| 2006/0223728 A1 | 10/2006 | Tokunaga |
| 2006/0272103 A1 | 12/2006 | Barbarat |
| 2006/0286655 A1 | 12/2006 | Philippe |
| 2008/0107614 A1 | 5/2008 | Fahnestock et al. |
| 2009/0130154 A1 | 5/2009 | Gupta |
| 2010/0015070 A1 | 1/2010 | Bollschweiler et al. |
| 2010/0272666 A1 | 10/2010 | Breakspear et al. |
| 2012/0087862 A1 | 4/2012 | Hood et al. |
| 2013/0059772 A1 | 3/2013 | Kumar |
| 2013/0224269 A1 | 8/2013 | Khan et al. |

(Continued)

FOREIGN PATENT DOCUMENTS

| | | |
|---|---|---|
| CA | 2309413 A1 | 11/2000 |
| CN | 103126949 A | 6/2013 |

(Continued)

OTHER PUBLICATIONS

PCT/US2023/026017 International Search Report and Written Opinion dated Dec. 13, 2023.

(Continued)

*Primary Examiner* — Lianko G Garyu
*Assistant Examiner* — Erinne R Dabkowski
(74) *Attorney, Agent, or Firm* — Sughrue Mion, PLLC

(57) ABSTRACT

The current application discloses a composition that comprises at least one peptide with a sequence length of 6-12 amino acids, where 2-5 of those amino acids are cysteines for the treatment and cosmetics of animal hair, in preference human hair. There are several hair styling methods that involve breakage and reestablishment of disulfide bonds, allowing relaxation and straightening of the hair. However, the most effective methods currently used to modulate hair contain harmful chemicals. Thus, there is a constant demand for formulations that efficiently model the hair fiber without damage. Thus, the present invention aims to provide a composition for treatment of the hair, including animal and human hair, without the use of chemicals harmful to the hair fiber and consumer health and uses of said compositions in shampoo, lotion, serum, cream, conditioner, foam, elixir, oil, aerosol or mask.

17 Claims, No Drawings
Specification includes a Sequence Listing.

(56) References Cited

U.S. PATENT DOCUMENTS

| | | | |
|---|---|---|---|
| 2016/0175209 A1 | 6/2016 | Walker et al. |
| 2016/0271043 A1 | 9/2016 | Cavaco Paulo et al. |
| 2020/0121581 A1 | 4/2020 | Shoseyov et al. |
| 2021/0393500 A1 | 12/2021 | Cavaco Paulo et al. |
| 2022/0287944 A1 | 9/2022 | Costache et al. |
| 2023/0248627 A1 | 8/2023 | Cavaco Paulo et al. |
| 2023/0248631 A1 | 8/2023 | Cavaco Paulo et al. |
| 2023/0301894 A1 | 9/2023 | Cavaco Paulo et al. |
| 2023/0338263 A1 | 10/2023 | Cavaco Paulo et al. |
| 2023/0355499 A1 | 11/2023 | Sahib et al. |
| 2023/0414478 A1 | 12/2023 | Cavaco et al. |
| 2023/0414479 A1 | 12/2023 | Cavaco et al. |
| 2023/0415070 A1 | 12/2023 | Cavaco et al. |
| 2024/0108560 A1 | 4/2024 | Staley et al. |
| 2024/0115481 A1 | 4/2024 | Cavaco Paulo et al. |
| 2024/0316187 A1 | 9/2024 | Von Mutius et al. |

FOREIGN PATENT DOCUMENTS

| | | |
|---|---|---|
| CN | 104940071 A | 9/2015 |
| EP | 0335654 A2 | 10/1989 |
| EP | 0488242 A1 | 6/1992 |
| EP | 1046390 A1 | 10/2000 |
| EP | 1238645 A2 | 9/2002 |
| EP | 1705188 A1 | 9/2006 |
| FR | 2706300 A1 | 12/1994 |
| FR | 2876286 A1 | 4/2006 |
| GB | 103484 A | 1/1918 |
| JP | H0656889 A | 3/1994 |
| JP | H1112138 A | 1/1999 |
| JP | 2005151849 A | 6/2005 |
| KR | 20090070272 A | 7/2009 |
| PT | 103484 A | 11/2007 |
| WO | WO-9711672 A1 | 4/1997 |
| WO | WO-0023039 A2 | 4/2000 |
| WO | WO-0051556 A1 | 9/2000 |
| WO | WO-0064405 A2 | 11/2000 |
| WO | WO-0112806 A2 | 2/2001 |
| WO | WO-0123890 A1 | 4/2001 |
| WO | WO-2004048399 A2 | 6/2004 |
| WO | WO-2005049834 A1 | 6/2005 |
| WO | WO-2006001536 A1 | 1/2006 |
| WO | WO-2007136286 A1 | 11/2007 |
| WO | WO-2008081348 A2 | 7/2008 |
| WO | WO-2010010145 A1 | 1/2010 |
| WO | WO-2010089228 A1 | 8/2010 |
| WO | WO-2011072991 A1 | 6/2011 |
| WO | WO-2012013593 A1 | 2/2012 |
| WO | WO-2015056216 A2 | 4/2015 |
| WO | WO-2018095813 A1 | 5/2018 |
| WO | WO-2020181395 A1 | 9/2020 |
| WO | WO-2021001289 A1 | 1/2021 |
| WO | WO-2022003655 A1 | 1/2022 |
| WO | WO-2022029147 A1 | 2/2022 |
| WO | WO-2022072696 A1 | 4/2022 |
| WO | WO-2023081711 A1 | 5/2023 |
| WO | WO-2023161711 A1 | 8/2023 |
| WO | WO-2023250104 A2 | 12/2023 |
| WO | WO-2023250105 A1 | 12/2023 |
| WO | WO-2024073683 A2 | 4/2024 |
| WO | WO-2024206473 A1 | 10/2024 |

OTHER PUBLICATIONS

PCT/US2023/026019 International Search Report and Written Opinion dated Dec. 5, 2023.
U.S. Appl. No. 18/194,372 Office Action dated Dec. 14, 2023.
U.S. Appl. No. 18/334,287 Office Action dated Feb. 6, 2024.
U.S. Appl. No. 18/339,889 Office Action dated Dec. 19, 2023.
U.S. Appl. No. 18/339,927 Office Action dated Jan. 24, 2024.
What is wrong with CANTU shampoo. https://forums.longhaircommunity.com/showthread.php?t=149761. Published: May 5, 2019.
Blast glossary downloaded from www.ncbi.nlm.nih.gov on May 2, 2020.
Blast search for Seq ID No. 1, downloaded May 2, 2020 (2020).
Blast search for Seq ID No. 2, downloaded May 2, 2020 (2020).
Co-pending U.S. Appl. No. 18/252,712, inventors Cavaco; Paulo Artur Manuel et al., filed May 11, 2023.
Co-pending U.S. Appl. No. 18/339,889, inventors Cavaco; Paulo Artur Manuel et al., filed Jun. 22, 2023.
Co-pending U.S. Appl. No. 18/339,927, inventors Cavaco; Paulo Artur Manuel et al., filed Jun. 22, 2023.
Co-pending U.S. Appl. No. 18/478,320, inventors Staley; Karis et al., filed Sep. 29, 2023.
Co-pending U.S. Appl. No. 18/520,428, inventors Cavaco Paulo; Artur Manuel et al., filed Nov. 27, 2023.
Dow, Carbowax Sentry Polyethylene Glycols, published online 2011.
Fernanda Reis Gavazzoni Dias. Hair Cosmetics: An Overview. International Journal of Trichology 7:2-15 (2015).
Fernandes et al. Keratin-based peptide: biological evaluation and strengthening properties on relaxed hair. International Journal of Cosmetic Science 34(4):338-346 (2012).
Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).
Marabotti et al. The misuse of terms in scientific literature. Bioinformatics 26(19):2498 (2010).
Naturally Curly, http://www.naturallycurly.com/curlreading/kinky-hair-type-4a/ingredients-commonly-used-in-hair-care-productspeg-modified-materials/, published online Jun. 8, 2010.
PCT/IB2014/065375 International Search Report and Written Opinion dated Jun. 7, 2015.
Romanowski. An introduction to cosmetic technology. American Oil Chemists' Society. Available at https://www.aocs.org/stay-informed/inform-magazine/featured-articles/an-introduction-to-cosmetic-technology-april2015?SSO=True (8 pgs.) (2015).
Shimomura et al. Human Hair Keratin-Associated Proteins. J Investig Dermatol Symp Proc 10:230-233 (2005).
Thesis from Celia Freitas Da Cruz, Unraveling and modulating human hair morphology features (192 pgs) (2012).
Uniprot Protein Database, protein accession A8MUX0 , Keratin-associated protein 16-1, accessed on Dec. 18, 2019.
Uniprot Protein Database, protein accession P26371 , Keratin-associated protein 5-9, accessed on Dec. 18, 2019.
Uniprot Protein Database, protein accession Q9NSB0, Type II hair keratin 6, accessed on Dec. 18, 2019.
Uniprot Protein Database, protein Accession Q9NSB5, accessed on Nov. 8, 2019.
Uniprot protein database, protein Type II hair keratin 1, protein accession Q9NSB5, accessed on Aug. 28, 2017.
U.S. Forest Service entry on soaps at www.fs.fed.us/wildflowers/ethnobotany/soaps.shtra, downloaded Sep. 29, 2020 (2020).
U.S. Appl. No. 15/030,313 Office Action dated Aug. 29, 2018.
U.S. Appl. No. 15/030,313 Office Action dated Aug. 31, 2017.
U.S. Appl. No. 15/030,313 Office Action dated Jan. 11, 2019.
U.S. Appl. No. 15/030,313 Office Action dated Jan. 24, 2018.
U.S. Appl. No. 15/030,313 Office Action dated Jul. 18, 2019.
U.S. Appl. No. 15/030,313 Office Action dated Mar. 2, 2017.
U.S. Appl. No. 16/122,796 Office Action dated Apr. 15, 2021.
U.S. Appl. No. 16/122,796 Office Action dated Apr. 28, 2023.
U.S. Appl. No. 16/122,796 Office Action dated Jan. 5, 2023.
U.S. Appl. No. 16/122,796 Office Action dated May 4, 2020.
U.S. Appl. No. 16/122,796 Office Action dated Oct. 1, 2020.
U.S. Appl. No. 16/122,796 Office Action dated Sep. 20, 2022.
U.S. Appl. No. 16/439,889 Office Action dated Apr. 1, 2022.
U.S. Appl. No. 16/439,889 Office Action dated Jan. 3, 2020.
U.S. Appl. No. 16/439,889 Office Action dated Sep. 15, 2022.
U.S. Appl. No. 18/164,515 Office Action dated Oct. 12, 2023.
U.S. Appl. No. 18/334,287 Office Action dated Oct. 10, 2023.
Yang. Chapter 36: Hair Care Cosmetics. Cosmetic Science and Technology: Theoretical Principles and Applications (pp. 601-615) (2017).

(56) References Cited

OTHER PUBLICATIONS

Altschul, Stephen F et al. Basic Local Alignment Search Tool. Journal of Molecular Biology 215(3):403-410 (1990).
Archunan. Odorant Binding Proteins: a key player in the sense of smell. Bioinformation 14(1):36-37 (2018).
Berendsen, HJ., A glimpse of the Holy Grail? Science 282(5389):642-643 (1998).
Bignetti et al. Purification and characterisation of an odorant-binding protein from cow nasal tissue. Eur. J. Biochem. 149:227-231 (1985).
Bignetti et al. The pyrazine-binding protein and olfaction. Comp. Biochem. Physiol., 90(1):1-5 (1988).
Bradley et al. Limits of cooperativity in a structurally modular protein: response of the Notch ankyrin domain to analogous alanine substitutions in each repeat. J Mol Biol. 324(2):373-386 (2002).
Breer. Olfactory receptors: molecular basis for recognition and discrimination of odors. Anal Bioanal Chem 377(3):427-33 (2003).
Briand et al. Evidence of an Odorant-Binding Protein in the Human Olfactory Mucus: Location, Structural Characterization, and Odorant-Binding Properties. Biochemistry 41:7241-7252 (2002).
Campanella et al., MatGAT: An application that generates similarity/identity matrices using protein or DNA sequences. BMC Bioinformatics 4:29 (2003).
Capo et al. The porcine odorant-binding protein as molecular probe for benzene detection. PloS One 13(9):e0202630 (2018).
Castro et al. The Structural Properties of Odorants Modulate Their Association to Human Odorant Binding Protein. Biomolecules 11(2):145 (2021).
Cave et al. Progress in the development of olfactory-based bioelectronic chemosensors. Biosens Bioelectron 123:211-222 (2019).
Cennamo et al. Easy to Use Plastic Optical Fiber-Based Biosensor for Detection of Butanal. PloS One 10(3):e0116770 (2015).
Chemists Corner, https://chemistscorner.com/cosmeticsciencetalk/discussion/sodium-pca-vs-glycerin/. Published: Dec. 1, 2020.
CN104940071A English Translation Published: Sep. 30, 2015.
Dal Monte et al. Purification and characterization of two odorant-binding proteins from nasal tisue of rabbit and pig. Comp Biochem Physiol 99(2):445-451 (1991).
Di Pietrantonio et al. Detection of odorant molecules via surface acoustic wave biosensor array based on odorant-binding proteins. Biosens Bioelectron 41:328-34 (2013).
EP1238645A2 English Translation Published: Sep. 11, 2002.
Flower. Beyond the superfamily: the lipocalin receptors. Biochim Biophys Acta 1482:327-336 (2000).
Flower. The lipocalin protein family : structure and function. Biochem. J. 318(Pt 1)(Pt 1):1-14 (1996).
Garibotti et al. Three Odorant-binding Proteins from Rabbit Nasal Mucosa. Chem Senses 22(4):383-390 (1997).
Goncalves et al. OBP fused with cell-penetrating peptides promotes liposomal transduction. Colloids Surf B Biointerfaces 161:645-653 (2018).
Goncalves et al. Release of Fragrances from Cotton Functionalized with Carbohydrate-Binding Module Proteins. ACS Applied Mater Interfaces 11(31):28499-28506 (2019).
Goncalves et al. Two Engineered OBPs with opposite temperature-dependent affinities towards 1-aminoanthracene. Sci Rep 8 (1):14844 (2018).
Gongalves et al. 1-Aminoanthracene Transduction into Liposomes Driven by Odorant-Binding Protein Proximity. ACS Applied Mater Interfaces 10(32):27531-27539 (2018).
Han et al. Operating Mechanism and Molecular Dynamics of Pheromone-Binding Protein ASP1 as Influenced by pH. PLoS One 9(10):e110565 (2014).
Kozlowski. IPC—Isoelectric Point Calculator. Biol Direct 11(1):55 (2016).
Lazar et al. Molecular and Functional Characterization of an Odorant Binding Protein of the Asian Elephant, Elephas maximus: Implications for the Role of Lipocalins in Mammalian Olfaction. Biochemistry 41:11786-11794 (2002).
Lobel et al. Odorant of different chemical classes interact with distinct odorant binding protein subtypes. Chem Senses 27:39-44 (2002).
Malpeli et al. Chapter 9: Purification and Fluorescent Titration of Cellular Retinol-Binding Protein. In Methods in Molecular Biology; Redfern, C. P. F., Ed.; pp. 111-122 (1998).
Mazzini et al. Dissociation and unfolding of bovine odorant binding protein at acidic pH. J Struct Biol 159(1):82-91 (2007).
Mulla et al. Capacitance-modulated transistor detects odorant binding protein chiral interactions. Nature Commun 6:6010 (2015).
Needleman, Saul B et al. A General Method Applicable to the Search for Similarities in the Amino Acid Sequence of Two Proteins. Journal of Molecular Biology 48(3):444-453 (1970).
Ngo, Thomas, et al., Computational Complexity, Protein Structure Prediction, and the Levinthal Paradox. Birkhauser Boston 491-495 (1994).
Nogueira et al. Peptide anchor for folate-targeted liposomal delivery. Biomacromolecules 16(9):2904-2910 (2015).
Ozeki et al. A study of the suppression of body odour in elderly subjects by anti-fungal agents. Int J Cosmet Sci 38(3):312-8 (2016).
Paolini et al. Porcine odorant-binding protein: structural stability and ligand affinities measured by Fourier-transform infrared spectroscopy and fluorescence spectroscopy. Biochim Biophys Acta 1431:179-188 (1999).
Parisi et al. Unfolding and refolding of porcine odorant binding protein in guanidinium hydrochloride: equilibrium studies at neutral pH. Biochim Biophys Acta 652(2):115-125 (2003).
PCT/IB2021/056011 International Search Report and Written Opinion dated Oct. 6, 2021.
Pelosi et al. Odorant-Binding Proteins as Sensing Elements for Odour Monitoring. Sensors (Basel) 18(10):3248 (2018).
Pelosi et al. Structure and biotechnological applications of odorant-binding proteins. Appl Microbiol Biotechnol 98(1):61-70 (2014).
Pelosi. Odorant-Binding Proteins: Structural Aspects. In Annals New York academy of sciences; Olfaction and Taste XII: an international symposium, pp. 281-293 (1998).
Perduca et al. Crystal Structure of a Truncated Form of Porcine Odorant-Binding Protein. Proteins 42:201-209 (2001).
Pes et al. Isolation of two odorant-binding proteins from mouse nasal tissue. Comp. Biochem. Physiol. 103 (4):1011-1017 (1992).
Pevsner et al. Odorant-binding protein: characterization of ligand binding. J Biol Chem 265(11):6118-6125 (1990).
Rudinger, J., Characteristics of the amino acids as components of a peptide hormone sequence. Peptide Hormones, J.A, Parsons , MA, BM, BCh, 1-7 (1976).
Sankaran et al. Biology and applications of olfactory sensing system: A review. Sensors and Actuators B: Chemical 171-172:1-17 (2012).
Schinzel, R, et al., The Phosphate Recognition Site of *Escherichia coli* Maltodextrin Phosphorylase. FEBS Letters 286(1-2):125-128 (1991).
Sigma, Designing Custom Peptides, pp. 1-2. (2004).
Silva et al. Odorant binding proteins: a biotechnological tool for odour control. Appl Microbiol Biotechnol 98(8):3629-3638 (2014).
Solu Shampoo. https://web.archive.Org/web/20200929001233/https://www.thekindestcut.com/product-page/solu-shampoo. Published: Sep. 29, 2020.
Sorokowska et al. Does Personality Smell? Accuracy of Personality Assessments Based on Body Odour. European Journal of Personality 26(5):496-503 (2012).
Spinelli et al. The Structure of the Monomeric Porcine Odorant Binding Protein Sheds Light on the Domain Swapping Mechanism. Biochemistry 37:7913-7918 (1998).
Tegoni et al. Mammalian odorant binding proteins. Biochim Biophys Acta 1482:229-240 (2000).
U.S. Appl. No. 18/164,515 Office Action dated Feb. 15, 2024.
U.S. Appl. No. 18/164,515 Office Action dated Jun. 5, 2024.
U.S. Appl. No. 18/339,927 Office Action dated May 8, 2024.
U.S. Appl. No. 18/520,428 Office Action dated Mar. 25, 2024.
U.S. Appl. No. 18/339,889 Office Action dated Mar. 27, 2024.
Vincent et al. Crystal structures of bovine odorant-binding protein in complex with odorant molecules. Eur J Biochem 271(19):3832-42 (2004).

(56) References Cited

OTHER PUBLICATIONS

Voet, Judith., Biochemistry, Second Edition, John Wiley & Sons, Inc., 235-241 (1995).
Whitson et al. Human Odorant Binding Protein 2a has Two Affinity States and is Capable of Binding Some Uremic Toxins. Biochem Anal Biochem 3:2 (2014).
Yampolsky, Lev, et al., The Exchangeability of Amino Acids in Proteins. Genetics 170(4):1459-1472 (2005).
PCT/US2024/021721 International Search Report and Written Opinion dated Jul. 11, 2024.
The PH of Hair—The Difficult Truth About Shampoo. Love Curly Hair, Jun. 23, 2021: [Retrieved on Nov. 19, 2024]. Available at URL:https://web.archive.org/web/20210623093539/https://www.lovecurlyhair.com/the-ph-of-hair-the-difficult-truth-about-shampoo// pp. 1-22.
U.S. Appl. No. 18/003,127 Office Action dated Nov. 14, 2024.
U.S. Appl. No. 18/164,515 Office Action dated Sep. 16, 2024.
U.S. Appl. No. 18/339,927 Office Action dated Nov. 26, 2024.
U.S. Appl. No. 18/520,428 Office Action dated Jul. 11, 2024.

PEPTIDE COMPOSITION AND RESPECTIVE USES

CROSS-REFERENCE

This application is a divisional of 18/334,287, filed Jun. 13, 2023, which is a continuation of U.S. application Ser. No. 18/194,372, filed Mar. 31, 2023, which is a continuation of U.S. application Ser. No. 16/439,889, filed Jun. 13, 2019, now U.S. Pat. No. 11,642,298, issued May 9, 2023, which is a continuation of U.S. application Ser. No. 15/030,313, filed Apr. 18, 2016, now U.S. Pat. No. 10,709,655, issued Jul. 14, 2020, which is a U.S. National Stage Entry of International Application PCT/IB2014/065375, filed Oct. 16, 2014, which claims priority to Portuguese Application No. 107244, filed Oct. 18, 2013, all of which are hereby incorporated by reference in their entirety.

SEQUENCE LISTING

The instant application contains a Sequence Listing which has been submitted electronically in XML format and is hereby incorporated by reference in its entirety. Said XML copy, created on Feb. 2, 2023, is named 63230-710-401_SL.xml and is 1,068.431 bytes in size.

TECHNICAL HELD

The current application corresponds to a composition that comprises at least one peptide, based on keratin and keratin associated proteins, containing 2 to 5 cysteines with the purpose of treatment and cosmetics of animal hair, in preference human hair.

BACKGROUND

Human hair has a significant social role in most of the various world cultures, particularly for female population. Thus, there is a constant desire to improve and change hair characteristics, such as its natural texture. There are several differences in hair characteristics between different human ethnicities, as well as between individuals of the same ethnicity, such as length, thickness, color and texture.

Hair is composed of approximately 65% to 95% protein. The remaining constituents include water, lipids, pigments and trace elements. The majority of the proteins present in human hair correspond to keratin and keratin-associated proteins.

Human hair fiber's structure consists of cuticle, cortex and medulla. The cuticle constitutes about 15% by weight of the hair and consists of overlapping layers of cells, similar to a system of scales, with high content of cysteine. It provides a protective character to the hair fiber. The cortex is the middle region of the hair being responsible for the strength, elasticity and hair color. It is composed of several cell types and represents about 80% of the weight of the hair. The medulla corresponds to a central beam of cells and is absent in some hairs.

Keratins and mainly keratin-associated proteins have high sulfur content, present in the cysteine amino acid. The presence of sulfur is essential to the hair structure, as it allows the formation of disulfide bonds between amino acids of the polypeptide chains, due to oxidation of cysteine. The existence of these bonds is largely responsible for the structure and texture of the hair.

There are several hair styling methods that involve breakage and reestablishment of disulfide bonds, allowing relaxation and straightening of the hair. However, the most effective methods currently used to modulate hair contain harmful chemicals such as sodium hydroxide, potassium hydroxide, lithium hydroxide, guanidine hydroxide, ammonium thioglycolate or sodium sulfate. These methods can damage the scalp and the hair fiber, leading to its weakening and reducing its tensile strength. Formaldehyde, an extremely toxic chemical, is also used in hair straightening products. Other hair treatments that do not involve so much damage to the hair and the consumer are usually very expensive, time-consuming and/or have low efficacy. Thus, there is a constant demand for formulations that efficiently model the hair fiber without damage.

Peptides, proteins, amino acids and its derivatives have also been used in compositions for personal care products, namely hair conditioning and strengthening. For example, the document WO 00/23039 discloses a composition for hair treatment containing intermediate filament proteins, namely artificial keratin. The document EP 0488242 discloses a hair treating agent containing 3% to 10% by weight of cysteine and salts thereof, a polyhydric alcohol or a saccharide containing four to twenty carbon atoms, three or more hydroxyl groups in the molecule and no aldehyde or ketone group, The current invention is distinguished by the use of peptides, while the other applications refer the use of, respectively, proteins and amino acids in isolation and together with other types of compounds. The peptides in this innovation peptide can penetrate into the Human hair in order to improve hair fiber resistance.

The document WO 00/51556 discloses a hair treatment composition that contains four or more discrete amino acids selected from histidine, lysine, methionine, tyrosine, tryptophan or cysteine. This document describes peptides without referring sequences and providing a composition essentially based on histidine, lysine, methionine, tyrosine, tryptophan or cysteine.

The document PT 103484 describes a formulation for cosmetic applications that uses hydrophobic binding domains and/or carbohydrates, in order to enhance its properties and to repair hair damage. The binding domains used are hydrolyzed milk protein, a model of human surfactant protein as well as biologically active and synthetic peptides. The current invention is distinguished by the innovative use of synthetic peptide sequences analogous to keratin proteins instead of surfactant proteins. Furthermore, it does not rely on hydrophobic binding domains and/or carbohydrates, but in other interactions, namely disulfide bonds.

Enzymes have also been used as activating agents for hair treatment, such as in the document WO 00/64405. The document WO 2012/13593 discloses a cosmetic kit for hair conformational change that acts specifically in the disulfide bonds of the hair keratin, through enzyme activating agents and proteolytic enzymes.

As described in the last document there are hair treatments that include actions at the level of the hair disulfide bonds. Below we highlight some examples.

The document WO 97/11672 reports a method for permanent hair processing using tris(2-carboxyethyl)phosphine (TCEP), and other water-soluble tertiary phosphines to break disulfide bonds, whose reaction occurs in acidicic environment. The document U.S. Pat. No. 5,635,170 discloses a composition for permanent shaping of hair based on a keratin reducing agent, which contains N-glycyl-L-cysteine and/or L-cysteinyl-glycine. The pH range of this composition is 6.5 to 9.0. The document WO 2008/081348 refers a method and composition for permanent modulation of hair, through the use of 1% to 30% of N-alkyl-2-mercapto acetamide as a keratin reducing agent. It also contains at least one cationic surfactant for permanently shaping hair and the resulting process. The document WO 2006/001536 describes an agent for permanent hair processing that contains a derivative of mercaptocarboxylic acid, which allows processing and reduction of hair keratin in the acidic and neutral range of the pH. The document US 2010/0272666 discloses a hair cosmetic composition for hair treatment, containing 5 to 50 amino acids, without containing cysteine or its derivatives. Thus, this invention is distinguished by the existence of specific amino acid sequences, which contain cysteine, allowing the formation of disulfide bonds that stabilize and protect the hair fiber.

In a previous article by Fernandes et al. (Fernandes, Lima, Loureiro, Gomes, & Cavaco-Paulo, 2012), it is performed the toxicology evaluation of a peptide sequence for hair care use, containing 13 amino acids with two cysteines in its composition. However, in this article it is not mentioned or suggested that the percentage of cysteine in a peptide sequence may have some effect on the resistance of the hair. Also, in the present innovation, the number of amino acids of each peptide sequence is 6 to 12.

SUMMARY

Thus, the present invention aims to provide a composition for treatment of the hair, including animal and human hair, without the use of chemicals harmful to the hair fiber and consumer health and that does not present the drawbacks found in the state of the art.

The compositions described in the current invention, after prolonged use, provide hair with soft, shiny, undamaged texture and with the desired features. The peptide compositions with a specific number of amino acids and cysteines act synergically providing resistance to strength, toughness and elasticity to the hair. Therefore, the compositions of the current invention are particularly relevant for hair treatment, hair dying, hair perms, etc.

The present application describes a peptide composition for hair treatment, in particular human or animal hair, which comprises at least one peptide with 6-12 amino acids length (namely 6, 7, 8, 9, 10, 11, 12 amino acids), where 2-5 of those amino acids correspond to cysteine, preferably 2, 3, 4 or 5 of those amino acids are cysteines and dermatologically suitable excipients, which penetrates the hair, increasing it resistance and reducing it breakage.

In the embodiment, for improved results, the peptide (or peptides) of the peptide composition for hair care can comprise 10-11 amino acids.

In the embodiment of the peptide composition for hair care treatment, the referred peptides can also contain a percentage of hydrophobic amino acids, not higher than 60%, and preferably less than 41% for better results. Preferably, the composition can also comprise at least one hydrophobic amino acid selected from the following list: phenylalanine, alanine, leucine, methionine, isoleucine, tryptophan, proline, valine or their mixtures.

In yet another embodiment, the amount of cysteine of the peptide composition for hair treatment may vary from 10% to 50% of the total of amino acids of the peptide sequence, preferably 20-30%, and even more preferably 25%.

In an embodiment of the composition, with better results of the peptide (or peptides) of the peptide composition for hair treatment, the sequence of peptide(s) can comprise at least one sequence of the following list with a with a degree of homology greater than or equal to 90%: SEQ. ID NO: 1-SEQ. ID NO: 1239, preferably with a degree of homology greater than or equal to 91%, 92%, 93%, 94%, 95%, 96%, 97%, 98%, 99%, 100%.

In an embodiment, improved results for the peptide (or peptides) of the peptide composition for hair treatment can comprise at least one of the sequences of the following list with a degree of homology equal or greater than 90%: SEQ.ID NO:5, SEQ.ID NO:75; SEQ.ID NO:94; SEQ.ID NO:409; SEQ.ID NO:411; SEQ.ID NO:412; SEQ ID. NO:432; SEQ.ID NO:618; SEQ.ID NO:717; SEQ.ID NO:951; SEQ.ID NO:1088; SEQ.ID NO:1131; SEQ.ID NO:1149, preferably with a degree of homology equal or greater than 91%, 92%, 93%, 94%, 95%, 96%, 97%, 98%, 99%, 100%.

In other embodiment, the concentration of the peptide of the peptide composition for hair treatment can vary between 0.001%-20% (w/w), preferably 0.01-5% w/w).

In yet other embodiment, the peptide composition for hair treatment can comprise at least one excipient, selected from the following list: surfactants, emulsifiers, preservatives, thickeners, organic polymers, humectants, silicones, oils, fragrances, vitamins, buffers.

In another embodiment, the peptide composition for hair treatment can compose at least one anionic surfactant selected from the following list: alkylbenzene sulfonates, ammonium lauryl sulfate, ammonium lauryl sulfate, ammonium xylenesulfonate, sodium C14-16 olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, or any mixture thereof.

In an embodiment, the peptide composition for hair treatment can comprise at least one amphoteric surfactant selected from the following list: cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, or any mixture thereof.

In other embodiment, the peptide composition for hair treatment can comprise at least one cationic surfactant selected from the following list: quaternary ammonium compounds, behentrimonium chloride, behentrimonium methosulfate, benzalkonium chloride, betrimonium chloride, binnamidopropyltrimonium chloride, cocotrimonium chloride, dicetyldimonium chloride, dicocodimonium chloride, dihydrogenated tallow dimethylammonium chloride, hydrogenated Palm trimethylammonium chloride, laurtrimonium chloride, quatemium-15, quaternium-18 bentonite, quatemium-22 hectonite, stearalkonium chloride, tallowtrimonium chloride, tricetyldimonium chloride, or any mixture thereof.

In yet other embodiment, the peptide composition for hair treatment can comprise at least one non-ionic surfactant selected from the following list: decyl glucoside, laureth-10 (lauryl ether 10), laureth-23, Laureth-4, PEG-10 sorbitan laurate, polysorbate-(20, 21, 40, 60, 61, 65, 80, 81), PPG-1 trideceth-6, sorbitol, steareth-(2, 10, 15, 20), C11-21 pareth-(3-30), C12-20 acid PEG-8 ester, or their mixtures.

In yet other embodiment, the peptide composition for hair treatment can comprise at least one emulsifier selected from the following list: caprylic/capric/diglyceryl succinate, C10-15 pareth-(2,4,6,8) phosphate, C14-16 glycol palmitate, C18-20 glycol isostearate, ceteareth-(4-60), cocamidopropyl lauryl ether, deceth-(3-10), DTPA-hydrogenated cocoate, dipentaerythrityl hydroxystearate, dipentaerythrityl hydroxyisostearate, dipentaerythrityl hexacapratelcaprylate, dodoxynol-(5,6,7,9,12), nonoxynol-(1-35), octoxynol-(1-70), Octyldodeceth-(2,5,16,20,25), Palm kernel glycerides, or any mixture thereof.

In other embodiment, the peptide composition for hair treatment can comprise at least one preservative selected from the following list: butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, or any mixture thereof.

In other embodiment, the peptide composition for hair treatment can comprise at least one thickener selected from the following list: aluminum stearates/isostearates/myristates/laurates/palmitates, glycol distearate, hydrogenated castor oil, hydrogenated castor oil hydroxystearate, hydrogenated castor oil isostearate, hydrogenated castor oil stearate, hydrogenated castor PEG-8 esters, PEG-150 distearate, or any mixture thereof.

In other embodiment, the peptide composition for hair treatment can comprise at least one natural polymer derived selected from the following list: carboxymethyl hydroxyethyl celulose, carboxymethyl hydroxypropyl guar, cellulose, ethyl celulose, hydroxy-butyl methylcellulose, hydroxyethylcellulose, hydroxymethylcellulose, lauryl polyglucose, or any mixture thereof.

In other embodiment, the peptide composition for hair treatment can comprise at least one humectant selected from the following list: 1,2,6 hexanetriol, dipropylene glycol, glycerin, hexylene glycol, panthenol, phytantriol, propylene glycol, sodium PCA, sorbitol, triethylene glycol, polyglyceryl sorbitol, glucose, fructose, polydextrose, potassium PCA, hydrogenated honey, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50), or any mixture thereof.

In other embodiment, the peptide composition for hair treatment can comprise at least one cationic polymer selected from the following list: polyquatemium-10, polyquatemium-7, polvquaternium-11m guar hydroxypropyltrimonium chloride, or any mixture thereof.

In other embodiment, the peptide composition for hair treatment can comprise at least one silicone selected from the following list: amodimethicone, amodimethicone, trideceth-12, cetrimonium, chlotide mixture, behenoxy, dimethicone sparingly, cetearyl methicone, cetyl dimethicone, cyclomethicone, cyclopentasiloxane, dimethicone, dimethicone copolyol, dimethicone copolyol, dimethiconol, hydrolyzed wheat protein hydroxypropyl polysiloxane, stearoxy dimethicone sparingly, stearyl dimethicone, trimethylsitylamodimethicone, lauryl methicone copolyol, or any mixture thereof.

In yet other embodiment, the peptide composition for hair treatment can comprise at least one organic oil selected from the following list: mineral oil, paraffin, petrolatum, or any mixture thereof.

In yet other embodiment, the peptide composition for hair treatment can comprise at least one protein selected from the following list: cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed wheat protein, keratin, potassium cocoyl hydrolyzed collagen, TEA-cocoyl hydrolyzed collagen, TEA-cocoyl hydrolyzed soy protein, or any mixture thereof.

In other embodiment, the peptide composition for hair treatment can comprise at least one vitamin selected from the following list: retinol, retinyl palmitate tocopherol acetate, or any mixture thereof.

In other embodiment, the peptide composition for hair treatment can comprise at least one ester emollient selected from the following list: butyl myristate, butyl stearate, C12-15 alkyl benzoate, caprylicicapric triglyceride, cetyl octanoate, cetyl stearate, cetearyl stearate, decyl oleate, dimethyl lauramine isostearate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, Sorbitan laurate, sorbitan tristearate, stearyl stearate, tocopheryl linoleate, or any mixture thereof.

In other embodiment, the peptide composition for hair treatment can comprise at least one alkanolamide selected from the following list: acetamide MEA, cocamide DEA, cocarnide MEA, lactamide MEA, lauramide DEA, lauramide DEA, propylene glycol, lauramide MEA, lecithinamide DEA, linolearnide DEA, linolearnide MEA, linoleamide MIPA, myristamide DEA, myristamide MEA, myristamide MIPA, oleamide DEA, oleamide DEA, oleamide MEA, oleamide MIPA, soyamide DEA, stearamide MEA, or any mixture thereof.

In yet other embodiment, the peptide composition for hair treatment can comprise at least one amine selected from the following list: behentamidopropyl dimethylamine, cocamidopropyl dimethylamine, isostearamidopropyl dimethylamine, lauramidopropyl dimethylamine, myristamidopropyl dimethylamine, oleamidopropyl dimethylamine, palmitamidopropyl dimethylamine, stearamidopropyl dimethylamine, tallamidopropyl dimethylamine, or any mixture thereof.

In yet other embodiment, the peptide composition for hair treatment can comprise at least one pH adjuster selected from the following list: ascorbic acid, citric acid, sodium hydroxide, triethanolamine, or any mixture thereof.

In yet other embodiment, the peptide composition for hair treatment can comprise at least one salt selected from the following list: calcium chloride, magnesium chloride, magnesium sulfate, potassium chloride, potassium glycol sulfate, sodium chloride, or any mixture thereof.

In yet other embodiment, the peptide composition for hair treatment can comprise at least one aliphatic alcohol selected from the following list: behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, or any mixture thereof.

In another embodiment, the peptide composition for hair treatment can comprise at least one UV filter/sunscreen selected from the following list: benzophenone-(2, 3, 4, 5, 6, 7, 8, 9, or 10), benzophenone-4, benzyl salicylate, benzylidene camphor sulfonic acid, bornelone, ethyl cinnamate, ethylhexyl methoxycinnamate (octyl methoxycinnamate), octoxynol-40, octoxynol-20, octyl methoxycinnamate, octyl salicylate, oxybenzone, phenyl ketone, PEG-25 PABA, polyacrylamidomethyl benzylidene camphor, or any mixture thereof.

In other embodiment, the peptide composition for hair treatment can comprise at least one natural oil selected from the following list: coconut oil, jojoba oil, olive oil, palm Oil, safflower oil, sesame seed oil, shea butter, sweet almond oil, wheat germ oil, or any mixture thereof.

In yet other embodiment, the peptide composition for hair treatment can comprise at least one amine oxide selected from the following list: cocamine oxide, lauramine oxide, or any mixture thereof.

In other embodiment, the peptide composition for hair treatment can comprise at least one chelate selected from the following list: diiospropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, or any mixture thereof.

In other embodiment, the peptide composition for hair treatment can comprise at least one fatty acid selected from the following list: arichidonic acid, capric acid, coconut fatty acid, lauric acid, linoleic acid, linolenic acid, myristic acid, palmitic acid, pantothenic acid, stearin; acid, caproic acid, capryleth-(4, 6, 9) carboxylic acid, isostearic acid, or any mixture thereof.

In other embodiment, the peptide composition for hair treatment can comprise at least one agent antimicrobial/antibacterial selected from the following list: glyoxal, triclosan, or any mixture thereof.

In other embodiment, the peptide composition for hair treatment can comprise at least one PEG-modified material selected from the following list: PEG-150 pentaerythirtyl tetrastearate, PEG-(-2, -3, -4, -6, -8, -12, -20, -32, -50, -150, -175) distearate, PEG-10 castor oil, PEG-10 cocamine, PEG-10 cocoate, PEG-10 coconut oil esters, PEG-10 glyceryl oleate, PEG-10 glyceryl pibsa tallate, PEG-10 glyceryl stearate, PEG-10 hydrogenated lanolin, PEG-10 hydrogenated tallow amine, PEG-10 isolauryl thioether, PEG-10 isostearate, PEG-10 lanolate, PEG-10 lanolin, PEG-10 laurate, PEG-10 oleate, PEG-10 olive glycerides, PEG-10 polyglyceryl-2 laurate, PEG-10 propylene glycol, PEG-10 sorbitan laurate, PEG-10 soya sterol, PEG-10 soyamine, PEG-10 stearamine, PEG-10 stearate, PEG-10 stearyl benzonium chloride, PEG-10 tallate, PEG-10 tallow aminopropylarnine, PEG-100, PEG-100 castor oil, PEG-100 hydrogenated castor oil, PEG-100 lanolin, PEG-100 stearate, PEG-40 hydrogenated castor Oil, PEG-60, PEG-55 propylene glycol distearate, or any mixture thereof.

In other embodiment, the peptide composition for hair treatment can comprise at least one polymer selected from the following list: carbomer, dodecanedioic acid/cetearyl alcohol/glycol copolymer, hydrogenated C6-14 olefin polymers, hydrogenated ethylene/propylene/styrene copolymer: polyacrylic acid, polymethyl methacrylate: polymer, polyvinyl acetate, polyvinyl alcohol, PPG, PPG-25-laureth-25, PPG-5 pentaerithrityl ether, PPG-75-PEG-300-hexylene glycol, polyvinylpyrrolidone, PVP/VA (polyvinylpyrrolidone/vinyl acetate copolymer), sodium carbomer, TEA-carbomer, poloxamer (100-407), poloxamine, polyacrylamidomethylpropane sulfonic acid, polyethylene terephthalate, or any mixture thereof.

In other embodiment, the peptide composition for hair treatment can comprise at least one antistatic agent selected from the following list: apricotamidopropyl ethyldimonium ethosulfate, apricotamidopropyl ethyldimonium lactate, cocamidopropyl ethyldimonium ethosulfate, cocamidopropyl ethyldimonium lactate, lauramidopropyl ethyldimonium ethosulfate, lauramidopropyl ethyldimonium lactate, linoleamidopropyl ethyldimonium ethosulfate, linoleamidopropyl ethyldimonium lactate, myristamidopropyl ethyldimonium ethosulfate, myristamidopropyl ethyldimonium lactate, oleamidopropyl ethyldimonium ethosulfate, olearnidopropyl ethyldimonium lactate, stearamidopropyl ethyldimonium ethosulfate, stearamidopropyl ethyldimonium lactate, or any mixture thereof.

In other embodiment, the peptide composition for hair treatment can comprise at least one alcohol selected from the following list: SD alcohol 40, witch hazel, isopropanol, or any mixture thereof.

In yet other embodiment, the peptide composition for hair treatment can comprise fragrances, oils or any mixture thereof.

In other embodiment, the peptide composition for hair treatment can be used in medicine, veterinary and/or for cosmetics, preferably for the treatment of hair, mainly for animal or human, particularly for treating diseases of the scalp, particularly scalp irritation, alopecia areata, lichen planus, folliculitis keloid of the neck, trichorrhexis nodosa, tricodistrophy, pili torti, tricorrexis
invaginata, moniletrix, uncombable hair syndrome.[0058] In other embodiment, the composition may comprise a dye agent linked to the N or C-terminal of the referred peptides.

In yet other embodiment is the use of the described composition for hair coloring.

Other aspect of the embodiment is the use of the described composition as a hair strengthener or as fixer of perms and/or curly hairs.

It is also described in this application shampoo, lotion, serum, cream, conditioner, foam, elixir, oil, aerosol or mask comprising the composition presented in this application.

The present application discloses a composition for hair treatment that comprise, in whole or in part, one or more peptide sequences of 6 to 12 amino acid residues based on keratin and keratin-associated proteins having 2 to 5 cysteine residues, preferably having 3 to 5 residues of cysteine, for treatment and cosmetics of the hair, preferably human hair, chemically pre-treated or not. Thus, the presence of cysteine in the peptide sequence (higher than 10%, preferably more than 15%) in combination with a percentage of hydrophobic amino acids ensures that the peptides can have a lasting fixation in the hair, improving the human hair properties such as elasticity and strength.

Surprisingly, the described peptide compositions in which the peptide(s) comprising 2 to 5 cysteines allow penetration of the peptide(s) and enhance the properties of hair, preferably 3-5 cysteines. Thus, described peptide(s) containing 2-5 cysteine in order to allow hair penetration and enrichment of the hair properties, such as elasticity, resistance, reduce eventual hair damage, as well as improve and change hair characteristics.

The peptide compositions described in the present application surprisingly enrich and improve the properties and characteristics of the hair, such as elasticity, strength and appearance, repairing damaged keratinous fiber. Therefore, formulation's high cysteine content is used to improve and/or change its characteristics, such as hair curl or uncurl. The sequence of peptides can have also preferably a percentage of hydrophobic amino acids not exceeding 60%, improving even further the results. Examples of hydrophobic amino acids are phenylalanine, alanine, leucine, methionine, isoleucine, tryptophan, proline, valine, and others.

In the context of the present description, the peptide composition can also be applied to the hair and in particular to the human hair as, but not limited to, aqueous solution or conventional shampoo or conditioner. It can also be used as a lotion, foam, aerosol, gel, mask, and application formulation with or without subsequent rinsing.

The concentration of peptide to be used depends on several features such as the condition of the hair, the origin and the formulation of the hair care product.

DETAILED DESCRIPTION

It should be understood that the detailed description and specific examples are indicative of preferred embodiments of the invention and are provided to be illustrative only. This patent is not limited to those mentioned applications.

The present application describes a composition for hair treatment that comprises different peptides, which are based in the structure of keratin and keratin associated proteins.

The compositions described in the present application allow surprisingly the dermo-cosmetic treatment of animal hair, including human hair, chemically pre-treated or not. The composition described in the present invention, through the use of specific peptides, allows the preparation of keratinous fiber damages, due to the high binding capacity of the keratin peptides, including through disulfide bridges.

The described compositions improve the properties and characteristics of the hair, such as elasticity, resistance and appearance, repairing putative damages of the hair.

The peptides here defined are peptide sequences which bind with a certain affinity to the hair. The peptides used in this invention are composed by 6 to 12 amino acids and are constituted by a minimum of 2 and a maximum of 5 cysteines, preferably 3-5 cysteines.

The peptide composition for hair treatment described allows a resistance increase due to the presence of the cysteine-rich peptide, which leads to the resistance of the hair even after several rinsing.

Every peptide can be used together or separately, as well as all or part of the peptide sequence in the hair composition. Each peptide sequence contains amino acids with sulfur, specifically cysteine, which interacts with the hair and allows the formation of intermolecular cross-linking, stabilizing the keratinous fiber.

The peptide composition described uses a high content on cysteine in order to enrich the hair properties, such as improve elasticity and resistance, reduce putative damage of the hair, improve and/or change hair characteristics. Regarding the interaction with the keratinous fibers, the cysteine is 10% to 50% of the total amount of amino acids of the peptide sequence. Additionally, the number of amino acids of the peptide sequence is preferable from 6 to 12.

The peptides can be used separately or in combination of two or more peptides. The concentration of the peptide to be used depends on several characteristics, such as hair condition, origin and the formulation of the product for hair treatment. The content of the hair composition of the present invention is as example 1-0.001% (w/w) in mass.

The peptides of the present invention can be prepared by conventional methods of peptide synthesis, well known in the state of the art.

Additionally, many companies provide customized services for peptide synthesis.

An embodiment of the current invention describes peptides that link to the hair, and which sequence of amino acids includes cysteines where the sequence is selected from the group between the sequences ID NO: 1 to sequence ID NO: 1239.

The sequence of the 1239 peptides referred is listed in the table of the FIG. 1, As example of hair, it was used virgin human hair tresses, acquired from the International Hair Importers and Products, Inc. (New York), The term virgin hair is applied to all the hair that was never subject or was at least 10 years without making any chemical treatment. Several different hair samples such as African, Asian and Caucasian hair are commercially available in several companies, such as the company mentioned above. Optionally, the hair samples can be treated, for example, using hydrogen peroxide to bleach the hair, needed for techniques such as hair dying.

In the context of this invention, the peptides can be applied to the hair, such as the human hair in the form of, but not limited to, aqueous or conventional preparation of shampoo or conditioner. It can also be in the form of lotion, foam, spray, gel, mask, formulation applied with or without subsequent rinsing.

This invention can be prepared by peptide coupling with an agent of these preparations directly or via a spacer.

This coupling interaction can be performed by covalent or non-covalent bonds, such as hydrogen bond, electrostatic interactions, hydrophobic interactions or van der Waals interactions. The spacer can be used to separate the peptide from the preparation agent, ensuring that the agent does not interfere with the peptide linkage to the hair.

The present invention can be understood more clearly and accurately by reading the following examples, which are indicative of preferred embodiments of the invention. They are provided for illustration in greater detail of the present invention, without introducing any limitation and without being limited to those applications.

EXAMPLES

The examples that are within the scope of the claims represent different embodiments of the invention; all other examples are comparative examples.

Example 1

The present application treats human hair through several commercial formulations with and without the use of the peptides from the sequence ID NO: 5. As The hair was supplied from International Hair Importers and Products, Inc. (New York).

The tests were performed with in human hair after 8 treatments of bleaching, at 50° C., in 0.1 M $Na_2CO_3$/$NaHCO_3$ buffer, at pH=9, 10% $H_2O_2$, for 1 hour.

Several formulations were tested:
hair serum with 15% PCG;
hair mask.

The mask used in this application was a basic commercial formulation with water, denaturing alcohol, propylene glycol, ether dicaprylic, cetylstearyl alcohol, behentrimonium chloride, cetyl ester, polysorbate 20, hydrolyzed wheat protein, hydrolyzed wheat starch, benzyl alcohol and fragrance.

The hair serum used in this application was a basic commercial formulation with water, denaturing alcohol, propylene glycol, polysorbate 20, hydrolyzed wheat protein, hydrolyzed wheat starch, crosslinked polymer alkyl acrylate/C10-30, triethanolamine, benzyl alcohol, fragrance.

Each of the formulations was tested with and without the peptide sequence ID NO:5, which contains in the sequence 15% of cysteine. The formulations containing the peptide SEQ ID NO:5 had a concentration of peptide of 0.1 mg/mL, in a ratio 1:1 (v/v).

To demonstrate the effect was also tested:
a peptide whose sequence does not contain cysteine, with approximately 41% hydrophobic amino acids;
a peptide which contains in it sequence 8% cysteine, with approximately 58% hydrophobic amino acids.

The hair mask was applied to the hair after 8 bleaching treatments, being left to act for 15 minutes, mimicking the procedure indicated in commercial masks. Posteriorly, the hair was washed. The serum was applied to the hair after 8 bleaching treatments, being left to act for 1 hour at 37° C. Posteriorly, the hair was not washed, as in typical commercial procedures the serum should be applied in dry hair. The hair was also tested after 5 applications.

The peptide from the sequence ID NO: 5 was able to penetrate in the hair fiber for all the formulations.

After the treatment, mechanical tests were performed, using a cell with 2.5 N maximum load and a deformation rate of 1.5 mm/min. Each hair was individually mounted in the tensile jig by means of a paper template with a fixed gauge length of 20 mm.

TABLE 1

Young modulus of virgin hair without treatments and after 8 times bleaching treatments.

| Hair type | Young modulus (MPa) |
| --- | --- |
| Virgin hair | 6579 |
| Hair after 8 time bleaching | 5294 |
| Serum(with a 15% cysteine and 50% hydrophobic amino acids peptide) | 7149 |
| Serum for comparison(with a 41% hydrophobic amino acid without cysteine peptide) | 6180 |
| Serum for comparison (with a 8% cysteine and 58% hydrophobic amino acid peptide) | 6456 |
| Serum for comparison (without peptide) | 6034 |

TABLE 2

Young modulus for different types of hair treatment.

| Type of treatment | Young modulus after 1 application (MPa) | Young modulus after 5 applications (MPa) |
| --- | --- | --- |
| Serum (with a 15% cysteine and 50% hydrophobic amino acid peptide) | 7149 | 7318 |
| Serum for comparison (without peptide) | 6034 | 6112 |
| Mask (with a 15% cysteine and 50% hydrophobic amino acid peptide) | 6175 | 7075 |
| Mask for comparison(without peptide) | 5514 | 5685 |

The peptide in these treatments is the peptide from sequence ID NO: 5, The formulations which contain the sequence ID NO:5 induce an increase in mechanical resistance of the damaged hair. After 5 applications, the hair treated with the sequence ID NO: 5 maintain the high resistance, having a higher increase in the resistance than without the peptide.

Example 2

This example discloses the treatment of human hair with peptides containing cysteine, and in this case the peptide containing the sequence ID NO: 409, based in the assumption that small peptides are able to penetrate in the hair fiber cuticle.

The hair was supplied from International Hair Importers and Products, Inc. (New York). Hair fibers were pre-treated by bleaching. The formulation was tested in different hair types:
virgin hair washed, with the cuticle intact and absence of chemical damages;
hair after 8 bleaching treatments, at 50° C. in 0.1 M Na2CO3/NaHCO3 buffer, at pH=9, 10% H2O2, for 1 hour.

The incorporation of the peptides was performed by direct application in the hair surface. The mechanical resistance tests were performed after the treatment of the hair with the peptide.

The measurements of mechanical resistance were performed using a cell with 2.5 N maximum load and a deformation rate of 1.5 mm/min. Each hair was individually mounted in the tensile jig by means of a paper template with a fixed gauge length of 20 mm.

As for the results obtained for the mechanical test showed that compared to the control, i.e., virgin hair without bleaching or peptide treatment (Young modulus: 4142±590 MPa), bleaching reduced the Young modulus (2478±567 MPa), while the treatment with the peptide sequence ID NO: 409 after bleaching increased the Young modulus to higher valued than the virgin hair with no treatment (5649±1022 MPa).

Example 3

This example discloses the treatment of human hair with a composition comprising peptides. In this example, the peptide with the sequence ID NO: 412 was tested. The hair was supplied from International Hair Importers and Products, Inc. (New York).

The formulation was tested in different hair types:
virgin hair washed, with the cuticle intact and absence of chemical damages;
hair after reduction treatment, at 37° C. in phosphate buffer at pH=8, with 3M GndHCl and 0.05M DTT for 2 hours.

For the treatment with the peptide SEQ ID NO: 412, concentrations of 0.01% (w/w) were used.

The average of the Young's modulus for relaxed hair is 3002 MPa, while for relaxed hair fiber after peptide treatment at 0.01% is 4190 MPa. The Young modulus value for virgin hair without treatment is 5214 MPa.

In the maximum load test, for the relaxed hair fiber, the maximum resistance was 96 MPa, while for the hair fiber relaxed after peptide treatment 126 MPa and for the virgin hair with no treatment 203 MPa.

Regarding hair stretching, the relaxed hair has an average of 51%, while after treatment with the peptide sequence ID NO: 412, has a stretching of 72%. For virgin hair, the average of hair stretching is 58%.

Therefore, it is evident that the peptides are capable to prevent the hair surface degradation and consequently, the hair treated with these peptides has a longer life span.

Example 4

In order to assess the interactions between the keratin and some peptides, a keratin solution was prepared. This procedure was performed by immersing African hair, acquired from the International Hair Importers and Products, Inc. (New York), in a solution containing 8 M urea, 0.2 M sodium dodecyl sulfate and 0.5 M sodium bisulfite. The mixture was heated to 50° C. for 24 h in a shaker bath. The solution was dialyzed for several days against doubledistilled water. The keratin solution was then concentrated using AMICON with a 3 kDa cut-off The keratin was then conjugated with Alexa Fluor 647 carboxylic acid, succinimidyl ester in DMSO anhydrous 5%.

The reaction was incubated for 1 h 30 min at room temperature and in the dark. The Alexa Fluor 647 that did not link to the keratin solution was separated by centrifugation in AMICON with a 3 kDa cut-off for 1 h at 25° C. and 5000×g.

The keratin was then diluted to 1 μg./mL in blocking buffer (3% BSA in tris-buffered saline (TBS) with 0.05% Tween 20). The peptides tested were SEQ.ID NO: 179, SEQ. ID NO:75, SEQ.ID NO:432, SEQ.ID NO:951, SEQ.ID NO:1108, SEQ.ID NO: 1131 and a peptide containing 13 amino acids, including 2 cysteines (X3CX5CX3), where X represents one of known amino acid residues, with the exception of cysteine residue that is represented by the letter C. This peptide is similar to the one tested in Fernandes et at (Fernandes, Lima, Loureiro, Goines, & Cavaco-Paulo, 2012).

Several peptides in a concentration of 15 fmol/mm2, were attached to a glass through a hydrophilic linked moiety, and were then incubated with the keratin, marked with Alexa Fluor 647, for 2 hours at 37° C.

After incubation, the glasses were rinsed in successive washing solutions: TBS+0.1% Tween 20 and blocking buffer with 3%BSA in TBS+0.1% Tween 20, for 3 minutes in each solution.

The imaging of the glasses was performed in Agilent G2565CA Microarray Scanner System. Three replicas of each peptide incubation were performed and analyzed.

TABLE 3

Normalized intensity levels of peptide sequences.

| Sequence | Number of amino acids | Cysteine content | Hydrophobic amino acids content | Intensity level (average ± standard deviation) |
|---|---|---|---|---|
| SEQ. ID NO: 179 | 10 | 20% | 50% | 0.990 ± 0.014 |
| SEQ. ID NO: 75 | 10 | 30% | 60% | 1.000 ± 0.000 |
| SEQ. ID NO: 432 | 10 | 30% | 40% | 1.000 ± 0.000 |
| SEQ. ID NO: 951 | 10 | 40% | 30% | 1.000 ± 0.000 |
| SEQ. ID NO: 1108 | 11 | 46% | 18% | 1.000 ± 0.000 |
| SEQ. ID NO: 1131 | 11 | 46% | 9% | 1.000 ± 0.000 |
| $X_3CX_5CX_3$ | 13 | 15% | 38% | 0.184 ± 0.084 |

The peptides SEQ.ID NO:75, SEQ.ID NO:432, SEQ.ID NO:951, SEQ.ID NO:1108, SEQ.ID NO:1131, with percentage of cysteine ranging from 30% to 46%, such as and percentage of hydrophobic amino acids ranging from 9% to 60% were able to obtain an intensity of 1, indicating a very high affinity to keratin. The peptide SEQ.ID NO:179, with 20% and 50% of cysteine and hydrophobic content, respectively showed a slightly inferior but still very high intensity (0.990+0.014). These peptides were compared with a peptide similar to the one described in Fernandes et al. (Fernandes, Lima, Loureiro, Gomes, & Cavaco-Paulo, 2012) containing 2 cysteines in a 13 amino acids sequence. The reduced percentage of cysteine (15%) and higher number of amino acids in the sequence (13 amino acids) lead to a decrease in the intensity to 0.184±0.084, showing an inferior affinity to keratin. This suggests that the higher number of amino acids difficult the reaction of the peptide with the hair keratins, This inferior affinity to keratin leads to less fixation of the peptides in the hair in posterior treatments and consequently providing less improvements in the recovery of the hair characteristics.

The sequences of peptides are described by one letter code of amino acids. The code is as follows:

```
List of peptide sequences
   Amino acid—One Letter Code
   Histidine—H
   Arginine—R
   Lysine—K
   Isoleucine—I
   Phenylalanine—F
   Leucine—L
   Tryptophan—W
   Alanine—A
   Methionine—M
   Proline—P
   Valine—V
   Cysteine—C
   Asparagine—N
   Glycine—G
   Serine—S
   Glutamine—Q
   Tyrosine—Y
   Threonine—T
   Aspartic acid—D
   Glutamic acid—E SEQ. ID NO: 1           APCAPRPSCG
   SEQ. ID NO: 2           EACVPSVPCP
   SEQ. ID NO: 3           ESCGTASGCA
   SEQ. ID NO: 4           GLCAGTSACL
   SEQ. ID NO: 5           GVCGPSPPCI
   SEQ. ID NO: 6           HGCTLPGACN
   SEQ. ID NO: 7           HSCTLPGACN
   SEQ. ID NO: 8           KDCLQNSLCE
   SEQ. ID NO: 9           LPCLPAASCG
   SEQ. ID NO: 10          LPCYFTGSCN
   SEQ. ID NO: 11          NFCLPSLSCR
   SEQ. ID NO: 12          NPCATTNACD
   SEQ. ID NO: 13          NPCATTNACE
   SEQ. ID NO: 14          NPCATTNACS
```

-continued

| List of peptide sequences | |
|---|---|
| SEQ. ID NO: 15 | NPCGLRARCG |
| SEQ. ID NO: 16 | NPCGPRSRCG |
| SEQ. ID NO: 17 | NPCSTPASCT |
| SEQ. ID NO: 18 | NPCSTSPSCV |
| SEQ. ID NO: 19 | PACTSSSPCS |
| SEQ. ID NO: 20 | SKCHESTVCP |
| SEQ. ID NO: 21 | SPCVPRTVCV |
| SEQ. ID NO: 22 | SSCSVETACL |
| SEQ. ID NO: 23 | SVCSSGVNCR |
| SEQ. ID NO: 24 | TACPLPGTCH |
| SEQ. ID NO: 25 | TNCSPRPICV |
| SEQ. ID NO: 26 | TSCVPPAPCT |
| SEQ. ID NO: 27 | TTCTSSNTCE |
| SEQ. ID NO: 28 | VPCVPSVPCT |
| SEQ. ID NO: 29 | ATCGPSACIT |
| SEQ. ID NO: 30 | GPCISNPCGL |
| SEQ. ID NO: 31 | GPCLSNPCTS |
| SEQ. ID NO: 32 | GSCVTNPCGP |
| SEQ. ID NO: 33 | LTCFSITCSS |
| SEQ. ID NO: 34 | NPCSTPSCTT |
| SEQ. ID NO: 35 | PSCVTAPCAP |
| SEQ. ID NO: 36 | SDCSSTHCSP |
| SEQ. ID NO: 37 | SLCLPPTCHT |
| SEQ. ID NO: 38 | SLCNLGSCGP |
| SEQ. ID NO: 39 | SPCLVGNCAW |
| SEQ. ID NO: 40 | TACLPGTCAT |
| SEQ. ID NO: 41 | TSCLPALCLP |
| SEQ. ID NO: 42 | TSCSSRPCVP |
| SEQ. ID NO: 43 | TTCGGGSCGV |
| SEQ. ID NO: 44 | VNCRPELCLG |
| SEQ. ID NO: 45 | YVCQPMACLP |
| SEQ. ID NO: 46 | AFSCISACGP |
| SEQ. ID NO: 47 | GSVCSAPCNG |
| SEQ. ID NO: 48 | GVVCGDLCAS |
| SEQ. ID NO: 49 | GVVCGDLCVS |
| SEQ. ID NO: 50 | LTGCLLPCYF |
| SEQ. ID NO: 51 | NEDCKLPCNP |
| SEQ. ID NO: 52 | NFSCVSACGP |
| SEQ. ID NO: 53 | PPTCHTACPL |
| SEQ. ID NO: 54 | PQPCATACKP |
| SEQ. ID NO: 55 | SEDCKLPCNP |
| SEQ. ID NO: 56 | SLGCRTSCSS |
| SEQ. ID NO: 57 | SLSCRTSCSS |
| SEQ. ID NO: 58 | SSSCPLGCTM |
| SEQ. ID NO: 59 | TGSCNSPCLV |
| SEQ. ID NO: 60 | TSSCPLGCTM |
| SEQ. ID NO: 61 | VGSCGSSCRK |
| SEQ. ID NO: 62 | VGVCGGSCKR |
| SEQ. ID NO: 63 | VSNCNWFCEG |
| SEQ. ID NO: 64 | ACGPRPGRCC |
| SEQ. ID NO: 65 | ACGPRPSRCC |
| SEQ. ID NO: 66 | CAPRPSCGPC |
| SEQ. ID NO: 67 | CEPCSAYVIC |
| SEQ. ID NO: 68 | CGLRARCGPC |
| SEQ. ID NO: 69 | CGPRPGRCCI |
| SEQ. ID NO: 70 | CGPRPSRCCI |
| SEQ. ID NO: 71 | CGPRSRCGPC |
| SEQ. ID NO: 72 | CGTSQKGCCN |
| SEQ. ID NO: 73 | CHGCTLPGAC |
| SEQ. ID NO: 74 | CHSCTLPGAC |
| SEQ. ID NO: 75 | CLPCLPAASC |
| SEQ. ID NO: 76 | CLPPTCHTAC |
| SEQ. ID NO: 77 | CLSNPCTSCV |
| SEQ. ID NO: 78 | CLVGNCAWCE |
| SEQ. ID NO: 79 | CNPCSTPASC |
| SEQ. ID NO: 80 | CNPCSTPSCT |
| SEQ. ID NO: 81 | CNPCSTSPSC |
| SEQ. ID NO: 82 | CNSPCLVGNC |
| SEQ. ID NO: 83 | CRTSCSSRPC |
| SEQ. ID NO: 84 | CSLKEHCSAC |
| SEQ. ID NO: 85 | CSPRPICVPC |
| SEQ. ID NO: 86 | CSSTMSYSCC |
| SEQ. ID NO: 87 | CSTPASCTSC |
| SEQ. ID NO: 88 | CSTPSCTTCV |
| SEQ. ID NO: 89 | CTSCVPPAPC |
| SEQ. ID NO: 90 | CTSSNTCEPC |
| SEQ. ID NO: 91 | CVPPAPCTPC |

-continued

| List of peptide sequences | |
|---|---|
| SEQ. ID NO: 92 | CVPPSCHGCT |
| SEQ. ID NO: 93 | CVPPSCHSCT |
| SEQ. ID NO: 94 | DCKLPCNPCA |
| SEQ. ID NO: 95 | DCKLPCNPCS |
| SEQ. ID NO: 96 | PCGTSQKGCC |
| SEQ. ID NO: 97 | PCLSNPCTSC |
| SEQ. ID NO: 98 | PCLVGNCAWC |
| SEQ. ID NO: 99 | PCNPCSTPSC |
| SEQ. ID NO: 100 | PCSTPSCTTC |
| SEQ. ID NO: 101 | PCTTCGPTCG |
| SEQ. ID NO: 102 | PCVPPSCHGC |
| SEQ. ID NO: 103 | PCVPPSCHSC |
| SEQ. ID NO: 104 | SCCLPSLGCR |
| SEQ. ID NO: 105 | SCSEELQCCQ |
| SEQ. ID NO: 106 | SCSPCSTTCT |
| SEQ. ID NO: 107 | ASCSTSGTCG |
| SEQ. ID NO: 108 | ASCYIPVGCQ |
| SEQ. ID NO: 109 | ASCYVPVSCQ |
| SEQ. ID NO: 110 | AVCTLPSSCQ |
| SEQ. ID NO: 111 | DLCPTSVSCG |
| SEQ. ID NO: 112 | EICWEPTSCQ |
| SEQ. ID NO: 113 | ETCGEPTSCQ |
| SEQ. ID NO: 114 | ETCNETTSCQ |
| SEQ. ID NO: 115 | ETCWRPNSCQ |
| SEQ. ID NO: 116 | GYCGYRPFCF |
| SEQ. ID NO: 117 | KTCWEPASCQ |
| SEQ. ID NO: 118 | KTCWEPTSCQ |
| SEQ. ID NO: 119 | LDCVDTTPCK |
| SEQ. ID NO: 120 | LGCGYGSFCG |
| SEQ. ID NO: 121 | NSCGYGSGCG |
| SEQ. ID NO: 122 | NYCPSNTMCE |
| SEQ. ID NO: 123 | PACVTSYSCR |
| SEQ. ID NO: 124 | PDCHVEGTCL |
| SEQ. ID NO: 125 | PDCRVEGTCL |
| SEQ. ID NO: 126 | PICSEPSPCS |
| SEQ. ID NO: 127 | PICYIFKPCQ |
| SEQ. ID NO: 128 | PLCYISNSCQ |
| SEQ. ID NO: 129 | PPCGQPTPCS |
| SEQ. ID NO: 130 | PPCHIPQPCV |
| SEQ. ID NO: 131 | PSCGRLASCG |
| SEQ. ID NO: 132 | PSCSESSICQ |
| SEQ. ID NO: 133 | PSCSEVTSCP |
| SEQ. ID NO: 134 | PSCSTSGTCG |
| SEQ. ID NO: 135 | PSCSVSSGCQ |
| SEQ. ID NO: 136 | PSCTESDSCK |
| SEQ. ID NO: 137 | PSCYQTSSCG |
| SEQ. ID NO: 138 | PTCFLLNSCQ |
| SEQ. ID NO: 139 | PTCSVTSSCQ |
| SEQ. ID NO: 140 | PTCWLLNNCH |
| SEQ. ID NO: 141 | PTCYQRTSCV |
| SEQ. ID NO: 142 | PTCYRRTSCV |
| SEQ. ID NO: 143 | PTCYVVKRCP |
| SEQ. ID NO: 144 | PVCFEATICE |
| SEQ. ID NO: 145 | PVCFEATVCE |
| SEQ. ID NO: 146 | PVCSRPASCS |
| SEQ. ID NO: 147 | PVCSWVPACS |
| SEQ. ID NO: 148 | QTCNESSYCL |
| SEQ. ID NO: 149 | QTCWEPTSCQ |
| SEQ. ID NO: 150 | SFCRLGYGCG |
| SEQ. ID NO: 151 | SFCRRGSGCG |
| SEQ. ID NO: 152 | SLCGYGYGCG |
| SEQ. ID NO: 153 | SLCSTEVSCG |
| SEQ. ID NO: 154 | SNCFGQLNCL |
| SEQ. ID NO: 155 | SPCGQPTPCS |
| SEQ. ID NO: 156 | SSCDQSSSCA |
| SEQ. ID NO: 157 | SSCGQSSSCA |
| SEQ. ID NO: 158 | SVCPEPVSCP |
| SEQ. ID NO: 159 | TFCSFDKSCR |
| SEQ. ID NO: 160 | TICSSDKSCR |
| SEQ. ID NO: 161 | TLCVESSPCH |
| SEQ. ID NO: 162 | TPCYQQSSCQ |
| SEQ. ID NO: 163 | VTCSRQTTCI |
| SEQ. ID NO: 164 | YGCGYGSGCG |
| SEQ. ID NO: 165 | YGCGYGSGCR |
| SEQ. ID NO: 166 | YGCIHSTHCG |
| SEQ. ID NO: 167 | AACEPSACQS |
| SEQ. ID NO: 168 | AACEPSPCQS |

-continued

| List of peptide sequences | |
|---|---|
| SEQ. ID NO: 169 | AACTMSVCSS |
| SEQ. ID NO: 170 | ADCLGGICLP |
| SEQ. ID NO: 171 | ALCLPSSCHS |
| SEQ. ID NO: 172 | ALCSPSTCQL |
| SEQ. ID NO: 173 | APCLALVCAP |
| SEQ. ID NO: 174 | APCLSLVCTP |
| SEQ. ID NO: 175 | APCLTLVCTP |
| SEQ. ID NO: 176 | APCVALLCRP |
| SEQ. ID NO: 177 | ASCGSLLCRP |
| SEQ. ID NO: 178 | ASCLSFLCRP |
| SEQ. ID NO: 179 | ASCVSLLCRP |
| SEQ. ID NO: 180 | AVCEPSPCQS |
| SEQ. ID NO: 181 | AVCLPVSCQS |
| SEQ. ID NO: 182 | AVCVPVRCQS |
| SEQ. ID NO: 183 | AVCVPVSCQS |
| SEQ. ID NO: 184 | DLCSPSTCQL |
| SEQ. ID NO: 185 | DSCGSSSCGP |
| SEQ. ID NO: 186 | DSCVQSNCFP |
| SEQ. ID NO: 187 | FNCSTRNCSS |
| SEQ. ID NO: 188 | GGCGSYGCSQ |
| SEQ. ID NO: 189 | GSCGFGSCYG |
| SEQ. ID NO: 190 | GSCSSRKCFS |
| SEQ. ID NO: 191 | GVCLPSTCPH |
| SEQ. ID NO: 192 | HSCEGYLCYS |
| SEQ. ID NO: 193 | IVCAAPSCQS |
| SEQ. ID NO: 194 | KTCSTTGCDP |
| SEQ. ID NO: 195 | LACVSQPCQS |
| SEQ. ID NO: 196 | LGCGYGGCGY |
| SEQ. ID NO: 197 | LSCGSRSCSS |
| SEQ. ID NO: 198 | LVCTPVSCVS |
| SEQ. ID NO: 199 | NGCQETYCEP |
| SEQ. ID NO: 200 | NSCRSLSCGS |
| SEQ. ID NO: 201 | PACVISTCPR |
| SEQ. ID NO: 202 | PGCLNQSCGS |
| SEQ. ID NO: 203 | PPCGTAPCLT |
| SEQ. ID NO: 204 | PPCTTALCRP |
| SEQ. ID NO: 205 | PPCYLVSCTP |
| SEQ. ID NO: 206 | PRCTRPICEP |
| SEQ. ID NO: 207 | PSCPVSSCAQ |
| SEQ. ID NO: 208 | PSCQPSVCVP |
| SEQ. ID NO: 209 | PSCSVSNCYQ |
| SEQ. ID NO: 210 | PSCSVSSCAQ |
| SEQ. ID NO: 211 | PSCTSVLCRP |
| SEQ. ID NO: 212 | PTCKSPSCEP |
| SEQ. ID NO: 213 | PTCVISSCPR |
| SEQ. ID NO: 214 | PTCVISTCPR |
| SEQ. ID NO: 215 | PTCYQTICFR |
| SEQ. ID NO: 216 | PVCGGVSCHT |
| SEQ. ID NO: 217 | PVCGRVSCHT |
| SEQ. ID NO: 218 | PVCNKPVCFV |
| SEQ. ID NO: 219 | PVCPTPTCSV |
| SEQ. ID NO: 220 | PVCRSTYCVP |
| SEQ. ID NO: 221 | PVCSKSVCYV |
| SEQ. ID NO: 222 | PVCSRPACYS |
| SEQ. ID NO: 223 | PVCYVPTCSE |
| SEQ. ID NO: 224 | QFCLSKSCQP |
| SEQ. ID NO: 225 | RPCERTACQS |
| SEQ. ID NO: 226 | RSCQTSFCGF |
| SEQ. ID NO: 227 | RSCSSLGCGS |
| SEQ. ID NO: 228 | RSCYSVGCGS |
| SEQ. ID NO: 229 | RVCLPGSCDS |
| SEQ. ID NO: 230 | SFCGFPSCST |
| SEQ. ID NO: 231 | SFCGYPSCST |
| SEQ. ID NO: 232 | SGCDPASCQP |
| SEQ. ID NO: 233 | SGCGGSGCGG |
| SEQ. ID NO: 234 | SGCQPSSCLA |
| SEQ. ID NO: 235 | SHCQPPHCQL |
| SEQ. ID NO: 236 | SICQPATCVA |
| SEQ. ID NO: 237 | SLCVPVSCRP |
| SEQ. ID NO: 238 | SNCLPTSCQP |
| SEQ. ID NO: 239 | SPCLVSSCQP |
| SEQ. ID NO: 240 | SPCQQSSCQE |
| SEQ. ID NO: 241 | SPCQQSYCVP |
| SEQ. ID NO: 242 | SPCSPAVCVS |
| SEQ. ID NO: 243 | SRCQQPSCQP |
| SEQ. ID NO: 244 | SRCYRPHCGQ |
| SEQ. ID NO: 245 | SSCAPIYCRR |

List of peptide sequences

| | |
|---|---|
| SEQ. ID NO: 246 | SSCAPVYCRR |
| SEQ. ID NO: 247 | SSCGKGGCGS |
| SEQ. ID NO: 248 | SSCGKRGCGS |
| SEQ. ID NO: 249 | SSCLPVSCRP |
| SEQ. ID NO: 250 | SSCQPAYCTS |
| SEQ. ID NO: 251 | SSCQPSYCRQ |
| SEQ. ID NO: 252 | SSCQPVVCEP |
| SEQ. ID NO: 253 | SSCTAVVCRP |
| SEQ. ID NO: 254 | SSCYQPFCRS |
| SEQ. ID NO: 255 | SSCYRPICGS |
| SEQ. ID NO: 256 | SSCYRPTCGS |
| SEQ. ID NO: 257 | SVCMSGSCQA |
| SEQ. ID NO: 258 | SVCSDQGCDQ |
| SEQ. ID NO: 259 | SVCSDOGCGL |
| SEQ. ID NO: 260 | SVCSDQGCGQ |
| SEQ. ID NO: 261 | SVCSDQGCSQ |
| SEQ. ID NO: 262 | SVCSDQSCGQ |
| SEQ. ID NO: 263 | SVCSHQGCGQ |
| SEQ. ID NO: 264 | SVCSHQGCGR |
| SEQ. ID NO: 265 | SVCVPVSCRP |
| SEQ. ID NO: 266 | SYCRQASCVS |
| SEQ. ID NO: 267 | TACEPSACQS |
| SEQ. ID NO: 268 | TICTASPCQP |
| SEQ. ID NO: 269 | TSCPETSCLP |
| SEQ. ID NO: 270 | TSCQMTNCEQ |
| SEQ. ID NO: 271 | TSCQPVHCET |
| SEQ. ID NO: 272 | TSCQPVLCKS |
| SEQ. ID NO: 273 | TSCQPVLCVP |
| SEQ. ID NO: 274 | TSCVGFVCQP |
| SEQ. ID NO: 275 | TSCVSNPCQV |
| SEQ. ID NO: 276 | TTCFQPTCVS |
| SEQ. ID NO: 277 | TTCFQPTCVT |
| SEQ. ID NO: 278 | TTCFQPTCVY |
| SEQ. ID NO: 279 | TTCISNPCST |
| SEQ. ID NO: 280 | TWCQGSSCQP |
| SEQ. ID NO: 281 | VGCQSSVCVP |
| SEQ. ID NO: 282 | VPCQPSTCVF |
| SEQ. ID NO: 283 | VSCEPSPCQS |
| SEQ. ID NO: 284 | VSCGGPICLP |
| SEQ. ID NO: 285 | VSCKPVLCVA |
| SEQ. ID NO: 286 | VSCPSTSCRP |
| SEQ. ID NO: 287 | VSCQSSVCMP |
| SEQ. ID NO: 288 | VSCTRIVCVA |
| SEQ. ID NO: 289 | VTCEPSPCQS |
| SEQ. ID NO: 290 | VTCQTTVCRP |
| SEQ. ID NO: 291 | YGCGYEGCRY |
| SEQ. ID NO: 292 | AGSCQPSCSE |
| SEQ. ID NO: 293 | ALLCRPLCGV |
| SEQ. ID NO: 294 | ALVCEPVCLR |
| SEQ. ID NO: 295 | ATICEPSCSV |
| SEQ. ID NO: 296 | ATTCEPSCSV |
| SEQ. ID NO: 297 | ATVCEPSCSV |
| SEQ. ID NO: 298 | EGTCLPPCYL |
| SEQ. ID NO: 299 | FSTCRPSCSG |
| SEQ. ID NO: 300 | GFVCQPMCSH |
| SEQ. ID NO: 301 | GLDCGYGCGY |
| SEQ. ID NO: 302 | GLGCGYGCGY |
| SEQ. ID NO: 303 | GLGCSYGCGH |
| SEQ. ID NO: 304 | GLGCSYGCGL |
| SEQ. ID NO: 305 | GSGCGYGCGY |
| SEQ. ID NO: 306 | GTGCGYGCGY |
| SEQ. ID NO: 307 | GVSCHTTCYR |
| SEQ. ID NO: 308 | GYACNFPCSY |
| SEQ. ID NO: 309 | GYGCGYGCGF |
| SEQ. ID NO: 310 | HSPCQASCYV |
| SEQ. ID NO: 311 | HTSCSPACQP |
| SEQ. ID NO: 312 | HTSCSSGCQP |
| SEQ. ID NO: 313 | IRWCHPDCHV |
| SEQ. ID NO: 314 | IRWCRPDCRV |
| SEQ. ID NO: 315 | ISSCGTGCGI |
| SEQ. ID NO: 316 | KGGCGSGCGG |
| SEQ. ID NO: 317 | KGGCGSSCSQ |
| SEQ. ID NO: 318 | LVTCQDSCGS |
| SEQ. ID NO: 319 | LVTCQESCQP |
| SEQ. ID NO: 320 | MSICSSACTD |
| SEQ. ID NO: 321 | MSICSSACTN |
| SEQ. ID NO: 322 | MSVCSSACSD |

| List of peptide sequences | |
|---|---|
| SEQ. ID NO: 323 | PAICEPSCSV |
| SEQ. ID NO: 324 | PASCQKSCYR |
| SEQ. ID NO: 325 | PIYCRRTCYH |
| SEQ. ID NO: 326 | PNSCQTLCVE |
| SEQ. ID NO: 327 | PQPCVPTCFL |
| SEQ. ID NO: 328 | PSACQSGCTS |
| SEQ. ID NO: 329 | PSPCEPSCSE |
| SEQ. ID NO: 330 | PSPCQASCYI |
| SEQ. ID NO: 331 | PSPCQSGCIS |
| SEQ. ID NO: 332 | PSPCQSGCTD |
| SEQ. ID NO: 333 | PSPCQSGCTS |
| SEQ. ID NO: 334 | PTACQPTCYQ |
| SEQ. ID NO: 335 | PTACQPTCYR |
| SEQ. ID NO: 336 | PTPCSTTCRT |
| SEQ. ID NO: 337 | PTSCQKSCYR |
| SEQ. ID NO: 338 | PTSCQPSCES |
| SEQ. ID NO: 339 | PTSCQTSCTL |
| SEQ. ID NO: 340 | PVICEPSCSV |
| SEQ. ID NO: 341 | PVSCVPVCSG |
| SEQ. ID NO: 342 | PVTCVPRCTR |
| SEQ. ID NO: 343 | PVYCRRTCYH |
| SEQ. ID NO: 344 | PVYCRRTCYY |
| SEQ. ID NO: 345 | PVYCVPVCSG |
| SEQ. ID NO: 346 | QPGCESPCEP |
| SEQ. ID NO: 347 | QQSCVSSCRR |
| SEQ. ID NO: 348 | QTSCGSSCGQ |
| SEQ. ID NO: 349 | QTTCHPSCGM |
| SEQ. ID NO: 350 | QTTCRPSCGV |
| SEQ. ID NO: 351 | RGGCGSGCGG |
| SEQ. ID NO: 352 | RLACYSLCSG |
| SEQ. ID NO: 353 | RPACYRPCYS |
| SEQ. ID NO: 354 | RPFCFRRCYS |
| SEQ. ID NO: 355 | RPICRPICSG |
| SEQ. ID NO: 356 | RPLCYRRCYS |
| SEQ. ID NO: 357 | RSPCQASCYV |
| SEQ. ID NO: 358 | RVSCHTTCYR |
| SEQ. ID NO: 359 | SAICRPTCPR |
| SEQ. ID NO: 360 | SDSCKRDCKK |
| SEQ. ID NO: 361 | SEGCGSGCGG |
| SEQ. ID NO: 362 | SFLCRPACSR |
| SEQ. ID NO: 363 | SGGCGSGCGG |
| SEQ. ID NO: 364 | SGGCGSSCGG |
| SEQ. ID NO: 365 | SGSCQAACGQ |
| SEQ. ID NO: 366 | SLLCHPVCKS |
| SEQ. ID NO: 367 | SLLCHPVCRS |
| SEQ. ID NO: 368 | SLLCRPACSP |
| SEQ. ID NO: 369 | SLLCRPACSR |
| SEQ. ID NO: 370 | SLLCRPICRP |
| SEQ. ID NO: 371 | SLLCRPMCSR |
| SEQ. ID NO: 372 | SLLCRPTCSR |
| SEQ. ID NO: 373 | SLLCRPVCQP |
| SEQ. ID NO: 374 | SLLCRPVCRP |
| SEQ. ID NO: 375 | SLLCRPVCRS |
| SEQ. ID NO: 376 | SLLCRPVCSR |
| SEQ. ID NO: 377 | SNPCQVTCSR |
| SEQ. ID NO: 378 | SRGCGSGCGG |
| SEQ. ID NO: 379 | SRSCQSPCYR |
| SEQ. ID NO: 380 | SRSCQSSCYR |
| SEQ. ID NO: 381 | SSGCGYGCGY |
| SEQ. ID NO: 382 | SSGCPMACPG |
| SEQ. ID NO: 383 | SSICQPICSE |
| SEQ. ID NO: 384 | SSPCHTSCYY |
| SEQ. ID NO: 385 | SSPCQPTCYV |
| SEQ. ID NO: 386 | SSPCQQSCYV |
| SEQ. ID NO: 387 | SSPCQTSCYR |
| SEQ. ID NO: 388 | SSSCQQSCRV |
| SEQ. ID NO: 389 | STVCQPACGV |
| SEQ. ID NO: 390 | TDNCQETCGE |
| SEQ. ID NO: 391 | TQPCYEPCLP |
| SEQ. ID NO: 392 | TSSCGTGCGI |
| SEQ. ID NO: 393 | TSSCQPSCGR |
| SEQ. ID NO: 394 | TSSCTTPCYQ |
| SEQ. ID NO: 395 | TSVCLPGCLN |
| SEQ. ID NO: 396 | TTVCLPGCLN |
| SEQ. ID NO: 397 | VANCQAPCST |
| SEQ. ID NO: 398 | VDDCPESCWP |
| SEQ. ID NO: 399 | VKRCPSVCPE |

-continued

| List of peptide sequences | |
|---|---|
| SEQ. ID NO: 400 | VSSCQPSCSE |
| SEQ. ID NO: 401 | YEGCRYGCGH |
| SEQ. ID NO: 402 | YGRCRHGCHS |
| SEQ. ID NO: 403 | YGYCRPSCYG |
| SEQ. ID NO: 404 | YRDCQKTCWE |
| SEQ. ID NO: 405 | YRGCQEICWE |
| SEQ. ID NO: 406 | YRGCQETCWR |
| SEQ. ID NO: 407 | YRGCQQTCWE |
| SEQ. ID NO: 408 | YRSCRPSCYG |
| SEQ. ID NO: 409 | GGVCGPSPPC |
| SEQ. ID NO: 410 | GVCGPSPPCI |
| SEQ. ID NO: 411 | VCGPSPPCIT |
| SEQ. ID NO: 412 | CGPSPPCITT |
| SEQ. ID NO: 413 | CAPIYCRRTC |
| SEQ. ID NO: 414 | CAPSPCQASC |
| SEQ. ID NO: 415 | CAPSPCQPAC |
| SEQ. ID NO: 416 | CAPVYCRRTC |
| SEQ. ID NO: 417 | CASSPCQQAC |
| SEQ. ID NO: 418 | CASSSCQPAC |
| SEQ. ID NO: 419 | CASSSCQQSC |
| SEQ. ID NO: 420 | CCGNFSSHSC |
| SEQ. ID NO: 421 | CCGYGGLGCG |
| SEQ. ID NO: 422 | CCNYYGNSCG |
| SEQ. ID NO: 423 | CCNYYRNSCG |
| SEQ. ID NO: 424 | CCSRNFSSCS |
| SEQ. ID NO: 425 | CDAGSCQPSC |
| SEQ. ID NO: 426 | CDPCSLQEGC |
| SEQ. ID NO: 427 | CDPSPCEPSC |
| SEQ. ID NO: 428 | CDPVICEPSC |
| SEQ. ID NO: 429 | CDQGLCQETC |
| SEQ. ID NO: 430 | CEATTCEPSC |
| SEQ. ID NO: 431 | CELPCGTPSC |
| SEQ. ID NO: 432 | CEPAICEPSC |
| SEQ. ID NO: 433 | CEPPCGTAPC |
| SEQ. ID NO: 434 | CEPPCSAPSC |
| SEQ. ID NO: 435 | CEPRSCASSC |
| SEQ. ID NO: 436 | CEPSACQSGC |
| SEQ. ID NO: 437 | CEPSCSVSNC |

-continued

| List of peptide sequences | |
|---|---|
| SEQ. ID NO: 438 | CEPSCSVSSC |
| SEQ. ID NO: 439 | CEPSPCQSGC |
| SEQ. ID NO: 440 | CEPTACQPTC |
| SEQ. ID NO: 441 | CEPTSCQTSC |
| SEQ. ID NO: 442 | CEPVCLRPVC |
| SEQ. ID NO: 443 | CETSSCQPRC |
| SEQ. ID NO: 444 | CETTCFQPTC |
| SEQ. ID NO: 445 | CFQPTCVSSC |
| SEQ. ID NO: 446 | CFQPTCVTSC |
| SEQ. ID NO: 447 | CFQPTCVYSC |
| SEQ. ID NO: 448 | CGCGFRRLGC |
| SEQ. ID NO: 449 | CGCGYRGLDC |
| SEQ. ID NO: 450 | CGCNGYYGCY |
| SEQ. ID NO: 451 | CGFGSCYGCG |
| SEQ. ID NO: 452 | CGGSGCGGSC |
| SEQ. ID NO: 453 | CGGSGSSCCV |
| SEQ. ID NO: 454 | CGGVSCHTTC |
| SEQ. ID NO: 455 | CGKGGCGSCG |
| SEQ. ID NO: 456 | CGKRGCGSCG |
| SEQ. ID NO: 457 | CGQDLCQETC |
| SEQ. ID NO: 458 | CGQTSCGSSC |
| SEQ. ID NO: 459 | CGQVLCQETC |
| SEQ. ID NO: 460 | CGRDLCQETC |
| SEQ. ID NO: 461 | CGRVSCHTTC |
| SEQ. ID NO: 462 | CGSCGFGSCY |
| SEQ. ID NO: 463 | CGSCGGSKGC |
| SEQ. ID NO: 464 | CGSGCGVPVC |
| SEQ. ID NO: 465 | CGSLLCRPTC |
| SEQ. ID NO: 466 | CGSRCYVPVC |
| SEQ. ID NO: 467 | CGSSSCGPQC |
| SEQ. ID NO: 468 | CGSVCSDQGC |
| SEQ. ID NO: 469 | CGSVCSDQSC |
| SEQ. ID NO: 470 | CGSVCSHQGC |
| SEQ. ID NO: 471 | CGSYGCSQCS |
| SEQ. ID NO: 472 | CGVCLPSTCP |
| SEQ. ID NO: 473 | CGYEGCRYGC |
| SEQ. ID NO: 474 | CGYGCGYGCG |
| SEQ. ID NO: 475 | CGYGGCGYGC |
| SEQ. ID NO: 476 | CGYGSFCGCG |

List of peptide sequences

| | |
|---|---|
| SEQ. ID NO: 477 | CGYGSGCGCG |
| SEQ. ID NO: 478 | CHPSCGMSSC |
| SEQ. ID NO: 479 | CHPSCSISSC |
| SEQ. ID NO: 480 | CHPTCYQTIC |
| SEQ. ID NO: 481 | CHTSCSPACQ |
| SEQ. ID NO: 482 | CHTSCSSGCQ |
| SEQ. ID NO: 483 | CHTTCYRPAC |
| SEQ. ID NO: 484 | CHTTCYRPTC |
| SEQ. ID NO: 485 | CIHSPCQASC |
| SEQ. ID NO: 486 | CIHSTHCGCN |
| SEQ. ID NO: 487 | CIRSPCQASC |
| SEQ. ID NO: 488 | CISSCYRPQC |
| SEQ. ID NO: 489 | CISSPCQQSC |
| SEQ. ID NO: 490 | CKPCSSQSSC |
| SEQ. ID NO: 491 | CKPSCSQSSC |
| SEQ. ID NO: 492 | CKPVCFKPIC |
| SEQ. ID NO: 493 | CKPVCYVPTC |
| SEQ. ID NO: 494 | CKPVSCVPVC |
| SEQ. ID NO: 495 | CKPVYCVPVC |
| SEQ. ID NO: 496 | CKTVYCKPIC |
| SEQ. ID NO: 497 | CLNQSCGSNC |
| SEQ. ID NO: 498 | CLNQSCGSSC |
| SEQ. ID NO: 499 | CLPGCLNQSC |
| SEQ. ID NO: 500 | CLPGSCDSCS |
| SEQ. ID NO: 501 | CLPPCYLVSC |
| SEQ. ID NO: 502 | CLPTSCQPSC |
| SEQ. ID NO: 503 | CLSFLCRPAC |
| SEQ. ID NO: 504 | CLVSSCQPSC |
| SEQ. ID NO: 505 | CMPSPCQPAC |
| SEQ. ID NO: 506 | CMSGSCQAAC |
| SEQ. ID NO: 507 | CNESSYCLPC |
| SEQ. ID NO: 508 | CPASCVSLLC |
| SEQ. ID NO: 509 | CPMACPGSPC |
| SEQ. ID NO: 510 | CPSSCTAVVC |
| SEQ. ID NO: 511 | CPVTCEPSPC |
| SEQ. ID NO: 512 | CQAACEPSAC |
| SEQ. ID NO: 513 | CQAACEPSPC |
| SEQ. ID NO: 514 | CQAACGQSVC |
| SEQ. ID NO: 515 | CQAPCSTKNC |
| SEQ. ID NO: 516 | CQAVCEPSPC |
| SEQ. ID NO: 517 | CQDSCGSSSC |
| SEQ. ID NO: 518 | CQHSSCQPTC |
| SEQ. ID NO: 519 | CQISSCGTGC |
| SEQ. ID NO: 520 | CQKSSCQPAC |
| SEQ. ID NO: 521 | CQPMCSHAAC |
| SEQ. ID NO: 522 | CQPPCTTALC |
| SEQ. ID NO: 523 | CQPSCESSFC |
| SEQ. ID NO: 524 | CQPSCSESTC |
| SEQ. ID NO: 525 | CQPSCTSVLC |
| SEQ. ID NO: 526 | CQPTCGGSSC |
| SEQ. ID NO: 527 | CQPTCSRPSC |
| SEQ. ID NO: 528 | CQPVCPTPTC |
| SEQ. ID NO: 529 | CQPVLCKSSC |
| SEQ. ID NO: 530 | CQPVVCEPSC |
| SEQ. ID NO: 531 | CQQPSCQPAC |
| SEQ. ID NO: 532 | CQQSCRVPVC |
| SEQ. ID NO: 533 | CQQSCYVPVC |
| SEQ. ID NO: 534 | CQQSGCQPAC |
| SEQ. ID NO: 535 | CQQSSCHPAC |
| SEQ. ID NO: 536 | CQQSSCKPAC |
| SEQ. ID NO: 537 | CQQSSCQLAC |
| SEQ. ID NO: 538 | CQQSSCQPAC |
| SEQ. ID NO: 539 | CQQSSCQPTC |
| SEQ. ID NO: 540 | CQQSSCQSAC |
| SEQ. ID NO: 541 | CQQSSCVSCV |
| SEQ. ID NO: 542 | CQQSYCVPVC |
| SEQ. ID NO: 543 | CQSGCISSCT |
| SEQ. ID NO: 544 | CQSGCTDSCT |
| SEQ. ID NO: 545 | CQSGCTSSCT |
| SEQ. ID NO: 546 | CQSSCYRPTC |
| SEQ. ID NO: 547 | CQSVCYQPTC |
| SEQ. ID NO: 548 | CQSVYCQPTC |
| SEQ. ID NO: 549 | CQTACEPSAC |
| SEQ. ID NO: 550 | CQTSSCGTGC |
| SEQ. ID NO: 551 | CQTTCHPSCG |
| SEQ. ID NO: 552 | CQTTCRPSCG |
| SEQ. ID NO: 553 | CQTTCYRTTC |

| List of peptide sequences | |
|---|---|
| SEQ. ID NO: 554 | CQTTRCRTTC |
| SEQ. ID NO: 555 | CQVTCEPSPC |
| SEQ. ID NO: 556 | CRNTSCQPTC |
| SEQ. ID NO: 557 | CRPACSPLAC |
| SEQ. ID NO: 558 | CRPACSRLAC |
| SEQ. ID NO: 559 | CRPACSRPAC |
| SEQ. ID NO: 560 | CRPMCSRPAC |
| SEQ. ID NO: 561 | CRPSCGQTTC |
| SEQ. ID NO: 562 | CRPSCGVSSC |
| SEQ. ID NO: 563 | CRPSCSISSC |
| SEQ. ID NO: 564 | CRPSCSQTTC |
| SEQ. ID NO: 565 | CRPSYCGQSC |
| SEQ. ID NO: 566 | CRPSYCISSC |
| SEQ. ID NO: 567 | CRPSYCQTTC |
| SEQ. ID NO: 568 | CRPTCSRLAC |
| SEQ. ID NO: 569 | CRPTCSSGSC |
| SEQ. ID NO: 570 | CRPTSCQNTC |
| SEQ. ID NO: 571 | CRPVCRSTYC |
| SEQ. ID NO: 572 | CRPVCSRPAC |
| SEQ. ID NO: 573 | CRPVTCVPRC |
| SEQ. ID NO: 574 | CRQSSCQPAC |
| SEQ. ID NO: 575 | CRTTCFHPIC |
| SEQ. ID NO: 576 | CRTTCFQPTC |
| SEQ. ID NO: 577 | CRTTCYRPSC |
| SEQ. ID NO: 578 | CRTTYCRPSC |
| SEQ. ID NO: 579 | CRVTCEPSPC |
| SEQ. ID NO: 580 | CRYGCGHRGC |
| SEQ. ID NO: 581 | CSAPCVALLC |
| SEQ. ID NO: 582 | CSDDSGSCCQ |
| SEQ. ID NO: 583 | CSEDSSSCCQ |
| SEQ. ID NO: 584 | CSEDSYSCCQ |
| SEQ. ID NO: 585 | CSEGCGSGCG |
| SEQ. ID NO: 586 | CSESSPSCCQ |
| SEQ. ID NO: 587 | CSESSSSCCQ |
| SEQ. ID NO: 588 | CSFDKSCRCG |
| SEQ. ID NO: 589 | CSGASSLCCQ |
| SEQ. ID NO: 590 | CSGASSPCCQ |
| SEQ. ID NO: 591 | CSGASSSCCQ |
| SEQ. ID NO: 592 | CSGASTSCCQ |
| SEQ. ID NO: 593 | CSGGCGSGCG |
| SEQ. ID NO: 594 | CSGGCGSSCG |
| SEQ. ID NO: 595 | CSGISSSCCQ |
| SEQ. ID NO: 596 | CSKDSSSCCQ |
| SEQ. ID NO: 597 | CSKGACGSCG |
| SEQ. ID NO: 598 | CSLSCGSRSC |
| SEQ. ID NO: 599 | CSQDLCQETC |
| SEQ. ID NO: 600 | CSRGCGSGCG |
| SEQ. ID NO: 601 | CSRLSSACCG |
| SEQ. ID NO: 602 | CSSCGKGGCG |
| SEQ. ID NO: 603 | CSSCGKRGCG |
| SEQ. ID NO: 604 | CSSDKSCRCG |
| SEQ. ID NO: 605 | CSSGNFSSCC |
| SEQ. ID NO: 606 | CSSSGCGSFC |
| SEQ. ID NO: 607 | CSSSGCGSSC |
| SEQ. ID NO: 608 | CSTPCYQPIC |
| SEQ. ID NO: 609 | CSTTCRTSSC |
| SEQ. ID NO: 610 | CSWVPACSCT |
| SEQ. ID NO: 611 | CTFSPCQQAC |
| SEQ. ID NO: 612 | CTMSVCSSAC |
| SEQ. ID NO: 613 | CTRPICEPCR |
| SEQ. ID NO: 614 | CTSSPCQHAC |
| SEQ. ID NO: 615 | CTSSPCQQAC |
| SEQ. ID NO: 616 | CTSSPCQQSC |
| SEQ. ID NO: 617 | CTSSSCQQAC |
| SEQ. ID NO: 618 | CVALLCRPLC |
| SEQ. ID NO: 619 | CVALVCEPVC |
| SEQ. ID NO: 620 | CVFSSCNTTC |
| SEQ. ID NO: 621 | CVGFVCQPMC |
| SEQ. ID NO: 622 | CVPRCTRPIC |
| SEQ. ID NO: 623 | CVPSPCQVAC |
| SEQ. ID NO: 624 | CVPSRCQASC |
| SEQ. ID NO: 625 | CVPSSCQASC |
| SEQ. ID NO: 626 | CVPVCNKPVC |
| SEQ. ID NO: 627 | CVPVCSKSVC |
| SEQ. ID NO: 628 | CVPVRCKPVC |
| SEQ. ID NO: 629 | CVSLLCRPAC |
| SEQ. ID NO: 630 | CVSLLCRPMC |

| List of peptide sequences | |
|---|---|
| SEQ. ID NO: 631 | CVSLLCRPTC |
| SEQ. ID NO: 632 | CVSLLCRPVC |
| SEQ. ID NO: 633 | CVSNPCQVTC |
| SEQ. ID NO: 634 | CVSRCYRPHC |
| SEQ. ID NO: 635 | CVSSCFRPQC |
| SEQ. ID NO: 636 | CVSSICQPIC |
| SEQ. ID NO: 637 | CVSSPCQPTC |
| SEQ. ID NO: 638 | CVVSCTPPSC |
| SEQ. ID NO: 639 | CVVSCTPPTC |
| SEQ. ID NO: 640 | CYCPKNSIFC |
| SEQ. ID NO: 641 | CYEPCLPRGC |
| SEQ. ID NO: 642 | CYRRCYSSCY |
| SEQ. ID NO: 643 | GCCGYGGLGC |
| SEQ. ID NO: 644 | GCGGCGSGCA |
| SEQ. ID NO: 645 | GCGGCGSGCG |
| SEQ. ID NO: 646 | GCGGCGSSCG |
| SEQ. ID NO: 647 | GCGGCSSSCG |
| SEQ. ID NO: 648 | GCGGSGSSCC |
| SEQ. ID NO: 649 | GCGSGCAGCG |
| SEQ. ID NO: 650 | GCGSGCGGCG |
| SEQ. ID NO: 651 | GCGSGCGGCS |
| SEQ. ID NO: 652 | GCGSSCGGCD |
| SEQ. ID NO: 653 | GCGSSCGGCG |
| SEQ. ID NO: 654 | GCGSSCSQCS |
| SEQ. ID NO: 655 | GCGYSSSCCG |
| SEQ. ID NO: 656 | GCKGGCGSCG |
| SEQ. ID NO: 657 | GCSGCSGGCG |
| SEQ. ID NO: 658 | ICSGASSLCC |
| SEQ. ID NO: 659 | ICSGASSPCC |
| SEQ. ID NO: 660 | MCCNYYGNSC |
| SEQ. ID NO: 661 | MCCNYYRNSC |
| SEQ. ID NO: 662 | MCYGYGCGCG |
| SEQ. ID NO: 663 | NCCSRNFSSC |
| SEQ. ID NO: 664 | PCSLQEGCCR |
| SEQ. ID NO: 665 | PCSSQSSCCV |
| SEQ. ID NO: 666 | SCCAPASSCQ |
| SEQ. ID NO: 667 | SCCAPASTCQ |
| SEQ. ID NO: 668 | SCCAPTSSCQ |
| SEQ. ID NO: 669 | SCCGYRPLCY |
| SEQ. ID NO: 670 | SCCVPASSCQ |
| SEQ. ID NO: 671 | SCCVPTSSCQ |
| SEQ. ID NO: 672 | SCGCSKGACG |
| SEQ. ID NO: 673 | SCGGCDSSCG |
| SEQ. ID NO: 674 | SCGGCGSGCG |
| SEQ. ID NO: 675 | SCGGCGSSCG |
| SEQ. ID NO: 676 | SCGGCKGGCG |
| SEQ. ID NO: 677 | SCGGSKGCCG |
| SEQ. ID NO: 678 | SCGSGCRGCG |
| SEQ. ID NO: 679 | SCYGCGYGCI |
| SEQ. ID NO: 680 | TCCVPVPSCG |
| SEQ. ID NO: 681 | TCSDDSGSCC |
| SEQ. ID NO: 682 | TCSEDSSSCC |
| SEQ. ID NO: 683 | TCSEDSYSCC |
| SEQ. ID NO: 684 | TCSESSPSCC |
| SEQ. ID NO: 685 | TCSESSSSCC |
| SEQ. ID NO: 686 | TCSKDSSSCC |
| SEQ. ID NO: 687 | TCSRLSSACC |
| SEQ. ID NO: 688 | VCCQPTPICD |
| SEQ. ID NO: 689 | VCSEDSSSCC |
| SEQ. ID NO: 690 | VCSGASSLCC |
| SEQ. ID NO: 691 | VCSGASSPCC |
| SEQ. ID NO: 692 | VCSGASSSCC |
| SEQ. ID NO: 693 | VCSGASTSCC |
| SEQ. ID NO: 694 | VCSGDSSCCQ |
| SEQ. ID NO: 695 | VCSGISSSCC |
| SEQ. ID NO: 696 | YCVPIPSCCA |
| SEQ. ID NO: 697 | CASSCCTPSC |
| SEQ. ID NO: 698 | CCDNCPPPCH |
| SEQ. ID NO: 699 | CCEPCLPRGC |
| SEQ. ID NO: 700 | CCGAASSCCR |
| SEQ. ID NO: 701 | CCGCGGSGCG |
| SEQ. ID NO: 702 | CCGPSSSCCQ |
| SEQ. ID NO: 703 | CCGSGCGGCG |
| SEQ. ID NO: 704 | CCKPYCSQCS |
| SEQ. ID NO: 705 | CCMPVSSCCA |
| SEQ. ID NO: 706 | CCNYYRNCCG |
| SEQ. ID NO: 707 | CCPSCVVSSC |

| List of peptide sequences | |
|---|---|
| SEQ. ID NO: 708 | CCPSYCVSSC |
| SEQ. ID NO: 709 | CCQPICGSSC |
| SEQ. ID NO: 710 | CCQPICVTSC |
| SEQ. ID NO: 711 | CCQPTCLSSC |
| SEQ. ID NO: 712 | CCQPTCLTSC |
| SEQ. ID NO: 713 | CCQPTCVASC |
| SEQ. ID NO: 714 | CCQPTCVTSC |
| SEQ. ID NO: 715 | CCQPYCHPTC |
| SEQ. ID NO: 716 | CCQQSSCVSC |
| SEQ. ID NO: 717 | CCQSSCFKPC |
| SEQ. ID NO: 718 | CCQSSCSKPC |
| SEQ. ID NO: 719 | CCQSSCYKPC |
| SEQ. ID NO: 720 | CCQTICRSTC |
| SEQ. ID NO: 721 | CCQTTCHPSC |
| SEQ. ID NO: 722 | CCQTTCRPSC |
| SEQ. ID NO: 723 | CCRVPTCSCS |
| SEQ. ID NO: 724 | CCSPGCQPTC |
| SEQ. ID NO: 725 | CCSSGCGSSC |
| SEQ. ID NO: 726 | CCSSSCGSCG |
| SEQ. ID NO: 727 | CCTQEQNCCE |
| SEQ. ID NO: 728 | CCVPIPSCCA |
| SEQ. ID NO: 729 | CCVPISSCCA |
| SEQ. ID NO: 730 | CCVPVCYQCK |
| SEQ. ID NO: 731 | CCVPVPSCCA |
| SEQ. ID NO: 732 | CCVPVPSCCV |
| SEQ. ID NO: 733 | CCVPVSSCCA |
| SEQ. ID NO: 734 | CDSSCCQPSC |
| SEQ. ID NO: 735 | CDTCPPPCCK |
| SEQ. ID NO: 736 | CEPCRRPVCC |
| SEQ. ID NO: 737 | CEPSCCQPVC |
| SEQ. ID NO: 738 | CEPSCCSAVC |
| SEQ. ID NO: 739 | CETSCCQPSC |
| SEQ. ID NO: 740 | CETTCCRTTC |
| SEQ. ID NO: 741 | CFSGCGSSCC |
| SEQ. ID NO: 742 | CGCSQSNCCK |
| SEQ. ID NO: 743 | CGCSQSSCCK |
| SEQ. ID NO: 744 | CGGCGGCGGC |
| SEQ. ID NO: 745 | CGGCGGGCCG |
| SEQ. ID NO: 746 | CGGCGSGCCV |
| SEQ. ID NO: 747 | CGGCGSSCCV |
| SEQ. ID NO: 748 | CGGGCCGSSC |
| SEQ. ID NO: 749 | CGGSCCGSSC |
| SEQ. ID NO: 750 | CGQSCCRPAC |
| SEQ. ID NO: 751 | CGQSCCRPVC |
| SEQ. ID NO: 752 | CGSCGCSQCN |
| SEQ. ID NO: 753 | CGSCGCSQCS |
| SEQ. ID NO: 754 | CGSFCCQSSC |
| SEQ. ID NO: 755 | CGSGCCVPVC |
| SEQ. ID NO: 756 | CGSSCCGSGC |
| SEQ. ID NO: 757 | CGSSCCQPCY |
| SEQ. ID NO: 758 | CGSSCCQPIC |
| SEQ. ID NO: 759 | CGSSCCQPSC |
| SEQ. ID NO: 760 | CGSSCCQSSC |
| SEQ. ID NO: 761 | CGSSCCVPIC |
| SEQ. ID NO: 762 | CGSSCCVPVC |
| SEQ. ID NO: 763 | CGSSCSQCSC |
| SEQ. ID NO: 764 | CGYGSCCGCG |
| SEQ. ID NO: 765 | CHPRCCISSC |
| SEQ. ID NO: 766 | CHPSCCESSC |
| SEQ. ID NO: 767 | CHPSCCISSC |
| SEQ. ID NO: 768 | CHPTCCQNTC |
| SEQ. ID NO: 769 | CHPTCCQTIC |
| SEQ. ID NO: 770 | CHPVCCQTTC |
| SEQ. ID NO: 771 | CHPVCKSTCC |
| SEQ. ID NO: 772 | CHPVCRSTCC |
| SEQ. ID NO: 773 | CISSCCHPSC |
| SEQ. ID NO: 774 | CISSCCKPSC |
| SEQ. ID NO: 775 | CISSCCRPSC |
| SEQ. ID NO: 776 | CISSCTPSCC |
| SEQ. ID NO: 777 | CISSSCCPSC |
| SEQ. ID NO: 778 | CKAVCCVPTC |
| SEQ. ID NO: 779 | CKPCCSQASC |
| SEQ. ID NO: 780 | CKPCCSQSRC |
| SEQ. ID NO: 781 | CKPCCSQSSC |
| SEQ. ID NO: 782 | CKPCCSSSGC |
| SEQ. ID NO: 783 | CKPCSCFSGC |
| SEQ. ID NO: 784 | CKPCSCSSGC |

List of peptide sequences

| | |
|---|---|
| SEQ. ID NO: 785 | CKPCYCSSGC |
| SEQ. ID NO: 786 | CKPICCVPVC |
| SEQ. ID NO: 787 | CKPQCCQSVC |
| SEQ. ID NO: 788 | CKPSCCQTTC |
| SEQ. ID NO: 789 | CKPVCCAPTC |
| SEQ. ID NO: 790 | CKPVCCKPIC |
| SEQ. ID NO: 791 | CKPVCCKSIC |
| SEQ. ID NO: 792 | CKPVCCLPTC |
| SEQ. ID NO: 793 | CKPVCCVPTC |
| SEQ. ID NO: 794 | CKPVCCVPVC |
| SEQ. ID NO: 795 | CKPVCCVSTC |
| SEQ. ID NO: 796 | CKPYCCQSSC |
| SEQ. ID NO: 797 | CKPYCSQCSC |
| SEQ. ID NO: 798 | CKSNCCKPVC |
| SEQ. ID NO: 799 | CKTVCCKPVC |
| SEQ. ID NO: 800 | CLPPCCVVSC |
| SEQ. ID NO: 801 | CLTSCCQPSC |
| SEQ. ID NO: 802 | CNPCCSQSSC |
| SEQ. ID NO: 803 | CPESCCELPC |
| SEQ. ID NO: 804 | CPESCCEPHC |
| SEQ. ID NO: 805 | CPESCCEPPC |
| SEQ. ID NO: 806 | CPFSCPTTCC |
| SEQ. ID NO: 807 | CPGDCFTCCT |
| SEQ. ID NO: 808 | CPSCVVSSCC |
| SEQ. ID NO: 809 | CPSYCVSSCC |
| SEQ. ID NO: 810 | CPTTCCRTTC |
| SEQ. ID NO: 811 | CQETCCRPSC |
| SEQ. ID NO: 812 | CQHACCVPVC |
| SEQ. ID NO: 813 | CQNTCCRTTC |
| SEQ. ID NO: 814 | CQPACCQPTC |
| SEQ. ID NO: 815 | CQPACCTASC |
| SEQ. ID NO: 816 | CQPACCTSSC |
| SEQ. ID NO: 817 | CQPACCTTSC |
| SEQ. ID NO: 818 | CQPACCVPVC |
| SEQ. ID NO: 819 | CQPACCVSSC |
| SEQ. ID NO: 820 | CQPCCHPTCY |
| SEQ. ID NO: 821 | CQPCCRPTSC |
| SEQ. ID NO: 822 | CQPICCGSSC |
| SEQ. ID NO: 823 | CQPICGSSCC |
| SEQ. ID NO: 824 | CQPICVTSCC |
| SEQ. ID NO: 825 | CQPNCCRPSC |
| SEQ. ID NO: 826 | CQPRCCETSC |
| SEQ. ID NO: 827 | CQPSCCRPAC |
| SEQ. ID NO: 828 | CQPSCCSTPC |
| SEQ. ID NO: 829 | CQPSCCSTTC |
| SEQ. ID NO: 830 | CQPSCCVPSC |
| SEQ. ID NO: 831 | CQPSCCVSSC |
| SEQ. ID NO: 832 | CQPTCCGSSC |
| SEQ. ID NO: 833 | CQPTCCHPSC |
| SEQ. ID NO: 834 | CQPTCCQPTC |
| SEQ. ID NO: 835 | CQPTCCRPRC |
| SEQ. ID NO: 836 | CQPTCCRPSC |
| SEQ. ID NO: 837 | CQPTCCRTTC |
| SEQ. ID NO: 838 | CQPTCLSSCC |
| SEQ. ID NO: 839 | CQPTCLTSCC |
| SEQ. ID NO: 840 | CQPTCVASCC |
| SEQ. ID NO: 841 | CQPTCVTSCC |
| SEQ. ID NO: 842 | CQPVCCQPTC |
| SEQ. ID NO: 843 | CQPYCHPTCC |
| SEQ. ID NO: 844 | CQQACCMPVC |
| SEQ. ID NO: 845 | CQQACCVPIC |
| SEQ. ID NO: 846 | CQQACCVPVC |
| SEQ. ID NO: 847 | CQQSCCVPVC |
| SEQ. ID NO: 848 | CQQSCCVSVC |
| SEQ. ID NO: 849 | CQSMCCQPTC |
| SEQ. ID NO: 850 | CQSNCCVPVC |
| SEQ. ID NO: 851 | CQSSCCKPCS |
| SEQ. ID NO: 852 | CQSSCCQSSC |
| SEQ. ID NO: 853 | CQSSCCVPVC |
| SEQ. ID NO: 854 | CQSSCFKPCC |
| SEQ. ID NO: 855 | CQSSCSKPCC |
| SEQ. ID NO: 856 | CQSVCCQPTC |
| SEQ. ID NO: 857 | CQTICRSTCC |
| SEQ. ID NO: 858 | CQTTCCRPSC |
| SEQ. ID NO: 859 | CQTTCCRTTC |
| SEQ. ID NO: 860 | CRATCCRPSC |
| SEQ. ID NO: 861 | CRGCGPSCCA |

List of peptide sequences

| | |
|---|---|
| SEQ. ID NO: 862 | CRPACCETTC |
| SEQ. ID NO: 863 | CRPACCONTC |
| SEQ. ID NO: 864 | CRPCCWATTC |
| SEQ. ID NO: 865 | CRPICRPACC |
| SEQ. ID NO: 866 | CRPLCCQTTC |
| SEQ. ID NO: 867 | CRPQCCQSVC |
| SEQ. ID NO: 868 | CRPQCCQTTC |
| SEQ. ID NO: 869 | CRPRCCISSC |
| SEQ. ID NO: 870 | CRPSCCESSC |
| SEQ. ID NO: 871 | CRPSCCETTC |
| SEQ. ID NO: 872 | CRPSCCISSC |
| SEQ. ID NO: 873 | CRPSCCKPQC |
| SEQ. ID NO: 874 | CRPSCCMSSC |
| SEQ. ID NO: 875 | CRPSCCQTTC |
| SEQ. ID NO: 876 | CRPSCCRPSC |
| SEQ. ID NO: 877 | CRPSCCVSRC |
| SEQ. ID NO: 878 | CRPSCCVSSC |
| SEQ. ID NO: 879 | CRPTCCETTC |
| SEQ. ID NO: 880 | CRPTCCQNTC |
| SEQ. ID NO: 881 | CRPTCCQTTC |
| SEQ. ID NO: 882 | CRPVCCDPCS |
| SEQ. ID NO: 883 | CRPVCCQTTC |
| SEQ. ID NO: 884 | CRPVCQPACC |
| SEQ. ID NO: 885 | CRPVCRPACC |
| SEQ. ID NO: 886 | CRPVCRPTCC |
| SEQ. ID NO: 887 | CRPVCRSTCC |
| SEQ. ID NO: 888 | CRPYCCESSC |
| SEQ. ID NO: 889 | CRRPVCCDPC |
| SEQ. ID NO: 890 | CRSQCCQSVC |
| SEQ. ID NO: 891 | CRTTCCHPSC |
| SEQ. ID NO: 892 | CRTTCCQPIC |
| SEQ. ID NO: 893 | CRTTCCQPTC |
| SEQ. ID NO: 894 | CRTTCCRPSC |
| SEQ. ID NO: 895 | CRTTCCRTTC |
| SEQ. ID NO: 896 | CSCSSCGSCA |
| SEQ. ID NO: 897 | CSCSSCGSCG |
| SEQ. ID NO: 898 | CSCTSCGSCG |
| SEQ. ID NO: 899 | CSPACQPTCC |
| SEQ. ID NO: 900 | CSPGCQPTCC |
| SEQ. ID NO: 901 | CSPSCCQTTC |
| SEQ. ID NO: 902 | CSQCSCYKPC |
| SEQ. ID NO: 903 | CSQSNCCKPC |
| SEQ. ID NO: 904 | CSQSSCCKPC |
| SEQ. ID NO: 905 | CSSGCGSCCQ |
| SEQ. ID NO: 906 | CSSGCGSSCC |
| SEQ. ID NO: 907 | CSSGCQPACC |
| SEQ. ID NO: 908 | CSSSCCQPSC |
| SEQ. ID NO: 909 | CSTPCCQPTC |
| SEQ. ID NO: 910 | CSTTCCQPIC |
| SEQ. ID NO: 911 | CTAVVCRPCC |
| SEQ. ID NO: 912 | CTDSCTPSCC |
| SEQ. ID NO: 913 | CTPSCCQPAC |
| SEQ. ID NO: 914 | CTRPICEPCC |
| SEQ. ID NO: 915 | CTSSCTPSCC |
| SEQ. ID NO: 916 | CVPACSCSSC |
| SEQ. ID NO: 917 | CVPACSCTSC |
| SEQ. ID NO: 918 | CVPVCCKPVC |
| SEQ. ID NO: 919 | CVPVCCVPTC |
| SEQ. ID NO: 920 | CVPVCCVPVC |
| SEQ. ID NO: 921 | CVSCVSSPCC |
| SEQ. ID NO: 922 | CVSRCCRPQC |
| SEQ. ID NO: 923 | CVSSCCKPQC |
| SEQ. ID NO: 924 | CVSSCCQHSC |
| SEQ. ID NO: 925 | CVSSCCQPFC |
| SEQ. ID NO: 926 | CVSSCCQPSC |
| SEQ. ID NO: 927 | CVSSCCRPQC |
| SEQ. ID NO: 928 | CVSTCCRPTC |
| SEQ. ID NO: 929 | CVTRCCSTPC |
| SEQ. ID NO: 930 | CVTSCCQPAC |
| SEQ. ID NO: 931 | CVTSCCQPSC |
| SEQ. ID NO: 932 | CVYSCCQPFC |
| SEQ. ID NO: 933 | CVYSCCQPSC |
| SEQ. ID NO: 934 | GCCGCSEGCG |
| SEQ. ID NO: 935 | GCCGCSGGCG |
| SEQ. ID NO: 936 | GCCGCSRGCG |
| SEQ. ID NO: 937 | GCCRPITCCP |
| SEQ. ID NO: 938 | GCGSSCCQCS |

| List of peptide sequences | |
|---|---|
| SEQ. ID NO: 939 | GCGVPVCCCS |
| SEQ. ID NO: 940 | LCCPCQTTCS |
| SEQ. ID NO: 941 | PCCCLRPVCG |
| SEQ. ID NO: 942 | PCCCRPVTCQ |
| SEQ. ID NO: 943 | PCCCVRPVCG |
| SEQ. ID NO: 944 | PCCSQASCCV |
| SEQ. ID NO: 945 | PCCSQSRCCV |
| SEQ. ID NO: 946 | PCCSQSSCCK |
| SEQ. ID NO: 947 | PCCSQSSCCV |
| SEQ. ID NO: 948 | PCCWATTCCQ |
| SEQ. ID NO: 949 | QCSCCKPYCS |
| SEQ. ID NO: 950 | RCYVPVCCCK |
| SEQ. ID NO: 951 | SCCAPVYCCK |
| SEQ. ID NO: 952 | SCCISSSCCP |
| SEQ. ID NO: 953 | SCCVSSCRCP |
| SEQ. ID NO: 954 | SCGCSQCSCY |
| SEQ. ID NO: 955 | SCGLENCCCP |
| SEQ. ID NO: 956 | VCCGASSCCQ |
| SEQ. ID NO: 957 | VCCGDSSCCQ |
| SEQ. ID NO: 958 | CASSCCTPSCC |
| SEQ. ID NO: 959 | CCCPSCVVSSC |
| SEQ. ID NO: 960 | CCCPSYCVSSC |
| SEQ. ID NO: 961 | CCCSSGCGSSC |
| SEQ. ID NO: 962 | CCDTCPPPCCK |
| SEQ. ID NO: 963 | CCEPHCCALSC |
| SEQ. ID NO: 964 | CCEPPCCAPSC |
| SEQ. ID NO: 965 | CCEPPCCATSC |
| SEQ. ID NO: 966 | CCETSCCQPSC |
| SEQ. ID NO: 967 | CCGSSCCGSGC |
| SEQ. ID NO: 968 | CCGSSCCGSSC |
| SEQ. ID NO: 969 | CCHPRCCISSC |
| SEQ. ID NO: 970 | CCHPSCCESSC |
| SEQ. ID NO: 971 | CCHPSCCISSC |
| SEQ. ID NO: 972 | CCHPSCCVSSC |
| SEQ. ID NO: 973 | CCHPTCCQNTC |
| SEQ. ID NO: 974 | CCHPTCCQTIC |
| SEQ. ID NO: 975 | CCISSCCKPSC |
| SEQ. ID NO: 976 | CCISSCCRPSC |
| SEQ. ID NO: 977 | CCISSSCCPSC |
| SEQ. ID NO: 978 | CCKAVCCVPTC |
| SEQ. ID NO: 979 | CCKPCCSQASC |
| SEQ. ID NO: 980 | CCKPCCSQSRC |
| SEQ. ID NO: 981 | CCKPCCSQSSC |
| SEQ. ID NO: 982 | CCKPCCSSSGC |
| SEQ. ID NO: 983 | CCKPCSCFSGC |
| SEQ. ID NO: 984 | CCKPCSCSSGC |
| SEQ. ID NO: 985 | CCKPCYCSSGC |
| SEQ. ID NO: 986 | CCKPICCVPVC |
| SEQ. ID NO: 987 | CCKPQCCQSVC |
| SEQ. ID NO: 988 | CCKPVCCKPIC |
| SEQ. ID NO: 989 | CCKPYCCQSSC |
| SEQ. ID NO: 990 | CCKPYCSQCSC |
| SEQ. ID NO: 991 | CCMPVCCKPVC |
| SEQ. ID NO: 992 | CCMPVCCKTVC |
| SEQ. ID NO: 993 | CCMSSCCKPQC |
| SEQ. ID NO: 994 | CCNPCCSQSSC |
| SEQ. ID NO: 995 | CCPGDCFTCCT |
| SEQ. ID NO: 996 | CCPSCVVSSCC |
| SEQ. ID NO: 997 | CCPSYCVSSCC |
| SEQ. ID NO: 998 | CCQNTCCRTTC |
| SEQ. ID NO: 999 | CCQPACCVSSC |
| SEQ. ID NO: 1000 | CCQPCCHPTCY |
| SEQ. ID NO: 1001 | CCQPCCRPTSC |
| SEQ. ID NO: 1002 | CCQPICGSSCC |
| SEQ. ID NO: 1003 | CCQPICVTSCC |
| SEQ. ID NO: 1004 | CCQPNCCRPSC |
| SEQ. ID NO: 1005 | CCQPSCCETSC |
| SEQ. ID NO: 1006 | CCQPSCCRPAC |
| SEQ. ID NO: 1007 | CCQPSCCSTPC |
| SEQ. ID NO: 1008 | CCQPSCCSTTC |
| SEQ. ID NO: 1009 | CCQPSCCVPSC |
| SEQ. ID NO: 1010 | CCQPSCCVSSC |
| SEQ. ID NO: 1011 | CCQPTCCHPSC |
| SEQ. ID NO: 1012 | CCQPTCCQPTC |
| SEQ. ID NO: 1013 | CCQPTCCRPRC |
| SEQ. ID NO: 1014 | CCQPTCCRPSC |
| SEQ. ID NO: 1015 | CCQPTCCRPTC |

List of peptide sequences

| | |
|---|---|
| SEQ. ID NO: 1016 | CCQPTCCRTTC |
| SEQ. ID NO: 1017 | CCQPTCLSSCC |
| SEQ. ID NO: 1018 | CCQPTCLTSCC |
| SEQ. ID NO: 1019 | CCQPTCVASCC |
| SEQ. ID NO: 1020 | CCQPTCVTSCC |
| SEQ. ID NO: 1021 | CCQPYCHPTCC |
| SEQ. ID NO: 1022 | CCQSMCCQPTC |
| SEQ. ID NO: 1023 | CCQSNCCVPVC |
| SEQ. ID NO: 1024 | CCQSSCCKPCS |
| SEQ. ID NO: 1025 | CCQSSCCKPSC |
| SEQ. ID NO: 1026 | CCQSSCCKPYC |
| SEQ. ID NO: 1027 | CCQSSCCQSSC |
| SEQ. ID NO: 1028 | CCQSSCCVPVC |
| SEQ. ID NO: 1029 | CCQSSCFKPCC |
| SEQ. ID NO: 1030 | CCQSSCSKPCC |
| SEQ. ID NO: 1031 | CCQSSCYKPCC |
| SEQ. ID NO: 1032 | CCQSVCCQPTC |
| SEQ. ID NO: 1033 | CCQTICRSTCC |
| SEQ. ID NO: 1034 | CCQTTCCRPSC |
| SEQ. ID NO: 1035 | CCQTTCCRTTC |
| SEQ. ID NO: 1036 | CCRPACCETTC |
| SEQ. ID NO: 1037 | CCRPACCQNTC |
| SEQ. ID NO: 1038 | CCRPLCCQTTC |
| SEQ. ID NO: 1039 | CCRPQCCQSVC |
| SEQ. ID NO: 1040 | CCRPQCCQTTC |
| SEQ. ID NO: 1041 | CCRPSCCESSC |
| SEQ. ID NO: 1042 | CCRPSCCETTC |
| SEQ. ID NO: 1043 | CCRPSCCGSSC |
| SEQ. ID NO: 1044 | CCRPSCCISSC |
| SEQ. ID NO: 1045 | CCRPSCCKPQC |
| SEQ. ID NO: 1046 | CCRPSCCQTTC |
| SEQ. ID NO: 1047 | CCRPSCCVSRC |
| SEQ. ID NO: 1048 | CCRPSCCVSSC |
| SEQ. ID NO: 1049 | CCRPTCCQNTC |
| SEQ. ID NO: 1050 | CCRPTCCQTTC |
| SEQ. ID NO: 1051 | CCRPVCCDPCS |
| SEQ. ID NO: 1052 | CCRTTCCQPTC |
| SEQ. ID NO: 1053 | CCRTTCCRPSC |
| SEQ. ID NO: 1054 | CCRTTCCRTTC |
| SEQ. ID NO: 1055 | CCSCSSCGSCA |
| SEQ. ID NO: 1056 | CCSPGCQPTCC |
| SEQ. ID NO: 1057 | CCSQSSCCKPC |
| SEQ. ID NO: 1058 | CCSSGCGSCCQ |
| SEQ. ID NO: 1059 | CCSSGCGSSCC |
| SEQ. ID NO: 1060 | CCSTPCCQPTC |
| SEQ. ID NO: 1061 | CCVPACSCSSC |
| SEQ. ID NO: 1062 | CCVPACSCTSC |
| SEQ. ID NO: 1063 | CCVPICCKPIC |
| SEQ. ID NO: 1064 | CCVPICCKPVC |
| SEQ. ID NO: 1065 | CCVPVCCKPIC |
| SEQ. ID NO: 1066 | CCVPVCCKPVC |
| SEQ. ID NO: 1067 | CCVPVCCKSNC |
| SEQ. ID NO: 1068 | CCVPVCCKTVC |
| SEQ. ID NO: 1069 | CCVPVCCSSSC |
| SEQ. ID NO: 1070 | CCVPVCCVPVC |
| SEQ. ID NO: 1071 | CCVSSCCKPQC |
| SEQ. ID NO: 1072 | CCVSSCCQHSC |
| SEQ. ID NO: 1073 | CCVSSCCQPSC |
| SEQ. ID NO: 1074 | CCVSSCCRPQC |
| SEQ. ID NO: 1075 | CCVSTCCRPTC |
| SEQ. ID NO: 1076 | CCVSVCCKPVC |
| SEQ. ID NO: 1077 | CDSSCCQPSCC |
| SEQ. ID NO: 1078 | CEPCCRPVCCD |
| SEQ. ID NO: 1079 | CFKPCCCQSSC |
| SEQ. ID NO: 1080 | CGDGCCCPSCY |
| SEQ. ID NO: 1081 | CGGGCCGSSCC |
| SEQ. ID NO: 1082 | CGGSCCGSSCC |
| SEQ. ID NO: 1083 | CGLENCCCPSC |
| SEQ. ID NO: 1084 | CGQSCCRPACC |
| SEQ. ID NO: 1085 | CGQSCCRPVCC |
| SEQ. ID NO: 1086 | CGSCCQSSCCN |
| SEQ. ID NO: 1087 | CGSCGCSQCNC |
| SEQ. ID NO: 1088 | CGSCGCSQCSC |
| SEQ. ID NO: 1089 | CGSGCCGPVCC |
| SEQ. ID NO: 1090 | CGSGCCVPVCC |
| SEQ. ID NO: 1091 | CGSNCCQPCCR |
| SEQ. ID NO: 1092 | CGSSCCQPCCH |

-continued

| List of peptide sequences | |
|---|---|
| SEQ. ID NO: 1093 | CGSSCCQPCCR |
| SEQ. ID NO: 1094 | CGSSCCQPCYC |
| SEQ. ID NO: 1095 | CGSSCCQPSCC |
| SEQ. ID NO: 1096 | CGSSCCQSSCC |
| SEQ. ID NO: 1097 | CGSSCCVPICC |
| SEQ. ID NO: 1098 | CGSSCCVPVCC |
| SEQ. ID NO: 1099 | CGSSCSQCSCC |
| SEQ. ID NO: 1100 | CGVPVCCCSCS |
| SEQ. ID NO: 1101 | CHPRCCISSCC |
| SEQ. ID NO: 1102 | CHPSCCESSCC |
| SEQ. ID NO: 1103 | CHPSCCISSCC |
| SEQ. ID NO: 1104 | CHPTCCQNTCC |
| SEQ. ID NO: 1105 | CISSCCHPSCC |
| SEQ. ID NO: 1106 | CISSCCKPSCC |
| SEQ. ID NO: 1107 | CISSCCRPSCC |
| SEQ. ID NO: 1108 | CISSSCCPSCC |
| SEQ. ID NO: 1109 | CKPCCCSSGCG |
| SEQ. ID NO: 1110 | CKPCCSQASCC |
| SEQ. ID NO: 1111 | CKPCCSQSRCC |
| SEQ. ID NO: 1112 | CKPCCSQSSCC |
| SEQ. ID NO: 1113 | CKPQCCQSMCC |
| SEQ. ID NO: 1114 | CKPQCCQSVCC |
| SEQ. ID NO: 1115 | CKPVCCCVPAC |
| SEQ. ID NO: 1116 | CKPVCCKPICC |
| SEQ. ID NO: 1117 | CKPVCCMPVCC |
| SEQ. ID NO: 1118 | CKPVCCVPVCC |
| SEQ. ID NO: 1119 | CKPVCCVSVCC |
| SEQ. ID NO: 1120 | CKPYCSQCSCC |
| SEQ. ID NO: 1121 | CLPCCRPTCCQ |
| SEQ. ID NO: 1122 | CLTSCCQPSCC |
| SEQ. ID NO: 1123 | CMSSCCKPQCC |
| SEQ. ID NO: 1124 | CNPCCSQSSCC |
| SEQ. ID NO: 1125 | CPACCVSSCCQ |
| SEQ. ID NO: 1126 | CPESCCEPHCC |
| SEQ. ID NO: 1127 | CPESCCEPPCC |
| SEQ. ID NO: 1128 | CPSCCESSCCR |
| SEQ. ID NO: 1129 | CPSCCQTTCCR |
| SEQ. ID NO: 1130 | CPSCCVSSCCR |
| SEQ. ID NO: 1131 | CQCSCCKPYCS |
| SEQ. ID NO: 1132 | CQETCCRPSCC |
| SEQ. ID NO: 1133 | CQNTCCRTTCC |
| SEQ. ID NO: 1134 | CQPACCTASCC |
| SEQ. ID NO: 1135 | CQPACCTSSCC |
| SEQ. ID NO: 1136 | CQPACCTTSCC |
| SEQ. ID NO: 1137 | CQPACCVPVCC |
| SEQ. ID NO: 1138 | CQPACCVSSCC |
| SEQ. ID NO: 1139 | CQPCCHPTCCQ |
| SEQ. ID NO: 1140 | CQPCCRPACCE |
| SEQ. ID NO: 1141 | CQPCCRPACCQ |
| SEQ. ID NO: 1142 | CQPCCRPTCCQ |
| SEQ. ID NO: 1143 | CQPCYCPACCV |
| SEQ. ID NO: 1144 | CQPICCGSSCC |
| SEQ. ID NO: 1145 | CQPRCCETSCC |
| SEQ. ID NO: 1146 | CQPSCCETSCC |
| SEQ. ID NO: 1147 | CQPSCCRPACC |
| SEQ. ID NO: 1148 | CQPSCCVPSCC |
| SEQ. ID NO: 1149 | CQPSCCVSSCC |
| SEQ. ID NO: 1150 | CQPTCCCPSYC |
| SEQ. ID NO: 1151 | CQPTCCGSSCC |
| SEQ. ID NO: 1152 | CQPTCCHPSCC |
| SEQ. ID NO: 1153 | CQPTCCQPTCC |
| SEQ. ID NO: 1154 | CQPTCCRPSCC |
| SEQ. ID NO: 1155 | CQPTCCRPTCC |
| SEQ. ID NO: 1156 | CQPTCCRTTCC |
| SEQ. ID NO: 1157 | CQQACCMPVCC |
| SEQ. ID NO: 1158 | CQQACCVPICC |
| SEQ. ID NO: 1159 | CQQACCVPVCC |
| SEQ. ID NO: 1160 | CQQSCCVPVCC |
| SEQ. ID NO: 1161 | CQQSCCVSVCC |
| SEQ. ID NO: 1162 | CQSNCCVPVCC |
| SEQ. ID NO: 1163 | CQSSCCCPASC |
| SEQ. ID NO: 1164 | CQSSCCKPCCS |
| SEQ. ID NO: 1165 | CQSSCCKPCSC |
| SEQ. ID NO: 1166 | CQSSCCKPYCC |
| SEQ. ID NO: 1167 | CQSSCCNPCCS |
| SEQ. ID NO: 1168 | CQSSCCQSSCC |
| SEQ. ID NO: 1169 | CQSSCCVPVCC |

List of peptide sequences

| | |
|---|---|
| SEQ. ID NO: 1170 | CQSSCFKPCCC |
| SEQ. ID NO: 1171 | CQSSCSKPCCC |
| SEQ. ID NO: 1172 | CQSSCYKPCCC |
| SEQ. ID NO: 1173 | CQSVCCQPTCC |
| SEQ. ID NO: 1174 | CQTTCCCPSCV |
| SEQ. ID NO: 1175 | CQTTCCRPSCC |
| SEQ. ID NO: 1176 | CQTTCCRTTCC |
| SEQ. ID NO: 1177 | CRPACCETTCC |
| SEQ. ID NO: 1178 | CRPACCQNTCC |
| SEQ. ID NO: 1179 | CRPCCCLRPVC |
| SEQ. ID NO: 1180 | CRPCCCVRPVC |
| SEQ. ID NO: 1181 | CRPCCWATTCC |
| SEQ. ID NO: 1182 | CRPLCCQTTCC |
| SEQ. ID NO: 1183 | CRPQCCQSVCC |
| SEQ. ID NO: 1184 | CRPQCCQTTCC |
| SEQ. ID NO: 1185 | CRPRCCISSCC |
| SEQ. ID NO: 1186 | CRPSCCESSCC |
| SEQ. ID NO: 1187 | CRPSCCISSCC |
| SEQ. ID NO: 1188 | CRPSCCKPQCC |
| SEQ. ID NO: 1189 | CRPSCCPSCCQ |
| SEQ. ID NO: 1190 | CRPSCCQTTCC |
| SEQ. ID NO: 1191 | CRPSCCRPQCC |
| SEQ. ID NO: 1192 | CRPSCCVSRCC |
| SEQ. ID NO: 1193 | CRPSCCVSSCC |
| SEQ. ID NO: 1194 | CRPTCCQNTCC |
| SEQ. ID NO: 1195 | CRPVCCCEPTC |
| SEQ. ID NO: 1196 | CRPVCCCYSCE |
| SEQ. ID NO: 1197 | CRTTCCHPSCC |
| SEQ. ID NO: 1198 | CRTTCCRPSCC |
| SEQ. ID NO: 1199 | CSCCKPYCSQC |
| SEQ. ID NO: 1200 | CSKPCCCQSSC |
| SEQ. ID NO: 1201 | CSPCCQPTCCR |
| SEQ. ID NO: 1202 | CSPCCVSSCCQ |
| SEQ. ID NO: 1203 | CSQCSCCKPCY |
| SEQ. ID NO: 1204 | CSQCSCYKPCC |
| SEQ. ID NO: 1205 | CSQSNCCKPCC |
| SEQ. ID NO: 1206 | CSQSSCCKPCC |
| SEQ. ID NO: 1207 | CSSSCCQPSCC |
| SEQ. ID NO: 1208 | CTPSCCQPACC |
| SEQ. ID NO: 1209 | CVASCCQPSCC |
| SEQ. ID NO: 1210 | CVPICCCKPVC |
| SEQ. ID NO: 1211 | CVPSCCQPCCH |
| SEQ. ID NO: 1212 | CVPVCCCKPMC |
| SEQ. ID NO: 1213 | CVPVCCCKPVC |
| SEQ. ID NO: 1214 | CVPVCCKPVCC |
| SEQ. ID NO: 1215 | CVSSCCKPQCC |
| SEQ. ID NO: 1216 | CVSSCCQHSCC |
| SEQ. ID NO: 1217 | CVSSCCQPCCH |
| SEQ. ID NO: 1218 | CVSSCCQPCCR |
| SEQ. ID NO: 1219 | CVSSCCQPFCC |
| SEQ. ID NO: 1220 | CVSSCCQPSCC |
| SEQ. ID NO: 1221 | CVSSCCRPQCC |
| SEQ. ID NO: 1222 | CVTRCCSTPCC |
| SEQ. ID NO: 1223 | CVTSCCQPACC |
| SEQ. ID NO: 1224 | CVTSCCQPSCC |
| SEQ. ID NO: 1225 | CVYSCCQPFCC |
| SEQ. ID NO: 1226 | CVYSCCQPSCC |
| SEQ. ID NO: 1227 | CYCPACCVSSC |
| SEQ. ID NO: 1228 | CYKPCCCQSSC |
| SEQ. ID NO: 1229 | CYKPCCCSSGC |
| SEQ. ID NO: 1230 | MCCCVPACSCS |
| SEQ. ID NO: 1231 | NCCVPVCCQCK |
| SEQ. ID NO: 1232 | QCSCCKPCYCS |
| SEQ. ID NO: 1233 | QCSCYKPCCCS |
| SEQ. ID NO: 1234 | SCCVPICCQCK |
| SEQ. ID NO: 1235 | SCCVPVCCQCK |
| SEQ. ID NO: 1236 | SCGCSQCNCCK |
| SEQ. ID NO: 1237 | SCGCSQCSCCK |
| SEQ. ID NO: 1238 | VCCCVPACSCS |
| SEQ. ID NO: 1239 | VCCCVPACSCT |

The present invention is of course in any way restricted to the embodiments herein described and one with ordinary skill in the area can provide many possibilities to modifications and substitutions of technical characteristics by equivalent ones, depending on each situation, as defined in the claims.

The preferred embodiments described above may obviously be combined. The following claims define further preferred embodiments.

What is claimed:

1. A hair composition comprising:
   a keratin peptide fragment having about 15% to about 30% cysteine amino acid content, wherein the keratin peptide fragment comprises a peptide sequence at least 90% identical to SEQ ID NO: 412 or SEQ ID NO: 409;
   wherein the hair composition is a lotion or cream.

2. The hair composition of claim 1, wherein the peptide sequence of the keratin peptide fragment is at least 95% identical to SEQ ID NO: 412.

3. The hair composition of claim 1, wherein the peptide sequence of the keratin peptide fragment is at least 95% identical to SEQ ID NO: 409.

4. The hair composition of claim 1, wherein the peptide sequence of the keratin peptide fragment is identical to SEQ ID NO: 412.

5. The hair composition of claim 1, wherein the peptide sequence of the keratin peptide fragment is identical to SEQ ID NO: 409.

6. The hair composition of claim 1, wherein the keratin peptide fragment forms one or more molecular interactions with hair.

7. The hair composition of claim 6, wherein the one or more molecular interactions is one or more disulfide bonds.

8. The hair composition of claim 1, wherein the total number of cysteine amino acids in the keratin peptide fragment is 2 cysteine amino acids.

9. A hair composition comprising:
   a keratin peptide fragment having about 15% to about 30% cysteine amino acid content, wherein the keratin peptide fragment comprises a peptide sequence at least 90% identical to SEQ ID NO: 412 or SEQ ID NO: 409; and
   at least one excipient comprising propylene glycol, polysorbate 20, hydrolyzed wheat protein, hydrolyzed wheat starch, potassium sorbate, or an alcohol, or a combination of two or more thereof,
   wherein the total number of cysteine amino acids in the keratin peptide fragment is 2 cysteine amino acids.

10. The hair composition of claim 9, wherein the at least one excipient further comprises ether dicaprylic, cetyl ester, behentrimonium chloride, or tocopherol, or a combination of two or more thereof.

11. The hair composition of claim 9, wherein the at least one excipient further comprises potassium hydroxide, acrylate, or phenoxyethanol, or a combination or two or more thereof.

12. The hair composition of claim 9, wherein the peptide sequence of the keratin peptide fragment is identical to SEQ ID NO: 412.

13. The hair composition of claim 9, wherein the peptide sequence of the keratin peptide fragment is identical to SEQ ID NO: 409.

14. A hair composition comprising:
   a keratin peptide fragment having about 15% to about 30% cysteine amino acid content, wherein the keratin peptide fragment comprises a peptide sequence at least 90% identical to SEQ ID NO: 412 or SEQ ID NO: 409; and
   at least one excipient comprising an oil and/or an alcohol,
   wherein the total number of cysteine amino acids in the keratin peptide fragment is 2 cysteine amino acids.

15. The hair composition of claim 14, comprising the oil and the alcohol.

16. The hair composition of claim 14, wherein the peptide sequence of the keratin peptide fragment is identical to SEQ ID NO: 412.

17. The hair composition of claim 14, wherein the peptide sequence of the keratin peptide fragment is identical to SEQ ID NO: 409.

\* \* \* \* \*

SEQUENCE LISTING

```
Sequence total quantity: 1239
SEQ ID NO: 1                moltype = AA  length = 10
FEATURE                     Location/Qualifiers
source                      1..10
                            mol_type = protein
                            organism = Homo sapiens
SEQUENCE: 1
APCAPRPSCG                                                                      10

SEQ ID NO: 2                moltype = AA  length = 10
FEATURE                     Location/Qualifiers
source                      1..10
                            mol_type = protein
                            organism = Homo sapiens
SEQUENCE: 2
EACVPSVPCP                                                                      10

SEQ ID NO: 3                moltype = AA  length = 10
FEATURE                     Location/Qualifiers
source                      1..10
                            mol_type = protein
                            organism = Homo sapiens
SEQUENCE: 3
ESCGTASGCA                                                                      10

SEQ ID NO: 4                moltype = AA  length = 10
FEATURE                     Location/Qualifiers
source                      1..10
                            mol_type = protein
                            organism = Homo sapiens
SEQUENCE: 4
GLCAGTSACL                                                                      10

SEQ ID NO: 5                moltype = AA  length = 10
FEATURE                     Location/Qualifiers
source                      1..10
                            mol_type = protein
                            organism = Homo sapiens
SEQUENCE: 5
GVCGPSPPCI                                                                      10

SEQ ID NO: 6                moltype = AA  length = 10
FEATURE                     Location/Qualifiers
source                      1..10
                            mol_type = protein
                            organism = Homo sapiens
SEQUENCE: 6
HGCTLPGACN                                                                      10

SEQ ID NO: 7                moltype = AA  length = 10
FEATURE                     Location/Qualifiers
source                      1..10
                            mol_type = protein
                            organism = Homo sapiens
SEQUENCE: 7
HSCTLPGACN                                                                      10

SEQ ID NO: 8                moltype = AA  length = 10
FEATURE                     Location/Qualifiers
source                      1..10
                            mol_type = protein
                            organism = Homo sapiens
SEQUENCE: 8
KDCLQNSLCE                                                                      10

SEQ ID NO: 9                moltype = AA  length = 10
FEATURE                     Location/Qualifiers
source                      1..10
                            mol_type = protein
                            organism = Homo sapiens
SEQUENCE: 9
LPCLPAASCG                                                                      10

SEQ ID NO: 10               moltype = AA  length = 10
FEATURE                     Location/Qualifiers
source                      1..10
                            mol_type = protein
                            organism = Homo sapiens
```

```
SEQUENCE: 10
LPCYFTGSCN                                                                              10

SEQ ID NO: 11           moltype = AA  length = 10
FEATURE                 Location/Qualifiers
source                  1..10
                        mol_type = protein
                        organism = Homo sapiens
SEQUENCE: 11
NFCLPSLSCR                                                                              10

SEQ ID NO: 12           moltype = AA  length = 10
FEATURE                 Location/Qualifiers
source                  1..10
                        mol_type = protein
                        organism = Homo sapiens
SEQUENCE: 12
NPCATTNACD                                                                              10

SEQ ID NO: 13           moltype = AA  length = 10
FEATURE                 Location/Qualifiers
source                  1..10
                        mol_type = protein
                        organism = Homo sapiens
SEQUENCE: 13
NPCATTNACE                                                                              10

SEQ ID NO: 14           moltype = AA  length = 10
FEATURE                 Location/Qualifiers
source                  1..10
                        mol_type = protein
                        organism = Homo sapiens
SEQUENCE: 14
NPCATTNACS                                                                              10

SEQ ID NO: 15           moltype = AA  length = 10
FEATURE                 Location/Qualifiers
source                  1..10
                        mol_type = protein
                        organism = Homo sapiens
SEQUENCE: 15
NPCGLRARCG                                                                              10

SEQ ID NO: 16           moltype = AA  length = 10
FEATURE                 Location/Qualifiers
source                  1..10
                        mol_type = protein
                        organism = Homo sapiens
SEQUENCE: 16
NPCGPRSRCG                                                                              10

SEQ ID NO: 17           moltype = AA  length = 10
FEATURE                 Location/Qualifiers
source                  1..10
                        mol_type = protein
                        organism = Homo sapiens
SEQUENCE: 17
NPCSTPASCT                                                                              10

SEQ ID NO: 18           moltype = AA  length = 10
FEATURE                 Location/Qualifiers
source                  1..10
                        mol_type = protein
                        organism = Homo sapiens
SEQUENCE: 18
NPCSTSPSCV                                                                              10

SEQ ID NO: 19           moltype = AA  length = 10
FEATURE                 Location/Qualifiers
source                  1..10
                        mol_type = protein
                        organism = Homo sapiens
SEQUENCE: 19
PACTSSSPCS                                                                              10

SEQ ID NO: 20           moltype = AA  length = 10
FEATURE                 Location/Qualifiers
source                  1..10
                        mol_type = protein
```

```
                        organism = Homo sapiens
SEQUENCE: 20
SKCHESTVCP                                                                          10

SEQ ID NO: 21           moltype = AA   length = 10
FEATURE                 Location/Qualifiers
source                  1..10
                        mol_type = protein
                        organism = Homo sapiens
SEQUENCE: 21
SPCVPRTVCV                                                                          10

SEQ ID NO: 22           moltype = AA   length = 10
FEATURE                 Location/Qualifiers
source                  1..10
                        mol_type = protein
                        organism = Homo sapiens
SEQUENCE: 22
SSCSVETACL                                                                          10

SEQ ID NO: 23           moltype = AA   length = 10
FEATURE                 Location/Qualifiers
source                  1..10
                        mol_type = protein
                        organism = Homo sapiens
SEQUENCE: 23
SVCSSGVNCR                                                                          10

SEQ ID NO: 24           moltype = AA   length = 10
FEATURE                 Location/Qualifiers
source                  1..10
                        mol_type = protein
                        organism = Homo sapiens
SEQUENCE: 24
TACPLPGTCH                                                                          10

SEQ ID NO: 25           moltype = AA   length = 10
FEATURE                 Location/Qualifiers
source                  1..10
                        mol_type = protein
                        organism = Homo sapiens
SEQUENCE: 25
TNCSPRPICV                                                                          10

SEQ ID NO: 26           moltype = AA   length = 10
FEATURE                 Location/Qualifiers
source                  1..10
                        mol_type = protein
                        organism = Homo sapiens
SEQUENCE: 26
TSCVPPAPCT                                                                          10

SEQ ID NO: 27           moltype = AA   length = 10
FEATURE                 Location/Qualifiers
source                  1..10
                        mol_type = protein
                        organism = Homo sapiens
SEQUENCE: 27
TTCTSSNTCE                                                                          10

SEQ ID NO: 28           moltype = AA   length = 10
FEATURE                 Location/Qualifiers
source                  1..10
                        mol_type = protein
                        organism = Homo sapiens
SEQUENCE: 28
VPCVPSVPCT                                                                          10

SEQ ID NO: 29           moltype = AA   length = 10
FEATURE                 Location/Qualifiers
source                  1..10
                        mol_type = protein
                        organism = Homo sapiens
SEQUENCE: 29
ATCGPSACIT                                                                          10

SEQ ID NO: 30           moltype = AA   length = 10
FEATURE                 Location/Qualifiers
source                  1..10
```

```
                              mol_type = protein
                              organism = Homo sapiens
SEQUENCE: 30
GPCISNPCGL                                                                      10

SEQ ID NO: 31                 moltype = AA  length = 10
FEATURE                       Location/Qualifiers
source                        1..10
                              mol_type = protein
                              organism = Homo sapiens
SEQUENCE: 31
GPCLSNPCTS                                                                      10

SEQ ID NO: 32                 moltype = AA  length = 10
FEATURE                       Location/Qualifiers
source                        1..10
                              mol_type = protein
                              organism = Homo sapiens
SEQUENCE: 32
GSCVTNPCGP                                                                      10

SEQ ID NO: 33                 moltype = AA  length = 10
FEATURE                       Location/Qualifiers
source                        1..10
                              mol_type = protein
                              organism = Homo sapiens
SEQUENCE: 33
LTCFSITCSS                                                                      10

SEQ ID NO: 34                 moltype = AA  length = 10
FEATURE                       Location/Qualifiers
source                        1..10
                              mol_type = protein
                              organism = Homo sapiens
SEQUENCE: 34
NPCSTPSCTT                                                                      10

SEQ ID NO: 35                 moltype = AA  length = 10
FEATURE                       Location/Qualifiers
source                        1..10
                              mol_type = protein
                              organism = Homo sapiens
SEQUENCE: 35
PSCVTAPCAP                                                                      10

SEQ ID NO: 36                 moltype = AA  length = 10
FEATURE                       Location/Qualifiers
source                        1..10
                              mol_type = protein
                              organism = Homo sapiens
SEQUENCE: 36
SDCSSTHCSP                                                                      10

SEQ ID NO: 37                 moltype = AA  length = 10
FEATURE                       Location/Qualifiers
source                        1..10
                              mol_type = protein
                              organism = Homo sapiens
SEQUENCE: 37
SLCLPPTCHT                                                                      10

SEQ ID NO: 38                 moltype = AA  length = 10
FEATURE                       Location/Qualifiers
source                        1..10
                              mol_type = protein
                              organism = Homo sapiens
SEQUENCE: 38
SLCNLGSCGP                                                                      10

SEQ ID NO: 39                 moltype = AA  length = 10
FEATURE                       Location/Qualifiers
source                        1..10
                              mol_type = protein
                              organism = Homo sapiens
SEQUENCE: 39
SPCLVGNCAW                                                                      10

SEQ ID NO: 40                 moltype = AA  length = 10
FEATURE                       Location/Qualifiers
```

```
                              -continued source                  1..10
                        mol_type = protein
                        organism = Homo sapiens
SEQUENCE: 40
TACLPGTCAT                                                              10

SEQ ID NO: 41           moltype = AA  length = 10
FEATURE                 Location/Qualifiers
source                  1..10
                        mol_type = protein
                        organism = Homo sapiens
SEQUENCE: 41
TSCLPALCLP                                                              10

SEQ ID NO: 42           moltype = AA  length = 10
FEATURE                 Location/Qualifiers
source                  1..10
                        mol_type = protein
                        organism = Homo sapiens
SEQUENCE: 42
TSCSSRPCVP                                                              10

SEQ ID NO: 43           moltype = AA  length = 10
FEATURE                 Location/Qualifiers
source                  1..10
                        mol_type = protein
                        organism = Homo sapiens
SEQUENCE: 43
TTCGGGSCGV                                                              10

SEQ ID NO: 44           moltype = AA  length = 10
FEATURE                 Location/Qualifiers
source                  1..10
                        mol_type = protein
                        organism = Homo sapiens
SEQUENCE: 44
VNCRPELCLG                                                              10

SEQ ID NO: 45           moltype = AA  length = 10
FEATURE                 Location/Qualifiers
source                  1..10
                        mol_type = protein
                        organism = Homo sapiens
SEQUENCE: 45
YVCQPMACLP                                                              10

SEQ ID NO: 46           moltype = AA  length = 10
FEATURE                 Location/Qualifiers
source                  1..10
                        mol_type = protein
                        organism = Homo sapiens
SEQUENCE: 46
AFSCISACGP                                                              10

SEQ ID NO: 47           moltype = AA  length = 10
FEATURE                 Location/Qualifiers
source                  1..10
                        mol_type = protein
                        organism = Homo sapiens
SEQUENCE: 47
GSVCSAPCNG                                                              10

SEQ ID NO: 48           moltype = AA  length = 10
FEATURE                 Location/Qualifiers
source                  1..10
                        mol_type = protein
                        organism = Homo sapiens
SEQUENCE: 48
GVVCGDLCAS                                                              10

SEQ ID NO: 49           moltype = AA  length = 10
FEATURE                 Location/Qualifiers
source                  1..10
                        mol_type = protein
                        organism = Homo sapiens
SEQUENCE: 49
GVVCGDLCVS                                                              10

SEQ ID NO: 50           moltype = AA  length = 10
```

```
FEATURE              Location/Qualifiers
source               1..10
                     mol_type = protein
                     organism = Homo sapiens
SEQUENCE: 50
LTGCLLPCYF                                                               10

SEQ ID NO: 51        moltype = AA  length = 10
FEATURE              Location/Qualifiers
source               1..10
                     mol_type = protein
                     organism = Homo sapiens
SEQUENCE: 51
NEDCKLPCNP                                                               10

SEQ ID NO: 52        moltype = AA  length = 10
FEATURE              Location/Qualifiers
source               1..10
                     mol_type = protein
                     organism = Homo sapiens
SEQUENCE: 52
NFSCVSACGP                                                               10

SEQ ID NO: 53        moltype = AA  length = 10
FEATURE              Location/Qualifiers
source               1..10
                     mol_type = protein
                     organism = Homo sapiens
SEQUENCE: 53
PPTCHTACPL                                                               10

SEQ ID NO: 54        moltype = AA  length = 10
FEATURE              Location/Qualifiers
source               1..10
                     mol_type = protein
                     organism = Homo sapiens
SEQUENCE: 54
PQPCATACKP                                                               10

SEQ ID NO: 55        moltype = AA  length = 10
FEATURE              Location/Qualifiers
source               1..10
                     mol_type = protein
                     organism = Homo sapiens
SEQUENCE: 55
SEDCKLPCNP                                                               10

SEQ ID NO: 56        moltype = AA  length = 10
FEATURE              Location/Qualifiers
source               1..10
                     mol_type = protein
                     organism = Homo sapiens
SEQUENCE: 56
SLGCRTSCSS                                                               10

SEQ ID NO: 57        moltype = AA  length = 10
FEATURE              Location/Qualifiers
source               1..10
                     mol_type = protein
                     organism = Homo sapiens
SEQUENCE: 57
SLSCRTSCSS                                                               10

SEQ ID NO: 58        moltype = AA  length = 10
FEATURE              Location/Qualifiers
source               1..10
                     mol_type = protein
                     organism = Homo sapiens
SEQUENCE: 58
SSSCPLGCTM                                                               10

SEQ ID NO: 59        moltype = AA  length = 10
FEATURE              Location/Qualifiers
source               1..10
                     mol_type = protein
                     organism = Homo sapiens
SEQUENCE: 59
TGSCNSPCLV                                                               10
```

```
SEQ ID NO: 60          moltype = AA   length = 10
FEATURE                Location/Qualifiers
source                 1..10
                       mol_type = protein
                       organism = Homo sapiens
SEQUENCE: 60
TSSCPLGCTM                                                                10

SEQ ID NO: 61          moltype = AA   length = 10
FEATURE                Location/Qualifiers
source                 1..10
                       mol_type = protein
                       organism = Homo sapiens
SEQUENCE: 61
VGSCGSSCRK                                                                10

SEQ ID NO: 62          moltype = AA   length = 10
FEATURE                Location/Qualifiers
source                 1..10
                       mol_type = protein
                       organism = Homo sapiens
SEQUENCE: 62
VGVCGGSCKR                                                                10

SEQ ID NO: 63          moltype = AA   length = 10
FEATURE                Location/Qualifiers
source                 1..10
                       mol_type = protein
                       organism = Homo sapiens
SEQUENCE: 63
VSNCNWFCEG                                                                10

SEQ ID NO: 64          moltype = AA   length = 10
FEATURE                Location/Qualifiers
source                 1..10
                       mol_type = protein
                       organism = Homo sapiens
SEQUENCE: 64
ACGPRPGRCC                                                                10

SEQ ID NO: 65          moltype = AA   length = 10
FEATURE                Location/Qualifiers
source                 1..10
                       mol_type = protein
                       organism = Homo sapiens
SEQUENCE: 65
ACGPRPSRCC                                                                10

SEQ ID NO: 66          moltype = AA   length = 10
FEATURE                Location/Qualifiers
source                 1..10
                       mol_type = protein
                       organism = Homo sapiens
SEQUENCE: 66
CAPRPSCGPC                                                                10

SEQ ID NO: 67          moltype = AA   length = 10
FEATURE                Location/Qualifiers
source                 1..10
                       mol_type = protein
                       organism = Homo sapiens
SEQUENCE: 67
CEPCSAYVIC                                                                10

SEQ ID NO: 68          moltype = AA   length = 10
FEATURE                Location/Qualifiers
source                 1..10
                       mol_type = protein
                       organism = Homo sapiens
SEQUENCE: 68
CGLRARCGPC                                                                10

SEQ ID NO: 69          moltype = AA   length = 10
FEATURE                Location/Qualifiers
source                 1..10
                       mol_type = protein
                       organism = Homo sapiens
SEQUENCE: 69
CGPRPGRCCI                                                                10
```

```
SEQ ID NO: 70              moltype = AA   length = 10
FEATURE                    Location/Qualifiers
source                     1..10
                           mol_type = protein
                           organism = Homo sapiens SEQUENCE: 70
CGPRPSRCCI                                                                10

SEQ ID NO: 71              moltype = AA   length = 10
FEATURE                    Location/Qualifiers
source                     1..10
                           mol_type = protein
                           organism = Homo sapiens SEQUENCE: 71
CGPRSRCGPC                                                                10

SEQ ID NO: 72              moltype = AA   length = 10
FEATURE                    Location/Qualifiers
source                     1..10
                           mol_type = protein
                           organism = Homo sapiens SEQUENCE: 72
CGTSQKGCCN                                                                10

SEQ ID NO: 73              moltype = AA   length = 10
FEATURE                    Location/Qualifiers
source                     1..10
                           mol_type = protein
                           organism = Homo sapiens SEQUENCE: 73
CHGCTLPGAC                                                                10

SEQ ID NO: 74              moltype = AA   length = 10
FEATURE                    Location/Qualifiers
source                     1..10
                           mol_type = protein
                           organism = Homo sapiens SEQUENCE: 74
CHSCTLPGAC                                                                10

SEQ ID NO: 75              moltype = AA   length = 10
FEATURE                    Location/Qualifiers
source                     1..10
                           mol_type = protein
                           organism = Homo sapiens SEQUENCE: 75
CLPCLPAASC                                                                10

SEQ ID NO: 76              moltype = AA   length = 10
FEATURE                    Location/Qualifiers
source                     1..10
                           mol_type = protein
                           organism = Homo sapiens SEQUENCE: 76
CLPPTCHTAC                                                                10

SEQ ID NO: 77              moltype = AA   length = 10
FEATURE                    Location/Qualifiers
source                     1..10
                           mol_type = protein
                           organism = Homo sapiens SEQUENCE: 77
CLSNPCTSCV                                                                10

SEQ ID NO: 78              moltype = AA   length = 10
FEATURE                    Location/Qualifiers
source                     1..10
                           mol_type = protein
                           organism = Homo sapiens SEQUENCE: 78
CLVGNCAWCE                                                                10

SEQ ID NO: 79              moltype = AA   length = 10
FEATURE                    Location/Qualifiers
source                     1..10
                           mol_type = protein
                           organism = Homo sapiens

SEQUENCE: 79
```

```
CNPCSTPASC                                                                     10

SEQ ID NO: 80            moltype = AA   length = 10
FEATURE                  Location/Qualifiers
source                   1..10
                         mol_type = protein
                         organism = Homo sapiens
SEQUENCE: 80
CNPCSTPSCT                                                                     10

SEQ ID NO: 81            moltype = AA   length = 10
FEATURE                  Location/Qualifiers
source                   1..10
                         mol_type = protein
                         organism = Homo sapiens
SEQUENCE: 81
CNPCSTSPSC                                                                     10

SEQ ID NO: 82            moltype = AA   length = 10
FEATURE                  Location/Qualifiers
source                   1..10
                         mol_type = protein
                         organism = Homo sapiens
SEQUENCE: 82
CNSPCLVGNC                                                                     10

SEQ ID NO: 83            moltype = AA   length = 10
FEATURE                  Location/Qualifiers
source                   1..10
                         mol_type = protein
                         organism = Homo sapiens
SEQUENCE: 83
CRTSCSSRPC                                                                     10

SEQ ID NO: 84            moltype = AA   length = 10
FEATURE                  Location/Qualifiers
source                   1..10
                         mol_type = protein
                         organism = Homo sapiens
SEQUENCE: 84
CSLKEHCSAC                                                                     10

SEQ ID NO: 85            moltype = AA   length = 10
FEATURE                  Location/Qualifiers
source                   1..10
                         mol_type = protein
                         organism = Homo sapiens
SEQUENCE: 85
CSPRPICVPC                                                                     10

SEQ ID NO: 86            moltype = AA   length = 10
FEATURE                  Location/Qualifiers
source                   1..10
                         mol_type = protein
                         organism = Homo sapiens
SEQUENCE: 86
CSSTMSYSCC                                                                     10

SEQ ID NO: 87            moltype = AA   length = 10
FEATURE                  Location/Qualifiers
source                   1..10
                         mol_type = protein
                         organism = Homo sapiens
SEQUENCE: 87
CSTPASCTSC                                                                     10

SEQ ID NO: 88            moltype = AA   length = 10
FEATURE                  Location/Qualifiers
source                   1..10
                         mol_type = protein
                         organism = Homo sapiens
SEQUENCE: 88
CSTPSCTTCV                                                                     10

SEQ ID NO: 89            moltype = AA   length = 10
FEATURE                  Location/Qualifiers
source                   1..10
                         mol_type = protein
                         organism = Homo sapiens
```

```
SEQUENCE: 89
CTSCVPPAPC                                                                                       10

SEQ ID NO: 90         moltype = AA   length = 10
FEATURE               Location/Qualifiers
source                1..10
                      mol_type = protein
                      organism = Homo sapiens
SEQUENCE: 90
CTSSNTCEPC                                                                                       10

SEQ ID NO: 91         moltype = AA   length = 10
FEATURE               Location/Qualifiers
source                1..10
                      mol_type = protein
                      organism = Homo sapiens
SEQUENCE: 91
CVPPAPCTPC                                                                                       10

SEQ ID NO: 92         moltype = AA   length = 10
FEATURE               Location/Qualifiers
source                1..10
                      mol_type = protein
                      organism = Homo sapiens
SEQUENCE: 92
CVPPSCHGCT                                                                                       10

SEQ ID NO: 93         moltype = AA   length = 10
FEATURE               Location/Qualifiers
source                1..10
                      mol_type = protein
                      organism = Homo sapiens
SEQUENCE: 93
CVPPSCHSCT                                                                                       10

SEQ ID NO: 94         moltype = AA   length = 10
FEATURE               Location/Qualifiers
source                1..10
                      mol_type = protein
                      organism = Homo sapiens
SEQUENCE: 94
DCKLPCNPCA                                                                                       10

SEQ ID NO: 95         moltype = AA   length = 10
FEATURE               Location/Qualifiers
source                1..10
                      mol_type = protein
                      organism = Homo sapiens
SEQUENCE: 95
DCKLPCNPCS                                                                                       10

SEQ ID NO: 96         moltype = AA   length = 10
FEATURE               Location/Qualifiers
source                1..10
                      mol_type = protein
                      organism = Homo sapiens
SEQUENCE: 96
PCGTSQKGCC                                                                                       10

SEQ ID NO: 97         moltype = AA   length = 10
FEATURE               Location/Qualifiers
source                1..10
                      mol_type = protein
                      organism = Homo sapiens
SEQUENCE: 97
PCLSNPCTSC                                                                                       10

SEQ ID NO: 98         moltype = AA   length = 10
FEATURE               Location/Qualifiers
source                1..10
                      mol_type = protein
                      organism = Homo sapiens
SEQUENCE: 98
PCLVGNCAWC                                                                                       10

SEQ ID NO: 99         moltype = AA   length = 10
FEATURE               Location/Qualifiers
source                1..10
                      mol_type = protein
```

```
                                    -continued
                              organism = Homo sapiens
SEQUENCE: 99
PCNPCSTPSC                                                                    10

SEQ ID NO: 100               moltype = AA   length = 10
FEATURE                      Location/Qualifiers
source                       1..10
                             mol_type = protein
                             organism = Homo sapiens
SEQUENCE: 100
PCSTPSCTTC                                                                    10

SEQ ID NO: 101               moltype = AA   length = 10
FEATURE                      Location/Qualifiers
source                       1..10
                             mol_type = protein
                             organism = Homo sapiens
SEQUENCE: 101
PCTTCGPTCG                                                                    10

SEQ ID NO: 102               moltype = AA   length = 10
FEATURE                      Location/Qualifiers
source                       1..10
                             mol_type = protein
                             organism = Homo sapiens
SEQUENCE: 102
PCVPPSCHGC                                                                    10

SEQ ID NO: 103               moltype = AA   length = 10
FEATURE                      Location/Qualifiers
source                       1..10
                             mol_type = protein
                             organism = Homo sapiens
SEQUENCE: 103
PCVPPSCHSC                                                                    10

SEQ ID NO: 104               moltype = AA   length = 10
FEATURE                      Location/Qualifiers
source                       1..10
                             mol_type = protein
                             organism = Homo sapiens
SEQUENCE: 104
SCCLPSLGCR                                                                    10

SEQ ID NO: 105               moltype = AA   length = 10
FEATURE                      Location/Qualifiers
source                       1..10
                             mol_type = protein
                             organism = Homo sapiens
SEQUENCE: 105
SCSEELQCCQ                                                                    10

SEQ ID NO: 106               moltype = AA   length = 10
FEATURE                      Location/Qualifiers
source                       1..10
                             mol_type = protein
                             organism = Homo sapiens
SEQUENCE: 106
SCSPCSTTCT                                                                    10

SEQ ID NO: 107               moltype = AA   length = 10
FEATURE                      Location/Qualifiers
source                       1..10
                             mol_type = protein
                             organism = Homo sapiens
SEQUENCE: 107
ASCSTSGTCG                                                                    10

SEQ ID NO: 108               moltype = AA   length = 10
FEATURE                      Location/Qualifiers
source                       1..10
                             mol_type = protein
                             organism = Homo sapiens
SEQUENCE: 108
ASCYIPVGCQ                                                                    10

SEQ ID NO: 109               moltype = AA   length = 10
FEATURE                      Location/Qualifiers
source                       1..10
```

```
                        mol_type = protein
                        organism = Homo sapiens
SEQUENCE: 109
ASCYVPVSCQ                                                              10

SEQ ID NO: 110          moltype = AA  length = 10
FEATURE                 Location/Qualifiers
source                  1..10
                        mol_type = protein
                        organism = Homo sapiens
SEQUENCE: 110
AVCTLPSSCQ                                                              10

SEQ ID NO: 111          moltype = AA  length = 10
FEATURE                 Location/Qualifiers
source                  1..10
                        mol_type = protein
                        organism = Homo sapiens
SEQUENCE: 111
DLCPTSVSCG                                                              10

SEQ ID NO: 112          moltype = AA  length = 10
FEATURE                 Location/Qualifiers
source                  1..10
                        mol_type = protein
                        organism = Homo sapiens
SEQUENCE: 112
EICWEPTSCQ                                                              10

SEQ ID NO: 113          moltype = AA  length = 10
FEATURE                 Location/Qualifiers
source                  1..10
                        mol_type = protein
                        organism = Homo sapiens
SEQUENCE: 113
ETCGEPTSCQ                                                              10

SEQ ID NO: 114          moltype = AA  length = 10
FEATURE                 Location/Qualifiers
source                  1..10
                        mol_type = protein
                        organism = Homo sapiens
SEQUENCE: 114
ETCNETTSCQ                                                              10

SEQ ID NO: 115          moltype = AA  length = 10
FEATURE                 Location/Qualifiers
source                  1..10
                        mol_type = protein
                        organism = Homo sapiens
SEQUENCE: 115
ETCWRPNSCQ                                                              10

SEQ ID NO: 116          moltype = AA  length = 10
FEATURE                 Location/Qualifiers
source                  1..10
                        mol_type = protein
                        organism = Homo sapiens
SEQUENCE: 116
GYCGYRPFCF                                                              10

SEQ ID NO: 117          moltype = AA  length = 10
FEATURE                 Location/Qualifiers
source                  1..10
                        mol_type = protein
                        organism = Homo sapiens
SEQUENCE: 117
KTCWEPASCQ                                                              10

SEQ ID NO: 118          moltype = AA  length = 10
FEATURE                 Location/Qualifiers
source                  1..10
                        mol_type = protein
                        organism = Homo sapiens
SEQUENCE: 118
KTCWEPTSCQ                                                              10

SEQ ID NO: 119          moltype = AA  length = 10
FEATURE                 Location/Qualifiers
```

| | | |
|---|---|---|
| source | 1..10<br>mol_type = protein<br>organism = Homo sapiens | |
| SEQUENCE: 119<br>LDCVDTTPCK | | 10 |
| SEQ ID NO: 120<br>FEATURE<br>source | moltype = AA  length = 10<br>Location/Qualifiers<br>1..10<br>mol_type = protein<br>organism = Homo sapiens | |
| SEQUENCE: 120<br>LGCGYGSFCG | | 10 |
| SEQ ID NO: 121<br>FEATURE<br>source | moltype = AA  length = 10<br>Location/Qualifiers<br>1..10<br>mol_type = protein<br>organism = Homo sapiens | |
| SEQUENCE: 121<br>NSCGYGSGCG | | 10 |
| SEQ ID NO: 122<br>FEATURE<br>source | moltype = AA  length = 10<br>Location/Qualifiers<br>1..10<br>mol_type = protein<br>organism = Homo sapiens | |
| SEQUENCE: 122<br>NYCPSNTMCE | | 10 |
| SEQ ID NO: 123<br>FEATURE<br>source | moltype = AA  length = 10<br>Location/Qualifiers<br>1..10<br>mol_type = protein<br>organism = Homo sapiens | |
| SEQUENCE: 123<br>PACVTSYSCR | | 10 |
| SEQ ID NO: 124<br>FEATURE<br>source | moltype = AA  length = 10<br>Location/Qualifiers<br>1..10<br>mol_type = protein<br>organism = Homo sapiens | |
| SEQUENCE: 124<br>PDCHVEGTCL | | 10 |
| SEQ ID NO: 125<br>FEATURE<br>source | moltype = AA  length = 10<br>Location/Qualifiers<br>1..10<br>mol_type = protein<br>organism = Homo sapiens | |
| SEQUENCE: 125<br>PDCRVEGTCL | | 10 |
| SEQ ID NO: 126<br>FEATURE<br>source | moltype = AA  length = 10<br>Location/Qualifiers<br>1..10<br>mol_type = protein<br>organism = Homo sapiens | |
| SEQUENCE: 126<br>PICSEPSPCS | | 10 |
| SEQ ID NO: 127<br>FEATURE<br>source | moltype = AA  length = 10<br>Location/Qualifiers<br>1..10<br>mol_type = protein<br>organism = Homo sapiens | |
| SEQUENCE: 127<br>PICYIFKPCQ | | 10 |
| SEQ ID NO: 128<br>FEATURE<br>source | moltype = AA  length = 10<br>Location/Qualifiers<br>1..10<br>mol_type = protein<br>organism = Homo sapiens | |
| SEQUENCE: 128<br>PLCYISNSCQ | | 10 |
| SEQ ID NO: 129 | moltype = AA  length = 10 | |

```
FEATURE                     Location/Qualifiers
source                      1..10
                            mol_type = protein
                            organism = Homo sapiens
SEQUENCE: 129
PPCGQPTPCS                                                                      10

SEQ ID NO: 130              moltype = AA  length = 10
FEATURE                     Location/Qualifiers
source                      1..10
                            mol_type = protein
                            organism = Homo sapiens
SEQUENCE: 130
PPCHIPQPCV                                                                      10

SEQ ID NO: 131              moltype = AA  length = 10
FEATURE                     Location/Qualifiers
source                      1..10
                            mol_type = protein
                            organism = Homo sapiens
SEQUENCE: 131
PSCGRLASCG                                                                      10

SEQ ID NO: 132              moltype = AA  length = 10
FEATURE                     Location/Qualifiers
source                      1..10
                            mol_type = protein
                            organism = Homo sapiens
SEQUENCE: 132
PSCSESSICQ                                                                      10

SEQ ID NO: 133              moltype = AA  length = 10
FEATURE                     Location/Qualifiers
source                      1..10
                            mol_type = protein
                            organism = Homo sapiens
SEQUENCE: 133
PSCSEVTSCP                                                                      10

SEQ ID NO: 134              moltype = AA  length = 10
FEATURE                     Location/Qualifiers
source                      1..10
                            mol_type = protein
                            organism = Homo sapiens
SEQUENCE: 134
PSCSTSGTCG                                                                      10

SEQ ID NO: 135              moltype = AA  length = 10
FEATURE                     Location/Qualifiers
source                      1..10
                            mol_type = protein
                            organism = Homo sapiens
SEQUENCE: 135
PSCSVSSGCQ                                                                      10

SEQ ID NO: 136              moltype = AA  length = 10
FEATURE                     Location/Qualifiers
source                      1..10
                            mol_type = protein
                            organism = Homo sapiens
SEQUENCE: 136
PSCTESDSCK                                                                      10

SEQ ID NO: 137              moltype = AA  length = 10
FEATURE                     Location/Qualifiers
source                      1..10
                            mol_type = protein
                            organism = Homo sapiens
SEQUENCE: 137
PSCYQTSSCG                                                                      10

SEQ ID NO: 138              moltype = AA  length = 10
FEATURE                     Location/Qualifiers
source                      1..10
                            mol_type = protein
                            organism = Homo sapiens
SEQUENCE: 138
PTCFLLNSCQ                                                                      10
```

| | | |
|---|---|---|
| SEQ ID NO: 139<br>FEATURE<br>source | moltype = AA   length = 10<br>Location/Qualifiers<br>1..10<br>mol_type = protein<br>organism = Homo sapiens | |
| SEQUENCE: 139<br>PTCSVTSSCQ | | 10 |
| SEQ ID NO: 140<br>FEATURE<br>source | moltype = AA   length = 10<br>Location/Qualifiers<br>1..10<br>mol_type = protein<br>organism = Homo sapiens | |
| SEQUENCE: 140<br>PTCWLLNNCH | | 10 |
| SEQ ID NO: 141<br>FEATURE<br>source | moltype = AA   length = 10<br>Location/Qualifiers<br>1..10<br>mol_type = protein<br>organism = Homo sapiens | |
| SEQUENCE: 141<br>PTCYQRTSCV | | 10 |
| SEQ ID NO: 142<br>FEATURE<br>source | moltype = AA   length = 10<br>Location/Qualifiers<br>1..10<br>mol_type = protein<br>organism = Homo sapiens | |
| SEQUENCE: 142<br>PTCYRRTSCV | | 10 |
| SEQ ID NO: 143<br>FEATURE<br>source | moltype = AA   length = 10<br>Location/Qualifiers<br>1..10<br>mol_type = protein<br>organism = Homo sapiens | |
| SEQUENCE: 143<br>PTCYVVKRCP | | 10 |
| SEQ ID NO: 144<br>FEATURE<br>source | moltype = AA   length = 10<br>Location/Qualifiers<br>1..10<br>mol_type = protein<br>organism = Homo sapiens | |
| SEQUENCE: 144<br>PVCFEATICE | | 10 |
| SEQ ID NO: 145<br>FEATURE<br>source | moltype = AA   length = 10<br>Location/Qualifiers<br>1..10<br>mol_type = protein<br>organism = Homo sapiens | |
| SEQUENCE: 145<br>PVCFEATVCE | | 10 |
| SEQ ID NO: 146<br>FEATURE<br>source | moltype = AA   length = 10<br>Location/Qualifiers<br>1..10<br>mol_type = protein<br>organism = Homo sapiens | |
| SEQUENCE: 146<br>PVCSRPASCS | | 10 |
| SEQ ID NO: 147<br>FEATURE<br>source | moltype = AA   length = 10<br>Location/Qualifiers<br>1..10<br>mol_type = protein<br>organism = Homo sapiens | |
| SEQUENCE: 147<br>PVCSWVPACS | | 10 |
| SEQ ID NO: 148<br>FEATURE<br>source | moltype = AA   length = 10<br>Location/Qualifiers<br>1..10<br>mol_type = protein<br>organism = Homo sapiens | |
| SEQUENCE: 148<br>QTCNESSYCL | | 10 |

```
SEQ ID NO: 149          moltype = AA   length = 10
FEATURE                 Location/Qualifiers
source                  1..10
                        mol_type = protein
                        organism = Homo sapiens
SEQUENCE: 149
QTCWEPTSCQ                                                                  10

SEQ ID NO: 150          moltype = AA   length = 10
FEATURE                 Location/Qualifiers
source                  1..10
                        mol_type = protein
                        organism = Homo sapiens
SEQUENCE: 150
SFCRLGYGCG                                                                  10

SEQ ID NO: 151          moltype = AA   length = 10
FEATURE                 Location/Qualifiers
source                  1..10
                        mol_type = protein
                        organism = Homo sapiens
SEQUENCE: 151
SFCRRGSGCG                                                                  10

SEQ ID NO: 152          moltype = AA   length = 10
FEATURE                 Location/Qualifiers
source                  1..10
                        mol_type = protein
                        organism = Homo sapiens
SEQUENCE: 152
SLCGYGYGCG                                                                  10

SEQ ID NO: 153          moltype = AA   length = 10
FEATURE                 Location/Qualifiers
source                  1..10
                        mol_type = protein
                        organism = Homo sapiens
SEQUENCE: 153
SLCSTEVSCG                                                                  10

SEQ ID NO: 154          moltype = AA   length = 10
FEATURE                 Location/Qualifiers
source                  1..10
                        mol_type = protein
                        organism = Homo sapiens
SEQUENCE: 154
SNCFGQLNCL                                                                  10

SEQ ID NO: 155          moltype = AA   length = 10
FEATURE                 Location/Qualifiers
source                  1..10
                        mol_type = protein
                        organism = Homo sapiens
SEQUENCE: 155
SPCGQPTPCS                                                                  10

SEQ ID NO: 156          moltype = AA   length = 10
FEATURE                 Location/Qualifiers
source                  1..10
                        mol_type = protein
                        organism = Homo sapiens
SEQUENCE: 156
SSCDQSSSCA                                                                  10

SEQ ID NO: 157          moltype = AA   length = 10
FEATURE                 Location/Qualifiers
source                  1..10
                        mol_type = protein
                        organism = Homo sapiens
SEQUENCE: 157
SSCGQSSSCA                                                                  10

SEQ ID NO: 158          moltype = AA   length = 10
FEATURE                 Location/Qualifiers
source                  1..10
                        mol_type = protein
                        organism = Homo sapiens
SEQUENCE: 158
```

```
SVCPEPVSCP                                                                                  10

SEQ ID NO: 159           moltype = AA  length = 10
FEATURE                  Location/Qualifiers
source                   1..10
                         mol_type = protein
                         organism = Homo sapiens SEQUENCE: 159
TFCSFDKSCR                                                                                  10

SEQ ID NO: 160           moltype = AA  length = 10
FEATURE                  Location/Qualifiers
source                   1..10
                         mol_type = protein
                         organism = Homo sapiens SEQUENCE: 160
TICSSDKSCR                                                                                  10

SEQ ID NO: 161           moltype = AA  length = 10
FEATURE                  Location/Qualifiers
source                   1..10
                         mol_type = protein
                         organism = Homo sapiens SEQUENCE: 161
TLCVESSPCH                                                                                  10

SEQ ID NO: 162           moltype = AA  length = 10
FEATURE                  Location/Qualifiers
source                   1..10
                         mol_type = protein
                         organism = Homo sapiens SEQUENCE: 162
TPCYQQSSCQ                                                                                  10

SEQ ID NO: 163           moltype = AA  length = 10
FEATURE                  Location/Qualifiers
source                   1..10
                         mol_type = protein
                         organism = Homo sapiens SEQUENCE: 163
VTCSRQTTCI                                                                                  10

SEQ ID NO: 164           moltype = AA  length = 10
FEATURE                  Location/Qualifiers
source                   1..10
                         mol_type = protein
                         organism = Homo sapiens SEQUENCE: 164
YGCGYGSGCG                                                                                  10

SEQ ID NO: 165           moltype = AA  length = 10
FEATURE                  Location/Qualifiers
source                   1..10
                         mol_type = protein
                         organism = Homo sapiens SEQUENCE: 165
YGCGYGSGCR                                                                                  10

SEQ ID NO: 166           moltype = AA  length = 10
FEATURE                  Location/Qualifiers
source                   1..10
                         mol_type = protein
                         organism = Homo sapiens SEQUENCE: 166
YGCIHSTHCG                                                                                  10

SEQ ID NO: 167           moltype = AA  length = 10
FEATURE                  Location/Qualifiers
source                   1..10
                         mol_type = protein
                         organism = Homo sapiens SEQUENCE: 167
AACEPSACQS                                                                                  10

SEQ ID NO: 168           moltype = AA  length = 10
FEATURE                  Location/Qualifiers
source                   1..10
                         mol_type = protein
                         organism = Homo sapiens
```

-continued

```
SEQUENCE: 168
AACEPSPCQS                                                                    10

SEQ ID NO: 169         moltype = AA  length = 10
FEATURE                Location/Qualifiers
source                 1..10
                       mol_type = protein
                       organism = Homo sapiens
SEQUENCE: 169
AACTMSVCSS                                                                    10

SEQ ID NO: 170         moltype = AA  length = 10
FEATURE                Location/Qualifiers
source                 1..10
                       mol_type = protein
                       organism = Homo sapiens
SEQUENCE: 170
ADCLGGICLP                                                                    10

SEQ ID NO: 171         moltype = AA  length = 10
FEATURE                Location/Qualifiers
source                 1..10
                       mol_type = protein
                       organism = Homo sapiens
SEQUENCE: 171
ALCLPSSCHS                                                                    10

SEQ ID NO: 172         moltype = AA  length = 10
FEATURE                Location/Qualifiers
source                 1..10
                       mol_type = protein
                       organism = Homo sapiens
SEQUENCE: 172
ALCSPSTCQL                                                                    10

SEQ ID NO: 173         moltype = AA  length = 10
FEATURE                Location/Qualifiers
source                 1..10
                       mol_type = protein
                       organism = Homo sapiens
SEQUENCE: 173
APCLALVCAP                                                                    10

SEQ ID NO: 174         moltype = AA  length = 10
FEATURE                Location/Qualifiers
source                 1..10
                       mol_type = protein
                       organism = Homo sapiens
SEQUENCE: 174
APCLSLVCTP                                                                    10

SEQ ID NO: 175         moltype = AA  length = 10
FEATURE                Location/Qualifiers
source                 1..10
                       mol_type = protein
                       organism = Homo sapiens
SEQUENCE: 175
APCLTLVCTP                                                                    10

SEQ ID NO: 176         moltype = AA  length = 10
FEATURE                Location/Qualifiers
source                 1..10
                       mol_type = protein
                       organism = Homo sapiens
SEQUENCE: 176
APCVALLCRP                                                                    10

SEQ ID NO: 177         moltype = AA  length = 10
FEATURE                Location/Qualifiers
source                 1..10
                       mol_type = protein
                       organism = Homo sapiens
SEQUENCE: 177
ASCGSLLCRP                                                                    10

SEQ ID NO: 178         moltype = AA  length = 10
FEATURE                Location/Qualifiers
source                 1..10
                       mol_type = protein
```

```
                          organism = Homo sapiens
SEQUENCE: 178
ASCLSFLCRP                                                                          10

SEQ ID NO: 179            moltype = AA   length = 10
FEATURE                   Location/Qualifiers
source                    1..10
                          mol_type = protein
                          organism = Homo sapiens
SEQUENCE: 179
ASCVSLLCRP                                                                          10

SEQ ID NO: 180            moltype = AA   length = 10
FEATURE                   Location/Qualifiers
source                    1..10
                          mol_type = protein
                          organism = Homo sapiens
SEQUENCE: 180
AVCEPSPCQS                                                                          10

SEQ ID NO: 181            moltype = AA   length = 10
FEATURE                   Location/Qualifiers
source                    1..10
                          mol_type = protein
                          organism = Homo sapiens
SEQUENCE: 181
AVCLPVSCQS                                                                          10

SEQ ID NO: 182            moltype = AA   length = 10
FEATURE                   Location/Qualifiers
source                    1..10
                          mol_type = protein
                          organism = Homo sapiens
SEQUENCE: 182
AVCVPVRCQS                                                                          10

SEQ ID NO: 183            moltype = AA   length = 10
FEATURE                   Location/Qualifiers
source                    1..10
                          mol_type = protein
                          organism = Homo sapiens
SEQUENCE: 183
AVCVPVSCQS                                                                          10

SEQ ID NO: 184            moltype = AA   length = 10
FEATURE                   Location/Qualifiers
source                    1..10
                          mol_type = protein
                          organism = Homo sapiens
SEQUENCE: 184
DLCSPSTCQL                                                                          10

SEQ ID NO: 185            moltype = AA   length = 10
FEATURE                   Location/Qualifiers
source                    1..10
                          mol_type = protein
                          organism = Homo sapiens
SEQUENCE: 185
DSCGSSSCGP                                                                          10

SEQ ID NO: 186            moltype = AA   length = 10
FEATURE                   Location/Qualifiers
source                    1..10
                          mol_type = protein
                          organism = Homo sapiens
SEQUENCE: 186
DSCVQSNCFP                                                                          10

SEQ ID NO: 187            moltype = AA   length = 10
FEATURE                   Location/Qualifiers
source                    1..10
                          mol_type = protein
                          organism = Homo sapiens
SEQUENCE: 187
FNCSTRNCSS                                                                          10

SEQ ID NO: 188            moltype = AA   length = 10
FEATURE                   Location/Qualifiers
source                    1..10
```

```
                              mol_type = protein
                              organism = Homo sapiens
SEQUENCE: 188
GGCGSYGCSQ                                                                      10

SEQ ID NO: 189                moltype = AA   length = 10
FEATURE                       Location/Qualifiers
source                        1..10
                              mol_type = protein
                              organism = Homo sapiens
SEQUENCE: 189
GSCGFGSCYG                                                                      10

SEQ ID NO: 190                moltype = AA   length = 10
FEATURE                       Location/Qualifiers
source                        1..10
                              mol_type = protein
                              organism = Homo sapiens
SEQUENCE: 190
GSCSSRKCFS                                                                      10

SEQ ID NO: 191                moltype = AA   length = 10
FEATURE                       Location/Qualifiers
source                        1..10
                              mol_type = protein
                              organism = Homo sapiens
SEQUENCE: 191
GVCLPSTCPH                                                                      10

SEQ ID NO: 192                moltype = AA   length = 10
FEATURE                       Location/Qualifiers
source                        1..10
                              mol_type = protein
                              organism = Homo sapiens
SEQUENCE: 192
HSCEGYLCYS                                                                      10

SEQ ID NO: 193                moltype = AA   length = 10
FEATURE                       Location/Qualifiers
source                        1..10
                              mol_type = protein
                              organism = Homo sapiens
SEQUENCE: 193
IVCAAPSCQS                                                                      10

SEQ ID NO: 194                moltype = AA   length = 10
FEATURE                       Location/Qualifiers
source                        1..10
                              mol_type = protein
                              organism = Homo sapiens
SEQUENCE: 194
KTCSTTGCDP                                                                      10

SEQ ID NO: 195                moltype = AA   length = 10
FEATURE                       Location/Qualifiers
source                        1..10
                              mol_type = protein
                              organism = Homo sapiens
SEQUENCE: 195
LACVSQPCQS                                                                      10

SEQ ID NO: 196                moltype = AA   length = 10
FEATURE                       Location/Qualifiers
source                        1..10
                              mol_type = protein
                              organism = Homo sapiens
SEQUENCE: 196
LGCGYGGCGY                                                                      10

SEQ ID NO: 197                moltype = AA   length = 10
FEATURE                       Location/Qualifiers
source                        1..10
                              mol_type = protein
                              organism = Homo sapiens
SEQUENCE: 197
LSCGSRSCSS                                                                      10

SEQ ID NO: 198                moltype = AA   length = 10
FEATURE                       Location/Qualifiers
```

```
source                     1..10
                           mol_type = protein
                           organism = Homo sapiens
SEQUENCE: 198
LVCTPVSCVS                                                              10

SEQ ID NO: 199             moltype = AA   length = 10
FEATURE                    Location/Qualifiers
source                     1..10
                           mol_type = protein
                           organism = Homo sapiens
SEQUENCE: 199
NGCQETYCEP                                                              10

SEQ ID NO: 200             moltype = AA   length = 10
FEATURE                    Location/Qualifiers
source                     1..10
                           mol_type = protein
                           organism = Homo sapiens
SEQUENCE: 200
NSCRSLSCGS                                                              10

SEQ ID NO: 201             moltype = AA   length = 10
FEATURE                    Location/Qualifiers
source                     1..10
                           mol_type = protein
                           organism = Homo sapiens
SEQUENCE: 201
PACVISTCPR                                                              10

SEQ ID NO: 202             moltype = AA   length = 10
FEATURE                    Location/Qualifiers
source                     1..10
                           mol_type = protein
                           organism = Homo sapiens
SEQUENCE: 202
PGCLNQSCGS                                                              10

SEQ ID NO: 203             moltype = AA   length = 10
FEATURE                    Location/Qualifiers
source                     1..10
                           mol_type = protein
                           organism = Homo sapiens
SEQUENCE: 203
PPCGTAPCLT                                                              10

SEQ ID NO: 204             moltype = AA   length = 10
FEATURE                    Location/Qualifiers
source                     1..10
                           mol_type = protein
                           organism = Homo sapiens
SEQUENCE: 204
PPCTTALCRP                                                              10

SEQ ID NO: 205             moltype = AA   length = 10
FEATURE                    Location/Qualifiers
source                     1..10
                           mol_type = protein
                           organism = Homo sapiens
SEQUENCE: 205
PPCYLVSCTP                                                              10

SEQ ID NO: 206             moltype = AA   length = 10
FEATURE                    Location/Qualifiers
source                     1..10
                           mol_type = protein
                           organism = Homo sapiens
SEQUENCE: 206
PRCTRPICEP                                                              10

SEQ ID NO: 207             moltype = AA   length = 10
FEATURE                    Location/Qualifiers
source                     1..10
                           mol_type = protein
                           organism = Homo sapiens
SEQUENCE: 207
PSCPVSSCAQ                                                              10

SEQ ID NO: 208             moltype = AA   length = 10
```

```
FEATURE                 Location/Qualifiers
source                  1..10
                        mol_type = protein
                        organism = Homo sapiens
SEQUENCE: 208
PSCQPSVCVP                                                                      10

SEQ ID NO: 209          moltype = AA  length = 10
FEATURE                 Location/Qualifiers
source                  1..10
                        mol_type = protein
                        organism = Homo sapiens
SEQUENCE: 209
PSCSVSNCYQ                                                                      10

SEQ ID NO: 210          moltype = AA  length = 10
FEATURE                 Location/Qualifiers
source                  1..10
                        mol_type = protein
                        organism = Homo sapiens
SEQUENCE: 210
PSCSVSSCAQ                                                                      10

SEQ ID NO: 211          moltype = AA  length = 10
FEATURE                 Location/Qualifiers
source                  1..10
                        mol_type = protein
                        organism = Homo sapiens
SEQUENCE: 211
PSCTSVLCRP                                                                      10

SEQ ID NO: 212          moltype = AA  length = 10
FEATURE                 Location/Qualifiers
source                  1..10
                        mol_type = protein
                        organism = Homo sapiens
SEQUENCE: 212
PTCKSPSCEP                                                                      10

SEQ ID NO: 213          moltype = AA  length = 10
FEATURE                 Location/Qualifiers
source                  1..10
                        mol_type = protein
                        organism = Homo sapiens
SEQUENCE: 213
PTCVISSCPR                                                                      10

SEQ ID NO: 214          moltype = AA  length = 10
FEATURE                 Location/Qualifiers
source                  1..10
                        mol_type = protein
                        organism = Homo sapiens
SEQUENCE: 214
PTCVISTCPR                                                                      10

SEQ ID NO: 215          moltype = AA  length = 10
FEATURE                 Location/Qualifiers
source                  1..10
                        mol_type = protein
                        organism = Homo sapiens
SEQUENCE: 215
PTCYQTICFR                                                                      10

SEQ ID NO: 216          moltype = AA  length = 10
FEATURE                 Location/Qualifiers
source                  1..10
                        mol_type = protein
                        organism = Homo sapiens
SEQUENCE: 216
PVCGGVSCHT                                                                      10

SEQ ID NO: 217          moltype = AA  length = 10
FEATURE                 Location/Qualifiers
source                  1..10
                        mol_type = protein
                        organism = Homo sapiens
SEQUENCE: 217
PVCGRVSCHT                                                                      10
```

| | | |
|---|---|---|
| SEQ ID NO: 218<br>FEATURE<br>source | moltype = AA   length = 10<br>Location/Qualifiers<br>1..10<br>mol_type = protein<br>organism = Homo sapiens | |
| SEQUENCE: 218<br>PVCNKPVCFV | | 10 |
| SEQ ID NO: 219<br>FEATURE<br>source | moltype = AA   length = 10<br>Location/Qualifiers<br>1..10<br>mol_type = protein<br>organism = Homo sapiens | |
| SEQUENCE: 219<br>PVCPTPTCSV | | 10 |
| SEQ ID NO: 220<br>FEATURE<br>source | moltype = AA   length = 10<br>Location/Qualifiers<br>1..10<br>mol_type = protein<br>organism = Homo sapiens | |
| SEQUENCE: 220<br>PVCRSTYCVP | | 10 |
| SEQ ID NO: 221<br>FEATURE<br>source | moltype = AA   length = 10<br>Location/Qualifiers<br>1..10<br>mol_type = protein<br>organism = Homo sapiens | |
| SEQUENCE: 221<br>PVCSKSVCYV | | 10 |
| SEQ ID NO: 222<br>FEATURE<br>source | moltype = AA   length = 10<br>Location/Qualifiers<br>1..10<br>mol_type = protein<br>organism = Homo sapiens | |
| SEQUENCE: 222<br>PVCSRPACYS | | 10 |
| SEQ ID NO: 223<br>FEATURE<br>source | moltype = AA   length = 10<br>Location/Qualifiers<br>1..10<br>mol_type = protein<br>organism = Homo sapiens | |
| SEQUENCE: 223<br>PVCYVPTCSE | | 10 |
| SEQ ID NO: 224<br>FEATURE<br>source | moltype = AA   length = 10<br>Location/Qualifiers<br>1..10<br>mol_type = protein<br>organism = Homo sapiens | |
| SEQUENCE: 224<br>QFCLSKSCQP | | 10 |
| SEQ ID NO: 225<br>FEATURE<br>source | moltype = AA   length = 10<br>Location/Qualifiers<br>1..10<br>mol_type = protein<br>organism = Homo sapiens | |
| SEQUENCE: 225<br>RPCERTACQS | | 10 |
| SEQ ID NO: 226<br>FEATURE<br>source | moltype = AA   length = 10<br>Location/Qualifiers<br>1..10<br>mol_type = protein<br>organism = Homo sapiens | |
| SEQUENCE: 226<br>RSCQTSFCGF | | 10 |
| SEQ ID NO: 227<br>FEATURE<br>source | moltype = AA   length = 10<br>Location/Qualifiers<br>1..10<br>mol_type = protein<br>organism = Homo sapiens | |
| SEQUENCE: 227<br>RSCSSLGCGS | | 10 |

```
SEQ ID NO: 228           moltype = AA  length = 10
FEATURE                  Location/Qualifiers
source                   1..10
                         mol_type = protein
                         organism = Homo sapiens SEQUENCE: 228
RSCYSVGCGS                                                                10

SEQ ID NO: 229           moltype = AA  length = 10
FEATURE                  Location/Qualifiers
source                   1..10
                         mol_type = protein
                         organism = Homo sapiens SEQUENCE: 229
RVCLPGSCDS                                                                10

SEQ ID NO: 230           moltype = AA  length = 10
FEATURE                  Location/Qualifiers
source                   1..10
                         mol_type = protein
                         organism = Homo sapiens SEQUENCE: 230
SFCGFPSCST                                                                10

SEQ ID NO: 231           moltype = AA  length = 10
FEATURE                  Location/Qualifiers
source                   1..10
                         mol_type = protein
                         organism = Homo sapiens SEQUENCE: 231
SFCGYPSCST                                                                10

SEQ ID NO: 232           moltype = AA  length = 10
FEATURE                  Location/Qualifiers
source                   1..10
                         mol_type = protein
                         organism = Homo sapiens SEQUENCE: 232
SGCDPASCQP                                                                10

SEQ ID NO: 233           moltype = AA  length = 10
FEATURE                  Location/Qualifiers
source                   1..10
                         mol_type = protein
                         organism = Homo sapiens SEQUENCE: 233
SGCGGSGCGG                                                                10

SEQ ID NO: 234           moltype = AA  length = 10
FEATURE                  Location/Qualifiers
source                   1..10
                         mol_type = protein
                         organism = Homo sapiens SEQUENCE: 234
SGCQPSSCLA                                                                10

SEQ ID NO: 235           moltype = AA  length = 10
FEATURE                  Location/Qualifiers
source                   1..10
                         mol_type = protein
                         organism = Homo sapiens SEQUENCE: 235
SHCQPPHCQL                                                                10

SEQ ID NO: 236           moltype = AA  length = 10
FEATURE                  Location/Qualifiers
source                   1..10
                         mol_type = protein
                         organism = Homo sapiens SEQUENCE: 236
SICQPATCVA                                                                10

SEQ ID NO: 237           moltype = AA  length = 10
FEATURE                  Location/Qualifiers
source                   1..10
                         mol_type = protein
                         organism = Homo sapiens

SEQUENCE: 237
```

```
SLCVPVSCRP                                                                    10

SEQ ID NO: 238            moltype = AA   length = 10
FEATURE                   Location/Qualifiers
source                    1..10
                          mol_type = protein
                          organism = Homo sapiens
SEQUENCE: 238
SNCLPTSCQP                                                                    10

SEQ ID NO: 239            moltype = AA   length = 10
FEATURE                   Location/Qualifiers
source                    1..10
                          mol_type = protein
                          organism = Homo sapiens
SEQUENCE: 239
SPCLVSSCQP                                                                    10

SEQ ID NO: 240            moltype = AA   length = 10
FEATURE                   Location/Qualifiers
source                    1..10
                          mol_type = protein
                          organism = Homo sapiens
SEQUENCE: 240
SPCQQSSCQE                                                                    10

SEQ ID NO: 241            moltype = AA   length = 10
FEATURE                   Location/Qualifiers
source                    1..10
                          mol_type = protein
                          organism = Homo sapiens
SEQUENCE: 241
SPCQQSYCVP                                                                    10

SEQ ID NO: 242            moltype = AA   length = 10
FEATURE                   Location/Qualifiers
source                    1..10
                          mol_type = protein
                          organism = Homo sapiens
SEQUENCE: 242
SPCSPAVCVS                                                                    10

SEQ ID NO: 243            moltype = AA   length = 10
FEATURE                   Location/Qualifiers
source                    1..10
                          mol_type = protein
                          organism = Homo sapiens
SEQUENCE: 243
SRCQQPSCQP                                                                    10

SEQ ID NO: 244            moltype = AA   length = 10
FEATURE                   Location/Qualifiers
source                    1..10
                          mol_type = protein
                          organism = Homo sapiens
SEQUENCE: 244
SRCYRPHCGQ                                                                    10

SEQ ID NO: 245            moltype = AA   length = 10
FEATURE                   Location/Qualifiers
source                    1..10
                          mol_type = protein
                          organism = Homo sapiens
SEQUENCE: 245
SSCAPIYCRR                                                                    10

SEQ ID NO: 246            moltype = AA   length = 10
FEATURE                   Location/Qualifiers
source                    1..10
                          mol_type = protein
                          organism = Homo sapiens
SEQUENCE: 246
SSCAPVYCRR                                                                    10

SEQ ID NO: 247            moltype = AA   length = 10
FEATURE                   Location/Qualifiers
source                    1..10
                          mol_type = protein
                          organism = Homo sapiens
```

-continued

```
SEQUENCE: 247
SSCGKGGCGS                                                                                  10

SEQ ID NO: 248          moltype = AA  length = 10
FEATURE                 Location/Qualifiers
source                  1..10
                        mol_type = protein
                        organism = Homo sapiens
SEQUENCE: 248
SSCGKRGCGS                                                                                  10

SEQ ID NO: 249          moltype = AA  length = 10
FEATURE                 Location/Qualifiers
source                  1..10
                        mol_type = protein
                        organism = Homo sapiens
SEQUENCE: 249
SSCLPVSCRP                                                                                  10

SEQ ID NO: 250          moltype = AA  length = 10
FEATURE                 Location/Qualifiers
source                  1..10
                        mol_type = protein
                        organism = Homo sapiens
SEQUENCE: 250
SSCQPAYCTS                                                                                  10

SEQ ID NO: 251          moltype = AA  length = 10
FEATURE                 Location/Qualifiers
source                  1..10
                        mol_type = protein
                        organism = Homo sapiens
SEQUENCE: 251
SSCQPSYCRQ                                                                                  10

SEQ ID NO: 252          moltype = AA  length = 10
FEATURE                 Location/Qualifiers
source                  1..10
                        mol_type = protein
                        organism = Homo sapiens
SEQUENCE: 252
SSCQPVVCEP                                                                                  10

SEQ ID NO: 253          moltype = AA  length = 10
FEATURE                 Location/Qualifiers
source                  1..10
                        mol_type = protein
                        organism = Homo sapiens
SEQUENCE: 253
SSCTAVVCRP                                                                                  10

SEQ ID NO: 254          moltype = AA  length = 10
FEATURE                 Location/Qualifiers
source                  1..10
                        mol_type = protein
                        organism = Homo sapiens
SEQUENCE: 254
SSCYQPFCRS                                                                                  10

SEQ ID NO: 255          moltype = AA  length = 10
FEATURE                 Location/Qualifiers
source                  1..10
                        mol_type = protein
                        organism = Homo sapiens
SEQUENCE: 255
SSCYRPICGS                                                                                  10

SEQ ID NO: 256          moltype = AA  length = 10
FEATURE                 Location/Qualifiers
source                  1..10
                        mol_type = protein
                        organism = Homo sapiens
SEQUENCE: 256
SSCYRPTCGS                                                                                  10

SEQ ID NO: 257          moltype = AA  length = 10
FEATURE                 Location/Qualifiers
source                  1..10
                        mol_type = protein
```

```
                        organism = Homo sapiens
SEQUENCE: 257
SVCMSGSCQA                                                              10

SEQ ID NO: 258          moltype = AA  length = 10
FEATURE                 Location/Qualifiers
source                  1..10
                        mol_type = protein
                        organism = Homo sapiens
SEQUENCE: 258
SVCSDQGCDQ                                                              10

SEQ ID NO: 259          moltype = AA  length = 10
FEATURE                 Location/Qualifiers
source                  1..10
                        mol_type = protein
                        organism = Homo sapiens
SEQUENCE: 259
SVCSDQGCGL                                                              10

SEQ ID NO: 260          moltype = AA  length = 10
FEATURE                 Location/Qualifiers
source                  1..10
                        mol_type = protein
                        organism = Homo sapiens
SEQUENCE: 260
SVCSDQGCGQ                                                              10

SEQ ID NO: 261          moltype = AA  length = 10
FEATURE                 Location/Qualifiers
source                  1..10
                        mol_type = protein
                        organism = Homo sapiens
SEQUENCE: 261
SVCSDQGCSQ                                                              10

SEQ ID NO: 262          moltype = AA  length = 10
FEATURE                 Location/Qualifiers
source                  1..10
                        mol_type = protein
                        organism = Homo sapiens
SEQUENCE: 262
SVCSDQSCGQ                                                              10

SEQ ID NO: 263          moltype = AA  length = 10
FEATURE                 Location/Qualifiers
source                  1..10
                        mol_type = protein
                        organism = Homo sapiens
SEQUENCE: 263
SVCSHQGCGQ                                                              10

SEQ ID NO: 264          moltype = AA  length = 10
FEATURE                 Location/Qualifiers
source                  1..10
                        mol_type = protein
                        organism = Homo sapiens
SEQUENCE: 264
SVCSHQGCGR                                                              10

SEQ ID NO: 265          moltype = AA  length = 10
FEATURE                 Location/Qualifiers
source                  1..10
                        mol_type = protein
                        organism = Homo sapiens
SEQUENCE: 265
SVCVPVSCRP                                                              10

SEQ ID NO: 266          moltype = AA  length = 10
FEATURE                 Location/Qualifiers
source                  1..10
                        mol_type = protein
                        organism = Homo sapiens
SEQUENCE: 266
SYCRQASCVS                                                              10

SEQ ID NO: 267          moltype = AA  length = 10
FEATURE                 Location/Qualifiers
source                  1..10
```

```
                          mol_type = protein
                          organism = Homo sapiens
SEQUENCE: 267
TACEPSACQS                                                           10

SEQ ID NO: 268           moltype = AA  length = 10
FEATURE                  Location/Qualifiers
source                   1..10
                         mol_type = protein
                         organism = Homo sapiens
SEQUENCE: 268
TICTASPCQP                                                           10

SEQ ID NO: 269           moltype = AA  length = 10
FEATURE                  Location/Qualifiers
source                   1..10
                         mol_type = protein
                         organism = Homo sapiens
SEQUENCE: 269
TSCPETSCLP                                                           10

SEQ ID NO: 270           moltype = AA  length = 10
FEATURE                  Location/Qualifiers
source                   1..10
                         mol_type = protein
                         organism = Homo sapiens
SEQUENCE: 270
TSCQMTNCEQ                                                           10

SEQ ID NO: 271           moltype = AA  length = 10
FEATURE                  Location/Qualifiers
source                   1..10
                         mol_type = protein
                         organism = Homo sapiens
SEQUENCE: 271
TSCQPVHCET                                                           10

SEQ ID NO: 272           moltype = AA  length = 10
FEATURE                  Location/Qualifiers
source                   1..10
                         mol_type = protein
                         organism = Homo sapiens
SEQUENCE: 272
TSCQPVLCKS                                                           10

SEQ ID NO: 273           moltype = AA  length = 10
FEATURE                  Location/Qualifiers
source                   1..10
                         mol_type = protein
                         organism = Homo sapiens
SEQUENCE: 273
TSCQPVLCVP                                                           10

SEQ ID NO: 274           moltype = AA  length = 10
FEATURE                  Location/Qualifiers
source                   1..10
                         mol_type = protein
                         organism = Homo sapiens
SEQUENCE: 274
TSCVGFVCQP                                                           10

SEQ ID NO: 275           moltype = AA  length = 10
FEATURE                  Location/Qualifiers
source                   1..10
                         mol_type = protein
                         organism = Homo sapiens
SEQUENCE: 275
TSCVSNPCQV                                                           10

SEQ ID NO: 276           moltype = AA  length = 10
FEATURE                  Location/Qualifiers
source                   1..10
                         mol_type = protein
                         organism = Homo sapiens
SEQUENCE: 276
TTCFQPTCVS                                                           10

SEQ ID NO: 277           moltype = AA  length = 10
FEATURE                  Location/Qualifiers
```

```
source                      1..10
                            mol_type = protein
                            organism = Homo sapiens
SEQUENCE: 277
TTCFQPTCVT                                                                      10

SEQ ID NO: 278              moltype = AA   length = 10
FEATURE                     Location/Qualifiers
source                      1..10
                            mol_type = protein
                            organism = Homo sapiens
SEQUENCE: 278
TTCFQPTCVY                                                                      10

SEQ ID NO: 279              moltype = AA   length = 10
FEATURE                     Location/Qualifiers
source                      1..10
                            mol_type = protein
                            organism = Homo sapiens
SEQUENCE: 279
TTCISNPCST                                                                      10

SEQ ID NO: 280              moltype = AA   length = 10
FEATURE                     Location/Qualifiers
source                      1..10
                            mol_type = protein
                            organism = Homo sapiens
SEQUENCE: 280
TWCQGSSCQP                                                                      10

SEQ ID NO: 281              moltype = AA   length = 10
FEATURE                     Location/Qualifiers
source                      1..10
                            mol_type = protein
                            organism = Homo sapiens
SEQUENCE: 281
VGCQSSVCVP                                                                      10

SEQ ID NO: 282              moltype = AA   length = 10
FEATURE                     Location/Qualifiers
source                      1..10
                            mol_type = protein
                            organism = Homo sapiens
SEQUENCE: 282
VPCQPSTCVF                                                                      10

SEQ ID NO: 283              moltype = AA   length = 10
FEATURE                     Location/Qualifiers
source                      1..10
                            mol_type = protein
                            organism = Homo sapiens
SEQUENCE: 283
VSCEPSPCQS                                                                      10

SEQ ID NO: 284              moltype = AA   length = 10
FEATURE                     Location/Qualifiers
source                      1..10
                            mol_type = protein
                            organism = Homo sapiens
SEQUENCE: 284
VSCGGPICLP                                                                      10

SEQ ID NO: 285              moltype = AA   length = 10
FEATURE                     Location/Qualifiers
source                      1..10
                            mol_type = protein
                            organism = Homo sapiens
SEQUENCE: 285
VSCKPVLCVA                                                                      10

SEQ ID NO: 286              moltype = AA   length = 10
FEATURE                     Location/Qualifiers
source                      1..10
                            mol_type = protein
                            organism = Homo sapiens
SEQUENCE: 286
VSCPSTSCRP                                                                      10

SEQ ID NO: 287              moltype = AA   length = 10
```

```
                          FEATURE         Location/Qualifiers
                          source          1..10
                                          mol_type = protein
                                          organism = Homo sapiens
SEQUENCE: 287
VSCQSSVCMP                                                                      10

SEQ ID NO: 288            moltype = AA   length = 10
FEATURE                   Location/Qualifiers
source                    1..10
                          mol_type = protein
                          organism = Homo sapiens
SEQUENCE: 288
VSCTRIVCVA                                                                      10

SEQ ID NO: 289            moltype = AA   length = 10
FEATURE                   Location/Qualifiers
source                    1..10
                          mol_type = protein
                          organism = Homo sapiens
SEQUENCE: 289
VTCEPSPCQS                                                                      10

SEQ ID NO: 290            moltype = AA   length = 10
FEATURE                   Location/Qualifiers
source                    1..10
                          mol_type = protein
                          organism = Homo sapiens
SEQUENCE: 290
VTCQTTVCRP                                                                      10

SEQ ID NO: 291            moltype = AA   length = 10
FEATURE                   Location/Qualifiers
source                    1..10
                          mol_type = protein
                          organism = Homo sapiens
SEQUENCE: 291
YGCGYEGCRY                                                                      10

SEQ ID NO: 292            moltype = AA   length = 10
FEATURE                   Location/Qualifiers
source                    1..10
                          mol_type = protein
                          organism = Homo sapiens
SEQUENCE: 292
AGSCQPSCSE                                                                      10

SEQ ID NO: 293            moltype = AA   length = 10
FEATURE                   Location/Qualifiers
source                    1..10
                          mol_type = protein
                          organism = Homo sapiens
SEQUENCE: 293
ALLCRPLCGV                                                                      10

SEQ ID NO: 294            moltype = AA   length = 10
FEATURE                   Location/Qualifiers
source                    1..10
                          mol_type = protein
                          organism = Homo sapiens
SEQUENCE: 294
ALVCEPVCLR                                                                      10

SEQ ID NO: 295            moltype = AA   length = 10
FEATURE                   Location/Qualifiers
source                    1..10
                          mol_type = protein
                          organism = Homo sapiens
SEQUENCE: 295
ATICEPSCSV                                                                      10

SEQ ID NO: 296            moltype = AA   length = 10
FEATURE                   Location/Qualifiers
source                    1..10
                          mol_type = protein
                          organism = Homo sapiens
SEQUENCE: 296
ATTCEPSCSV                                                                      10
```

| | | |
|---|---|---|
| SEQ ID NO: 297<br>FEATURE<br>source | moltype = AA  length = 10<br>Location/Qualifiers<br>1..10<br>mol_type = protein<br>organism = Homo sapiens | |
| SEQUENCE: 297<br>ATVCEPSCSV | | 10 |
| SEQ ID NO: 298<br>FEATURE<br>source | moltype = AA  length = 10<br>Location/Qualifiers<br>1..10<br>mol_type = protein<br>organism = Homo sapiens | |
| SEQUENCE: 298<br>EGTCLPPCYL | | 10 |
| SEQ ID NO: 299<br>FEATURE<br>source | moltype = AA  length = 10<br>Location/Qualifiers<br>1..10<br>mol_type = protein<br>organism = Homo sapiens | |
| SEQUENCE: 299<br>FSTCRPSCSG | | 10 |
| SEQ ID NO: 300<br>FEATURE<br>source | moltype = AA  length = 10<br>Location/Qualifiers<br>1..10<br>mol_type = protein<br>organism = Homo sapiens | |
| SEQUENCE: 300<br>GFVCQPMCSH | | 10 |
| SEQ ID NO: 301<br>FEATURE<br>source | moltype = AA  length = 10<br>Location/Qualifiers<br>1..10<br>mol_type = protein<br>organism = Homo sapiens | |
| SEQUENCE: 301<br>GLDCGYGCGY | | 10 |
| SEQ ID NO: 302<br>FEATURE<br>source | moltype = AA  length = 10<br>Location/Qualifiers<br>1..10<br>mol_type = protein<br>organism = Homo sapiens | |
| SEQUENCE: 302<br>GLGCGYGCGY | | 10 |
| SEQ ID NO: 303<br>FEATURE<br>source | moltype = AA  length = 10<br>Location/Qualifiers<br>1..10<br>mol_type = protein<br>organism = Homo sapiens | |
| SEQUENCE: 303<br>GLGCSYGCGH | | 10 |
| SEQ ID NO: 304<br>FEATURE<br>source | moltype = AA  length = 10<br>Location/Qualifiers<br>1..10<br>mol_type = protein<br>organism = Homo sapiens | |
| SEQUENCE: 304<br>GLGCSYGCGL | | 10 |
| SEQ ID NO: 305<br>FEATURE<br>source | moltype = AA  length = 10<br>Location/Qualifiers<br>1..10<br>mol_type = protein<br>organism = Homo sapiens | |
| SEQUENCE: 305<br>GSGCGYGCGY | | 10 |
| SEQ ID NO: 306<br>FEATURE<br>source | moltype = AA  length = 10<br>Location/Qualifiers<br>1..10<br>mol_type = protein<br>organism = Homo sapiens | |
| SEQUENCE: 306<br>GTGCGYGCGY | | 10 |

| | | |
|---|---|---|
| SEQ ID NO: 307<br>FEATURE<br>source | moltype = AA   length = 10<br>Location/Qualifiers<br>1..10<br>mol_type = protein<br>organism = Homo sapiens | |
| SEQUENCE: 307<br>GVSCHTTCYR | | 10 |
| SEQ ID NO: 308<br>FEATURE<br>source | moltype = AA   length = 10<br>Location/Qualifiers<br>1..10<br>mol_type = protein<br>organism = Homo sapiens | |
| SEQUENCE: 308<br>GYACNFPCSY | | 10 |
| SEQ ID NO: 309<br>FEATURE<br>source | moltype = AA   length = 10<br>Location/Qualifiers<br>1..10<br>mol_type = protein<br>organism = Homo sapiens | |
| SEQUENCE: 309<br>GYGCGYGCGF | | 10 |
| SEQ ID NO: 310<br>FEATURE<br>source | moltype = AA   length = 10<br>Location/Qualifiers<br>1..10<br>mol_type = protein<br>organism = Homo sapiens | |
| SEQUENCE: 310<br>HSPCQASCYV | | 10 |
| SEQ ID NO: 311<br>FEATURE<br>source | moltype = AA   length = 10<br>Location/Qualifiers<br>1..10<br>mol_type = protein<br>organism = Homo sapiens | |
| SEQUENCE: 311<br>HTSCSPACQP | | 10 |
| SEQ ID NO: 312<br>FEATURE<br>source | moltype = AA   length = 10<br>Location/Qualifiers<br>1..10<br>mol_type = protein<br>organism = Homo sapiens | |
| SEQUENCE: 312<br>HTSCSSGCQP | | 10 |
| SEQ ID NO: 313<br>FEATURE<br>source | moltype = AA   length = 10<br>Location/Qualifiers<br>1..10<br>mol_type = protein<br>organism = Homo sapiens | |
| SEQUENCE: 313<br>IRWCHPDCHV | | 10 |
| SEQ ID NO: 314<br>FEATURE<br>source | moltype = AA   length = 10<br>Location/Qualifiers<br>1..10<br>mol_type = protein<br>organism = Homo sapiens | |
| SEQUENCE: 314<br>IRWCRPDCRV | | 10 |
| SEQ ID NO: 315<br>FEATURE<br>source | moltype = AA   length = 10<br>Location/Qualifiers<br>1..10<br>mol_type = protein<br>organism = Homo sapiens | |
| SEQUENCE: 315<br>ISSCGTGCGI | | 10 |
| SEQ ID NO: 316<br>FEATURE<br>source | moltype = AA   length = 10<br>Location/Qualifiers<br>1..10<br>mol_type = protein<br>organism = Homo sapiens | |
| SEQUENCE: 316 | | |

-continued

KGGCGSGCGG                                                                                          10

SEQ ID NO: 317            moltype = AA   length = 10
FEATURE                   Location/Qualifiers
source                    1..10
                          mol_type = protein
                          organism = Homo sapiens SEQUENCE: 317
KGGCGSSCSQ                                                                                          10

SEQ ID NO: 318            moltype = AA   length = 10
FEATURE                   Location/Qualifiers
source                    1..10
                          mol_type = protein
                          organism = Homo sapiens SEQUENCE: 318
LVTCQDSCGS                                                                                          10

SEQ ID NO: 319            moltype = AA   length = 10
FEATURE                   Location/Qualifiers
source                    1..10
                          mol_type = protein
                          organism = Homo sapiens SEQUENCE: 319
LVTCQESCQP                                                                                          10

SEQ ID NO: 320            moltype = AA   length = 10
FEATURE                   Location/Qualifiers
source                    1..10
                          mol_type = protein
                          organism = Homo sapiens SEQUENCE: 320
MSICSSACTD                                                                                          10

SEQ ID NO: 321            moltype = AA   length = 10
FEATURE                   Location/Qualifiers
source                    1..10
                          mol_type = protein
                          organism = Homo sapiens SEQUENCE: 321
MSICSSACTN                                                                                          10

SEQ ID NO: 322            moltype = AA   length = 10
FEATURE                   Location/Qualifiers
source                    1..10
                          mol_type = protein
                          organism = Homo sapiens SEQUENCE: 322
MSVCSSACSD                                                                                          10

SEQ ID NO: 323            moltype = AA   length = 10
FEATURE                   Location/Qualifiers
source                    1..10
                          mol_type = protein
                          organism = Homo sapiens SEQUENCE: 323
PAICEPSCSV                                                                                          10

SEQ ID NO: 324            moltype = AA   length = 10
FEATURE                   Location/Qualifiers
source                    1..10
                          mol_type = protein
                          organism = Homo sapiens SEQUENCE: 324
PASCQKSCYR                                                                                          10

SEQ ID NO: 325            moltype = AA   length = 10
FEATURE                   Location/Qualifiers
source                    1..10
                          mol_type = protein
                          organism = Homo sapiens SEQUENCE: 325
PIYCRRTCYH                                                                                          10

SEQ ID NO: 326            moltype = AA   length = 10
FEATURE                   Location/Qualifiers
source                    1..10
                          mol_type = protein
                          organism = Homo sapiens

```
SEQUENCE: 326
PNSCQTLCVE                                                                    10

SEQ ID NO: 327          moltype = AA  length = 10
FEATURE                 Location/Qualifiers
source                  1..10
                        mol_type = protein
                        organism = Homo sapiens
SEQUENCE: 327
PQPCVPTCFL                                                                    10

SEQ ID NO: 328          moltype = AA  length = 10
FEATURE                 Location/Qualifiers
source                  1..10
                        mol_type = protein
                        organism = Homo sapiens
SEQUENCE: 328
PSACQSGCTS                                                                    10

SEQ ID NO: 329          moltype = AA  length = 10
FEATURE                 Location/Qualifiers
source                  1..10
                        mol_type = protein
                        organism = Homo sapiens
SEQUENCE: 329
PSPCEPSCSE                                                                    10

SEQ ID NO: 330          moltype = AA  length = 10
FEATURE                 Location/Qualifiers
source                  1..10
                        mol_type = protein
                        organism = Homo sapiens
SEQUENCE: 330
PSPCQASCYI                                                                    10

SEQ ID NO: 331          moltype = AA  length = 10
FEATURE                 Location/Qualifiers
source                  1..10
                        mol_type = protein
                        organism = Homo sapiens
SEQUENCE: 331
PSPCQSGCIS                                                                    10

SEQ ID NO: 332          moltype = AA  length = 10
FEATURE                 Location/Qualifiers
source                  1..10
                        mol_type = protein
                        organism = Homo sapiens
SEQUENCE: 332
PSPCQSGCTD                                                                    10

SEQ ID NO: 333          moltype = AA  length = 10
FEATURE                 Location/Qualifiers
source                  1..10
                        mol_type = protein
                        organism = Homo sapiens
SEQUENCE: 333
PSPCQSGCTS                                                                    10

SEQ ID NO: 334          moltype = AA  length = 10
FEATURE                 Location/Qualifiers
source                  1..10
                        mol_type = protein
                        organism = Homo sapiens
SEQUENCE: 334
PTACQPTCYQ                                                                    10

SEQ ID NO: 335          moltype = AA  length = 10
FEATURE                 Location/Qualifiers
source                  1..10
                        mol_type = protein
                        organism = Homo sapiens
SEQUENCE: 335
PTACQPTCYR                                                                    10

SEQ ID NO: 336          moltype = AA  length = 10
FEATURE                 Location/Qualifiers
source                  1..10
                        mol_type = protein
```

-continued

```
                        organism = Homo sapiens
SEQUENCE: 336
PTPCSTTCRT                                                              10

SEQ ID NO: 337          moltype = AA   length = 10
FEATURE                 Location/Qualifiers
source                  1..10
                        mol_type = protein
                        organism = Homo sapiens
SEQUENCE: 337
PTSCQKSCYR                                                              10

SEQ ID NO: 338          moltype = AA   length = 10
FEATURE                 Location/Qualifiers
source                  1..10
                        mol_type = protein
                        organism = Homo sapiens
SEQUENCE: 338
PTSCQPSCES                                                              10

SEQ ID NO: 339          moltype = AA   length = 10
FEATURE                 Location/Qualifiers
source                  1..10
                        mol_type = protein
                        organism = Homo sapiens
SEQUENCE: 339
PTSCQTSCTL                                                              10

SEQ ID NO: 340          moltype = AA   length = 10
FEATURE                 Location/Qualifiers
source                  1..10
                        mol_type = protein
                        organism = Homo sapiens
SEQUENCE: 340
PVICEPSCSV                                                              10

SEQ ID NO: 341          moltype = AA   length = 10
FEATURE                 Location/Qualifiers
source                  1..10
                        mol_type = protein
                        organism = Homo sapiens
SEQUENCE: 341
PVSCVPVCSG                                                              10

SEQ ID NO: 342          moltype = AA   length = 10
FEATURE                 Location/Qualifiers
source                  1..10
                        mol_type = protein
                        organism = Homo sapiens
SEQUENCE: 342
PVTCVPRCTR                                                              10

SEQ ID NO: 343          moltype = AA   length = 10
FEATURE                 Location/Qualifiers
source                  1..10
                        mol_type = protein
                        organism = Homo sapiens
SEQUENCE: 343
PVYCRRTCYH                                                              10

SEQ ID NO: 344          moltype = AA   length = 10
FEATURE                 Location/Qualifiers
source                  1..10
                        mol_type = protein
                        organism = Homo sapiens
SEQUENCE: 344
PVYCRRTCYY                                                              10

SEQ ID NO: 345          moltype = AA   length = 10
FEATURE                 Location/Qualifiers
source                  1..10
                        mol_type = protein
                        organism = Homo sapiens
SEQUENCE: 345
PVYCVPVCSG                                                              10

SEQ ID NO: 346          moltype = AA   length = 10
FEATURE                 Location/Qualifiers
source                  1..10
```

-continued

```
                            mol_type = protein
                            organism = Homo sapiens
SEQUENCE: 346
QPGCESPCEP                                                              10

SEQ ID NO: 347              moltype = AA  length = 10
FEATURE                     Location/Qualifiers
source                      1..10
                            mol_type = protein
                            organism = Homo sapiens
SEQUENCE: 347
QQSCVSSCRR                                                              10

SEQ ID NO: 348              moltype = AA  length = 10
FEATURE                     Location/Qualifiers
source                      1..10
                            mol_type = protein
                            organism = Homo sapiens
SEQUENCE: 348
QTSCGSSCGQ                                                              10

SEQ ID NO: 349              moltype = AA  length = 10
FEATURE                     Location/Qualifiers
source                      1..10
                            mol_type = protein
                            organism = Homo sapiens
SEQUENCE: 349
QTTCHPSCGM                                                              10

SEQ ID NO: 350              moltype = AA  length = 10
FEATURE                     Location/Qualifiers
source                      1..10
                            mol_type = protein
                            organism = Homo sapiens
SEQUENCE: 350
QTTCRPSCGV                                                              10

SEQ ID NO: 351              moltype = AA  length = 10
FEATURE                     Location/Qualifiers
source                      1..10
                            mol_type = protein
                            organism = Homo sapiens
SEQUENCE: 351
RGGCGSGCGG                                                              10

SEQ ID NO: 352              moltype = AA  length = 10
FEATURE                     Location/Qualifiers
source                      1..10
                            mol_type = protein
                            organism = Homo sapiens
SEQUENCE: 352
RLACYSLCSG                                                              10

SEQ ID NO: 353              moltype = AA  length = 10
FEATURE                     Location/Qualifiers
source                      1..10
                            mol_type = protein
                            organism = Homo sapiens
SEQUENCE: 353
RPACYRPCYS                                                              10

SEQ ID NO: 354              moltype = AA  length = 10
FEATURE                     Location/Qualifiers
source                      1..10
                            mol_type = protein
                            organism = Homo sapiens
SEQUENCE: 354
RPFCFRRCYS                                                              10

SEQ ID NO: 355              moltype = AA  length = 10
FEATURE                     Location/Qualifiers
source                      1..10
                            mol_type = protein
                            organism = Homo sapiens
SEQUENCE: 355
RPICRPICSG                                                              10

SEQ ID NO: 356              moltype = AA  length = 10
FEATURE                     Location/Qualifiers
```

```
source                    1..10
                          mol_type = protein
                          organism = Homo sapiens
SEQUENCE: 356
RPLCYRRCYS                                                                10

SEQ ID NO: 357            moltype = AA   length = 10
FEATURE                   Location/Qualifiers
source                    1..10
                          mol_type = protein
                          organism = Homo sapiens
SEQUENCE: 357
RSPCQASCYV                                                                10

SEQ ID NO: 358            moltype = AA   length = 10
FEATURE                   Location/Qualifiers
source                    1..10
                          mol_type = protein
                          organism = Homo sapiens
SEQUENCE: 358
RVSCHTTCYR                                                                10

SEQ ID NO: 359            moltype = AA   length = 10
FEATURE                   Location/Qualifiers
source                    1..10
                          mol_type = protein
                          organism = Homo sapiens
SEQUENCE: 359
SAICRPTCPR                                                                10

SEQ ID NO: 360            moltype = AA   length = 10
FEATURE                   Location/Qualifiers
source                    1..10
                          mol_type = protein
                          organism = Homo sapiens
SEQUENCE: 360
SDSCKRDCKK                                                                10

SEQ ID NO: 361            moltype = AA   length = 10
FEATURE                   Location/Qualifiers
source                    1..10
                          mol_type = protein
                          organism = Homo sapiens
SEQUENCE: 361
SEGCGSGCGG                                                                10

SEQ ID NO: 362            moltype = AA   length = 10
FEATURE                   Location/Qualifiers
source                    1..10
                          mol_type = protein
                          organism = Homo sapiens
SEQUENCE: 362
SFLCRPACSR                                                                10

SEQ ID NO: 363            moltype = AA   length = 10
FEATURE                   Location/Qualifiers
source                    1..10
                          mol_type = protein
                          organism = Homo sapiens
SEQUENCE: 363
SGGCGSGCGG                                                                10

SEQ ID NO: 364            moltype = AA   length = 10
FEATURE                   Location/Qualifiers
source                    1..10
                          mol_type = protein
                          organism = Homo sapiens
SEQUENCE: 364
SGGCGSSCGG                                                                10

SEQ ID NO: 365            moltype = AA   length = 10
FEATURE                   Location/Qualifiers
source                    1..10
                          mol_type = protein
                          organism = Homo sapiens
SEQUENCE: 365
SGSCQAACGQ                                                                10

SEQ ID NO: 366            moltype = AA   length = 10
```

```
FEATURE              Location/Qualifiers
source               1..10
                     mol_type = protein
                     organism = Homo sapiens
SEQUENCE: 366
SLLCHPVCKS                                                                      10

SEQ ID NO: 367       moltype = AA   length = 10
FEATURE              Location/Qualifiers
source               1..10
                     mol_type = protein
                     organism = Homo sapiens
SEQUENCE: 367
SLLCHPVCRS                                                                      10

SEQ ID NO: 368       moltype = AA   length = 10
FEATURE              Location/Qualifiers
source               1..10
                     mol_type = protein
                     organism = Homo sapiens
SEQUENCE: 368
SLLCRPACSP                                                                      10

SEQ ID NO: 369       moltype = AA   length = 10
FEATURE              Location/Qualifiers
source               1..10
                     mol_type = protein
                     organism = Homo sapiens
SEQUENCE: 369
SLLCRPACSR                                                                      10

SEQ ID NO: 370       moltype = AA   length = 10
FEATURE              Location/Qualifiers
source               1..10
                     mol_type = protein
                     organism = Homo sapiens
SEQUENCE: 370
SLLCRPICRP                                                                      10

SEQ ID NO: 371       moltype = AA   length = 10
FEATURE              Location/Qualifiers
source               1..10
                     mol_type = protein
                     organism = Homo sapiens
SEQUENCE: 371
SLLCRPMCSR                                                                      10

SEQ ID NO: 372       moltype = AA   length = 10
FEATURE              Location/Qualifiers
source               1..10
                     mol_type = protein
                     organism = Homo sapiens
SEQUENCE: 372
SLLCRPTCSR                                                                      10

SEQ ID NO: 373       moltype = AA   length = 10
FEATURE              Location/Qualifiers
source               1..10
                     mol_type = protein
                     organism = Homo sapiens
SEQUENCE: 373
SLLCRPVCQP                                                                      10

SEQ ID NO: 374       moltype = AA   length = 10
FEATURE              Location/Qualifiers
source               1..10
                     mol_type = protein
                     organism = Homo sapiens
SEQUENCE: 374
SLLCRPVCRP                                                                      10

SEQ ID NO: 375       moltype = AA   length = 10
FEATURE              Location/Qualifiers
source               1..10
                     mol_type = protein
                     organism = Homo sapiens
SEQUENCE: 375
SLLCRPVCRS                                                                      10
```

```
SEQ ID NO: 376         moltype = AA   length = 10
FEATURE                Location/Qualifiers
source                 1..10
                       mol_type = protein
                       organism = Homo sapiens
SEQUENCE: 376
SLLCRPVCSR                                                                10

SEQ ID NO: 377         moltype = AA   length = 10
FEATURE                Location/Qualifiers
source                 1..10
                       mol_type = protein
                       organism = Homo sapiens
SEQUENCE: 377
SNPCQVTCSR                                                                10

SEQ ID NO: 378         moltype = AA   length = 10
FEATURE                Location/Qualifiers
source                 1..10
                       mol_type = protein
                       organism = Homo sapiens
SEQUENCE: 378
SRGCGSGCGG                                                                10

SEQ ID NO: 379         moltype = AA   length = 10
FEATURE                Location/Qualifiers
source                 1..10
                       mol_type = protein
                       organism = Homo sapiens
SEQUENCE: 379
SRSCQSPCYR                                                                10

SEQ ID NO: 380         moltype = AA   length = 10
FEATURE                Location/Qualifiers
source                 1..10
                       mol_type = protein
                       organism = Homo sapiens
SEQUENCE: 380
SRSCQSSCYR                                                                10

SEQ ID NO: 381         moltype = AA   length = 10
FEATURE                Location/Qualifiers
source                 1..10
                       mol_type = protein
                       organism = Homo sapiens
SEQUENCE: 381
SSGCYGCGY                                                                 10

SEQ ID NO: 382         moltype = AA   length = 10
FEATURE                Location/Qualifiers
source                 1..10
                       mol_type = protein
                       organism = Homo sapiens
SEQUENCE: 382
SSGCPMACPG                                                                10

SEQ ID NO: 383         moltype = AA   length = 10
FEATURE                Location/Qualifiers
source                 1..10
                       mol_type = protein
                       organism = Homo sapiens
SEQUENCE: 383
SSICQPICSE                                                                10

SEQ ID NO: 384         moltype = AA   length = 10
FEATURE                Location/Qualifiers
source                 1..10
                       mol_type = protein
                       organism = Homo sapiens
SEQUENCE: 384
SSPCHTSCYY                                                                10

SEQ ID NO: 385         moltype = AA   length = 10
FEATURE                Location/Qualifiers
source                 1..10
                       mol_type = protein
                       organism = Homo sapiens
SEQUENCE: 385
SSPCQPTCYV                                                                10
```

```
SEQ ID NO: 386           moltype = AA   length = 10
FEATURE                  Location/Qualifiers
source                   1..10
                         mol_type = protein
                         organism = Homo sapiens SEQUENCE: 386
SSPCQQSCYV                                                                10

SEQ ID NO: 387           moltype = AA   length = 10
FEATURE                  Location/Qualifiers
source                   1..10
                         mol_type = protein
                         organism = Homo sapiens SEQUENCE: 387
SSPCQTSCYR                                                                10

SEQ ID NO: 388           moltype = AA   length = 10
FEATURE                  Location/Qualifiers
source                   1..10
                         mol_type = protein
                         organism = Homo sapiens SEQUENCE: 388
SSSCQQSCRV                                                                10

SEQ ID NO: 389           moltype = AA   length = 10
FEATURE                  Location/Qualifiers
source                   1..10
                         mol_type = protein
                         organism = Homo sapiens SEQUENCE: 389
STVCQPACGV                                                                10

SEQ ID NO: 390           moltype = AA   length = 10
FEATURE                  Location/Qualifiers
source                   1..10
                         mol_type = protein
                         organism = Homo sapiens SEQUENCE: 390
TDNCQETCGE                                                                10

SEQ ID NO: 391           moltype = AA   length = 10
FEATURE                  Location/Qualifiers
source                   1..10
                         mol_type = protein
                         organism = Homo sapiens SEQUENCE: 391
TQPCYEPCLP                                                                10

SEQ ID NO: 392           moltype = AA   length = 10
FEATURE                  Location/Qualifiers
source                   1..10
                         mol_type = protein
                         organism = Homo sapiens SEQUENCE: 392
TSSCGTGCGI                                                                10

SEQ ID NO: 393           moltype = AA   length = 10
FEATURE                  Location/Qualifiers
source                   1..10
                         mol_type = protein
                         organism = Homo sapiens SEQUENCE: 393
TSSCQPSCGR                                                                10

SEQ ID NO: 394           moltype = AA   length = 10
FEATURE                  Location/Qualifiers
source                   1..10
                         mol_type = protein
                         organism = Homo sapiens SEQUENCE: 394
TSSCTTPCYQ                                                                10

SEQ ID NO: 395           moltype = AA   length = 10
FEATURE                  Location/Qualifiers
source                   1..10
                         mol_type = protein
                         organism = Homo sapiens

SEQUENCE: 395
```

```
TSVCLPGCLN                                                                                  10

SEQ ID NO: 396          moltype = AA   length = 10
FEATURE                 Location/Qualifiers
source                  1..10
                        mol_type = protein
                        organism = Homo sapiens SEQUENCE: 396
TTVCLPGCLN                                                                                  10

SEQ ID NO: 397          moltype = AA   length = 10
FEATURE                 Location/Qualifiers
source                  1..10
                        mol_type = protein
                        organism = Homo sapiens SEQUENCE: 397
VANCQAPCST                                                                                  10

SEQ ID NO: 398          moltype = AA   length = 10
FEATURE                 Location/Qualifiers
source                  1..10
                        mol_type = protein
                        organism = Homo sapiens SEQUENCE: 398
VDDCPESCWP                                                                                  10

SEQ ID NO: 399          moltype = AA   length = 10
FEATURE                 Location/Qualifiers
source                  1..10
                        mol_type = protein
                        organism = Homo sapiens SEQUENCE: 399
VKRCPSVCPE                                                                                  10

SEQ ID NO: 400          moltype = AA   length = 10
FEATURE                 Location/Qualifiers
source                  1..10
                        mol_type = protein
                        organism = Homo sapiens SEQUENCE: 400
VSSCQPSCSE                                                                                  10

SEQ ID NO: 401          moltype = AA   length = 10
FEATURE                 Location/Qualifiers
source                  1..10
                        mol_type = protein
                        organism = Homo sapiens SEQUENCE: 401
YEGCRYGCGH                                                                                  10

SEQ ID NO: 402          moltype = AA   length = 10
FEATURE                 Location/Qualifiers
source                  1..10
                        mol_type = protein
                        organism = Homo sapiens SEQUENCE: 402
YGRCRHGCHS                                                                                  10

SEQ ID NO: 403          moltype = AA   length = 10
FEATURE                 Location/Qualifiers
source                  1..10
                        mol_type = protein
                        organism = Homo sapiens SEQUENCE: 403
YGYCRPSCYG                                                                                  10

SEQ ID NO: 404          moltype = AA   length = 10
FEATURE                 Location/Qualifiers
source                  1..10
                        mol_type = protein
                        organism = Homo sapiens SEQUENCE: 404
YRDCQKTCWE                                                                                  10

SEQ ID NO: 405          moltype = AA   length = 10
FEATURE                 Location/Qualifiers
source                  1..10
                        mol_type = protein
                        organism = Homo sapiens
```

```
SEQUENCE: 405
YRGCQEICWE                                                                              10

SEQ ID NO: 406         moltype = AA  length = 10
FEATURE                Location/Qualifiers
source                 1..10
                       mol_type = protein
                       organism = Homo sapiens
SEQUENCE: 406
YRGCQETCWR                                                                              10

SEQ ID NO: 407         moltype = AA  length = 10
FEATURE                Location/Qualifiers
source                 1..10
                       mol_type = protein
                       organism = Homo sapiens
SEQUENCE: 407
YRGCQQTCWE                                                                              10

SEQ ID NO: 408         moltype = AA  length = 10
FEATURE                Location/Qualifiers
source                 1..10
                       mol_type = protein
                       organism = Homo sapiens
SEQUENCE: 408
YRSCRPSCYG                                                                              10

SEQ ID NO: 409         moltype = AA  length = 10
FEATURE                Location/Qualifiers
source                 1..10
                       mol_type = protein
                       organism = Homo sapiens
SEQUENCE: 409
GGVCGPSPPC                                                                              10

SEQ ID NO: 410         moltype = AA  length = 10
FEATURE                Location/Qualifiers
source                 1..10
                       mol_type = protein
                       organism = Homo sapiens
SEQUENCE: 410
GVCGPSPPCI                                                                              10

SEQ ID NO: 411         moltype = AA  length = 10
FEATURE                Location/Qualifiers
source                 1..10
                       mol_type = protein
                       organism = Homo sapiens
SEQUENCE: 411
VCGPSPPCIT                                                                              10

SEQ ID NO: 412         moltype = AA  length = 10
FEATURE                Location/Qualifiers
source                 1..10
                       mol_type = protein
                       organism = Homo sapiens
SEQUENCE: 412
CGPSPPCITT                                                                              10

SEQ ID NO: 413         moltype = AA  length = 10
FEATURE                Location/Qualifiers
source                 1..10
                       mol_type = protein
                       organism = Homo sapiens
SEQUENCE: 413
CAPIYCRRTC                                                                              10

SEQ ID NO: 414         moltype = AA  length = 10
FEATURE                Location/Qualifiers
source                 1..10
                       mol_type = protein
                       organism = Homo sapiens
SEQUENCE: 414
CAPSPCQASC                                                                              10

SEQ ID NO: 415         moltype = AA  length = 10
FEATURE                Location/Qualifiers
source                 1..10
                       mol_type = protein
```

-continued

```
                        organism = Homo sapiens
SEQUENCE: 415
CAPSPCQPAC                                                                          10

SEQ ID NO: 416          moltype = AA   length = 10
FEATURE                 Location/Qualifiers
source                  1..10
                        mol_type = protein
                        organism = Homo sapiens
SEQUENCE: 416
CAPVYCRRTC                                                                          10

SEQ ID NO: 417          moltype = AA   length = 10
FEATURE                 Location/Qualifiers
source                  1..10
                        mol_type = protein
                        organism = Homo sapiens
SEQUENCE: 417
CASSPCQQAC                                                                          10

SEQ ID NO: 418          moltype = AA   length = 10
FEATURE                 Location/Qualifiers
source                  1..10
                        mol_type = protein
                        organism = Homo sapiens
SEQUENCE: 418
CASSSCQPAC                                                                          10

SEQ ID NO: 419          moltype = AA   length = 10
FEATURE                 Location/Qualifiers
source                  1..10
                        mol_type = protein
                        organism = Homo sapiens
SEQUENCE: 419
CASSSCQQSC                                                                          10

SEQ ID NO: 420          moltype = AA   length = 10
FEATURE                 Location/Qualifiers
source                  1..10
                        mol_type = protein
                        organism = Homo sapiens
SEQUENCE: 420
CCGNFSSHSC                                                                          10

SEQ ID NO: 421          moltype = AA   length = 10
FEATURE                 Location/Qualifiers
source                  1..10
                        mol_type = protein
                        organism = Homo sapiens
SEQUENCE: 421
CCGYGGLGCG                                                                          10

SEQ ID NO: 422          moltype = AA   length = 10
FEATURE                 Location/Qualifiers
source                  1..10
                        mol_type = protein
                        organism = Homo sapiens
SEQUENCE: 422
CCNYYGNSCG                                                                          10

SEQ ID NO: 423          moltype = AA   length = 10
FEATURE                 Location/Qualifiers
source                  1..10
                        mol_type = protein
                        organism = Homo sapiens
SEQUENCE: 423
CCNYYRNSCG                                                                          10

SEQ ID NO: 424          moltype = AA   length = 10
FEATURE                 Location/Qualifiers
source                  1..10
                        mol_type = protein
                        organism = Homo sapiens
SEQUENCE: 424
CCSRNFSSCS                                                                          10

SEQ ID NO: 425          moltype = AA   length = 10
FEATURE                 Location/Qualifiers
source                  1..10
```

```
                              mol_type = protein
                              organism = Homo sapiens
SEQUENCE: 425
CDAGSCQPSC                                                                   10

SEQ ID NO: 426                moltype = AA  length = 10
FEATURE                       Location/Qualifiers
source                        1..10
                              mol_type = protein
                              organism = Homo sapiens
SEQUENCE: 426
CDPCSLQEGC                                                                   10

SEQ ID NO: 427                moltype = AA  length = 10
FEATURE                       Location/Qualifiers
source                        1..10
                              mol_type = protein
                              organism = Homo sapiens
SEQUENCE: 427
CDPSPCEPSC                                                                   10

SEQ ID NO: 428                moltype = AA  length = 10
FEATURE                       Location/Qualifiers
source                        1..10
                              mol_type = protein
                              organism = Homo sapiens
SEQUENCE: 428
CDPVICEPSC                                                                   10

SEQ ID NO: 429                moltype = AA  length = 10
FEATURE                       Location/Qualifiers
source                        1..10
                              mol_type = protein
                              organism = Homo sapiens
SEQUENCE: 429
CDQGLCQETC                                                                   10

SEQ ID NO: 430                moltype = AA  length = 10
FEATURE                       Location/Qualifiers
source                        1..10
                              mol_type = protein
                              organism = Homo sapiens
SEQUENCE: 430
CEATTCEPSC                                                                   10

SEQ ID NO: 431                moltype = AA  length = 10
FEATURE                       Location/Qualifiers
source                        1..10
                              mol_type = protein
                              organism = Homo sapiens
SEQUENCE: 431
CELPCGTPSC                                                                   10

SEQ ID NO: 432                moltype = AA  length = 10
FEATURE                       Location/Qualifiers
source                        1..10
                              mol_type = protein
                              organism = Homo sapiens
SEQUENCE: 432
CEPAICEPSC                                                                   10

SEQ ID NO: 433                moltype = AA  length = 10
FEATURE                       Location/Qualifiers
source                        1..10
                              mol_type = protein
                              organism = Homo sapiens
SEQUENCE: 433
CEPPCGTAPC                                                                   10

SEQ ID NO: 434                moltype = AA  length = 10
FEATURE                       Location/Qualifiers
source                        1..10
                              mol_type = protein
                              organism = Homo sapiens
SEQUENCE: 434
CEPPCSAPSC                                                                   10

SEQ ID NO: 435                moltype = AA  length = 10
FEATURE                       Location/Qualifiers
```

```
source                  1..10
                        mol_type = protein
                        organism = Homo sapiens
SEQUENCE: 435
CEPRSCASSC                                                              10

SEQ ID NO: 436          moltype = AA   length = 10
FEATURE                 Location/Qualifiers
source                  1..10
                        mol_type = protein
                        organism = Homo sapiens
SEQUENCE: 436
CEPSACQSGC                                                              10

SEQ ID NO: 437          moltype = AA   length = 10
FEATURE                 Location/Qualifiers
source                  1..10
                        mol_type = protein
                        organism = Homo sapiens
SEQUENCE: 437
CEPSCSVSNC                                                              10

SEQ ID NO: 438          moltype = AA   length = 10
FEATURE                 Location/Qualifiers
source                  1..10
                        mol_type = protein
                        organism = Homo sapiens
SEQUENCE: 438
CEPSCSVSSC                                                              10

SEQ ID NO: 439          moltype = AA   length = 10
FEATURE                 Location/Qualifiers
source                  1..10
                        mol_type = protein
                        organism = Homo sapiens
SEQUENCE: 439
CEPSPCQSGC                                                              10

SEQ ID NO: 440          moltype = AA   length = 10
FEATURE                 Location/Qualifiers
source                  1..10
                        mol_type = protein
                        organism = Homo sapiens
SEQUENCE: 440
CEPTACQPTC                                                              10

SEQ ID NO: 441          moltype = AA   length = 10
FEATURE                 Location/Qualifiers
source                  1..10
                        mol_type = protein
                        organism = Homo sapiens
SEQUENCE: 441
CEPTSCQTSC                                                              10

SEQ ID NO: 442          moltype = AA   length = 10
FEATURE                 Location/Qualifiers
source                  1..10
                        mol_type = protein
                        organism = Homo sapiens
SEQUENCE: 442
CEPVCLRPVC                                                              10

SEQ ID NO: 443          moltype = AA   length = 10
FEATURE                 Location/Qualifiers
source                  1..10
                        mol_type = protein
                        organism = Homo sapiens
SEQUENCE: 443
CETSSCQPRC                                                              10

SEQ ID NO: 444          moltype = AA   length = 10
FEATURE                 Location/Qualifiers
source                  1..10
                        mol_type = protein
                        organism = Homo sapiens
SEQUENCE: 444
CETTCFQPTC                                                              10

SEQ ID NO: 445          moltype = AA   length = 10
```

```
                        FEATURE         Location/Qualifiers
                        source          1..10
                                        mol_type = protein
                                        organism = Homo sapiens
SEQUENCE: 445
CFQPTCVSSC                                                                          10

SEQ ID NO: 446          moltype = AA   length = 10
FEATURE                 Location/Qualifiers
source                  1..10
                        mol_type = protein
                        organism = Homo sapiens
SEQUENCE: 446
CFQPTCVTSC                                                                          10

SEQ ID NO: 447          moltype = AA   length = 10
FEATURE                 Location/Qualifiers
source                  1..10
                        mol_type = protein
                        organism = Homo sapiens
SEQUENCE: 447
CFQPTCVYSC                                                                          10

SEQ ID NO: 448          moltype = AA   length = 10
FEATURE                 Location/Qualifiers
source                  1..10
                        mol_type = protein
                        organism = Homo sapiens
SEQUENCE: 448
CGCGFRRLGC                                                                          10

SEQ ID NO: 449          moltype = AA   length = 10
FEATURE                 Location/Qualifiers
source                  1..10
                        mol_type = protein
                        organism = Homo sapiens
SEQUENCE: 449
CGCGYRGLDC                                                                          10

SEQ ID NO: 450          moltype = AA   length = 10
FEATURE                 Location/Qualifiers
source                  1..10
                        mol_type = protein
                        organism = Homo sapiens
SEQUENCE: 450
CGCNGYYGCY                                                                          10

SEQ ID NO: 451          moltype = AA   length = 10
FEATURE                 Location/Qualifiers
source                  1..10
                        mol_type = protein
                        organism = Homo sapiens
SEQUENCE: 451
CGFGSCYGCG                                                                          10

SEQ ID NO: 452          moltype = AA   length = 10
FEATURE                 Location/Qualifiers
source                  1..10
                        mol_type = protein
                        organism = Homo sapiens
SEQUENCE: 452
CGGSGCGGSC                                                                          10

SEQ ID NO: 453          moltype = AA   length = 10
FEATURE                 Location/Qualifiers
source                  1..10
                        mol_type = protein
                        organism = Homo sapiens
SEQUENCE: 453
CGGSGSSCCV                                                                          10

SEQ ID NO: 454          moltype = AA   length = 10
FEATURE                 Location/Qualifiers
source                  1..10
                        mol_type = protein
                        organism = Homo sapiens
SEQUENCE: 454
CGGVSCHTTC                                                                          10
```

-continued

| | | |
|---|---|---|
| SEQ ID NO: 455<br>FEATURE<br>source | moltype = AA   length = 10<br>Location/Qualifiers<br>1..10<br>mol_type = protein<br>organism = Homo sapiens | |
| SEQUENCE: 455<br>CGKGGCGSCG | | 10 |
| SEQ ID NO: 456<br>FEATURE<br>source | moltype = AA   length = 10<br>Location/Qualifiers<br>1..10<br>mol_type = protein<br>organism = Homo sapiens | |
| SEQUENCE: 456<br>CGKRGCGSCG | | 10 |
| SEQ ID NO: 457<br>FEATURE<br>source | moltype = AA   length = 10<br>Location/Qualifiers<br>1..10<br>mol_type = protein<br>organism = Homo sapiens | |
| SEQUENCE: 457<br>CGQDLCQETC | | 10 |
| SEQ ID NO: 458<br>FEATURE<br>source | moltype = AA   length = 10<br>Location/Qualifiers<br>1..10<br>mol_type = protein<br>organism = Homo sapiens | |
| SEQUENCE: 458<br>CGQTSCGSSC | | 10 |
| SEQ ID NO: 459<br>FEATURE<br>source | moltype = AA   length = 10<br>Location/Qualifiers<br>1..10<br>mol_type = protein<br>organism = Homo sapiens | |
| SEQUENCE: 459<br>CGQVLCQETC | | 10 |
| SEQ ID NO: 460<br>FEATURE<br>source | moltype = AA   length = 10<br>Location/Qualifiers<br>1..10<br>mol_type = protein<br>organism = Homo sapiens | |
| SEQUENCE: 460<br>CGRDLCQETC | | 10 |
| SEQ ID NO: 461<br>FEATURE<br>source | moltype = AA   length = 10<br>Location/Qualifiers<br>1..10<br>mol_type = protein<br>organism = Homo sapiens | |
| SEQUENCE: 461<br>CGRVSCHTTC | | 10 |
| SEQ ID NO: 462<br>FEATURE<br>source | moltype = AA   length = 10<br>Location/Qualifiers<br>1..10<br>mol_type = protein<br>organism = Homo sapiens | |
| SEQUENCE: 462<br>CGSCGFGSCY | | 10 |
| SEQ ID NO: 463<br>FEATURE<br>source | moltype = AA   length = 10<br>Location/Qualifiers<br>1..10<br>mol_type = protein<br>organism = Homo sapiens | |
| SEQUENCE: 463<br>CGSCGGSKGC | | 10 |
| SEQ ID NO: 464<br>FEATURE<br>source | moltype = AA   length = 10<br>Location/Qualifiers<br>1..10<br>mol_type = protein<br>organism = Homo sapiens | |
| SEQUENCE: 464<br>CGSGCGVPVC | | 10 |

| | | |
|---|---|---|
| SEQ ID NO: 465<br>FEATURE<br>source | moltype = AA   length = 10<br>Location/Qualifiers<br>1..10<br>mol_type = protein<br>organism = Homo sapiens | |
| SEQUENCE: 465<br>CGSLLCRPTC | | 10 |
| SEQ ID NO: 466<br>FEATURE<br>source | moltype = AA   length = 10<br>Location/Qualifiers<br>1..10<br>mol_type = protein<br>organism = Homo sapiens | |
| SEQUENCE: 466<br>CGSRCYVPVC | | 10 |
| SEQ ID NO: 467<br>FEATURE<br>source | moltype = AA   length = 10<br>Location/Qualifiers<br>1..10<br>mol_type = protein<br>organism = Homo sapiens | |
| SEQUENCE: 467<br>CGSSSCGPQC | | 10 |
| SEQ ID NO: 468<br>FEATURE<br>source | moltype = AA   length = 10<br>Location/Qualifiers<br>1..10<br>mol_type = protein<br>organism = Homo sapiens | |
| SEQUENCE: 468<br>CGSVCSDQGC | | 10 |
| SEQ ID NO: 469<br>FEATURE<br>source | moltype = AA   length = 10<br>Location/Qualifiers<br>1..10<br>mol_type = protein<br>organism = Homo sapiens | |
| SEQUENCE: 469<br>CGSVCSDQSC | | 10 |
| SEQ ID NO: 470<br>FEATURE<br>source | moltype = AA   length = 10<br>Location/Qualifiers<br>1..10<br>mol_type = protein<br>organism = Homo sapiens | |
| SEQUENCE: 470<br>CGSVCSHQGC | | 10 |
| SEQ ID NO: 471<br>FEATURE<br>source | moltype = AA   length = 10<br>Location/Qualifiers<br>1..10<br>mol_type = protein<br>organism = Homo sapiens | |
| SEQUENCE: 471<br>CGSYGCSQCS | | 10 |
| SEQ ID NO: 472<br>FEATURE<br>source | moltype = AA   length = 10<br>Location/Qualifiers<br>1..10<br>mol_type = protein<br>organism = Homo sapiens | |
| SEQUENCE: 472<br>CGVCLPSTCP | | 10 |
| SEQ ID NO: 473<br>FEATURE<br>source | moltype = AA   length = 10<br>Location/Qualifiers<br>1..10<br>mol_type = protein<br>organism = Homo sapiens | |
| SEQUENCE: 473<br>CGYEGCRYGC | | 10 |
| SEQ ID NO: 474<br>FEATURE<br>source | moltype = AA   length = 10<br>Location/Qualifiers<br>1..10<br>mol_type = protein<br>organism = Homo sapiens | |
| SEQUENCE: 474 | | |

```
CGYGCGYGCG                                                                              10

SEQ ID NO: 475          moltype = AA  length = 10
FEATURE                 Location/Qualifiers
source                  1..10
                        mol_type = protein
                        organism = Homo sapiens SEQUENCE: 475
CGYGGCGYGC                                                                              10

SEQ ID NO: 476          moltype = AA  length = 10
FEATURE                 Location/Qualifiers
source                  1..10
                        mol_type = protein
                        organism = Homo sapiens SEQUENCE: 476
CGYGSFCGCG                                                                              10

SEQ ID NO: 477          moltype = AA  length = 10
FEATURE                 Location/Qualifiers
source                  1..10
                        mol_type = protein
                        organism = Homo sapiens SEQUENCE: 477
CGYGSGCGCG                                                                              10

SEQ ID NO: 478          moltype = AA  length = 10
FEATURE                 Location/Qualifiers
source                  1..10
                        mol_type = protein
                        organism = Homo sapiens SEQUENCE: 478
CHPSCGMSSC                                                                              10

SEQ ID NO: 479          moltype = AA  length = 10
FEATURE                 Location/Qualifiers
source                  1..10
                        mol_type = protein
                        organism = Homo sapiens SEQUENCE: 479
CHPSCSISSC                                                                              10

SEQ ID NO: 480          moltype = AA  length = 10
FEATURE                 Location/Qualifiers
source                  1..10
                        mol_type = protein
                        organism = Homo sapiens SEQUENCE: 480
CHPTCYQTIC                                                                              10

SEQ ID NO: 481          moltype = AA  length = 10
FEATURE                 Location/Qualifiers
source                  1..10
                        mol_type = protein
                        organism = Homo sapiens SEQUENCE: 481
CHTSCSPACQ                                                                              10

SEQ ID NO: 482          moltype = AA  length = 10
FEATURE                 Location/Qualifiers
source                  1..10
                        mol_type = protein
                        organism = Homo sapiens SEQUENCE: 482
CHTSCSSGCQ                                                                              10

SEQ ID NO: 483          moltype = AA  length = 10
FEATURE                 Location/Qualifiers
source                  1..10
                        mol_type = protein
                        organism = Homo sapiens SEQUENCE: 483
CHTTCYRPAC                                                                              10

SEQ ID NO: 484          moltype = AA  length = 10
FEATURE                 Location/Qualifiers
source                  1..10
                        mol_type = protein
                        organism = Homo sapiens
```

```
SEQUENCE: 484
CHTTCYRPTC                                                                      10

SEQ ID NO: 485         moltype = AA  length = 10
FEATURE                Location/Qualifiers
source                 1..10
                       mol_type = protein
                       organism = Homo sapiens
SEQUENCE: 485
CIHSPCQASC                                                                      10

SEQ ID NO: 486         moltype = AA  length = 10
FEATURE                Location/Qualifiers
source                 1..10
                       mol_type = protein
                       organism = Homo sapiens
SEQUENCE: 486
CIHSTHCGCN                                                                      10

SEQ ID NO: 487         moltype = AA  length = 10
FEATURE                Location/Qualifiers
source                 1..10
                       mol_type = protein
                       organism = Homo sapiens
SEQUENCE: 487
CIRSPCQASC                                                                      10

SEQ ID NO: 488         moltype = AA  length = 10
FEATURE                Location/Qualifiers
source                 1..10
                       mol_type = protein
                       organism = Homo sapiens
SEQUENCE: 488
CISSCYRPQC                                                                      10

SEQ ID NO: 489         moltype = AA  length = 10
FEATURE                Location/Qualifiers
source                 1..10
                       mol_type = protein
                       organism = Homo sapiens
SEQUENCE: 489
CISSPCQQSC                                                                      10

SEQ ID NO: 490         moltype = AA  length = 10
FEATURE                Location/Qualifiers
source                 1..10
                       mol_type = protein
                       organism = Homo sapiens
SEQUENCE: 490
CKPCSSQSSC                                                                      10

SEQ ID NO: 491         moltype = AA  length = 10
FEATURE                Location/Qualifiers
source                 1..10
                       mol_type = protein
                       organism = Homo sapiens
SEQUENCE: 491
CKPSCSQSSC                                                                      10

SEQ ID NO: 492         moltype = AA  length = 10
FEATURE                Location/Qualifiers
source                 1..10
                       mol_type = protein
                       organism = Homo sapiens
SEQUENCE: 492
CKPVCFKPIC                                                                      10

SEQ ID NO: 493         moltype = AA  length = 10
FEATURE                Location/Qualifiers
source                 1..10
                       mol_type = protein
                       organism = Homo sapiens
SEQUENCE: 493
CKPVCYVPTC                                                                      10

SEQ ID NO: 494         moltype = AA  length = 10
FEATURE                Location/Qualifiers
source                 1..10
                       mol_type = protein
```

```
                                        organism = Homo sapiens
SEQUENCE: 494
CKPVSCVPVC                                                                              10

SEQ ID NO: 495          moltype = AA   length = 10
FEATURE                 Location/Qualifiers
source                  1..10
                        mol_type = protein
                        organism = Homo sapiens
SEQUENCE: 495
CKPVYCVPVC                                                                              10

SEQ ID NO: 496          moltype = AA   length = 10
FEATURE                 Location/Qualifiers
source                  1..10
                        mol_type = protein
                        organism = Homo sapiens
SEQUENCE: 496
CKTVYCKPIC                                                                              10

SEQ ID NO: 497          moltype = AA   length = 10
FEATURE                 Location/Qualifiers
source                  1..10
                        mol_type = protein
                        organism = Homo sapiens
SEQUENCE: 497
CLNQSCGSNC                                                                              10

SEQ ID NO: 498          moltype = AA   length = 10
FEATURE                 Location/Qualifiers
source                  1..10
                        mol_type = protein
                        organism = Homo sapiens
SEQUENCE: 498
CLNQSCGSSC                                                                              10

SEQ ID NO: 499          moltype = AA   length = 10
FEATURE                 Location/Qualifiers
source                  1..10
                        mol_type = protein
                        organism = Homo sapiens
SEQUENCE: 499
CLPGCLNQSC                                                                              10

SEQ ID NO: 500          moltype = AA   length = 10
FEATURE                 Location/Qualifiers
source                  1..10
                        mol_type = protein
                        organism = Homo sapiens
SEQUENCE: 500
CLPGSCDSCS                                                                              10

SEQ ID NO: 501          moltype = AA   length = 10
FEATURE                 Location/Qualifiers
source                  1..10
                        mol_type = protein
                        organism = Homo sapiens
SEQUENCE: 501
CLPPCYLVSC                                                                              10

SEQ ID NO: 502          moltype = AA   length = 10
FEATURE                 Location/Qualifiers
source                  1..10
                        mol_type = protein
                        organism = Homo sapiens
SEQUENCE: 502
CLPTSCQPSC                                                                              10

SEQ ID NO: 503          moltype = AA   length = 10
FEATURE                 Location/Qualifiers
source                  1..10
                        mol_type = protein
                        organism = Homo sapiens
SEQUENCE: 503
CLSFLCRPAC                                                                              10

SEQ ID NO: 504          moltype = AA   length = 10
FEATURE                 Location/Qualifiers
source                  1..10
```

```
                            mol_type = protein
                            organism = Homo sapiens
SEQUENCE: 504
CLVSSCQPSC                                                              10

SEQ ID NO: 505              moltype = AA  length = 10
FEATURE                     Location/Qualifiers
source                      1..10
                            mol_type = protein
                            organism = Homo sapiens
SEQUENCE: 505
CMPSPCQPAC                                                              10

SEQ ID NO: 506              moltype = AA  length = 10
FEATURE                     Location/Qualifiers
source                      1..10
                            mol_type = protein
                            organism = Homo sapiens
SEQUENCE: 506
CMSGSCQAAC                                                              10

SEQ ID NO: 507              moltype = AA  length = 10
FEATURE                     Location/Qualifiers
source                      1..10
                            mol_type = protein
                            organism = Homo sapiens
SEQUENCE: 507
CNESSYCLPC                                                              10

SEQ ID NO: 508              moltype = AA  length = 10
FEATURE                     Location/Qualifiers
source                      1..10
                            mol_type = protein
                            organism = Homo sapiens
SEQUENCE: 508
CPASCVSLLC                                                              10

SEQ ID NO: 509              moltype = AA  length = 10
FEATURE                     Location/Qualifiers
source                      1..10
                            mol_type = protein
                            organism = Homo sapiens
SEQUENCE: 509
CPMACPGSPC                                                              10

SEQ ID NO: 510              moltype = AA  length = 10
FEATURE                     Location/Qualifiers
source                      1..10
                            mol_type = protein
                            organism = Homo sapiens
SEQUENCE: 510
CPSSCTAVVC                                                              10

SEQ ID NO: 511              moltype = AA  length = 10
FEATURE                     Location/Qualifiers
source                      1..10
                            mol_type = protein
                            organism = Homo sapiens
SEQUENCE: 511
CPVTCEPSPC                                                              10

SEQ ID NO: 512              moltype = AA  length = 10
FEATURE                     Location/Qualifiers
source                      1..10
                            mol_type = protein
                            organism = Homo sapiens
SEQUENCE: 512
CQAACEPSAC                                                              10

SEQ ID NO: 513              moltype = AA  length = 10
FEATURE                     Location/Qualifiers
source                      1..10
                            mol_type = protein
                            organism = Homo sapiens
SEQUENCE: 513
CQAACEPSPC                                                              10

SEQ ID NO: 514              moltype = AA  length = 10
FEATURE                     Location/Qualifiers
```

```
                             -continued source                  1..10
                        mol_type = protein
                        organism = Homo sapiens
SEQUENCE: 514
CQAACGQSVC                                                              10

SEQ ID NO: 515          moltype = AA   length = 10
FEATURE                 Location/Qualifiers
source                  1..10
                        mol_type = protein
                        organism = Homo sapiens
SEQUENCE: 515
CQAPCSTKNC                                                              10

SEQ ID NO: 516          moltype = AA   length = 10
FEATURE                 Location/Qualifiers
source                  1..10
                        mol_type = protein
                        organism = Homo sapiens
SEQUENCE: 516
CQAVCEPSPC                                                              10

SEQ ID NO: 517          moltype = AA   length = 10
FEATURE                 Location/Qualifiers
source                  1..10
                        mol_type = protein
                        organism = Homo sapiens
SEQUENCE: 517
CQDSCGSSSC                                                              10

SEQ ID NO: 518          moltype = AA   length = 10
FEATURE                 Location/Qualifiers
source                  1..10
                        mol_type = protein
                        organism = Homo sapiens
SEQUENCE: 518
CQHSSCQPTC                                                              10

SEQ ID NO: 519          moltype = AA   length = 10
FEATURE                 Location/Qualifiers
source                  1..10
                        mol_type = protein
                        organism = Homo sapiens
SEQUENCE: 519
CQISSCGTGC                                                              10

SEQ ID NO: 520          moltype = AA   length = 10
FEATURE                 Location/Qualifiers
source                  1..10
                        mol_type = protein
                        organism = Homo sapiens
SEQUENCE: 520
CQKSSCQPAC                                                              10

SEQ ID NO: 521          moltype = AA   length = 10
FEATURE                 Location/Qualifiers
source                  1..10
                        mol_type = protein
                        organism = Homo sapiens
SEQUENCE: 521
CQPMCSHAAC                                                              10

SEQ ID NO: 522          moltype = AA   length = 10
FEATURE                 Location/Qualifiers
source                  1..10
                        mol_type = protein
                        organism = Homo sapiens
SEQUENCE: 522
CQPPCTTALC                                                              10

SEQ ID NO: 523          moltype = AA   length = 10
FEATURE                 Location/Qualifiers
source                  1..10
                        mol_type = protein
                        organism = Homo sapiens
SEQUENCE: 523
CQPSCESSFC                                                              10

SEQ ID NO: 524          moltype = AA   length = 10
```

-continued

```
FEATURE            Location/Qualifiers
source             1..10
                   mol_type = protein
                   organism = Homo sapiens
SEQUENCE: 524
CQPSCSESTC                                                                      10

SEQ ID NO: 525     moltype = AA  length = 10
FEATURE            Location/Qualifiers
source             1..10
                   mol_type = protein
                   organism = Homo sapiens
SEQUENCE: 525
CQPSCTSVLC                                                                      10

SEQ ID NO: 526     moltype = AA  length = 10
FEATURE            Location/Qualifiers
source             1..10
                   mol_type = protein
                   organism = Homo sapiens
SEQUENCE: 526
CQPTCGGSSC                                                                      10

SEQ ID NO: 527     moltype = AA  length = 10
FEATURE            Location/Qualifiers
source             1..10
                   mol_type = protein
                   organism = Homo sapiens
SEQUENCE: 527
CQPTCSRPSC                                                                      10

SEQ ID NO: 528     moltype = AA  length = 10
FEATURE            Location/Qualifiers
source             1..10
                   mol_type = protein
                   organism = Homo sapiens
SEQUENCE: 528
CQPVCPTPTC                                                                      10

SEQ ID NO: 529     moltype = AA  length = 10
FEATURE            Location/Qualifiers
source             1..10
                   mol_type = protein
                   organism = Homo sapiens
SEQUENCE: 529
CQPVLCKSSC                                                                      10

SEQ ID NO: 530     moltype = AA  length = 10
FEATURE            Location/Qualifiers
source             1..10
                   mol_type = protein
                   organism = Homo sapiens
SEQUENCE: 530
CQPVVCEPSC                                                                      10

SEQ ID NO: 531     moltype = AA  length = 10
FEATURE            Location/Qualifiers
source             1..10
                   mol_type = protein
                   organism = Homo sapiens
SEQUENCE: 531
CQQPSCQPAC                                                                      10

SEQ ID NO: 532     moltype = AA  length = 10
FEATURE            Location/Qualifiers
source             1..10
                   mol_type = protein
                   organism = Homo sapiens
SEQUENCE: 532
CQQSCRVPVC                                                                      10

SEQ ID NO: 533     moltype = AA  length = 10
FEATURE            Location/Qualifiers
source             1..10
                   mol_type = protein
                   organism = Homo sapiens
SEQUENCE: 533
CQQSCYVPVC                                                                      10
```

| | | |
|---|---|---|
| SEQ ID NO: 534<br>FEATURE<br>source | moltype = AA   length = 10<br>Location/Qualifiers<br>1..10<br>mol_type = protein<br>organism = Homo sapiens | |
| SEQUENCE: 534<br>CQQSGCQPAC | | 10 |
| SEQ ID NO: 535<br>FEATURE<br>source | moltype = AA   length = 10<br>Location/Qualifiers<br>1..10<br>mol_type = protein<br>organism = Homo sapiens | |
| SEQUENCE: 535<br>CQQSSCHPAC | | 10 |
| SEQ ID NO: 536<br>FEATURE<br>source | moltype = AA   length = 10<br>Location/Qualifiers<br>1..10<br>mol_type = protein<br>organism = Homo sapiens | |
| SEQUENCE: 536<br>CQQSSCKPAC | | 10 |
| SEQ ID NO: 537<br>FEATURE<br>source | moltype = AA   length = 10<br>Location/Qualifiers<br>1..10<br>mol_type = protein<br>organism = Homo sapiens | |
| SEQUENCE: 537<br>CQQSSCQLAC | | 10 |
| SEQ ID NO: 538<br>FEATURE<br>source | moltype = AA   length = 10<br>Location/Qualifiers<br>1..10<br>mol_type = protein<br>organism = Homo sapiens | |
| SEQUENCE: 538<br>CQQSSCQPAC | | 10 |
| SEQ ID NO: 539<br>FEATURE<br>source | moltype = AA   length = 10<br>Location/Qualifiers<br>1..10<br>mol_type = protein<br>organism = Homo sapiens | |
| SEQUENCE: 539<br>CQQSSCQPTC | | 10 |
| SEQ ID NO: 540<br>FEATURE<br>source | moltype = AA   length = 10<br>Location/Qualifiers<br>1..10<br>mol_type = protein<br>organism = Homo sapiens | |
| SEQUENCE: 540<br>CQQSSCQSAC | | 10 |
| SEQ ID NO: 541<br>FEATURE<br>source | moltype = AA   length = 10<br>Location/Qualifiers<br>1..10<br>mol_type = protein<br>organism = Homo sapiens | |
| SEQUENCE: 541<br>CQQSSCVSCV | | 10 |
| SEQ ID NO: 542<br>FEATURE<br>source | moltype = AA   length = 10<br>Location/Qualifiers<br>1..10<br>mol_type = protein<br>organism = Homo sapiens | |
| SEQUENCE: 542<br>CQQSYCVPVC | | 10 |
| SEQ ID NO: 543<br>FEATURE<br>source | moltype = AA   length = 10<br>Location/Qualifiers<br>1..10<br>mol_type = protein<br>organism = Homo sapiens | |
| SEQUENCE: 543<br>CQSGCISSCT | | 10 |

```
SEQ ID NO: 544         moltype = AA  length = 10
FEATURE                Location/Qualifiers
source                 1..10
                       mol_type = protein
                       organism = Homo sapiens SEQUENCE: 544
CQSGCTDSCT                                                                10

SEQ ID NO: 545         moltype = AA  length = 10
FEATURE                Location/Qualifiers
source                 1..10
                       mol_type = protein
                       organism = Homo sapiens SEQUENCE: 545
CQSGCTSSCT                                                                10

SEQ ID NO: 546         moltype = AA  length = 10
FEATURE                Location/Qualifiers
source                 1..10
                       mol_type = protein
                       organism = Homo sapiens SEQUENCE: 546
CQSSCYRPTC                                                                10

SEQ ID NO: 547         moltype = AA  length = 10
FEATURE                Location/Qualifiers
source                 1..10
                       mol_type = protein
                       organism = Homo sapiens SEQUENCE: 547
CQSVCYQPTC                                                                10

SEQ ID NO: 548         moltype = AA  length = 10
FEATURE                Location/Qualifiers
source                 1..10
                       mol_type = protein
                       organism = Homo sapiens SEQUENCE: 548
CQSVYCQPTC                                                                10

SEQ ID NO: 549         moltype = AA  length = 10
FEATURE                Location/Qualifiers
source                 1..10
                       mol_type = protein
                       organism = Homo sapiens SEQUENCE: 549
CQTACEPSAC                                                                10

SEQ ID NO: 550         moltype = AA  length = 10
FEATURE                Location/Qualifiers
source                 1..10
                       mol_type = protein
                       organism = Homo sapiens SEQUENCE: 550
CQTSSCGTGC                                                                10

SEQ ID NO: 551         moltype = AA  length = 10
FEATURE                Location/Qualifiers
source                 1..10
                       mol_type = protein
                       organism = Homo sapiens SEQUENCE: 551
CQTTCHPSCG                                                                10

SEQ ID NO: 552         moltype = AA  length = 10
FEATURE                Location/Qualifiers
source                 1..10
                       mol_type = protein
                       organism = Homo sapiens SEQUENCE: 552
CQTTCRPSCG                                                                10

SEQ ID NO: 553         moltype = AA  length = 10
FEATURE                Location/Qualifiers
source                 1..10
                       mol_type = protein
                       organism = Homo sapiens

SEQUENCE: 553
```

```
CQTTCYRTTC                                                                          10

SEQ ID NO: 554        moltype = AA   length = 10
FEATURE               Location/Qualifiers
source                1..10
                      mol_type = protein
                      organism = Homo sapiens
SEQUENCE: 554
CQTTRCRTTC                                                                          10

SEQ ID NO: 555        moltype = AA   length = 10
FEATURE               Location/Qualifiers
source                1..10
                      mol_type = protein
                      organism = Homo sapiens
SEQUENCE: 555
CQVTCEPSPC                                                                          10

SEQ ID NO: 556        moltype = AA   length = 10
FEATURE               Location/Qualifiers
source                1..10
                      mol_type = protein
                      organism = Homo sapiens
SEQUENCE: 556
CRNTSCQPTC                                                                          10

SEQ ID NO: 557        moltype = AA   length = 10
FEATURE               Location/Qualifiers
source                1..10
                      mol_type = protein
                      organism = Homo sapiens
SEQUENCE: 557
CRPACSPLAC                                                                          10

SEQ ID NO: 558        moltype = AA   length = 10
FEATURE               Location/Qualifiers
source                1..10
                      mol_type = protein
                      organism = Homo sapiens
SEQUENCE: 558
CRPACSRLAC                                                                          10

SEQ ID NO: 559        moltype = AA   length = 10
FEATURE               Location/Qualifiers
source                1..10
                      mol_type = protein
                      organism = Homo sapiens
SEQUENCE: 559
CRPACSRPAC                                                                          10

SEQ ID NO: 560        moltype = AA   length = 10
FEATURE               Location/Qualifiers
source                1..10
                      mol_type = protein
                      organism = Homo sapiens
SEQUENCE: 560
CRPMCSRPAC                                                                          10

SEQ ID NO: 561        moltype = AA   length = 10
FEATURE               Location/Qualifiers
source                1..10
                      mol_type = protein
                      organism = Homo sapiens
SEQUENCE: 561
CRPSCGQTTC                                                                          10

SEQ ID NO: 562        moltype = AA   length = 10
FEATURE               Location/Qualifiers
source                1..10
                      mol_type = protein
                      organism = Homo sapiens
SEQUENCE: 562
CRPSCGVSSC                                                                          10

SEQ ID NO: 563        moltype = AA   length = 10
FEATURE               Location/Qualifiers
source                1..10
                      mol_type = protein
                      organism = Homo sapiens
```

```
SEQUENCE: 563
CRPSCSISSC                                                                  10

SEQ ID NO: 564         moltype = AA  length = 10
FEATURE                Location/Qualifiers
source                 1..10
                       mol_type = protein
                       organism = Homo sapiens
SEQUENCE: 564
CRPSCSQTTC                                                                  10

SEQ ID NO: 565         moltype = AA  length = 10
FEATURE                Location/Qualifiers
source                 1..10
                       mol_type = protein
                       organism = Homo sapiens
SEQUENCE: 565
CRPSYCGQSC                                                                  10

SEQ ID NO: 566         moltype = AA  length = 10
FEATURE                Location/Qualifiers
source                 1..10
                       mol_type = protein
                       organism = Homo sapiens
SEQUENCE: 566
CRPSYCISSC                                                                  10

SEQ ID NO: 567         moltype = AA  length = 10
FEATURE                Location/Qualifiers
source                 1..10
                       mol_type = protein
                       organism = Homo sapiens
SEQUENCE: 567
CRPSYCQTTC                                                                  10

SEQ ID NO: 568         moltype = AA  length = 10
FEATURE                Location/Qualifiers
source                 1..10
                       mol_type = protein
                       organism = Homo sapiens
SEQUENCE: 568
CRPTCSRLAC                                                                  10

SEQ ID NO: 569         moltype = AA  length = 10
FEATURE                Location/Qualifiers
source                 1..10
                       mol_type = protein
                       organism = Homo sapiens
SEQUENCE: 569
CRPTCSSGSC                                                                  10

SEQ ID NO: 570         moltype = AA  length = 10
FEATURE                Location/Qualifiers
source                 1..10
                       mol_type = protein
                       organism = Homo sapiens
SEQUENCE: 570
CRPTSCQNTC                                                                  10

SEQ ID NO: 571         moltype = AA  length = 10
FEATURE                Location/Qualifiers
source                 1..10
                       mol_type = protein
                       organism = Homo sapiens
SEQUENCE: 571
CRPVCRSTYC                                                                  10

SEQ ID NO: 572         moltype = AA  length = 10
FEATURE                Location/Qualifiers
source                 1..10
                       mol_type = protein
                       organism = Homo sapiens
SEQUENCE: 572
CRPVCSRPAC                                                                  10

SEQ ID NO: 573         moltype = AA  length = 10
FEATURE                Location/Qualifiers
source                 1..10
                       mol_type = protein
```

```
                        organism = Homo sapiens
SEQUENCE: 573
CRPVTCVPRC                                                                      10

SEQ ID NO: 574          moltype = AA  length = 10
FEATURE                 Location/Qualifiers
source                  1..10
                        mol_type = protein
                        organism = Homo sapiens
SEQUENCE: 574
CRQSSCQPAC                                                                      10

SEQ ID NO: 575          moltype = AA  length = 10
FEATURE                 Location/Qualifiers
source                  1..10
                        mol_type = protein
                        organism = Homo sapiens
SEQUENCE: 575
CRTTCFHPIC                                                                      10

SEQ ID NO: 576          moltype = AA  length = 10
FEATURE                 Location/Qualifiers
source                  1..10
                        mol_type = protein
                        organism = Homo sapiens
SEQUENCE: 576
CRTTCFQPTC                                                                      10

SEQ ID NO: 577          moltype = AA  length = 10
FEATURE                 Location/Qualifiers
source                  1..10
                        mol_type = protein
                        organism = Homo sapiens
SEQUENCE: 577
CRTTCYRPSC                                                                      10

SEQ ID NO: 578          moltype = AA  length = 10
FEATURE                 Location/Qualifiers
source                  1..10
                        mol_type = protein
                        organism = Homo sapiens
SEQUENCE: 578
CRTTYCRPSC                                                                      10

SEQ ID NO: 579          moltype = AA  length = 10
FEATURE                 Location/Qualifiers
source                  1..10
                        mol_type = protein
                        organism = Homo sapiens
SEQUENCE: 579
CRVTCEPSPC                                                                      10

SEQ ID NO: 580          moltype = AA  length = 10
FEATURE                 Location/Qualifiers
source                  1..10
                        mol_type = protein
                        organism = Homo sapiens
SEQUENCE: 580
CRYGCGHRGC                                                                      10

SEQ ID NO: 581          moltype = AA  length = 10
FEATURE                 Location/Qualifiers
source                  1..10
                        mol_type = protein
                        organism = Homo sapiens
SEQUENCE: 581
CSAPCVALLC                                                                      10

SEQ ID NO: 582          moltype = AA  length = 10
FEATURE                 Location/Qualifiers
source                  1..10
                        mol_type = protein
                        organism = Homo sapiens
SEQUENCE: 582
CSDDSGSCCQ                                                                      10

SEQ ID NO: 583          moltype = AA  length = 10
FEATURE                 Location/Qualifiers
source                  1..10
```

```
                              mol_type = protein
                              organism = Homo sapiens
SEQUENCE: 583
CSEDSSSCCQ                                                                          10

SEQ ID NO: 584                moltype = AA  length = 10
FEATURE                       Location/Qualifiers
source                        1..10
                              mol_type = protein
                              organism = Homo sapiens
SEQUENCE: 584
CSEDSYSCCQ                                                                          10

SEQ ID NO: 585                moltype = AA  length = 10
FEATURE                       Location/Qualifiers
source                        1..10
                              mol_type = protein
                              organism = Homo sapiens
SEQUENCE: 585
CSEGCGSGCG                                                                          10

SEQ ID NO: 586                moltype = AA  length = 10
FEATURE                       Location/Qualifiers
source                        1..10
                              mol_type = protein
                              organism = Homo sapiens
SEQUENCE: 586
CSESSPSCCQ                                                                          10

SEQ ID NO: 587                moltype = AA  length = 10
FEATURE                       Location/Qualifiers
source                        1..10
                              mol_type = protein
                              organism = Homo sapiens
SEQUENCE: 587
CSESSSSCCQ                                                                          10

SEQ ID NO: 588                moltype = AA  length = 10
FEATURE                       Location/Qualifiers
source                        1..10
                              mol_type = protein
                              organism = Homo sapiens
SEQUENCE: 588
CSFDKSCRCG                                                                          10

SEQ ID NO: 589                moltype = AA  length = 10
FEATURE                       Location/Qualifiers
source                        1..10
                              mol_type = protein
                              organism = Homo sapiens
SEQUENCE: 589
CSGASSLCCQ                                                                          10

SEQ ID NO: 590                moltype = AA  length = 10
FEATURE                       Location/Qualifiers
source                        1..10
                              mol_type = protein
                              organism = Homo sapiens
SEQUENCE: 590
CSGASSPCCQ                                                                          10

SEQ ID NO: 591                moltype = AA  length = 10
FEATURE                       Location/Qualifiers
source                        1..10
                              mol_type = protein
                              organism = Homo sapiens
SEQUENCE: 591
CSGASSSCCQ                                                                          10

SEQ ID NO: 592                moltype = AA  length = 10
FEATURE                       Location/Qualifiers
source                        1..10
                              mol_type = protein
                              organism = Homo sapiens
SEQUENCE: 592
CSGASTSCCQ                                                                          10

SEQ ID NO: 593                moltype = AA  length = 10
FEATURE                       Location/Qualifiers
```

```
source                    1..10
                          mol_type = protein
                          organism = Homo sapiens
SEQUENCE: 593
CSGGCGSGCG                                                                              10

SEQ ID NO: 594            moltype = AA   length = 10
FEATURE                   Location/Qualifiers
source                    1..10
                          mol_type = protein
                          organism = Homo sapiens
SEQUENCE: 594
CSGGCGSSCG                                                                              10

SEQ ID NO: 595            moltype = AA   length = 10
FEATURE                   Location/Qualifiers
source                    1..10
                          mol_type = protein
                          organism = Homo sapiens
SEQUENCE: 595
CSGISSSCCQ                                                                              10

SEQ ID NO: 596            moltype = AA   length = 10
FEATURE                   Location/Qualifiers
source                    1..10
                          mol_type = protein
                          organism = Homo sapiens
SEQUENCE: 596
CSKDSSSCCQ                                                                              10

SEQ ID NO: 597            moltype = AA   length = 10
FEATURE                   Location/Qualifiers
source                    1..10
                          mol_type = protein
                          organism = Homo sapiens
SEQUENCE: 597
CSKGACGSCG                                                                              10

SEQ ID NO: 598            moltype = AA   length = 10
FEATURE                   Location/Qualifiers
source                    1..10
                          mol_type = protein
                          organism = Homo sapiens
SEQUENCE: 598
CSLSCGSRSC                                                                              10

SEQ ID NO: 599            moltype = AA   length = 10
FEATURE                   Location/Qualifiers
source                    1..10
                          mol_type = protein
                          organism = Homo sapiens
SEQUENCE: 599
CSQDLCQETC                                                                              10

SEQ ID NO: 600            moltype = AA   length = 10
FEATURE                   Location/Qualifiers
source                    1..10
                          mol_type = protein
                          organism = Homo sapiens
SEQUENCE: 600
CSRGCGSGCG                                                                              10

SEQ ID NO: 601            moltype = AA   length = 10
FEATURE                   Location/Qualifiers
source                    1..10
                          mol_type = protein
                          organism = Homo sapiens
SEQUENCE: 601
CSRLSSACCG                                                                              10

SEQ ID NO: 602            moltype = AA   length = 10
FEATURE                   Location/Qualifiers
source                    1..10
                          mol_type = protein
                          organism = Homo sapiens
SEQUENCE: 602
CSSCGKGGCG                                                                              10

SEQ ID NO: 603            moltype = AA   length = 10
```

```
                        -continued

FEATURE                 Location/Qualifiers
source                  1..10
                        mol_type = protein
                        organism = Homo sapiens
SEQUENCE: 603
CSSCGKRGCG                                                              10

SEQ ID NO: 604          moltype = AA  length = 10
FEATURE                 Location/Qualifiers
source                  1..10
                        mol_type = protein
                        organism = Homo sapiens
SEQUENCE: 604
CSSDKSCRCG                                                              10

SEQ ID NO: 605          moltype = AA  length = 10
FEATURE                 Location/Qualifiers
source                  1..10
                        mol_type = protein
                        organism = Homo sapiens
SEQUENCE: 605
CSSGNFSSCC                                                              10

SEQ ID NO: 606          moltype = AA  length = 10
FEATURE                 Location/Qualifiers
source                  1..10
                        mol_type = protein
                        organism = Homo sapiens
SEQUENCE: 606
CSSSGCGSFC                                                              10

SEQ ID NO: 607          moltype = AA  length = 10
FEATURE                 Location/Qualifiers
source                  1..10
                        mol_type = protein
                        organism = Homo sapiens
SEQUENCE: 607
CSSSGCGSSC                                                              10

SEQ ID NO: 608          moltype = AA  length = 10
FEATURE                 Location/Qualifiers
source                  1..10
                        mol_type = protein
                        organism = Homo sapiens
SEQUENCE: 608
CSTPCYQPIC                                                              10

SEQ ID NO: 609          moltype = AA  length = 10
FEATURE                 Location/Qualifiers
source                  1..10
                        mol_type = protein
                        organism = Homo sapiens
SEQUENCE: 609
CSTTCRTSSC                                                              10

SEQ ID NO: 610          moltype = AA  length = 10
FEATURE                 Location/Qualifiers
source                  1..10
                        mol_type = protein
                        organism = Homo sapiens
SEQUENCE: 610
CSWVPACSCT                                                              10

SEQ ID NO: 611          moltype = AA  length = 10
FEATURE                 Location/Qualifiers
source                  1..10
                        mol_type = protein
                        organism = Homo sapiens
SEQUENCE: 611
CTFSPCQQAC                                                              10

SEQ ID NO: 612          moltype = AA  length = 10
FEATURE                 Location/Qualifiers
source                  1..10
                        mol_type = protein
                        organism = Homo sapiens
SEQUENCE: 612
CTMSVCSSAC                                                              10
```

```
SEQ ID NO: 613          moltype = AA  length = 10
FEATURE                 Location/Qualifiers
source                  1..10
                        mol_type = protein
                        organism = Homo sapiens
SEQUENCE: 613
CTRPICEPCR                                                                10

SEQ ID NO: 614          moltype = AA  length = 10
FEATURE                 Location/Qualifiers
source                  1..10
                        mol_type = protein
                        organism = Homo sapiens
SEQUENCE: 614
CTSSPCQHAC                                                                10

SEQ ID NO: 615          moltype = AA  length = 10
FEATURE                 Location/Qualifiers
source                  1..10
                        mol_type = protein
                        organism = Homo sapiens
SEQUENCE: 615
CTSSPCQQAC                                                                10

SEQ ID NO: 616          moltype = AA  length = 10
FEATURE                 Location/Qualifiers
source                  1..10
                        mol_type = protein
                        organism = Homo sapiens
SEQUENCE: 616
CTSSPCQQSC                                                                10

SEQ ID NO: 617          moltype = AA  length = 10
FEATURE                 Location/Qualifiers
source                  1..10
                        mol_type = protein
                        organism = Homo sapiens
SEQUENCE: 617
CTSSSCQQAC                                                                10

SEQ ID NO: 618          moltype = AA  length = 10
FEATURE                 Location/Qualifiers
source                  1..10
                        mol_type = protein
                        organism = Homo sapiens
SEQUENCE: 618
CVALLCRPLC                                                                10

SEQ ID NO: 619          moltype = AA  length = 10
FEATURE                 Location/Qualifiers
source                  1..10
                        mol_type = protein
                        organism = Homo sapiens
SEQUENCE: 619
CVALVCEPVC                                                                10

SEQ ID NO: 620          moltype = AA  length = 10
FEATURE                 Location/Qualifiers
source                  1..10
                        mol_type = protein
                        organism = Homo sapiens
SEQUENCE: 620
CVFSSCNTTC                                                                10

SEQ ID NO: 621          moltype = AA  length = 10
FEATURE                 Location/Qualifiers
source                  1..10
                        mol_type = protein
                        organism = Homo sapiens
SEQUENCE: 621
CVGFVCQPMC                                                                10

SEQ ID NO: 622          moltype = AA  length = 10
FEATURE                 Location/Qualifiers
source                  1..10
                        mol_type = protein
                        organism = Homo sapiens
SEQUENCE: 622
CVPRCTRPIC                                                                10
```

| | | |
|---|---|---|
| SEQ ID NO: 623<br>FEATURE<br>source | moltype = AA length = 10<br>Location/Qualifiers<br>1..10<br>mol_type = protein<br>organism = Homo sapiens | |
| SEQUENCE: 623<br>CVPSPCQVAC | | 10 |
| SEQ ID NO: 624<br>FEATURE<br>source | moltype = AA length = 10<br>Location/Qualifiers<br>1..10<br>mol_type = protein<br>organism = Homo sapiens | |
| SEQUENCE: 624<br>CVPSRCQASC | | 10 |
| SEQ ID NO: 625<br>FEATURE<br>source | moltype = AA length = 10<br>Location/Qualifiers<br>1..10<br>mol_type = protein<br>organism = Homo sapiens | |
| SEQUENCE: 625<br>CVPSSCQASC | | 10 |
| SEQ ID NO: 626<br>FEATURE<br>source | moltype = AA length = 10<br>Location/Qualifiers<br>1..10<br>mol_type = protein<br>organism = Homo sapiens | |
| SEQUENCE: 626<br>CVPVCNKPVC | | 10 |
| SEQ ID NO: 627<br>FEATURE<br>source | moltype = AA length = 10<br>Location/Qualifiers<br>1..10<br>mol_type = protein<br>organism = Homo sapiens | |
| SEQUENCE: 627<br>CVPVCSKSVC | | 10 |
| SEQ ID NO: 628<br>FEATURE<br>source | moltype = AA length = 10<br>Location/Qualifiers<br>1..10<br>mol_type = protein<br>organism = Homo sapiens | |
| SEQUENCE: 628<br>CVPVRCKPVC | | 10 |
| SEQ ID NO: 629<br>FEATURE<br>source | moltype = AA length = 10<br>Location/Qualifiers<br>1..10<br>mol_type = protein<br>organism = Homo sapiens | |
| SEQUENCE: 629<br>CVSLLCRPAC | | 10 |
| SEQ ID NO: 630<br>FEATURE<br>source | moltype = AA length = 10<br>Location/Qualifiers<br>1..10<br>mol_type = protein<br>organism = Homo sapiens | |
| SEQUENCE: 630<br>CVSLLCRPMC | | 10 |
| SEQ ID NO: 631<br>FEATURE<br>source | moltype = AA length = 10<br>Location/Qualifiers<br>1..10<br>mol_type = protein<br>organism = Homo sapiens | |
| SEQUENCE: 631<br>CVSLLCRPTC | | 10 |
| SEQ ID NO: 632<br>FEATURE<br>source | moltype = AA length = 10<br>Location/Qualifiers<br>1..10<br>mol_type = protein<br>organism = Homo sapiens | |
| SEQUENCE: 632 | | |

CVSLLCRPVC                                                                          10

SEQ ID NO: 633           moltype = AA  length = 10
FEATURE                  Location/Qualifiers
source                   1..10
                         mol_type = protein
                         organism = Homo sapiens SEQUENCE: 633
CVSNPCQVTC                                                                          10

SEQ ID NO: 634           moltype = AA  length = 10
FEATURE                  Location/Qualifiers
source                   1..10
                         mol_type = protein
                         organism = Homo sapiens SEQUENCE: 634
CVSRCYRPHC                                                                          10

SEQ ID NO: 635           moltype = AA  length = 10
FEATURE                  Location/Qualifiers
source                   1..10
                         mol_type = protein
                         organism = Homo sapiens SEQUENCE: 635
CVSSCFRPQC                                                                          10

SEQ ID NO: 636           moltype = AA  length = 10
FEATURE                  Location/Qualifiers
source                   1..10
                         mol_type = protein
                         organism = Homo sapiens SEQUENCE: 636
CVSSICQPIC                                                                          10

SEQ ID NO: 637           moltype = AA  length = 10
FEATURE                  Location/Qualifiers
source                   1..10
                         mol_type = protein
                         organism = Homo sapiens SEQUENCE: 637
CVSSPCQPTC                                                                          10

SEQ ID NO: 638           moltype = AA  length = 10
FEATURE                  Location/Qualifiers
source                   1..10
                         mol_type = protein
                         organism = Homo sapiens SEQUENCE: 638
CVVSCTPPSC                                                                          10

SEQ ID NO: 639           moltype = AA  length = 10
FEATURE                  Location/Qualifiers
source                   1..10
                         mol_type = protein
                         organism = Homo sapiens SEQUENCE: 639
CVVSCTPPTC                                                                          10

SEQ ID NO: 640           moltype = AA  length = 10
FEATURE                  Location/Qualifiers
source                   1..10
                         mol_type = protein
                         organism = Homo sapiens SEQUENCE: 640
CYCPKNSIFC                                                                          10

SEQ ID NO: 641           moltype = AA  length = 10
FEATURE                  Location/Qualifiers
source                   1..10
                         mol_type = protein
                         organism = Homo sapiens SEQUENCE: 641
CYEPCLPRGC                                                                          10

SEQ ID NO: 642           moltype = AA  length = 10
FEATURE                  Location/Qualifiers
source                   1..10
                         mol_type = protein
                         organism = Homo sapiens

```
SEQUENCE: 642
CYRRCYSSCY                                                                              10

SEQ ID NO: 643         moltype = AA  length = 10
FEATURE                Location/Qualifiers
source                 1..10
                       mol_type = protein
                       organism = Homo sapiens
SEQUENCE: 643
GCCGYGGLGC                                                                              10

SEQ ID NO: 644         moltype = AA  length = 10
FEATURE                Location/Qualifiers
source                 1..10
                       mol_type = protein
                       organism = Homo sapiens
SEQUENCE: 644
GCGGCGSGCA                                                                              10

SEQ ID NO: 645         moltype = AA  length = 10
FEATURE                Location/Qualifiers
source                 1..10
                       mol_type = protein
                       organism = Homo sapiens
SEQUENCE: 645
GCGGCGSGCG                                                                              10

SEQ ID NO: 646         moltype = AA  length = 10
FEATURE                Location/Qualifiers
source                 1..10
                       mol_type = protein
                       organism = Homo sapiens
SEQUENCE: 646
GCGGCGSSCG                                                                              10

SEQ ID NO: 647         moltype = AA  length = 10
FEATURE                Location/Qualifiers
source                 1..10
                       mol_type = protein
                       organism = Homo sapiens
SEQUENCE: 647
GCGGCSSSCG                                                                              10

SEQ ID NO: 648         moltype = AA  length = 10
FEATURE                Location/Qualifiers
source                 1..10
                       mol_type = protein
                       organism = Homo sapiens
SEQUENCE: 648
GCGGSGSSCC                                                                              10

SEQ ID NO: 649         moltype = AA  length = 10
FEATURE                Location/Qualifiers
source                 1..10
                       mol_type = protein
                       organism = Homo sapiens
SEQUENCE: 649
GCGSGCAGCG                                                                              10

SEQ ID NO: 650         moltype = AA  length = 10
FEATURE                Location/Qualifiers
source                 1..10
                       mol_type = protein
                       organism = Homo sapiens
SEQUENCE: 650
GCGSGCGGCG                                                                              10

SEQ ID NO: 651         moltype = AA  length = 10
FEATURE                Location/Qualifiers
source                 1..10
                       mol_type = protein
                       organism = Homo sapiens
SEQUENCE: 651
GCGSGCGGCS                                                                              10

SEQ ID NO: 652         moltype = AA  length = 10
FEATURE                Location/Qualifiers
source                 1..10
                       mol_type = protein
```

```
SEQUENCE: 652
GCGSSCGGCD                                                          10

SEQ ID NO: 653         moltype = AA   length = 10
FEATURE                Location/Qualifiers
source                 1..10
                       mol_type = protein
                       organism = Homo sapiens
SEQUENCE: 653
GCGSSCGGCG                                                          10

SEQ ID NO: 654         moltype = AA   length = 10
FEATURE                Location/Qualifiers
source                 1..10
                       mol_type = protein
                       organism = Homo sapiens
SEQUENCE: 654
GCGSSCSQCS                                                          10

SEQ ID NO: 655         moltype = AA   length = 10
FEATURE                Location/Qualifiers
source                 1..10
                       mol_type = protein
                       organism = Homo sapiens
SEQUENCE: 655
GCGYSSSCCG                                                          10

SEQ ID NO: 656         moltype = AA   length = 10
FEATURE                Location/Qualifiers
source                 1..10
                       mol_type = protein
                       organism = Homo sapiens
SEQUENCE: 656
GCKGGCGSCG                                                          10

SEQ ID NO: 657         moltype = AA   length = 10
FEATURE                Location/Qualifiers
source                 1..10
                       mol_type = protein
                       organism = Homo sapiens
SEQUENCE: 657
GCSGCSGGCG                                                          10

SEQ ID NO: 658         moltype = AA   length = 10
FEATURE                Location/Qualifiers
source                 1..10
                       mol_type = protein
                       organism = Homo sapiens
SEQUENCE: 658
ICSGASSLCC                                                          10

SEQ ID NO: 659         moltype = AA   length = 10
FEATURE                Location/Qualifiers
source                 1..10
                       mol_type = protein
                       organism = Homo sapiens
SEQUENCE: 659
ICSGASSPCC                                                          10

SEQ ID NO: 660         moltype = AA   length = 10
FEATURE                Location/Qualifiers
source                 1..10
                       mol_type = protein
                       organism = Homo sapiens
SEQUENCE: 660
MCCNYYGNSC                                                          10

SEQ ID NO: 661         moltype = AA   length = 10
FEATURE                Location/Qualifiers
source                 1..10
                       mol_type = protein
                       organism = Homo sapiens
SEQUENCE: 661
MCCNYYRNSC                                                          10

SEQ ID NO: 662         moltype = AA   length = 10
FEATURE                Location/Qualifiers
source                 1..10
```

```
                        mol_type = protein
                        organism = Homo sapiens
SEQUENCE: 662
MCYGYGCGCG                                                              10

SEQ ID NO: 663          moltype = AA  length = 10
FEATURE                 Location/Qualifiers
source                  1..10
                        mol_type = protein
                        organism = Homo sapiens
SEQUENCE: 663
NCCSRNFSSC                                                              10

SEQ ID NO: 664          moltype = AA  length = 10
FEATURE                 Location/Qualifiers
source                  1..10
                        mol_type = protein
                        organism = Homo sapiens
SEQUENCE: 664
PCSLQEGCCR                                                              10

SEQ ID NO: 665          moltype = AA  length = 10
FEATURE                 Location/Qualifiers
source                  1..10
                        mol_type = protein
                        organism = Homo sapiens
SEQUENCE: 665
PCSSQSSCCV                                                              10

SEQ ID NO: 666          moltype = AA  length = 10
FEATURE                 Location/Qualifiers
source                  1..10
                        mol_type = protein
                        organism = Homo sapiens
SEQUENCE: 666
SCCAPASSCQ                                                              10

SEQ ID NO: 667          moltype = AA  length = 10
FEATURE                 Location/Qualifiers
source                  1..10
                        mol_type = protein
                        organism = Homo sapiens
SEQUENCE: 667
SCCAPASTCQ                                                              10

SEQ ID NO: 668          moltype = AA  length = 10
FEATURE                 Location/Qualifiers
source                  1..10
                        mol_type = protein
                        organism = Homo sapiens
SEQUENCE: 668
SCCAPTSSCQ                                                              10

SEQ ID NO: 669          moltype = AA  length = 10
FEATURE                 Location/Qualifiers
source                  1..10
                        mol_type = protein
                        organism = Homo sapiens
SEQUENCE: 669
SCCGYRPLCY                                                              10

SEQ ID NO: 670          moltype = AA  length = 10
FEATURE                 Location/Qualifiers
source                  1..10
                        mol_type = protein
                        organism = Homo sapiens
SEQUENCE: 670
SCCVPASSCQ                                                              10

SEQ ID NO: 671          moltype = AA  length = 10
FEATURE                 Location/Qualifiers
source                  1..10
                        mol_type = protein
                        organism = Homo sapiens
SEQUENCE: 671
SCCVPTSSCQ                                                              10

SEQ ID NO: 672          moltype = AA  length = 10
FEATURE                 Location/Qualifiers
```

-continued

| | | |
|---|---|---|
| source | 1..10<br>mol_type = protein<br>organism = Homo sapiens | |
| SEQUENCE: 672<br>SCGCSKGACG | | 10 |
| SEQ ID NO: 673<br>FEATURE<br>source | moltype = AA  length = 10<br>Location/Qualifiers<br>1..10<br>mol_type = protein<br>organism = Homo sapiens | |
| SEQUENCE: 673<br>SCGGCDSSCG | | 10 |
| SEQ ID NO: 674<br>FEATURE<br>source | moltype = AA  length = 10<br>Location/Qualifiers<br>1..10<br>mol_type = protein<br>organism = Homo sapiens | |
| SEQUENCE: 674<br>SCGGCGSGCG | | 10 |
| SEQ ID NO: 675<br>FEATURE<br>source | moltype = AA  length = 10<br>Location/Qualifiers<br>1..10<br>mol_type = protein<br>organism = Homo sapiens | |
| SEQUENCE: 675<br>SCGGCGSSCG | | 10 |
| SEQ ID NO: 676<br>FEATURE<br>source | moltype = AA  length = 10<br>Location/Qualifiers<br>1..10<br>mol_type = protein<br>organism = Homo sapiens | |
| SEQUENCE: 676<br>SCGGCKGGCG | | 10 |
| SEQ ID NO: 677<br>FEATURE<br>source | moltype = AA  length = 10<br>Location/Qualifiers<br>1..10<br>mol_type = protein<br>organism = Homo sapiens | |
| SEQUENCE: 677<br>SCGGSKGCCG | | 10 |
| SEQ ID NO: 678<br>FEATURE<br>source | moltype = AA  length = 10<br>Location/Qualifiers<br>1..10<br>mol_type = protein<br>organism = Homo sapiens | |
| SEQUENCE: 678<br>SCGSGCRGCG | | 10 |
| SEQ ID NO: 679<br>FEATURE<br>source | moltype = AA  length = 10<br>Location/Qualifiers<br>1..10<br>mol_type = protein<br>organism = Homo sapiens | |
| SEQUENCE: 679<br>SCYGCGYGCI | | 10 |
| SEQ ID NO: 680<br>FEATURE<br>source | moltype = AA  length = 10<br>Location/Qualifiers<br>1..10<br>mol_type = protein<br>organism = Homo sapiens | |
| SEQUENCE: 680<br>TCCVPVPSCG | | 10 |
| SEQ ID NO: 681<br>FEATURE<br>source | moltype = AA  length = 10<br>Location/Qualifiers<br>1..10<br>mol_type = protein<br>organism = Homo sapiens | |
| SEQUENCE: 681<br>TCSDDSGSCC | | 10 |
| SEQ ID NO: 682 | moltype = AA  length = 10 | |

```
                        -continued

FEATURE                 Location/Qualifiers
source                  1..10
                        mol_type = protein
                        organism = Homo sapiens
SEQUENCE: 682
TCSEDSSSCC                                                              10

SEQ ID NO: 683          moltype = AA  length = 10
FEATURE                 Location/Qualifiers
source                  1..10
                        mol_type = protein
                        organism = Homo sapiens
SEQUENCE: 683
TCSEDSYSCC                                                              10

SEQ ID NO: 684          moltype = AA  length = 10
FEATURE                 Location/Qualifiers
source                  1..10
                        mol_type = protein
                        organism = Homo sapiens
SEQUENCE: 684
TCSESSPSCC                                                              10

SEQ ID NO: 685          moltype = AA  length = 10
FEATURE                 Location/Qualifiers
source                  1..10
                        mol_type = protein
                        organism = Homo sapiens
SEQUENCE: 685
TCSESSSSCC                                                              10

SEQ ID NO: 686          moltype = AA  length = 10
FEATURE                 Location/Qualifiers
source                  1..10
                        mol_type = protein
                        organism = Homo sapiens
SEQUENCE: 686
TCSKDSSSCC                                                              10

SEQ ID NO: 687          moltype = AA  length = 10
FEATURE                 Location/Qualifiers
source                  1..10
                        mol_type = protein
                        organism = Homo sapiens
SEQUENCE: 687
TCSRLSSACC                                                              10

SEQ ID NO: 688          moltype = AA  length = 10
FEATURE                 Location/Qualifiers
source                  1..10
                        mol_type = protein
                        organism = Homo sapiens
SEQUENCE: 688
VCCQPTPICD                                                              10

SEQ ID NO: 689          moltype = AA  length = 10
FEATURE                 Location/Qualifiers
source                  1..10
                        mol_type = protein
                        organism = Homo sapiens
SEQUENCE: 689
VCSEDSSSCC                                                              10

SEQ ID NO: 690          moltype = AA  length = 10
FEATURE                 Location/Qualifiers
source                  1..10
                        mol_type = protein
                        organism = Homo sapiens
SEQUENCE: 690
VCSGASSLCC                                                              10

SEQ ID NO: 691          moltype = AA  length = 10
FEATURE                 Location/Qualifiers
source                  1..10
                        mol_type = protein
                        organism = Homo sapiens
SEQUENCE: 691
VCSGASSPCC                                                              10
```

```
SEQ ID NO: 692          moltype = AA   length = 10
FEATURE                 Location/Qualifiers
source                  1..10
                        mol_type = protein
                        organism = Homo sapiens
SEQUENCE: 692
VCSGASSSCC                                                                10

SEQ ID NO: 693          moltype = AA   length = 10
FEATURE                 Location/Qualifiers
source                  1..10
                        mol_type = protein
                        organism = Homo sapiens
SEQUENCE: 693
VCSGASTSCC                                                                10

SEQ ID NO: 694          moltype = AA   length = 10
FEATURE                 Location/Qualifiers
source                  1..10
                        mol_type = protein
                        organism = Homo sapiens
SEQUENCE: 694
VCSGDSSCCQ                                                                10

SEQ ID NO: 695          moltype = AA   length = 10
FEATURE                 Location/Qualifiers
source                  1..10
                        mol_type = protein
                        organism = Homo sapiens
SEQUENCE: 695
VCSGISSSCC                                                                10

SEQ ID NO: 696          moltype = AA   length = 10
FEATURE                 Location/Qualifiers
source                  1..10
                        mol_type = protein
                        organism = Homo sapiens
SEQUENCE: 696
YCVPIPSCCA                                                                10

SEQ ID NO: 697          moltype = AA   length = 10
FEATURE                 Location/Qualifiers
source                  1..10
                        mol_type = protein
                        organism = Homo sapiens
SEQUENCE: 697
CASSCCTPSC                                                                10

SEQ ID NO: 698          moltype = AA   length = 10
FEATURE                 Location/Qualifiers
source                  1..10
                        mol_type = protein
                        organism = Homo sapiens
SEQUENCE: 698
CCDNCPPPCH                                                                10

SEQ ID NO: 699          moltype = AA   length = 10
FEATURE                 Location/Qualifiers
source                  1..10
                        mol_type = protein
                        organism = Homo sapiens
SEQUENCE: 699
CCEPCLPRGC                                                                10

SEQ ID NO: 700          moltype = AA   length = 10
FEATURE                 Location/Qualifiers
source                  1..10
                        mol_type = protein
                        organism = Homo sapiens
SEQUENCE: 700
CCGAASSCCR                                                                10

SEQ ID NO: 701          moltype = AA   length = 10
FEATURE                 Location/Qualifiers
source                  1..10
                        mol_type = protein
                        organism = Homo sapiens
SEQUENCE: 701
CCGCGGSGCG                                                                10
```

```
SEQ ID NO: 702           moltype = AA  length = 10
FEATURE                  Location/Qualifiers
source                   1..10
                         mol_type = protein
                         organism = Homo sapiens
SEQUENCE: 702
CCGPSSSCCQ                                                                10

SEQ ID NO: 703           moltype = AA  length = 10
FEATURE                  Location/Qualifiers
source                   1..10
                         mol_type = protein
                         organism = Homo sapiens
SEQUENCE: 703
CCGSGCGGCG                                                                10

SEQ ID NO: 704           moltype = AA  length = 10
FEATURE                  Location/Qualifiers
source                   1..10
                         mol_type = protein
                         organism = Homo sapiens
SEQUENCE: 704
CCKPYCSQCS                                                                10

SEQ ID NO: 705           moltype = AA  length = 10
FEATURE                  Location/Qualifiers
source                   1..10
                         mol_type = protein
                         organism = Homo sapiens
SEQUENCE: 705
CCMPVSSCCA                                                                10

SEQ ID NO: 706           moltype = AA  length = 10
FEATURE                  Location/Qualifiers
source                   1..10
                         mol_type = protein
                         organism = Homo sapiens
SEQUENCE: 706
CCNYYRNCCG                                                                10

SEQ ID NO: 707           moltype = AA  length = 10
FEATURE                  Location/Qualifiers
source                   1..10
                         mol_type = protein
                         organism = Homo sapiens
SEQUENCE: 707
CCPSCVVSSC                                                                10

SEQ ID NO: 708           moltype = AA  length = 10
FEATURE                  Location/Qualifiers
source                   1..10
                         mol_type = protein
                         organism = Homo sapiens
SEQUENCE: 708
CCPSYCVSSC                                                                10

SEQ ID NO: 709           moltype = AA  length = 10
FEATURE                  Location/Qualifiers
source                   1..10
                         mol_type = protein
                         organism = Homo sapiens
SEQUENCE: 709
CCQPICGSSC                                                                10

SEQ ID NO: 710           moltype = AA  length = 10
FEATURE                  Location/Qualifiers
source                   1..10
                         mol_type = protein
                         organism = Homo sapiens
SEQUENCE: 710
CCQPICVTSC                                                                10

SEQ ID NO: 711           moltype = AA  length = 10
FEATURE                  Location/Qualifiers
source                   1..10
                         mol_type = protein
                         organism = Homo sapiens
SEQUENCE: 711
```

-continued

CCQPTCLSSC 10

| | | |
|---|---|---|
| SEQ ID NO: 712<br>FEATURE<br>source | moltype = AA  length = 10<br>Location/Qualifiers<br>1..10<br>mol_type = protein<br>organism = Homo sapiens | |

SEQUENCE: 712
CCQPTCLTSC 10

| | | |
|---|---|---|
| SEQ ID NO: 713<br>FEATURE<br>source | moltype = AA  length = 10<br>Location/Qualifiers<br>1..10<br>mol_type = protein<br>organism = Homo sapiens | |

SEQUENCE: 713
CCQPTCVASC 10

| | | |
|---|---|---|
| SEQ ID NO: 714<br>FEATURE<br>source | moltype = AA  length = 10<br>Location/Qualifiers<br>1..10<br>mol_type = protein<br>organism = Homo sapiens | |

SEQUENCE: 714
CCQPTCVTSC 10

| | | |
|---|---|---|
| SEQ ID NO: 715<br>FEATURE<br>source | moltype = AA  length = 10<br>Location/Qualifiers<br>1..10<br>mol_type = protein<br>organism = Homo sapiens | |

SEQUENCE: 715
CCQPYCHPTC 10

| | | |
|---|---|---|
| SEQ ID NO: 716<br>FEATURE<br>source | moltype = AA  length = 10<br>Location/Qualifiers<br>1..10<br>mol_type = protein<br>organism = Homo sapiens | |

SEQUENCE: 716
CCQQSSCVSC 10

| | | |
|---|---|---|
| SEQ ID NO: 717<br>FEATURE<br>source | moltype = AA  length = 10<br>Location/Qualifiers<br>1..10<br>mol_type = protein<br>organism = Homo sapiens | |

SEQUENCE: 717
CCQSSCFKPC 10

| | | |
|---|---|---|
| SEQ ID NO: 718<br>FEATURE<br>source | moltype = AA  length = 10<br>Location/Qualifiers<br>1..10<br>mol_type = protein<br>organism = Homo sapiens | |

SEQUENCE: 718
CCQSSCSKPC 10

| | | |
|---|---|---|
| SEQ ID NO: 719<br>FEATURE<br>source | moltype = AA  length = 10<br>Location/Qualifiers<br>1..10<br>mol_type = protein<br>organism = Homo sapiens | |

SEQUENCE: 719
CCQSSCYKPC 10

| | | |
|---|---|---|
| SEQ ID NO: 720<br>FEATURE<br>source | moltype = AA  length = 10<br>Location/Qualifiers<br>1..10<br>mol_type = protein<br>organism = Homo sapiens | |

SEQUENCE: 720
CCQTICRSTC 10

| | | |
|---|---|---|
| SEQ ID NO: 721<br>FEATURE<br>source | moltype = AA  length = 10<br>Location/Qualifiers<br>1..10<br>mol_type = protein<br>organism = Homo sapiens | |

```
SEQUENCE: 721
CCQTTCHPSC                                                                    10

SEQ ID NO: 722           moltype = AA  length = 10
FEATURE                  Location/Qualifiers
source                   1..10
                         mol_type = protein
                         organism = Homo sapiens
SEQUENCE: 722
CCQTTCRPSC                                                                    10

SEQ ID NO: 723           moltype = AA  length = 10
FEATURE                  Location/Qualifiers
source                   1..10
                         mol_type = protein
                         organism = Homo sapiens
SEQUENCE: 723
CCRVPTCSCS                                                                    10

SEQ ID NO: 724           moltype = AA  length = 10
FEATURE                  Location/Qualifiers
source                   1..10
                         mol_type = protein
                         organism = Homo sapiens
SEQUENCE: 724
CCSPGCQPTC                                                                    10

SEQ ID NO: 725           moltype = AA  length = 10
FEATURE                  Location/Qualifiers
source                   1..10
                         mol_type = protein
                         organism = Homo sapiens
SEQUENCE: 725
CCSSGCGSSC                                                                    10

SEQ ID NO: 726           moltype = AA  length = 10
FEATURE                  Location/Qualifiers
source                   1..10
                         mol_type = protein
                         organism = Homo sapiens
SEQUENCE: 726
CCSSSCGSCG                                                                    10

SEQ ID NO: 727           moltype = AA  length = 10
FEATURE                  Location/Qualifiers
source                   1..10
                         mol_type = protein
                         organism = Homo sapiens
SEQUENCE: 727
CCTQEQNCCE                                                                    10

SEQ ID NO: 728           moltype = AA  length = 10
FEATURE                  Location/Qualifiers
source                   1..10
                         mol_type = protein
                         organism = Homo sapiens
SEQUENCE: 728
CCVPIPSCCA                                                                    10

SEQ ID NO: 729           moltype = AA  length = 10
FEATURE                  Location/Qualifiers
source                   1..10
                         mol_type = protein
                         organism = Homo sapiens
SEQUENCE: 729
CCVPISSCCA                                                                    10

SEQ ID NO: 730           moltype = AA  length = 10
FEATURE                  Location/Qualifiers
source                   1..10
                         mol_type = protein
                         organism = Homo sapiens
SEQUENCE: 730
CCVPVCYQCK                                                                    10

SEQ ID NO: 731           moltype = AA  length = 10
FEATURE                  Location/Qualifiers
source                   1..10
                         mol_type = protein
```

```
                                organism = Homo sapiens
SEQUENCE: 731
CCVPVPSCCA                                                                      10

SEQ ID NO: 732                  moltype = AA   length = 10
FEATURE                         Location/Qualifiers
source                          1..10
                                mol_type = protein
                                organism = Homo sapiens
SEQUENCE: 732
CCVPVPSCCV                                                                      10

SEQ ID NO: 733                  moltype = AA   length = 10
FEATURE                         Location/Qualifiers
source                          1..10
                                mol_type = protein
                                organism = Homo sapiens
SEQUENCE: 733
CCVPVSSCCA                                                                      10

SEQ ID NO: 734                  moltype = AA   length = 10
FEATURE                         Location/Qualifiers
source                          1..10
                                mol_type = protein
                                organism = Homo sapiens
SEQUENCE: 734
CDSSCCQPSC                                                                      10

SEQ ID NO: 735                  moltype = AA   length = 10
FEATURE                         Location/Qualifiers
source                          1..10
                                mol_type = protein
                                organism = Homo sapiens
SEQUENCE: 735
CDTCPPPCCK                                                                      10

SEQ ID NO: 736                  moltype = AA   length = 10
FEATURE                         Location/Qualifiers
source                          1..10
                                mol_type = protein
                                organism = Homo sapiens
SEQUENCE: 736
CEPCRRPVCC                                                                      10

SEQ ID NO: 737                  moltype = AA   length = 10
FEATURE                         Location/Qualifiers
source                          1..10
                                mol_type = protein
                                organism = Homo sapiens
SEQUENCE: 737
CEPSCCQPVC                                                                      10

SEQ ID NO: 738                  moltype = AA   length = 10
FEATURE                         Location/Qualifiers
source                          1..10
                                mol_type = protein
                                organism = Homo sapiens
SEQUENCE: 738
CEPSCCSAVC                                                                      10

SEQ ID NO: 739                  moltype = AA   length = 10
FEATURE                         Location/Qualifiers
source                          1..10
                                mol_type = protein
                                organism = Homo sapiens
SEQUENCE: 739
CETSCCQPSC                                                                      10

SEQ ID NO: 740                  moltype = AA   length = 10
FEATURE                         Location/Qualifiers
source                          1..10
                                mol_type = protein
                                organism = Homo sapiens
SEQUENCE: 740
CETTCCRTTC                                                                      10

SEQ ID NO: 741                  moltype = AA   length = 10
FEATURE                         Location/Qualifiers
source                          1..10
```

```
SEQUENCE: 741
CFSGCGSSCC                                                                10

SEQ ID NO: 742         moltype = AA  length = 10
FEATURE                Location/Qualifiers
source                 1..10
                       mol_type = protein
                       organism = Homo sapiens
SEQUENCE: 742
CGCSQSNCCK                                                                10

SEQ ID NO: 743         moltype = AA  length = 10
FEATURE                Location/Qualifiers
source                 1..10
                       mol_type = protein
                       organism = Homo sapiens
SEQUENCE: 743
CGCSQSSCCK                                                                10

SEQ ID NO: 744         moltype = AA  length = 10
FEATURE                Location/Qualifiers
source                 1..10
                       mol_type = protein
                       organism = Homo sapiens
SEQUENCE: 744
CGGCGGCGGC                                                                10

SEQ ID NO: 745         moltype = AA  length = 10
FEATURE                Location/Qualifiers
source                 1..10
                       mol_type = protein
                       organism = Homo sapiens
SEQUENCE: 745
CGGCGGGCCG                                                                10

SEQ ID NO: 746         moltype = AA  length = 10
FEATURE                Location/Qualifiers
source                 1..10
                       mol_type = protein
                       organism = Homo sapiens
SEQUENCE: 746
CGGCGSGCCV                                                                10

SEQ ID NO: 747         moltype = AA  length = 10
FEATURE                Location/Qualifiers
source                 1..10
                       mol_type = protein
                       organism = Homo sapiens
SEQUENCE: 747
CGGCGSSCCV                                                                10

SEQ ID NO: 748         moltype = AA  length = 10
FEATURE                Location/Qualifiers
source                 1..10
                       mol_type = protein
                       organism = Homo sapiens
SEQUENCE: 748
CGGGCCGSSC                                                                10

SEQ ID NO: 749         moltype = AA  length = 10
FEATURE                Location/Qualifiers
source                 1..10
                       mol_type = protein
                       organism = Homo sapiens
SEQUENCE: 749
CGGSCCGSSC                                                                10

SEQ ID NO: 750         moltype = AA  length = 10
FEATURE                Location/Qualifiers
source                 1..10
                       mol_type = protein
                       organism = Homo sapiens
SEQUENCE: 750
CGQSCCRPAC                                                                10

SEQ ID NO: 751         moltype = AA  length = 10
FEATURE                Location/Qualifiers
```

| | |
|---|---|
| source | 1..10<br>mol_type = protein<br>organism = Homo sapiens |

SEQUENCE: 751
CGQSCCRPVC                                                                                  10

| | |
|---|---|
| SEQ ID NO: 752<br>FEATURE<br>source | moltype = AA   length = 10<br>Location/Qualifiers<br>1..10<br>mol_type = protein<br>organism = Homo sapiens |

SEQUENCE: 752
CGSCGCSQCN                                                                                  10

| | |
|---|---|
| SEQ ID NO: 753<br>FEATURE<br>source | moltype = AA   length = 10<br>Location/Qualifiers<br>1..10<br>mol_type = protein<br>organism = Homo sapiens |

SEQUENCE: 753
CGSCGCSQCS                                                                                  10

| | |
|---|---|
| SEQ ID NO: 754<br>FEATURE<br>source | moltype = AA   length = 10<br>Location/Qualifiers<br>1..10<br>mol_type = protein<br>organism = Homo sapiens |

SEQUENCE: 754
CGSFCCQSSC                                                                                  10

| | |
|---|---|
| SEQ ID NO: 755<br>FEATURE<br>source | moltype = AA   length = 10<br>Location/Qualifiers<br>1..10<br>mol_type = protein<br>organism = Homo sapiens |

SEQUENCE: 755
CGSGCCVPVC                                                                                  10

| | |
|---|---|
| SEQ ID NO: 756<br>FEATURE<br>source | moltype = AA   length = 10<br>Location/Qualifiers<br>1..10<br>mol_type = protein<br>organism = Homo sapiens |

SEQUENCE: 756
CGSSCCGSGC                                                                                  10

| | |
|---|---|
| SEQ ID NO: 757<br>FEATURE<br>source | moltype = AA   length = 10<br>Location/Qualifiers<br>1..10<br>mol_type = protein<br>organism = Homo sapiens |

SEQUENCE: 757
CGSSCCQPCY                                                                                  10

| | |
|---|---|
| SEQ ID NO: 758<br>FEATURE<br>source | moltype = AA   length = 10<br>Location/Qualifiers<br>1..10<br>mol_type = protein<br>organism = Homo sapiens |

SEQUENCE: 758
CGSSCCQPIC                                                                                  10

| | |
|---|---|
| SEQ ID NO: 759<br>FEATURE<br>source | moltype = AA   length = 10<br>Location/Qualifiers<br>1..10<br>mol_type = protein<br>organism = Homo sapiens |

SEQUENCE: 759
CGSSCCQPSC                                                                                  10

| | |
|---|---|
| SEQ ID NO: 760<br>FEATURE<br>source | moltype = AA   length = 10<br>Location/Qualifiers<br>1..10<br>mol_type = protein<br>organism = Homo sapiens |

SEQUENCE: 760
CGSSCCQSSC                                                                                  10

| | |
|---|---|
| SEQ ID NO: 761 | moltype = AA   length = 10 |

-continued

```
FEATURE              Location/Qualifiers
source               1..10
                     mol_type = protein
                     organism = Homo sapiens
SEQUENCE: 761
CGSSCCVPIC                                                          10

SEQ ID NO: 762       moltype = AA  length = 10
FEATURE              Location/Qualifiers
source               1..10
                     mol_type = protein
                     organism = Homo sapiens
SEQUENCE: 762
CGSSCCVPVC                                                          10

SEQ ID NO: 763       moltype = AA  length = 10
FEATURE              Location/Qualifiers
source               1..10
                     mol_type = protein
                     organism = Homo sapiens
SEQUENCE: 763
CGSSCSQCSC                                                          10

SEQ ID NO: 764       moltype = AA  length = 10
FEATURE              Location/Qualifiers
source               1..10
                     mol_type = protein
                     organism = Homo sapiens
SEQUENCE: 764
CGYGSCCGCG                                                          10

SEQ ID NO: 765       moltype = AA  length = 10
FEATURE              Location/Qualifiers
source               1..10
                     mol_type = protein
                     organism = Homo sapiens
SEQUENCE: 765
CHPRCCISSC                                                          10

SEQ ID NO: 766       moltype = AA  length = 10
FEATURE              Location/Qualifiers
source               1..10
                     mol_type = protein
                     organism = Homo sapiens
SEQUENCE: 766
CHPSCCESSC                                                          10

SEQ ID NO: 767       moltype = AA  length = 10
FEATURE              Location/Qualifiers
source               1..10
                     mol_type = protein
                     organism = Homo sapiens
SEQUENCE: 767
CHPSCCISSC                                                          10

SEQ ID NO: 768       moltype = AA  length = 10
FEATURE              Location/Qualifiers
source               1..10
                     mol_type = protein
                     organism = Homo sapiens
SEQUENCE: 768
CHPTCCQNTC                                                          10

SEQ ID NO: 769       moltype = AA  length = 10
FEATURE              Location/Qualifiers
source               1..10
                     mol_type = protein
                     organism = Homo sapiens
SEQUENCE: 769
CHPTCCQTIC                                                          10

SEQ ID NO: 770       moltype = AA  length = 10
FEATURE              Location/Qualifiers
source               1..10
                     mol_type = protein
                     organism = Homo sapiens
SEQUENCE: 770
CHPVCCQTTC                                                          10
```

```
SEQ ID NO: 771          moltype = AA   length = 10
FEATURE                 Location/Qualifiers
source                  1..10
                        mol_type = protein
                        organism = Homo sapiens
SEQUENCE: 771
CHPVCKSTCC                                                                10

SEQ ID NO: 772          moltype = AA   length = 10
FEATURE                 Location/Qualifiers
source                  1..10
                        mol_type = protein
                        organism = Homo sapiens
SEQUENCE: 772
CHPVCRSTCC                                                                10

SEQ ID NO: 773          moltype = AA   length = 10
FEATURE                 Location/Qualifiers
source                  1..10
                        mol_type = protein
                        organism = Homo sapiens
SEQUENCE: 773
CISSCCHPSC                                                                10

SEQ ID NO: 774          moltype = AA   length = 10
FEATURE                 Location/Qualifiers
source                  1..10
                        mol_type = protein
                        organism = Homo sapiens
SEQUENCE: 774
CISSCCKPSC                                                                10

SEQ ID NO: 775          moltype = AA   length = 10
FEATURE                 Location/Qualifiers
source                  1..10
                        mol_type = protein
                        organism = Homo sapiens
SEQUENCE: 775
CISSCCRPSC                                                                10

SEQ ID NO: 776          moltype = AA   length = 10
FEATURE                 Location/Qualifiers
source                  1..10
                        mol_type = protein
                        organism = Homo sapiens
SEQUENCE: 776
CISSCTPSCC                                                                10

SEQ ID NO: 777          moltype = AA   length = 10
FEATURE                 Location/Qualifiers
source                  1..10
                        mol_type = protein
                        organism = Homo sapiens
SEQUENCE: 777
CISSSCCPSC                                                                10

SEQ ID NO: 778          moltype = AA   length = 10
FEATURE                 Location/Qualifiers
source                  1..10
                        mol_type = protein
                        organism = Homo sapiens
SEQUENCE: 778
CKAVCCVPTC                                                                10

SEQ ID NO: 779          moltype = AA   length = 10
FEATURE                 Location/Qualifiers
source                  1..10
                        mol_type = protein
                        organism = Homo sapiens
SEQUENCE: 779
CKPCCSQASC                                                                10

SEQ ID NO: 780          moltype = AA   length = 10
FEATURE                 Location/Qualifiers
source                  1..10
                        mol_type = protein
                        organism = Homo sapiens
SEQUENCE: 780
CKPCCSQSRC                                                                10
```

| | | |
|---|---|---|
| SEQ ID NO: 781<br>FEATURE<br>source | moltype = AA   length = 10<br>Location/Qualifiers<br>1..10<br>mol_type = protein<br>organism = Homo sapiens | |
| SEQUENCE: 781<br>CKPCCSQSSC | | 10 |
| SEQ ID NO: 782<br>FEATURE<br>source | moltype = AA   length = 10<br>Location/Qualifiers<br>1..10<br>mol_type = protein<br>organism = Homo sapiens | |
| SEQUENCE: 782<br>CKPCCSSSGC | | 10 |
| SEQ ID NO: 783<br>FEATURE<br>source | moltype = AA   length = 10<br>Location/Qualifiers<br>1..10<br>mol_type = protein<br>organism = Homo sapiens | |
| SEQUENCE: 783<br>CKPCSCFSGC | | 10 |
| SEQ ID NO: 784<br>FEATURE<br>source | moltype = AA   length = 10<br>Location/Qualifiers<br>1..10<br>mol_type = protein<br>organism = Homo sapiens | |
| SEQUENCE: 784<br>CKPCSCSSGC | | 10 |
| SEQ ID NO: 785<br>FEATURE<br>source | moltype = AA   length = 10<br>Location/Qualifiers<br>1..10<br>mol_type = protein<br>organism = Homo sapiens | |
| SEQUENCE: 785<br>CKPCYCSSGC | | 10 |
| SEQ ID NO: 786<br>FEATURE<br>source | moltype = AA   length = 10<br>Location/Qualifiers<br>1..10<br>mol_type = protein<br>organism = Homo sapiens | |
| SEQUENCE: 786<br>CKPICCVPVC | | 10 |
| SEQ ID NO: 787<br>FEATURE<br>source | moltype = AA   length = 10<br>Location/Qualifiers<br>1..10<br>mol_type = protein<br>organism = Homo sapiens | |
| SEQUENCE: 787<br>CKPQCCQSVC | | 10 |
| SEQ ID NO: 788<br>FEATURE<br>source | moltype = AA   length = 10<br>Location/Qualifiers<br>1..10<br>mol_type = protein<br>organism = Homo sapiens | |
| SEQUENCE: 788<br>CKPSCCQTTC | | 10 |
| SEQ ID NO: 789<br>FEATURE<br>source | moltype = AA   length = 10<br>Location/Qualifiers<br>1..10<br>mol_type = protein<br>organism = Homo sapiens | |
| SEQUENCE: 789<br>CKPVCCAPTC | | 10 |
| SEQ ID NO: 790<br>FEATURE<br>source | moltype = AA   length = 10<br>Location/Qualifiers<br>1..10<br>mol_type = protein<br>organism = Homo sapiens | |
| SEQUENCE: 790 | | |

CKPVCCKPIC                                                                                      10

SEQ ID NO: 791          moltype = AA   length = 10
FEATURE                 Location/Qualifiers
source                  1..10
                        mol_type = protein
                        organism = Homo sapiens SEQUENCE: 791
CKPVCCKSIC                                                                                      10

SEQ ID NO: 792          moltype = AA   length = 10
FEATURE                 Location/Qualifiers
source                  1..10
                        mol_type = protein
                        organism = Homo sapiens SEQUENCE: 792
CKPVCCLPTC                                                                                      10

SEQ ID NO: 793          moltype = AA   length = 10
FEATURE                 Location/Qualifiers
source                  1..10
                        mol_type = protein
                        organism = Homo sapiens SEQUENCE: 793
CKPVCCVPTC                                                                                      10

SEQ ID NO: 794          moltype = AA   length = 10
FEATURE                 Location/Qualifiers
source                  1..10
                        mol_type = protein
                        organism = Homo sapiens SEQUENCE: 794
CKPVCCVPVC                                                                                      10

SEQ ID NO: 795          moltype = AA   length = 10
FEATURE                 Location/Qualifiers
source                  1..10
                        mol_type = protein
                        organism = Homo sapiens SEQUENCE: 795
CKPVCCVSTC                                                                                      10

SEQ ID NO: 796          moltype = AA   length = 10
FEATURE                 Location/Qualifiers
source                  1..10
                        mol_type = protein
                        organism = Homo sapiens SEQUENCE: 796
CKPYCCQSSC                                                                                      10

SEQ ID NO: 797          moltype = AA   length = 10
FEATURE                 Location/Qualifiers
source                  1..10
                        mol_type = protein
                        organism = Homo sapiens SEQUENCE: 797
CKPYCSQCSC                                                                                      10

SEQ ID NO: 798          moltype = AA   length = 10
FEATURE                 Location/Qualifiers
source                  1..10
                        mol_type = protein
                        organism = Homo sapiens SEQUENCE: 798
CKSNCCKPVC                                                                                      10

SEQ ID NO: 799          moltype = AA   length = 10
FEATURE                 Location/Qualifiers
source                  1..10
                        mol_type = protein
                        organism = Homo sapiens SEQUENCE: 799
CKTVCCKPVC                                                                                      10

SEQ ID NO: 800          moltype = AA   length = 10
FEATURE                 Location/Qualifiers
source                  1..10
                        mol_type = protein
                        organism = Homo sapiens

```
SEQUENCE: 800
CLPPCCVVSC                                                                      10

SEQ ID NO: 801         moltype = AA  length = 10
FEATURE                Location/Qualifiers
source                 1..10
                       mol_type = protein
                       organism = Homo sapiens
SEQUENCE: 801
CLTSCCQPSC                                                                      10

SEQ ID NO: 802         moltype = AA  length = 10
FEATURE                Location/Qualifiers
source                 1..10
                       mol_type = protein
                       organism = Homo sapiens
SEQUENCE: 802
CNPCCSQSSC                                                                      10

SEQ ID NO: 803         moltype = AA  length = 10
FEATURE                Location/Qualifiers
source                 1..10
                       mol_type = protein
                       organism = Homo sapiens
SEQUENCE: 803
CPESCCELPC                                                                      10

SEQ ID NO: 804         moltype = AA  length = 10
FEATURE                Location/Qualifiers
source                 1..10
                       mol_type = protein
                       organism = Homo sapiens
SEQUENCE: 804
CPESCCEPHC                                                                      10

SEQ ID NO: 805         moltype = AA  length = 10
FEATURE                Location/Qualifiers
source                 1..10
                       mol_type = protein
                       organism = Homo sapiens
SEQUENCE: 805
CPESCCEPPC                                                                      10

SEQ ID NO: 806         moltype = AA  length = 10
FEATURE                Location/Qualifiers
source                 1..10
                       mol_type = protein
                       organism = Homo sapiens
SEQUENCE: 806
CPFSCPTTCC                                                                      10

SEQ ID NO: 807         moltype = AA  length = 10
FEATURE                Location/Qualifiers
source                 1..10
                       mol_type = protein
                       organism = Homo sapiens
SEQUENCE: 807
CPGDCFTCCT                                                                      10

SEQ ID NO: 808         moltype = AA  length = 10
FEATURE                Location/Qualifiers
source                 1..10
                       mol_type = protein
                       organism = Homo sapiens
SEQUENCE: 808
CPSCVVSSCC                                                                      10

SEQ ID NO: 809         moltype = AA  length = 10
FEATURE                Location/Qualifiers
source                 1..10
                       mol_type = protein
                       organism = Homo sapiens
SEQUENCE: 809
CPSYCVSSCC                                                                      10

SEQ ID NO: 810         moltype = AA  length = 10
FEATURE                Location/Qualifiers
source                 1..10
                       mol_type = protein
```

```
                                    organism = Homo sapiens
SEQUENCE: 810
CPTTCCRTTC                                                                              10

SEQ ID NO: 811          moltype = AA  length = 10
FEATURE                 Location/Qualifiers
source                  1..10
                        mol_type = protein
                        organism = Homo sapiens
SEQUENCE: 811
CQETCCRPSC                                                                              10

SEQ ID NO: 812          moltype = AA  length = 10
FEATURE                 Location/Qualifiers
source                  1..10
                        mol_type = protein
                        organism = Homo sapiens
SEQUENCE: 812
CQHACCVPVC                                                                              10

SEQ ID NO: 813          moltype = AA  length = 10
FEATURE                 Location/Qualifiers
source                  1..10
                        mol_type = protein
                        organism = Homo sapiens
SEQUENCE: 813
CQNTCCRTTC                                                                              10

SEQ ID NO: 814          moltype = AA  length = 10
FEATURE                 Location/Qualifiers
source                  1..10
                        mol_type = protein
                        organism = Homo sapiens
SEQUENCE: 814
CQPACCQPTC                                                                              10

SEQ ID NO: 815          moltype = AA  length = 10
FEATURE                 Location/Qualifiers
source                  1..10
                        mol_type = protein
                        organism = Homo sapiens
SEQUENCE: 815
CQPACCTASC                                                                              10

SEQ ID NO: 816          moltype = AA  length = 10
FEATURE                 Location/Qualifiers
source                  1..10
                        mol_type = protein
                        organism = Homo sapiens
SEQUENCE: 816
CQPACCTSSC                                                                              10

SEQ ID NO: 817          moltype = AA  length = 10
FEATURE                 Location/Qualifiers
source                  1..10
                        mol_type = protein
                        organism = Homo sapiens
SEQUENCE: 817
CQPACCTTSC                                                                              10

SEQ ID NO: 818          moltype = AA  length = 10
FEATURE                 Location/Qualifiers
source                  1..10
                        mol_type = protein
                        organism = Homo sapiens
SEQUENCE: 818
CQPACCVPVC                                                                              10

SEQ ID NO: 819          moltype = AA  length = 10
FEATURE                 Location/Qualifiers
source                  1..10
                        mol_type = protein
                        organism = Homo sapiens
SEQUENCE: 819
CQPACCVSSC                                                                              10

SEQ ID NO: 820          moltype = AA  length = 10
FEATURE                 Location/Qualifiers
source                  1..10
```

```
                         mol_type = protein
                         organism = Homo sapiens
SEQUENCE: 820
CQPCCHPTCY                                                              10

SEQ ID NO: 821           moltype = AA  length = 10
FEATURE                  Location/Qualifiers
source                   1..10
                         mol_type = protein
                         organism = Homo sapiens
SEQUENCE: 821
CQPCCRPTSC                                                              10

SEQ ID NO: 822           moltype = AA  length = 10
FEATURE                  Location/Qualifiers
source                   1..10
                         mol_type = protein
                         organism = Homo sapiens
SEQUENCE: 822
CQPICCGSSC                                                              10

SEQ ID NO: 823           moltype = AA  length = 10
FEATURE                  Location/Qualifiers
source                   1..10
                         mol_type = protein
                         organism = Homo sapiens
SEQUENCE: 823
CQPICGSSCC                                                              10

SEQ ID NO: 824           moltype = AA  length = 10
FEATURE                  Location/Qualifiers
source                   1..10
                         mol_type = protein
                         organism = Homo sapiens
SEQUENCE: 824
CQPICVTSCC                                                              10

SEQ ID NO: 825           moltype = AA  length = 10
FEATURE                  Location/Qualifiers
source                   1..10
                         mol_type = protein
                         organism = Homo sapiens
SEQUENCE: 825
CQPNCCRPSC                                                              10

SEQ ID NO: 826           moltype = AA  length = 10
FEATURE                  Location/Qualifiers
source                   1..10
                         mol_type = protein
                         organism = Homo sapiens
SEQUENCE: 826
CQPRCCETSC                                                              10

SEQ ID NO: 827           moltype = AA  length = 10
FEATURE                  Location/Qualifiers
source                   1..10
                         mol_type = protein
                         organism = Homo sapiens
SEQUENCE: 827
CQPSCCRPAC                                                              10

SEQ ID NO: 828           moltype = AA  length = 10
FEATURE                  Location/Qualifiers
source                   1..10
                         mol_type = protein
                         organism = Homo sapiens
SEQUENCE: 828
CQPSCCSTPC                                                              10

SEQ ID NO: 829           moltype = AA  length = 10
FEATURE                  Location/Qualifiers
source                   1..10
                         mol_type = protein
                         organism = Homo sapiens
SEQUENCE: 829
CQPSCCSTTC                                                              10

SEQ ID NO: 830           moltype = AA  length = 10
FEATURE                  Location/Qualifiers
```

```
                                  -continued source                     1..10
                           mol_type = protein
                           organism = Homo sapiens
SEQUENCE: 830
CQPSCCVPSC                                                             10

SEQ ID NO: 831             moltype = AA   length = 10
FEATURE                    Location/Qualifiers
source                     1..10
                           mol_type = protein
                           organism = Homo sapiens
SEQUENCE: 831
CQPSCCVSSC                                                             10

SEQ ID NO: 832             moltype = AA   length = 10
FEATURE                    Location/Qualifiers
source                     1..10
                           mol_type = protein
                           organism = Homo sapiens
SEQUENCE: 832
CQPTCCGSSC                                                             10

SEQ ID NO: 833             moltype = AA   length = 10
FEATURE                    Location/Qualifiers
source                     1..10
                           mol_type = protein
                           organism = Homo sapiens
SEQUENCE: 833
CQPTCCHPSC                                                             10

SEQ ID NO: 834             moltype = AA   length = 10
FEATURE                    Location/Qualifiers
source                     1..10
                           mol_type = protein
                           organism = Homo sapiens
SEQUENCE: 834
CQPTCCQPTC                                                             10

SEQ ID NO: 835             moltype = AA   length = 10
FEATURE                    Location/Qualifiers
source                     1..10
                           mol_type = protein
                           organism = Homo sapiens
SEQUENCE: 835
CQPTCCRPRC                                                             10

SEQ ID NO: 836             moltype = AA   length = 10
FEATURE                    Location/Qualifiers
source                     1..10
                           mol_type = protein
                           organism = Homo sapiens
SEQUENCE: 836
CQPTCCRPSC                                                             10

SEQ ID NO: 837             moltype = AA   length = 10
FEATURE                    Location/Qualifiers
source                     1..10
                           mol_type = protein
                           organism = Homo sapiens
SEQUENCE: 837
CQPTCCRTTC                                                             10

SEQ ID NO: 838             moltype = AA   length = 10
FEATURE                    Location/Qualifiers
source                     1..10
                           mol_type = protein
                           organism = Homo sapiens
SEQUENCE: 838
CQPTCLSSCC                                                             10

SEQ ID NO: 839             moltype = AA   length = 10
FEATURE                    Location/Qualifiers
source                     1..10
                           mol_type = protein
                           organism = Homo sapiens
SEQUENCE: 839
CQPTCLTSCC                                                             10

SEQ ID NO: 840             moltype = AA   length = 10
```

-continued

```
FEATURE              Location/Qualifiers
source               1..10
                     mol_type = protein
                     organism = Homo sapiens
SEQUENCE: 840
CQPTCVASCC                                                              10

SEQ ID NO: 841       moltype = AA  length = 10
FEATURE              Location/Qualifiers
source               1..10
                     mol_type = protein
                     organism = Homo sapiens
SEQUENCE: 841
CQPTCVTSCC                                                              10

SEQ ID NO: 842       moltype = AA  length = 10
FEATURE              Location/Qualifiers
source               1..10
                     mol_type = protein
                     organism = Homo sapiens
SEQUENCE: 842
CQPVCCQPTC                                                              10

SEQ ID NO: 843       moltype = AA  length = 10
FEATURE              Location/Qualifiers
source               1..10
                     mol_type = protein
                     organism = Homo sapiens
SEQUENCE: 843
CQPYCHPTCC                                                              10

SEQ ID NO: 844       moltype = AA  length = 10
FEATURE              Location/Qualifiers
source               1..10
                     mol_type = protein
                     organism = Homo sapiens
SEQUENCE: 844
CQQACCMPVC                                                              10

SEQ ID NO: 845       moltype = AA  length = 10
FEATURE              Location/Qualifiers
source               1..10
                     mol_type = protein
                     organism = Homo sapiens
SEQUENCE: 845
CQQACCVPIC                                                              10

SEQ ID NO: 846       moltype = AA  length = 10
FEATURE              Location/Qualifiers
source               1..10
                     mol_type = protein
                     organism = Homo sapiens
SEQUENCE: 846
CQQACCVPVC                                                              10

SEQ ID NO: 847       moltype = AA  length = 10
FEATURE              Location/Qualifiers
source               1..10
                     mol_type = protein
                     organism = Homo sapiens
SEQUENCE: 847
CQQSCCVPVC                                                              10

SEQ ID NO: 848       moltype = AA  length = 10
FEATURE              Location/Qualifiers
source               1..10
                     mol_type = protein
                     organism = Homo sapiens
SEQUENCE: 848
CQQSCCVSVC                                                              10

SEQ ID NO: 849       moltype = AA  length = 10
FEATURE              Location/Qualifiers
source               1..10
                     mol_type = protein
                     organism = Homo sapiens
SEQUENCE: 849
CQSMCCQPTC                                                              10
```

| | | |
|---|---|---|
| SEQ ID NO: 850<br>FEATURE<br>source | moltype = AA   length = 10<br>Location/Qualifiers<br>1..10<br>mol_type = protein<br>organism = Homo sapiens | |
| SEQUENCE: 850<br>CQSNCCVPVC | | 10 |
| SEQ ID NO: 851<br>FEATURE<br>source | moltype = AA   length = 10<br>Location/Qualifiers<br>1..10<br>mol_type = protein<br>organism = Homo sapiens | |
| SEQUENCE: 851<br>CQSSCCKPCS | | 10 |
| SEQ ID NO: 852<br>FEATURE<br>source | moltype = AA   length = 10<br>Location/Qualifiers<br>1..10<br>mol_type = protein<br>organism = Homo sapiens | |
| SEQUENCE: 852<br>CQSSCCQSSC | | 10 |
| SEQ ID NO: 853<br>FEATURE<br>source | moltype = AA   length = 10<br>Location/Qualifiers<br>1..10<br>mol_type = protein<br>organism = Homo sapiens | |
| SEQUENCE: 853<br>CQSSCCVPVC | | 10 |
| SEQ ID NO: 854<br>FEATURE<br>source | moltype = AA   length = 10<br>Location/Qualifiers<br>1..10<br>mol_type = protein<br>organism = Homo sapiens | |
| SEQUENCE: 854<br>CQSSCFKPCC | | 10 |
| SEQ ID NO: 855<br>FEATURE<br>source | moltype = AA   length = 10<br>Location/Qualifiers<br>1..10<br>mol_type = protein<br>organism = Homo sapiens | |
| SEQUENCE: 855<br>CQSSCSKPCC | | 10 |
| SEQ ID NO: 856<br>FEATURE<br>source | moltype = AA   length = 10<br>Location/Qualifiers<br>1..10<br>mol_type = protein<br>organism = Homo sapiens | |
| SEQUENCE: 856<br>CQSVCCQPTC | | 10 |
| SEQ ID NO: 857<br>FEATURE<br>source | moltype = AA   length = 10<br>Location/Qualifiers<br>1..10<br>mol_type = protein<br>organism = Homo sapiens | |
| SEQUENCE: 857<br>CQTICRSTCC | | 10 |
| SEQ ID NO: 858<br>FEATURE<br>source | moltype = AA   length = 10<br>Location/Qualifiers<br>1..10<br>mol_type = protein<br>organism = Homo sapiens | |
| SEQUENCE: 858<br>CQTTCCRPSC | | 10 |
| SEQ ID NO: 859<br>FEATURE<br>source | moltype = AA   length = 10<br>Location/Qualifiers<br>1..10<br>mol_type = protein<br>organism = Homo sapiens | |
| SEQUENCE: 859<br>CQTTCCRTTC | | 10 |

```
SEQ ID NO: 860           moltype = AA  length = 10
FEATURE                  Location/Qualifiers
source                   1..10
                         mol_type = protein
                         organism = Homo sapiens SEQUENCE: 860
CRATCCRPSC                                                              10

SEQ ID NO: 861           moltype = AA  length = 10
FEATURE                  Location/Qualifiers
source                   1..10
                         mol_type = protein
                         organism = Homo sapiens SEQUENCE: 861
CRGCGPSCCA                                                              10

SEQ ID NO: 862           moltype = AA  length = 10
FEATURE                  Location/Qualifiers
source                   1..10
                         mol_type = protein
                         organism = Homo sapiens SEQUENCE: 862
CRPACCETTC                                                              10

SEQ ID NO: 863           moltype = AA  length = 10
FEATURE                  Location/Qualifiers
source                   1..10
                         mol_type = protein
                         organism = Homo sapiens SEQUENCE: 863
CRPACCQNTC                                                              10

SEQ ID NO: 864           moltype = AA  length = 10
FEATURE                  Location/Qualifiers
source                   1..10
                         mol_type = protein
                         organism = Homo sapiens SEQUENCE: 864
CRPCCWATTC                                                              10

SEQ ID NO: 865           moltype = AA  length = 10
FEATURE                  Location/Qualifiers
source                   1..10
                         mol_type = protein
                         organism = Homo sapiens SEQUENCE: 865
CRPICRPACC                                                              10

SEQ ID NO: 866           moltype = AA  length = 10
FEATURE                  Location/Qualifiers
source                   1..10
                         mol_type = protein
                         organism = Homo sapiens SEQUENCE: 866
CRPLCCQTTC                                                              10

SEQ ID NO: 867           moltype = AA  length = 10
FEATURE                  Location/Qualifiers
source                   1..10
                         mol_type = protein
                         organism = Homo sapiens SEQUENCE: 867
CRPQCCQSVC                                                              10

SEQ ID NO: 868           moltype = AA  length = 10
FEATURE                  Location/Qualifiers
source                   1..10
                         mol_type = protein
                         organism = Homo sapiens SEQUENCE: 868
CRPQCCQTTC                                                              10

SEQ ID NO: 869           moltype = AA  length = 10
FEATURE                  Location/Qualifiers
source                   1..10
                         mol_type = protein
                         organism = Homo sapiens

SEQUENCE: 869
```

```
CRPRCCISSC                                                                              10

SEQ ID NO: 870          moltype = AA  length = 10
FEATURE                 Location/Qualifiers
source                  1..10
                        mol_type = protein
                        organism = Homo sapiens SEQUENCE: 870
CRPSCCESSC                                                                              10

SEQ ID NO: 871          moltype = AA  length = 10
FEATURE                 Location/Qualifiers
source                  1..10
                        mol_type = protein
                        organism = Homo sapiens SEQUENCE: 871
CRPSCCETTC                                                                              10

SEQ ID NO: 872          moltype = AA  length = 10
FEATURE                 Location/Qualifiers
source                  1..10
                        mol_type = protein
                        organism = Homo sapiens SEQUENCE: 872
CRPSCCISSC                                                                              10

SEQ ID NO: 873          moltype = AA  length = 10
FEATURE                 Location/Qualifiers
source                  1..10
                        mol_type = protein
                        organism = Homo sapiens SEQUENCE: 873
CRPSCCKPQC                                                                              10

SEQ ID NO: 874          moltype = AA  length = 10
FEATURE                 Location/Qualifiers
source                  1..10
                        mol_type = protein
                        organism = Homo sapiens SEQUENCE: 874
CRPSCCMSSC                                                                              10

SEQ ID NO: 875          moltype = AA  length = 10
FEATURE                 Location/Qualifiers
source                  1..10
                        mol_type = protein
                        organism = Homo sapiens SEQUENCE: 875
CRPSCCQTTC                                                                              10

SEQ ID NO: 876          moltype = AA  length = 10
FEATURE                 Location/Qualifiers
source                  1..10
                        mol_type = protein
                        organism = Homo sapiens SEQUENCE: 876
CRPSCCRPSC                                                                              10

SEQ ID NO: 877          moltype = AA  length = 10
FEATURE                 Location/Qualifiers
source                  1..10
                        mol_type = protein
                        organism = Homo sapiens SEQUENCE: 877
CRPSCCVSRC                                                                              10

SEQ ID NO: 878          moltype = AA  length = 10
FEATURE                 Location/Qualifiers
source                  1..10
                        mol_type = protein
                        organism = Homo sapiens SEQUENCE: 878
CRPSCCVSSC                                                                              10

SEQ ID NO: 879          moltype = AA  length = 10
FEATURE                 Location/Qualifiers
source                  1..10
                        mol_type = protein
                        organism = Homo sapiens
```

```
SEQUENCE: 879
CRPTCCETTC                                                                          10

SEQ ID NO: 880          moltype = AA  length = 10
FEATURE                 Location/Qualifiers
source                  1..10
                        mol_type = protein
                        organism = Homo sapiens
SEQUENCE: 880
CRPTCCQNTC                                                                          10

SEQ ID NO: 881          moltype = AA  length = 10
FEATURE                 Location/Qualifiers
source                  1..10
                        mol_type = protein
                        organism = Homo sapiens
SEQUENCE: 881
CRPTCCQTTC                                                                          10

SEQ ID NO: 882          moltype = AA  length = 10
FEATURE                 Location/Qualifiers
source                  1..10
                        mol_type = protein
                        organism = Homo sapiens
SEQUENCE: 882
CRPVCCDPCS                                                                          10

SEQ ID NO: 883          moltype = AA  length = 10
FEATURE                 Location/Qualifiers
source                  1..10
                        mol_type = protein
                        organism = Homo sapiens
SEQUENCE: 883
CRPVCCQTTC                                                                          10

SEQ ID NO: 884          moltype = AA  length = 10
FEATURE                 Location/Qualifiers
source                  1..10
                        mol_type = protein
                        organism = Homo sapiens
SEQUENCE: 884
CRPVCQPACC                                                                          10

SEQ ID NO: 885          moltype = AA  length = 10
FEATURE                 Location/Qualifiers
source                  1..10
                        mol_type = protein
                        organism = Homo sapiens
SEQUENCE: 885
CRPVCRPACC                                                                          10

SEQ ID NO: 886          moltype = AA  length = 10
FEATURE                 Location/Qualifiers
source                  1..10
                        mol_type = protein
                        organism = Homo sapiens
SEQUENCE: 886
CRPVCRPTCC                                                                          10

SEQ ID NO: 887          moltype = AA  length = 10
FEATURE                 Location/Qualifiers
source                  1..10
                        mol_type = protein
                        organism = Homo sapiens
SEQUENCE: 887
CRPVCRSTCC                                                                          10

SEQ ID NO: 888          moltype = AA  length = 10
FEATURE                 Location/Qualifiers
source                  1..10
                        mol_type = protein
                        organism = Homo sapiens
SEQUENCE: 888
CRPYCCESSC                                                                          10

SEQ ID NO: 889          moltype = AA  length = 10
FEATURE                 Location/Qualifiers
source                  1..10
                        mol_type = protein
```

```
                              organism = Homo sapiens
SEQUENCE: 889
CRRPVCCDPC                                                                    10

SEQ ID NO: 890               moltype = AA  length = 10
FEATURE                      Location/Qualifiers
source                       1..10
                             mol_type = protein
                             organism = Homo sapiens
SEQUENCE: 890
CRSQCCQSVC                                                                    10

SEQ ID NO: 891               moltype = AA  length = 10
FEATURE                      Location/Qualifiers
source                       1..10
                             mol_type = protein
                             organism = Homo sapiens
SEQUENCE: 891
CRTTCCHPSC                                                                    10

SEQ ID NO: 892               moltype = AA  length = 10
FEATURE                      Location/Qualifiers
source                       1..10
                             mol_type = protein
                             organism = Homo sapiens
SEQUENCE: 892
CRTTCCQPIC                                                                    10

SEQ ID NO: 893               moltype = AA  length = 10
FEATURE                      Location/Qualifiers
source                       1..10
                             mol_type = protein
                             organism = Homo sapiens
SEQUENCE: 893
CRTTCCQPTC                                                                    10

SEQ ID NO: 894               moltype = AA  length = 10
FEATURE                      Location/Qualifiers
source                       1..10
                             mol_type = protein
                             organism = Homo sapiens
SEQUENCE: 894
CRTTCCRPSC                                                                    10

SEQ ID NO: 895               moltype = AA  length = 10
FEATURE                      Location/Qualifiers
source                       1..10
                             mol_type = protein
                             organism = Homo sapiens
SEQUENCE: 895
CRTTCCRTTC                                                                    10

SEQ ID NO: 896               moltype = AA  length = 10
FEATURE                      Location/Qualifiers
source                       1..10
                             mol_type = protein
                             organism = Homo sapiens
SEQUENCE: 896
CSCSSCGSCA                                                                    10

SEQ ID NO: 897               moltype = AA  length = 10
FEATURE                      Location/Qualifiers
source                       1..10
                             mol_type = protein
                             organism = Homo sapiens
SEQUENCE: 897
CSCSSCGSCG                                                                    10

SEQ ID NO: 898               moltype = AA  length = 10
FEATURE                      Location/Qualifiers
source                       1..10
                             mol_type = protein
                             organism = Homo sapiens
SEQUENCE: 898
CSCTSCGSCG                                                                    10

SEQ ID NO: 899               moltype = AA  length = 10
FEATURE                      Location/Qualifiers
source                       1..10
```

```
                        mol_type = protein
                        organism = Homo sapiens
SEQUENCE: 899
CSPACQPTCC                                                              10

SEQ ID NO: 900          moltype = AA  length = 10
FEATURE                 Location/Qualifiers
source                  1..10
                        mol_type = protein
                        organism = Homo sapiens
SEQUENCE: 900
CSPGCQPTCC                                                              10

SEQ ID NO: 901          moltype = AA  length = 10
FEATURE                 Location/Qualifiers
source                  1..10
                        mol_type = protein
                        organism = Homo sapiens
SEQUENCE: 901
CSPSCCQTTC                                                              10

SEQ ID NO: 902          moltype = AA  length = 10
FEATURE                 Location/Qualifiers
source                  1..10
                        mol_type = protein
                        organism = Homo sapiens
SEQUENCE: 902
CSQCSCYKPC                                                              10

SEQ ID NO: 903          moltype = AA  length = 10
FEATURE                 Location/Qualifiers
source                  1..10
                        mol_type = protein
                        organism = Homo sapiens
SEQUENCE: 903
CSQSNCCKPC                                                              10

SEQ ID NO: 904          moltype = AA  length = 10
FEATURE                 Location/Qualifiers
source                  1..10
                        mol_type = protein
                        organism = Homo sapiens
SEQUENCE: 904
CSQSSCCKPC                                                              10

SEQ ID NO: 905          moltype = AA  length = 10
FEATURE                 Location/Qualifiers
source                  1..10
                        mol_type = protein
                        organism = Homo sapiens
SEQUENCE: 905
CSSGCGSCCQ                                                              10

SEQ ID NO: 906          moltype = AA  length = 10
FEATURE                 Location/Qualifiers
source                  1..10
                        mol_type = protein
                        organism = Homo sapiens
SEQUENCE: 906
CSSGCGSSCC                                                              10

SEQ ID NO: 907          moltype = AA  length = 10
FEATURE                 Location/Qualifiers
source                  1..10
                        mol_type = protein
                        organism = Homo sapiens
SEQUENCE: 907
CSSGCQPACC                                                              10

SEQ ID NO: 908          moltype = AA  length = 10
FEATURE                 Location/Qualifiers
source                  1..10
                        mol_type = protein
                        organism = Homo sapiens
SEQUENCE: 908
CSSSCCQPSC                                                              10

SEQ ID NO: 909          moltype = AA  length = 10
FEATURE                 Location/Qualifiers
```

```
source                       1..10
                             mol_type = protein
                             organism = Homo sapiens
SEQUENCE: 909
CSTPCCQPTC                                                                      10

SEQ ID NO: 910               moltype = AA  length = 10
FEATURE                      Location/Qualifiers
source                       1..10
                             mol_type = protein
                             organism = Homo sapiens
SEQUENCE: 910
CSTTCCQPIC                                                                      10

SEQ ID NO: 911               moltype = AA  length = 10
FEATURE                      Location/Qualifiers
source                       1..10
                             mol_type = protein
                             organism = Homo sapiens
SEQUENCE: 911
CTAVVCRPCC                                                                      10

SEQ ID NO: 912               moltype = AA  length = 10
FEATURE                      Location/Qualifiers
source                       1..10
                             mol_type = protein
                             organism = Homo sapiens
SEQUENCE: 912
CTDSCTPSCC                                                                      10

SEQ ID NO: 913               moltype = AA  length = 10
FEATURE                      Location/Qualifiers
source                       1..10
                             mol_type = protein
                             organism = Homo sapiens
SEQUENCE: 913
CTPSCCQPAC                                                                      10

SEQ ID NO: 914               moltype = AA  length = 10
FEATURE                      Location/Qualifiers
source                       1..10
                             mol_type = protein
                             organism = Homo sapiens
SEQUENCE: 914
CTRPICEPCC                                                                      10

SEQ ID NO: 915               moltype = AA  length = 10
FEATURE                      Location/Qualifiers
source                       1..10
                             mol_type = protein
                             organism = Homo sapiens
SEQUENCE: 915
CTSSCTPSCC                                                                      10

SEQ ID NO: 916               moltype = AA  length = 10
FEATURE                      Location/Qualifiers
source                       1..10
                             mol_type = protein
                             organism = Homo sapiens
SEQUENCE: 916
CVPACSCSSC                                                                      10

SEQ ID NO: 917               moltype = AA  length = 10
FEATURE                      Location/Qualifiers
source                       1..10
                             mol_type = protein
                             organism = Homo sapiens
SEQUENCE: 917
CVPACSCTSC                                                                      10

SEQ ID NO: 918               moltype = AA  length = 10
FEATURE                      Location/Qualifiers
source                       1..10
                             mol_type = protein
                             organism = Homo sapiens
SEQUENCE: 918
CVPVCCKPVC                                                                      10

SEQ ID NO: 919               moltype = AA  length = 10
```

```
FEATURE              Location/Qualifiers
source               1..10
                     mol_type = protein
                     organism = Homo sapiens
SEQUENCE: 919
CVPVCCVPTC                                                                      10

SEQ ID NO: 920       moltype = AA  length = 10
FEATURE              Location/Qualifiers
source               1..10
                     mol_type = protein
                     organism = Homo sapiens
SEQUENCE: 920
CVPVCCVPVC                                                                      10

SEQ ID NO: 921       moltype = AA  length = 10
FEATURE              Location/Qualifiers
source               1..10
                     mol_type = protein
                     organism = Homo sapiens
SEQUENCE: 921
CVSCVSSPCC                                                                      10

SEQ ID NO: 922       moltype = AA  length = 10
FEATURE              Location/Qualifiers
source               1..10
                     mol_type = protein
                     organism = Homo sapiens
SEQUENCE: 922
CVSRCCRPQC                                                                      10

SEQ ID NO: 923       moltype = AA  length = 10
FEATURE              Location/Qualifiers
source               1..10
                     mol_type = protein
                     organism = Homo sapiens
SEQUENCE: 923
CVSSCCKPQC                                                                      10

SEQ ID NO: 924       moltype = AA  length = 10
FEATURE              Location/Qualifiers
source               1..10
                     mol_type = protein
                     organism = Homo sapiens
SEQUENCE: 924
CVSSCCQHSC                                                                      10

SEQ ID NO: 925       moltype = AA  length = 10
FEATURE              Location/Qualifiers
source               1..10
                     mol_type = protein
                     organism = Homo sapiens
SEQUENCE: 925
CVSSCCQPFC                                                                      10

SEQ ID NO: 926       moltype = AA  length = 10
FEATURE              Location/Qualifiers
source               1..10
                     mol_type = protein
                     organism = Homo sapiens
SEQUENCE: 926
CVSSCCQPSC                                                                      10

SEQ ID NO: 927       moltype = AA  length = 10
FEATURE              Location/Qualifiers
source               1..10
                     mol_type = protein
                     organism = Homo sapiens
SEQUENCE: 927
CVSSCCRPQC                                                                      10

SEQ ID NO: 928       moltype = AA  length = 10
FEATURE              Location/Qualifiers
source               1..10
                     mol_type = protein
                     organism = Homo sapiens
SEQUENCE: 928
CVSTCCRPTC                                                                      10
```

```
SEQ ID NO: 929         moltype = AA  length = 10
FEATURE                Location/Qualifiers
source                 1..10
                       mol_type = protein
                       organism = Homo sapiens
SEQUENCE: 929
CVTRCCSTPC                                                              10

SEQ ID NO: 930         moltype = AA  length = 10
FEATURE                Location/Qualifiers
source                 1..10
                       mol_type = protein
                       organism = Homo sapiens
SEQUENCE: 930
CVTSCCQPAC                                                              10

SEQ ID NO: 931         moltype = AA  length = 10
FEATURE                Location/Qualifiers
source                 1..10
                       mol_type = protein
                       organism = Homo sapiens
SEQUENCE: 931
CVTSCCQPSC                                                              10

SEQ ID NO: 932         moltype = AA  length = 10
FEATURE                Location/Qualifiers
source                 1..10
                       mol_type = protein
                       organism = Homo sapiens
SEQUENCE: 932
CVYSCCQPFC                                                              10

SEQ ID NO: 933         moltype = AA  length = 10
FEATURE                Location/Qualifiers
source                 1..10
                       mol_type = protein
                       organism = Homo sapiens
SEQUENCE: 933
CVYSCCQPSC                                                              10

SEQ ID NO: 934         moltype = AA  length = 10
FEATURE                Location/Qualifiers
source                 1..10
                       mol_type = protein
                       organism = Homo sapiens
SEQUENCE: 934
GCCGCSEGCG                                                              10

SEQ ID NO: 935         moltype = AA  length = 10
FEATURE                Location/Qualifiers
source                 1..10
                       mol_type = protein
                       organism = Homo sapiens
SEQUENCE: 935
GCCGCSGGCG                                                              10

SEQ ID NO: 936         moltype = AA  length = 10
FEATURE                Location/Qualifiers
source                 1..10
                       mol_type = protein
                       organism = Homo sapiens
SEQUENCE: 936
GCCGCSRGCG                                                              10

SEQ ID NO: 937         moltype = AA  length = 10
FEATURE                Location/Qualifiers
source                 1..10
                       mol_type = protein
                       organism = Homo sapiens
SEQUENCE: 937
GCCRPITCCP                                                              10

SEQ ID NO: 938         moltype = AA  length = 10
FEATURE                Location/Qualifiers
source                 1..10
                       mol_type = protein
                       organism = Homo sapiens
SEQUENCE: 938
GCGSSCCQCS                                                              10
```

```
SEQ ID NO: 939            moltype = AA   length = 10
FEATURE                   Location/Qualifiers
source                    1..10
                          mol_type = protein
                          organism = Homo sapiens SEQUENCE: 939
GCGVPVCCCS                                                                10

SEQ ID NO: 940            moltype = AA   length = 10
FEATURE                   Location/Qualifiers
source                    1..10
                          mol_type = protein
                          organism = Homo sapiens SEQUENCE: 940
LCCPCQTTCS                                                                10

SEQ ID NO: 941            moltype = AA   length = 10
FEATURE                   Location/Qualifiers
source                    1..10
                          mol_type = protein
                          organism = Homo sapiens SEQUENCE: 941
PCCCLRPVCG                                                                10

SEQ ID NO: 942            moltype = AA   length = 10
FEATURE                   Location/Qualifiers
source                    1..10
                          mol_type = protein
                          organism = Homo sapiens SEQUENCE: 942
PCCCRPVTCQ                                                                10

SEQ ID NO: 943            moltype = AA   length = 10
FEATURE                   Location/Qualifiers
source                    1..10
                          mol_type = protein
                          organism = Homo sapiens SEQUENCE: 943
PCCCVRPVCG                                                                10

SEQ ID NO: 944            moltype = AA   length = 10
FEATURE                   Location/Qualifiers
source                    1..10
                          mol_type = protein
                          organism = Homo sapiens SEQUENCE: 944
PCCSQASCCV                                                                10

SEQ ID NO: 945            moltype = AA   length = 10
FEATURE                   Location/Qualifiers
source                    1..10
                          mol_type = protein
                          organism = Homo sapiens SEQUENCE: 945
PCCSQSRCCV                                                                10

SEQ ID NO: 946            moltype = AA   length = 10
FEATURE                   Location/Qualifiers
source                    1..10
                          mol_type = protein
                          organism = Homo sapiens SEQUENCE: 946
PCCSQSSCCK                                                                10

SEQ ID NO: 947            moltype = AA   length = 10
FEATURE                   Location/Qualifiers
source                    1..10
                          mol_type = protein
                          organism = Homo sapiens SEQUENCE: 947
PCCSQSSCCV                                                                10

SEQ ID NO: 948            moltype = AA   length = 10
FEATURE                   Location/Qualifiers
source                    1..10
                          mol_type = protein
                          organism = Homo sapiens

SEQUENCE: 948
```

```
PCCWATTCCQ                                                                          10

SEQ ID NO: 949           moltype = AA   length = 10
FEATURE                  Location/Qualifiers
source                   1..10
                         mol_type = protein
                         organism = Homo sapiens SEQUENCE: 949
QCSCCKPYCS                                                                          10

SEQ ID NO: 950           moltype = AA   length = 10
FEATURE                  Location/Qualifiers
source                   1..10
                         mol_type = protein
                         organism = Homo sapiens SEQUENCE: 950
RCYVPVCCCK                                                                          10

SEQ ID NO: 951           moltype = AA   length = 10
FEATURE                  Location/Qualifiers
source                   1..10
                         mol_type = protein
                         organism = Homo sapiens SEQUENCE: 951
SCCAPVYCCK                                                                          10

SEQ ID NO: 952           moltype = AA   length = 10
FEATURE                  Location/Qualifiers
source                   1..10
                         mol_type = protein
                         organism = Homo sapiens SEQUENCE: 952
SCCISSSCCP                                                                          10

SEQ ID NO: 953           moltype = AA   length = 10
FEATURE                  Location/Qualifiers
source                   1..10
                         mol_type = protein
                         organism = Homo sapiens SEQUENCE: 953
SCCVSSCRCP                                                                          10

SEQ ID NO: 954           moltype = AA   length = 10
FEATURE                  Location/Qualifiers
source                   1..10
                         mol_type = protein
                         organism = Homo sapiens SEQUENCE: 954
SCGCSQCSCY                                                                          10

SEQ ID NO: 955           moltype = AA   length = 10
FEATURE                  Location/Qualifiers
source                   1..10
                         mol_type = protein
                         organism = Homo sapiens SEQUENCE: 955
SCGLENCCCP                                                                          10

SEQ ID NO: 956           moltype = AA   length = 10
FEATURE                  Location/Qualifiers
source                   1..10
                         mol_type = protein
                         organism = Homo sapiens SEQUENCE: 956
VCCGASSCCQ                                                                          10

SEQ ID NO: 957           moltype = AA   length = 10
FEATURE                  Location/Qualifiers
source                   1..10
                         mol_type = protein
                         organism = Homo sapiens SEQUENCE: 957
VCCGDSSCCQ                                                                          10

SEQ ID NO: 958           moltype = AA   length = 11
FEATURE                  Location/Qualifiers
source                   1..11
                         mol_type = protein
                         organism = Homo sapiens
```

| | | |
|---|---|---|
| SEQUENCE: 958 CASSCCTPSC C | | 11 |
| SEQ ID NO: 959 FEATURE source | moltype = AA  length = 11 Location/Qualifiers 1..11 mol_type = protein organism = Homo sapiens | |
| SEQUENCE: 959 CCCPSCVVSS C | | 11 |
| SEQ ID NO: 960 FEATURE source | moltype = AA  length = 11 Location/Qualifiers 1..11 mol_type = protein organism = Homo sapiens | |
| SEQUENCE: 960 CCCPSYCVSS C | | 11 |
| SEQ ID NO: 961 FEATURE source | moltype = AA  length = 11 Location/Qualifiers 1..11 mol_type = protein organism = Homo sapiens | |
| SEQUENCE: 961 CCCSSGCGSS C | | 11 |
| SEQ ID NO: 962 FEATURE source | moltype = AA  length = 11 Location/Qualifiers 1..11 mol_type = protein organism = Homo sapiens | |
| SEQUENCE: 962 CCDTCPPPCC K | | 11 |
| SEQ ID NO: 963 FEATURE source | moltype = AA  length = 11 Location/Qualifiers 1..11 mol_type = protein organism = Homo sapiens | |
| SEQUENCE: 963 CCEPHCCALS C | | 11 |
| SEQ ID NO: 964 FEATURE source | moltype = AA  length = 11 Location/Qualifiers 1..11 mol_type = protein organism = Homo sapiens | |
| SEQUENCE: 964 CCEPPCCAPS C | | 11 |
| SEQ ID NO: 965 FEATURE source | moltype = AA  length = 11 Location/Qualifiers 1..11 mol_type = protein organism = Homo sapiens | |
| SEQUENCE: 965 CCEPPCCATS C | | 11 |
| SEQ ID NO: 966 FEATURE source | moltype = AA  length = 11 Location/Qualifiers 1..11 mol_type = protein organism = Homo sapiens | |
| SEQUENCE: 966 CCETSCCQPS C | | 11 |
| SEQ ID NO: 967 FEATURE source | moltype = AA  length = 11 Location/Qualifiers 1..11 mol_type = protein organism = Homo sapiens | |
| SEQUENCE: 967 CCGSSCCGSG C | | 11 |
| SEQ ID NO: 968 FEATURE source | moltype = AA  length = 11 Location/Qualifiers 1..11 mol_type = protein | |

```
                              organism = Homo sapiens
SEQUENCE: 968
CCGSSCCGSS C                                                              11

SEQ ID NO: 969           moltype = AA   length = 11
FEATURE                  Location/Qualifiers
source                   1..11
                         mol_type = protein
                         organism = Homo sapiens
SEQUENCE: 969
CCHPRCCISS C                                                              11

SEQ ID NO: 970           moltype = AA   length = 11
FEATURE                  Location/Qualifiers
source                   1..11
                         mol_type = protein
                         organism = Homo sapiens
SEQUENCE: 970
CCHPSCCESS C                                                              11

SEQ ID NO: 971           moltype = AA   length = 11
FEATURE                  Location/Qualifiers
source                   1..11
                         mol_type = protein
                         organism = Homo sapiens
SEQUENCE: 971
CCHPSCCISS C                                                              11

SEQ ID NO: 972           moltype = AA   length = 11
FEATURE                  Location/Qualifiers
source                   1..11
                         mol_type = protein
                         organism = Homo sapiens
SEQUENCE: 972
CCHPSCCVSS C                                                              11

SEQ ID NO: 973           moltype = AA   length = 11
FEATURE                  Location/Qualifiers
source                   1..11
                         mol_type = protein
                         organism = Homo sapiens
SEQUENCE: 973
CCHPTCCQNT C                                                              11

SEQ ID NO: 974           moltype = AA   length = 11
FEATURE                  Location/Qualifiers
source                   1..11
                         mol_type = protein
                         organism = Homo sapiens
SEQUENCE: 974
CCHPTCCQTI C                                                              11

SEQ ID NO: 975           moltype = AA   length = 11
FEATURE                  Location/Qualifiers
source                   1..11
                         mol_type = protein
                         organism = Homo sapiens
SEQUENCE: 975
CCISSCCKPS C                                                              11

SEQ ID NO: 976           moltype = AA   length = 11
FEATURE                  Location/Qualifiers
source                   1..11
                         mol_type = protein
                         organism = Homo sapiens
SEQUENCE: 976
CCISSCCRPS C                                                              11

SEQ ID NO: 977           moltype = AA   length = 11
FEATURE                  Location/Qualifiers
source                   1..11
                         mol_type = protein
                         organism = Homo sapiens
SEQUENCE: 977
CCISSSCCPS C                                                              11

SEQ ID NO: 978           moltype = AA   length = 11
FEATURE                  Location/Qualifiers
source                   1..11
```

```
                         mol_type = protein
                         organism = Homo sapiens
SEQUENCE: 978
CCKAVCCVPT C                                                            11

SEQ ID NO: 979           moltype = AA  length = 11
FEATURE                  Location/Qualifiers
source                   1..11
                         mol_type = protein
                         organism = Homo sapiens
SEQUENCE: 979
CCKPCCSQAS C                                                            11

SEQ ID NO: 980           moltype = AA  length = 11
FEATURE                  Location/Qualifiers
source                   1..11
                         mol_type = protein
                         organism = Homo sapiens
SEQUENCE: 980
CCKPCCSQSR C                                                            11

SEQ ID NO: 981           moltype = AA  length = 11
FEATURE                  Location/Qualifiers
source                   1..11
                         mol_type = protein
                         organism = Homo sapiens
SEQUENCE: 981
CCKPCCSQSS C                                                            11

SEQ ID NO: 982           moltype = AA  length = 11
FEATURE                  Location/Qualifiers
source                   1..11
                         mol_type = protein
                         organism = Homo sapiens
SEQUENCE: 982
CCKPCCSSSG C                                                            11

SEQ ID NO: 983           moltype = AA  length = 11
FEATURE                  Location/Qualifiers
source                   1..11
                         mol_type = protein
                         organism = Homo sapiens
SEQUENCE: 983
CCKPCSCFSG C                                                            11

SEQ ID NO: 984           moltype = AA  length = 11
FEATURE                  Location/Qualifiers
source                   1..11
                         mol_type = protein
                         organism = Homo sapiens
SEQUENCE: 984
CCKPCSCSSG C                                                            11

SEQ ID NO: 985           moltype = AA  length = 11
FEATURE                  Location/Qualifiers
source                   1..11
                         mol_type = protein
                         organism = Homo sapiens
SEQUENCE: 985
CCKPCYCSSG C                                                            11

SEQ ID NO: 986           moltype = AA  length = 11
FEATURE                  Location/Qualifiers
source                   1..11
                         mol_type = protein
                         organism = Homo sapiens
SEQUENCE: 986
CCKPICCVPV C                                                            11

SEQ ID NO: 987           moltype = AA  length = 11
FEATURE                  Location/Qualifiers
source                   1..11
                         mol_type = protein
                         organism = Homo sapiens
SEQUENCE: 987
CCKPQCCQSV C                                                            11

SEQ ID NO: 988           moltype = AA  length = 11
FEATURE                  Location/Qualifiers
```

-continued

| | | |
|---|---|---|
| source | 1..11<br>mol_type = protein<br>organism = Homo sapiens | |
| SEQUENCE: 988<br>CCKPVCCKPI C | | 11 |
| SEQ ID NO: 989<br>FEATURE<br>source | moltype = AA   length = 11<br>Location/Qualifiers<br>1..11<br>mol_type = protein<br>organism = Homo sapiens | |
| SEQUENCE: 989<br>CCKPYCCQSS C | | 11 |
| SEQ ID NO: 990<br>FEATURE<br>source | moltype = AA   length = 11<br>Location/Qualifiers<br>1..11<br>mol_type = protein<br>organism = Homo sapiens | |
| SEQUENCE: 990<br>CCKPYCSQCS C | | 11 |
| SEQ ID NO: 991<br>FEATURE<br>source | moltype = AA   length = 11<br>Location/Qualifiers<br>1..11<br>mol_type = protein<br>organism = Homo sapiens | |
| SEQUENCE: 991<br>CCMPVCCKPV C | | 11 |
| SEQ ID NO: 992<br>FEATURE<br>source | moltype = AA   length = 11<br>Location/Qualifiers<br>1..11<br>mol_type = protein<br>organism = Homo sapiens | |
| SEQUENCE: 992<br>CCMPVCCKTV C | | 11 |
| SEQ ID NO: 993<br>FEATURE<br>source | moltype = AA   length = 11<br>Location/Qualifiers<br>1..11<br>mol_type = protein<br>organism = Homo sapiens | |
| SEQUENCE: 993<br>CCMSSCCKPQ C | | 11 |
| SEQ ID NO: 994<br>FEATURE<br>source | moltype = AA   length = 11<br>Location/Qualifiers<br>1..11<br>mol_type = protein<br>organism = Homo sapiens | |
| SEQUENCE: 994<br>CCNPCCSQSS C | | 11 |
| SEQ ID NO: 995<br>FEATURE<br>source | moltype = AA   length = 11<br>Location/Qualifiers<br>1..11<br>mol_type = protein<br>organism = Homo sapiens | |
| SEQUENCE: 995<br>CCPGDCFTCC T | | 11 |
| SEQ ID NO: 996<br>FEATURE<br>source | moltype = AA   length = 11<br>Location/Qualifiers<br>1..11<br>mol_type = protein<br>organism = Homo sapiens | |
| SEQUENCE: 996<br>CCPSCVVSSC C | | 11 |
| SEQ ID NO: 997<br>FEATURE<br>source | moltype = AA   length = 11<br>Location/Qualifiers<br>1..11<br>mol_type = protein<br>organism = Homo sapiens | |
| SEQUENCE: 997<br>CCPSYCVSSC C | | 11 |
| SEQ ID NO: 998 | moltype = AA   length = 11 | |

```
FEATURE                 Location/Qualifiers
source                  1..11
                        mol_type = protein
                        organism = Homo sapiens
SEQUENCE: 998
CCQNTCCRTT C                                                                    11

SEQ ID NO: 999          moltype = AA  length = 11
FEATURE                 Location/Qualifiers
source                  1..11
                        mol_type = protein
                        organism = Homo sapiens
SEQUENCE: 999
CCQPACCVSS C                                                                    11

SEQ ID NO: 1000         moltype = AA  length = 11
FEATURE                 Location/Qualifiers
source                  1..11
                        mol_type = protein
                        organism = Homo sapiens
SEQUENCE: 1000
CCQPCCHPTC Y                                                                    11

SEQ ID NO: 1001         moltype = AA  length = 11
FEATURE                 Location/Qualifiers
source                  1..11
                        mol_type = protein
                        organism = Homo sapiens
SEQUENCE: 1001
CCQPCCRPTS C                                                                    11

SEQ ID NO: 1002         moltype = AA  length = 11
FEATURE                 Location/Qualifiers
source                  1..11
                        mol_type = protein
                        organism = Homo sapiens
SEQUENCE: 1002
CCQPICGSSC C                                                                    11

SEQ ID NO: 1003         moltype = AA  length = 11
FEATURE                 Location/Qualifiers
source                  1..11
                        mol_type = protein
                        organism = Homo sapiens
SEQUENCE: 1003
CCQPICVTSC C                                                                    11

SEQ ID NO: 1004         moltype = AA  length = 11
FEATURE                 Location/Qualifiers
source                  1..11
                        mol_type = protein
                        organism = Homo sapiens
SEQUENCE: 1004
CCQPNCCRPS C                                                                    11

SEQ ID NO: 1005         moltype = AA  length = 11
FEATURE                 Location/Qualifiers
source                  1..11
                        mol_type = protein
                        organism = Homo sapiens
SEQUENCE: 1005
CCQPSCCETS C                                                                    11

SEQ ID NO: 1006         moltype = AA  length = 11
FEATURE                 Location/Qualifiers
source                  1..11
                        mol_type = protein
                        organism = Homo sapiens
SEQUENCE: 1006
CCQPSCCRPA C                                                                    11

SEQ ID NO: 1007         moltype = AA  length = 11
FEATURE                 Location/Qualifiers
source                  1..11
                        mol_type = protein
                        organism = Homo sapiens
SEQUENCE: 1007
CCQPSCCSTP C                                                                    11
```

```
SEQ ID NO: 1008          moltype = AA  length = 11
FEATURE                  Location/Qualifiers
source                   1..11
                         mol_type = protein
                         organism = Homo sapiens
SEQUENCE: 1008
CCQPSCCSTT C                                                              11

SEQ ID NO: 1009          moltype = AA  length = 11
FEATURE                  Location/Qualifiers
source                   1..11
                         mol_type = protein
                         organism = Homo sapiens
SEQUENCE: 1009
CCQPSCCVPS C                                                              11

SEQ ID NO: 1010          moltype = AA  length = 11
FEATURE                  Location/Qualifiers
source                   1..11
                         mol_type = protein
                         organism = Homo sapiens
SEQUENCE: 1010
CCQPSCCVSS C                                                              11

SEQ ID NO: 1011          moltype = AA  length = 11
FEATURE                  Location/Qualifiers
source                   1..11
                         mol_type = protein
                         organism = Homo sapiens
SEQUENCE: 1011
CCQPTCCHPS C                                                              11

SEQ ID NO: 1012          moltype = AA  length = 11
FEATURE                  Location/Qualifiers
source                   1..11
                         mol_type = protein
                         organism = Homo sapiens
SEQUENCE: 1012
CCQPTCCQPT C                                                              11

SEQ ID NO: 1013          moltype = AA  length = 11
FEATURE                  Location/Qualifiers
source                   1..11
                         mol_type = protein
                         organism = Homo sapiens
SEQUENCE: 1013
CCQPTCCRPR C                                                              11

SEQ ID NO: 1014          moltype = AA  length = 11
FEATURE                  Location/Qualifiers
source                   1..11
                         mol_type = protein
                         organism = Homo sapiens
SEQUENCE: 1014
CCQPTCCRPS C                                                              11

SEQ ID NO: 1015          moltype = AA  length = 11
FEATURE                  Location/Qualifiers
source                   1..11
                         mol_type = protein
                         organism = Homo sapiens
SEQUENCE: 1015
CCQPTCCRPT C                                                              11

SEQ ID NO: 1016          moltype = AA  length = 11
FEATURE                  Location/Qualifiers
source                   1..11
                         mol_type = protein
                         organism = Homo sapiens
SEQUENCE: 1016
CCQPTCCRTT C                                                              11

SEQ ID NO: 1017          moltype = AA  length = 11
FEATURE                  Location/Qualifiers
source                   1..11
                         mol_type = protein
                         organism = Homo sapiens
SEQUENCE: 1017
CCQPTCLSSC C                                                              11
```

```
SEQ ID NO: 1018              moltype = AA   length = 11
FEATURE                      Location/Qualifiers
source                       1..11
                             mol_type = protein
                             organism = Homo sapiens
SEQUENCE: 1018
CCQPTCLTSC C                                                                    11

SEQ ID NO: 1019              moltype = AA   length = 11
FEATURE                      Location/Qualifiers
source                       1..11
                             mol_type = protein
                             organism = Homo sapiens
SEQUENCE: 1019
CCQPTCVASC C                                                                    11

SEQ ID NO: 1020              moltype = AA   length = 11
FEATURE                      Location/Qualifiers
source                       1..11
                             mol_type = protein
                             organism = Homo sapiens
SEQUENCE: 1020
CCQPTCVTSC C                                                                    11

SEQ ID NO: 1021              moltype = AA   length = 11
FEATURE                      Location/Qualifiers
source                       1..11
                             mol_type = protein
                             organism = Homo sapiens
SEQUENCE: 1021
CCQPYCHPTC C                                                                    11

SEQ ID NO: 1022              moltype = AA   length = 11
FEATURE                      Location/Qualifiers
source                       1..11
                             mol_type = protein
                             organism = Homo sapiens
SEQUENCE: 1022
CCQSMCCQPT C                                                                    11

SEQ ID NO: 1023              moltype = AA   length = 11
FEATURE                      Location/Qualifiers
source                       1..11
                             mol_type = protein
                             organism = Homo sapiens
SEQUENCE: 1023
CCQSNCCVPV C                                                                    11

SEQ ID NO: 1024              moltype = AA   length = 11
FEATURE                      Location/Qualifiers
source                       1..11
                             mol_type = protein
                             organism = Homo sapiens
SEQUENCE: 1024
CCQSSCCKPC S                                                                    11

SEQ ID NO: 1025              moltype = AA   length = 11
FEATURE                      Location/Qualifiers
source                       1..11
                             mol_type = protein
                             organism = Homo sapiens
SEQUENCE: 1025
CCQSSCCKPS C                                                                    11

SEQ ID NO: 1026              moltype = AA   length = 11
FEATURE                      Location/Qualifiers
source                       1..11
                             mol_type = protein
                             organism = Homo sapiens
SEQUENCE: 1026
CCQSSCCKPY C                                                                    11

SEQ ID NO: 1027              moltype = AA   length = 11
FEATURE                      Location/Qualifiers
source                       1..11
                             mol_type = protein
                             organism = Homo sapiens
SEQUENCE: 1027
```

-continued

CCQSSCCQSS C                                                                                              11

SEQ ID NO: 1028         moltype = AA   length = 11
FEATURE                 Location/Qualifiers
source                  1..11
                        mol_type = protein
                        organism = Homo sapiens SEQUENCE: 1028
CCQSSCCVPV C                                                                                              11

SEQ ID NO: 1029         moltype = AA   length = 11
FEATURE                 Location/Qualifiers
source                  1..11
                        mol_type = protein
                        organism = Homo sapiens SEQUENCE: 1029
CCQSSCFKPC C                                                                                              11

SEQ ID NO: 1030         moltype = AA   length = 11
FEATURE                 Location/Qualifiers
source                  1..11
                        mol_type = protein
                        organism = Homo sapiens SEQUENCE: 1030
CCQSSCSKPC C                                                                                              11

SEQ ID NO: 1031         moltype = AA   length = 11
FEATURE                 Location/Qualifiers
source                  1..11
                        mol_type = protein
                        organism = Homo sapiens SEQUENCE: 1031
CCQSSCYKPC C                                                                                              11

SEQ ID NO: 1032         moltype = AA   length = 11
FEATURE                 Location/Qualifiers
source                  1..11
                        mol_type = protein
                        organism = Homo sapiens SEQUENCE: 1032
CCQSVCCQPT C                                                                                              11

SEQ ID NO: 1033         moltype = AA   length = 11
FEATURE                 Location/Qualifiers
source                  1..11
                        mol_type = protein
                        organism = Homo sapiens SEQUENCE: 1033
CCQTICRSTC C                                                                                              11

SEQ ID NO: 1034         moltype = AA   length = 11
FEATURE                 Location/Qualifiers
source                  1..11
                        mol_type = protein
                        organism = Homo sapiens SEQUENCE: 1034
CCQTTCCRPS C                                                                                              11

SEQ ID NO: 1035         moltype = AA   length = 11
FEATURE                 Location/Qualifiers
source                  1..11
                        mol_type = protein
                        organism = Homo sapiens SEQUENCE: 1035
CCQTTCCRTT C                                                                                              11

SEQ ID NO: 1036         moltype = AA   length = 11
FEATURE                 Location/Qualifiers
source                  1..11
                        mol_type = protein
                        organism = Homo sapiens SEQUENCE: 1036
CCRPACCETT C                                                                                              11

SEQ ID NO: 1037         moltype = AA   length = 11
FEATURE                 Location/Qualifiers
source                  1..11
                        mol_type = protein
                        organism = Homo sapiens -continued

```
SEQUENCE: 1037
CCRPACCQNT C                                                                 11

SEQ ID NO: 1038         moltype = AA  length = 11
FEATURE                 Location/Qualifiers
source                  1..11
                        mol_type = protein
                        organism = Homo sapiens
SEQUENCE: 1038
CCRPLCCQTT C                                                                 11

SEQ ID NO: 1039         moltype = AA  length = 11
FEATURE                 Location/Qualifiers
source                  1..11
                        mol_type = protein
                        organism = Homo sapiens
SEQUENCE: 1039
CCRPQCCQSV C                                                                 11

SEQ ID NO: 1040         moltype = AA  length = 11
FEATURE                 Location/Qualifiers
source                  1..11
                        mol_type = protein
                        organism = Homo sapiens
SEQUENCE: 1040
CCRPQCCQTT C                                                                 11

SEQ ID NO: 1041         moltype = AA  length = 11
FEATURE                 Location/Qualifiers
source                  1..11
                        mol_type = protein
                        organism = Homo sapiens
SEQUENCE: 1041
CCRPSCCESS C                                                                 11

SEQ ID NO: 1042         moltype = AA  length = 11
FEATURE                 Location/Qualifiers
source                  1..11
                        mol_type = protein
                        organism = Homo sapiens
SEQUENCE: 1042
CCRPSCCETT C                                                                 11

SEQ ID NO: 1043         moltype = AA  length = 11
FEATURE                 Location/Qualifiers
source                  1..11
                        mol_type = protein
                        organism = Homo sapiens
SEQUENCE: 1043
CCRPSCCGSS C                                                                 11

SEQ ID NO: 1044         moltype = AA  length = 11
FEATURE                 Location/Qualifiers
source                  1..11
                        mol_type = protein
                        organism = Homo sapiens
SEQUENCE: 1044
CCRPSCCISS C                                                                 11

SEQ ID NO: 1045         moltype = AA  length = 11
FEATURE                 Location/Qualifiers
source                  1..11
                        mol_type = protein
                        organism = Homo sapiens
SEQUENCE: 1045
CCRPSCCKPQ C                                                                 11

SEQ ID NO: 1046         moltype = AA  length = 11
FEATURE                 Location/Qualifiers
source                  1..11
                        mol_type = protein
                        organism = Homo sapiens
SEQUENCE: 1046
CCRPSCCQTT C                                                                 11

SEQ ID NO: 1047         moltype = AA  length = 11
FEATURE                 Location/Qualifiers
source                  1..11
                        mol_type = protein
```

```
                              organism = Homo sapiens
SEQUENCE: 1047
CCRPSCCVSR C                                                               11

SEQ ID NO: 1048       moltype = AA   length = 11
FEATURE               Location/Qualifiers
source                1..11
                      mol_type = protein
                      organism = Homo sapiens
SEQUENCE: 1048
CCRPSCCVSS C                                                               11

SEQ ID NO: 1049       moltype = AA   length = 11
FEATURE               Location/Qualifiers
source                1..11
                      mol_type = protein
                      organism = Homo sapiens
SEQUENCE: 1049
CCRPTCCQNT C                                                               11

SEQ ID NO: 1050       moltype = AA   length = 11
FEATURE               Location/Qualifiers
source                1..11
                      mol_type = protein
                      organism = Homo sapiens
SEQUENCE: 1050
CCRPTCCQTT C                                                               11

SEQ ID NO: 1051       moltype = AA   length = 11
FEATURE               Location/Qualifiers
source                1..11
                      mol_type = protein
                      organism = Homo sapiens
SEQUENCE: 1051
CCRPVCCDPC S                                                               11

SEQ ID NO: 1052       moltype = AA   length = 11
FEATURE               Location/Qualifiers
source                1..11
                      mol_type = protein
                      organism = Homo sapiens
SEQUENCE: 1052
CCRTTCCQPT C                                                               11

SEQ ID NO: 1053       moltype = AA   length = 11
FEATURE               Location/Qualifiers
source                1..11
                      mol_type = protein
                      organism = Homo sapiens
SEQUENCE: 1053
CCRTTCCRPS C                                                               11

SEQ ID NO: 1054       moltype = AA   length = 11
FEATURE               Location/Qualifiers
source                1..11
                      mol_type = protein
                      organism = Homo sapiens
SEQUENCE: 1054
CCRTTCCRTT C                                                               11

SEQ ID NO: 1055       moltype = AA   length = 11
FEATURE               Location/Qualifiers
source                1..11
                      mol_type = protein
                      organism = Homo sapiens
SEQUENCE: 1055
CCSCSSCGSC A                                                               11

SEQ ID NO: 1056       moltype = AA   length = 11
FEATURE               Location/Qualifiers
source                1..11
                      mol_type = protein
                      organism = Homo sapiens
SEQUENCE: 1056
CCSPGCQPTC C                                                               11

SEQ ID NO: 1057       moltype = AA   length = 11
FEATURE               Location/Qualifiers
source                1..11
```

-continued

```
                        mol_type = protein
                        organism = Homo sapiens
SEQUENCE: 1057
CCSQSSCCKP C                                                            11

SEQ ID NO: 1058         moltype = AA   length = 11
FEATURE                 Location/Qualifiers
source                  1..11
                        mol_type = protein
                        organism = Homo sapiens
SEQUENCE: 1058
CCSSGCGSCC Q                                                            11

SEQ ID NO: 1059         moltype = AA   length = 11
FEATURE                 Location/Qualifiers
source                  1..11
                        mol_type = protein
                        organism = Homo sapiens
SEQUENCE: 1059
CCSSGCGSSC C                                                            11

SEQ ID NO: 1060         moltype = AA   length = 11
FEATURE                 Location/Qualifiers
source                  1..11
                        mol_type = protein
                        organism = Homo sapiens
SEQUENCE: 1060
CCSTPCCQPT C                                                            11

SEQ ID NO: 1061         moltype = AA   length = 11
FEATURE                 Location/Qualifiers
source                  1..11
                        mol_type = protein
                        organism = Homo sapiens
SEQUENCE: 1061
CCVPACSCSS C                                                            11

SEQ ID NO: 1062         moltype = AA   length = 11
FEATURE                 Location/Qualifiers
source                  1..11
                        mol_type = protein
                        organism = Homo sapiens
SEQUENCE: 1062
CCVPACSCTS C                                                            11

SEQ ID NO: 1063         moltype = AA   length = 11
FEATURE                 Location/Qualifiers
source                  1..11
                        mol_type = protein
                        organism = Homo sapiens
SEQUENCE: 1063
CCVPICCKPI C                                                            11

SEQ ID NO: 1064         moltype = AA   length = 11
FEATURE                 Location/Qualifiers
source                  1..11
                        mol_type = protein
                        organism = Homo sapiens
SEQUENCE: 1064
CCVPICCKPV C                                                            11

SEQ ID NO: 1065         moltype = AA   length = 11
FEATURE                 Location/Qualifiers
source                  1..11
                        mol_type = protein
                        organism = Homo sapiens
SEQUENCE: 1065
CCVPVCCKPI C                                                            11

SEQ ID NO: 1066         moltype = AA   length = 11
FEATURE                 Location/Qualifiers
source                  1..11
                        mol_type = protein
                        organism = Homo sapiens
SEQUENCE: 1066
CCVPVCCKPV C                                                            11

SEQ ID NO: 1067         moltype = AA   length = 11
FEATURE                 Location/Qualifiers
```

```
source                      1..11
                            mol_type = protein
                            organism = Homo sapiens
SEQUENCE: 1067
CCVPVCCKSN C                                                                                   11

SEQ ID NO: 1068             moltype = AA   length = 11
FEATURE                     Location/Qualifiers
source                      1..11
                            mol_type = protein
                            organism = Homo sapiens
SEQUENCE: 1068
CCVPVCCKTV C                                                                                   11

SEQ ID NO: 1069             moltype = AA   length = 11
FEATURE                     Location/Qualifiers
source                      1..11
                            mol_type = protein
                            organism = Homo sapiens
SEQUENCE: 1069
CCVPVCCSSS C                                                                                   11

SEQ ID NO: 1070             moltype = AA   length = 11
FEATURE                     Location/Qualifiers
source                      1..11
                            mol_type = protein
                            organism = Homo sapiens
SEQUENCE: 1070
CCVPVCCVPV C                                                                                   11

SEQ ID NO: 1071             moltype = AA   length = 11
FEATURE                     Location/Qualifiers
source                      1..11
                            mol_type = protein
                            organism = Homo sapiens
SEQUENCE: 1071
CCVSSCCKPQ C                                                                                   11

SEQ ID NO: 1072             moltype = AA   length = 11
FEATURE                     Location/Qualifiers
source                      1..11
                            mol_type = protein
                            organism = Homo sapiens
SEQUENCE: 1072
CCVSSCCQHS C                                                                                   11

SEQ ID NO: 1073             moltype = AA   length = 11
FEATURE                     Location/Qualifiers
source                      1..11
                            mol_type = protein
                            organism = Homo sapiens
SEQUENCE: 1073
CCVSSCCQPS C                                                                                   11

SEQ ID NO: 1074             moltype = AA   length = 11
FEATURE                     Location/Qualifiers
source                      1..11
                            mol_type = protein
                            organism = Homo sapiens
SEQUENCE: 1074
CCVSSCCRPQ C                                                                                   11

SEQ ID NO: 1075             moltype = AA   length = 11
FEATURE                     Location/Qualifiers
source                      1..11
                            mol_type = protein
                            organism = Homo sapiens
SEQUENCE: 1075
CCVSTCCRPT C                                                                                   11

SEQ ID NO: 1076             moltype = AA   length = 11
FEATURE                     Location/Qualifiers
source                      1..11
                            mol_type = protein
                            organism = Homo sapiens
SEQUENCE: 1076
CCVSVCCKPV C                                                                                   11

SEQ ID NO: 1077             moltype = AA   length = 11
```

```
FEATURE                 Location/Qualifiers
source                  1..11
                        mol_type = protein
                        organism = Homo sapiens
SEQUENCE: 1077
CDSSCCQPSC C                                                                    11

SEQ ID NO: 1078         moltype = AA   length = 11
FEATURE                 Location/Qualifiers
source                  1..11
                        mol_type = protein
                        organism = Homo sapiens
SEQUENCE: 1078
CEPCCRPVCC D                                                                    11

SEQ ID NO: 1079         moltype = AA   length = 11
FEATURE                 Location/Qualifiers
source                  1..11
                        mol_type = protein
                        organism = Homo sapiens
SEQUENCE: 1079
CFKPCCCQSS C                                                                    11

SEQ ID NO: 1080         moltype = AA   length = 11
FEATURE                 Location/Qualifiers
source                  1..11
                        mol_type = protein
                        organism = Homo sapiens
SEQUENCE: 1080
CGDGCCCPSC Y                                                                    11

SEQ ID NO: 1081         moltype = AA   length = 11
FEATURE                 Location/Qualifiers
source                  1..11
                        mol_type = protein
                        organism = Homo sapiens
SEQUENCE: 1081
CGGGCCGSSC C                                                                    11

SEQ ID NO: 1082         moltype = AA   length = 11
FEATURE                 Location/Qualifiers
source                  1..11
                        mol_type = protein
                        organism = Homo sapiens
SEQUENCE: 1082
CGGSCCGSSC C                                                                    11

SEQ ID NO: 1083         moltype = AA   length = 11
FEATURE                 Location/Qualifiers
source                  1..11
                        mol_type = protein
                        organism = Homo sapiens
SEQUENCE: 1083
CGLENCCCPS C                                                                    11

SEQ ID NO: 1084         moltype = AA   length = 11
FEATURE                 Location/Qualifiers
source                  1..11
                        mol_type = protein
                        organism = Homo sapiens
SEQUENCE: 1084
CGQSCCRPAC C                                                                    11

SEQ ID NO: 1085         moltype = AA   length = 11
FEATURE                 Location/Qualifiers
source                  1..11
                        mol_type = protein
                        organism = Homo sapiens
SEQUENCE: 1085
CGQSCCRPVC C                                                                    11

SEQ ID NO: 1086         moltype = AA   length = 11
FEATURE                 Location/Qualifiers
source                  1..11
                        mol_type = protein
                        organism = Homo sapiens
SEQUENCE: 1086
CGSCCQSSCC N                                                                    11
```

```
SEQ ID NO: 1087         moltype = AA   length = 11
FEATURE                 Location/Qualifiers
source                  1..11
                        mol_type = protein
                        organism = Homo sapiens
SEQUENCE: 1087
CGSCGCSQCN C                                                                 11

SEQ ID NO: 1088         moltype = AA   length = 11
FEATURE                 Location/Qualifiers
source                  1..11
                        mol_type = protein
                        organism = Homo sapiens
SEQUENCE: 1088
CGSCGCSQCS C                                                                 11

SEQ ID NO: 1089         moltype = AA   length = 11
FEATURE                 Location/Qualifiers
source                  1..11
                        mol_type = protein
                        organism = Homo sapiens
SEQUENCE: 1089
CGSGCCGPVC C                                                                 11

SEQ ID NO: 1090         moltype = AA   length = 11
FEATURE                 Location/Qualifiers
source                  1..11
                        mol_type = protein
                        organism = Homo sapiens
SEQUENCE: 1090
CGSGCCVPVC C                                                                 11

SEQ ID NO: 1091         moltype = AA   length = 11
FEATURE                 Location/Qualifiers
source                  1..11
                        mol_type = protein
                        organism = Homo sapiens
SEQUENCE: 1091
CGSNCCQPCC R                                                                 11

SEQ ID NO: 1092         moltype = AA   length = 11
FEATURE                 Location/Qualifiers
source                  1..11
                        mol_type = protein
                        organism = Homo sapiens
SEQUENCE: 1092
CGSSCCQPCC H                                                                 11

SEQ ID NO: 1093         moltype = AA   length = 11
FEATURE                 Location/Qualifiers
source                  1..11
                        mol_type = protein
                        organism = Homo sapiens
SEQUENCE: 1093
CGSSCCQPCC R                                                                 11

SEQ ID NO: 1094         moltype = AA   length = 11
FEATURE                 Location/Qualifiers
source                  1..11
                        mol_type = protein
                        organism = Homo sapiens
SEQUENCE: 1094
CGSSCCQPCY C                                                                 11

SEQ ID NO: 1095         moltype = AA   length = 11
FEATURE                 Location/Qualifiers
source                  1..11
                        mol_type = protein
                        organism = Homo sapiens
SEQUENCE: 1095
CGSSCCQPSC C                                                                 11

SEQ ID NO: 1096         moltype = AA   length = 11
FEATURE                 Location/Qualifiers
source                  1..11
                        mol_type = protein
                        organism = Homo sapiens
SEQUENCE: 1096
CGSSCCQSSC C                                                                 11
```

```
SEQ ID NO: 1097            moltype = AA  length = 11
FEATURE                    Location/Qualifiers
source                     1..11
                           mol_type = protein
                           organism = Homo sapiens
SEQUENCE: 1097
CGSSCCVPIC C                                                                        11

SEQ ID NO: 1098            moltype = AA  length = 11
FEATURE                    Location/Qualifiers
source                     1..11
                           mol_type = protein
                           organism = Homo sapiens
SEQUENCE: 1098
CGSSCCVPVC C                                                                        11

SEQ ID NO: 1099            moltype = AA  length = 11
FEATURE                    Location/Qualifiers
source                     1..11
                           mol_type = protein
                           organism = Homo sapiens
SEQUENCE: 1099
CGSSCSQCSC C                                                                        11

SEQ ID NO: 1100            moltype = AA  length = 11
FEATURE                    Location/Qualifiers
source                     1..11
                           mol_type = protein
                           organism = Homo sapiens
SEQUENCE: 1100
CGVPVCCCSC S                                                                        11

SEQ ID NO: 1101            moltype = AA  length = 11
FEATURE                    Location/Qualifiers
source                     1..11
                           mol_type = protein
                           organism = Homo sapiens
SEQUENCE: 1101
CHPRCCISSC C                                                                        11

SEQ ID NO: 1102            moltype = AA  length = 11
FEATURE                    Location/Qualifiers
source                     1..11
                           mol_type = protein
                           organism = Homo sapiens
SEQUENCE: 1102
CHPSCCESSC C                                                                        11

SEQ ID NO: 1103            moltype = AA  length = 11
FEATURE                    Location/Qualifiers
source                     1..11
                           mol_type = protein
                           organism = Homo sapiens
SEQUENCE: 1103
CHPSCCISSC C                                                                        11

SEQ ID NO: 1104            moltype = AA  length = 11
FEATURE                    Location/Qualifiers
source                     1..11
                           mol_type = protein
                           organism = Homo sapiens
SEQUENCE: 1104
CHPTCCQNTC C                                                                        11

SEQ ID NO: 1105            moltype = AA  length = 11
FEATURE                    Location/Qualifiers
source                     1..11
                           mol_type = protein
                           organism = Homo sapiens
SEQUENCE: 1105
CISSCCHPSC C                                                                        11

SEQ ID NO: 1106            moltype = AA  length = 11
FEATURE                    Location/Qualifiers
source                     1..11
                           mol_type = protein
                           organism = Homo sapiens
SEQUENCE: 1106
```

| | | |
|---|---|---|
| CISSCCKPSC C | | 11 |
| SEQ ID NO: 1107<br>FEATURE<br>source | moltype = AA  length = 11<br>Location/Qualifiers<br>1..11<br>mol_type = protein<br>organism = Homo sapiens | |
| SEQUENCE: 1107<br>CISSCCRPSC C | | 11 |
| SEQ ID NO: 1108<br>FEATURE<br>source | moltype = AA  length = 11<br>Location/Qualifiers<br>1..11<br>mol_type = protein<br>organism = Homo sapiens | |
| SEQUENCE: 1108<br>CISSSCCPSC C | | 11 |
| SEQ ID NO: 1109<br>FEATURE<br>source | moltype = AA  length = 11<br>Location/Qualifiers<br>1..11<br>mol_type = protein<br>organism = Homo sapiens | |
| SEQUENCE: 1109<br>CKPCCCSSGC G | | 11 |
| SEQ ID NO: 1110<br>FEATURE<br>source | moltype = AA  length = 11<br>Location/Qualifiers<br>1..11<br>mol_type = protein<br>organism = Homo sapiens | |
| SEQUENCE: 1110<br>CKPCCSQASC C | | 11 |
| SEQ ID NO: 1111<br>FEATURE<br>source | moltype = AA  length = 11<br>Location/Qualifiers<br>1..11<br>mol_type = protein<br>organism = Homo sapiens | |
| SEQUENCE: 1111<br>CKPCCSQSRC C | | 11 |
| SEQ ID NO: 1112<br>FEATURE<br>source | moltype = AA  length = 11<br>Location/Qualifiers<br>1..11<br>mol_type = protein<br>organism = Homo sapiens | |
| SEQUENCE: 1112<br>CKPCCSQSSC C | | 11 |
| SEQ ID NO: 1113<br>FEATURE<br>source | moltype = AA  length = 11<br>Location/Qualifiers<br>1..11<br>mol_type = protein<br>organism = Homo sapiens | |
| SEQUENCE: 1113<br>CKPQCCQSMC C | | 11 |
| SEQ ID NO: 1114<br>FEATURE<br>source | moltype = AA  length = 11<br>Location/Qualifiers<br>1..11<br>mol_type = protein<br>organism = Homo sapiens | |
| SEQUENCE: 1114<br>CKPQCCQSVC C | | 11 |
| SEQ ID NO: 1115<br>FEATURE<br>source | moltype = AA  length = 11<br>Location/Qualifiers<br>1..11<br>mol_type = protein<br>organism = Homo sapiens | |
| SEQUENCE: 1115<br>CKPVCCCVPA C | | 11 |
| SEQ ID NO: 1116<br>FEATURE<br>source | moltype = AA  length = 11<br>Location/Qualifiers<br>1..11<br>mol_type = protein<br>organism = Homo sapiens | |

```
SEQUENCE: 1116
CKPVCCKPIC C                                                                  11

SEQ ID NO: 1117         moltype = AA  length = 11
FEATURE                 Location/Qualifiers
source                  1..11
                        mol_type = protein
                        organism = Homo sapiens
SEQUENCE: 1117
CKPVCCMPVC C                                                                  11

SEQ ID NO: 1118         moltype = AA  length = 11
FEATURE                 Location/Qualifiers
source                  1..11
                        mol_type = protein
                        organism = Homo sapiens
SEQUENCE: 1118
CKPVCCVPVC C                                                                  11

SEQ ID NO: 1119         moltype = AA  length = 11
FEATURE                 Location/Qualifiers
source                  1..11
                        mol_type = protein
                        organism = Homo sapiens
SEQUENCE: 1119
CKPVCCVSVC C                                                                  11

SEQ ID NO: 1120         moltype = AA  length = 11
FEATURE                 Location/Qualifiers
source                  1..11
                        mol_type = protein
                        organism = Homo sapiens
SEQUENCE: 1120
CKPYCSQCSC C                                                                  11

SEQ ID NO: 1121         moltype = AA  length = 11
FEATURE                 Location/Qualifiers
source                  1..11
                        mol_type = protein
                        organism = Homo sapiens
SEQUENCE: 1121
CLPCCRPTCC Q                                                                  11

SEQ ID NO: 1122         moltype = AA  length = 11
FEATURE                 Location/Qualifiers
source                  1..11
                        mol_type = protein
                        organism = Homo sapiens
SEQUENCE: 1122
CLTSCCQPSC C                                                                  11

SEQ ID NO: 1123         moltype = AA  length = 11
FEATURE                 Location/Qualifiers
source                  1..11
                        mol_type = protein
                        organism = Homo sapiens
SEQUENCE: 1123
CMSSCCKPQC C                                                                  11

SEQ ID NO: 1124         moltype = AA  length = 11
FEATURE                 Location/Qualifiers
source                  1..11
                        mol_type = protein
                        organism = Homo sapiens
SEQUENCE: 1124
CNPCCSQSSC C                                                                  11

SEQ ID NO: 1125         moltype = AA  length = 11
FEATURE                 Location/Qualifiers
source                  1..11
                        mol_type = protein
                        organism = Homo sapiens
SEQUENCE: 1125
CPACCVSSCC Q                                                                  11

SEQ ID NO: 1126         moltype = AA  length = 11
FEATURE                 Location/Qualifiers
source                  1..11
                        mol_type = protein
```

```
                       organism = Homo sapiens
SEQUENCE: 1126
CPESCCEPHC C                                                                11

SEQ ID NO: 1127        moltype = AA   length = 11
FEATURE                Location/Qualifiers
source                 1..11
                       mol_type = protein
                       organism = Homo sapiens
SEQUENCE: 1127
CPESCCEPPC C                                                                11

SEQ ID NO: 1128        moltype = AA   length = 11
FEATURE                Location/Qualifiers
source                 1..11
                       mol_type = protein
                       organism = Homo sapiens
SEQUENCE: 1128
CPSCCESSCC R                                                                11

SEQ ID NO: 1129        moltype = AA   length = 11
FEATURE                Location/Qualifiers
source                 1..11
                       mol_type = protein
                       organism = Homo sapiens
SEQUENCE: 1129
CPSCCQTTCC R                                                                11

SEQ ID NO: 1130        moltype = AA   length = 11
FEATURE                Location/Qualifiers
source                 1..11
                       mol_type = protein
                       organism = Homo sapiens
SEQUENCE: 1130
CPSCCVSSCC R                                                                11

SEQ ID NO: 1131        moltype = AA   length = 11
FEATURE                Location/Qualifiers
source                 1..11
                       mol_type = protein
                       organism = Homo sapiens
SEQUENCE: 1131
CQCSCCKPYC S                                                                11

SEQ ID NO: 1132        moltype = AA   length = 11
FEATURE                Location/Qualifiers
source                 1..11
                       mol_type = protein
                       organism = Homo sapiens
SEQUENCE: 1132
CQETCCRPSC C                                                                11

SEQ ID NO: 1133        moltype = AA   length = 11
FEATURE                Location/Qualifiers
source                 1..11
                       mol_type = protein
                       organism = Homo sapiens
SEQUENCE: 1133
CQNTCCRTTC C                                                                11

SEQ ID NO: 1134        moltype = AA   length = 11
FEATURE                Location/Qualifiers
source                 1..11
                       mol_type = protein
                       organism = Homo sapiens
SEQUENCE: 1134
CQPACCTASC C                                                                11

SEQ ID NO: 1135        moltype = AA   length = 11
FEATURE                Location/Qualifiers
source                 1..11
                       mol_type = protein
                       organism = Homo sapiens
SEQUENCE: 1135
CQPACCTSSC C                                                                11

SEQ ID NO: 1136        moltype = AA   length = 11
FEATURE                Location/Qualifiers
source                 1..11
```

```
                              mol_type = protein
                              organism = Homo sapiens
SEQUENCE: 1136
CQPACCTTSC C                                                              11

SEQ ID NO: 1137               moltype = AA   length = 11
FEATURE                       Location/Qualifiers
source                        1..11
                              mol_type = protein
                              organism = Homo sapiens
SEQUENCE: 1137
CQPACCVPVC C                                                              11

SEQ ID NO: 1138               moltype = AA   length = 11
FEATURE                       Location/Qualifiers
source                        1..11
                              mol_type = protein
                              organism = Homo sapiens
SEQUENCE: 1138
CQPACCVSSC C                                                              11

SEQ ID NO: 1139               moltype = AA   length = 11
FEATURE                       Location/Qualifiers
source                        1..11
                              mol_type = protein
                              organism = Homo sapiens
SEQUENCE: 1139
CQPCCHPTCC Q                                                              11

SEQ ID NO: 1140               moltype = AA   length = 11
FEATURE                       Location/Qualifiers
source                        1..11
                              mol_type = protein
                              organism = Homo sapiens
SEQUENCE: 1140
CQPCCRPACC E                                                              11

SEQ ID NO: 1141               moltype = AA   length = 11
FEATURE                       Location/Qualifiers
source                        1..11
                              mol_type = protein
                              organism = Homo sapiens
SEQUENCE: 1141
CQPCCRPACC Q                                                              11

SEQ ID NO: 1142               moltype = AA   length = 11
FEATURE                       Location/Qualifiers
source                        1..11
                              mol_type = protein
                              organism = Homo sapiens
SEQUENCE: 1142
CQPCCRPTCC Q                                                              11

SEQ ID NO: 1143               moltype = AA   length = 11
FEATURE                       Location/Qualifiers
source                        1..11
                              mol_type = protein
                              organism = Homo sapiens
SEQUENCE: 1143
CQPCYCPACC V                                                              11

SEQ ID NO: 1144               moltype = AA   length = 11
FEATURE                       Location/Qualifiers
source                        1..11
                              mol_type = protein
                              organism = Homo sapiens
SEQUENCE: 1144
CQPICCGSSC C                                                              11

SEQ ID NO: 1145               moltype = AA   length = 11
FEATURE                       Location/Qualifiers
source                        1..11
                              mol_type = protein
                              organism = Homo sapiens
SEQUENCE: 1145
CQPRCCETSC C                                                              11

SEQ ID NO: 1146               moltype = AA   length = 11
FEATURE                       Location/Qualifiers
```

```
source                     1..11
                           mol_type = protein
                           organism = Homo sapiens
SEQUENCE: 1146
CQPSCCETSC C                                                                      11

SEQ ID NO: 1147            moltype = AA   length = 11
FEATURE                    Location/Qualifiers
source                     1..11
                           mol_type = protein
                           organism = Homo sapiens
SEQUENCE: 1147
CQPSCCRPAC C                                                                      11

SEQ ID NO: 1148            moltype = AA   length = 11
FEATURE                    Location/Qualifiers
source                     1..11
                           mol_type = protein
                           organism = Homo sapiens
SEQUENCE: 1148
CQPSCCVPSC C                                                                      11

SEQ ID NO: 1149            moltype = AA   length = 11
FEATURE                    Location/Qualifiers
source                     1..11
                           mol_type = protein
                           organism = Homo sapiens
SEQUENCE: 1149
CQPSCCVSSC C                                                                      11

SEQ ID NO: 1150            moltype = AA   length = 11
FEATURE                    Location/Qualifiers
source                     1..11
                           mol_type = protein
                           organism = Homo sapiens
SEQUENCE: 1150
CQPTCCCPSY C                                                                      11

SEQ ID NO: 1151            moltype = AA   length = 11
FEATURE                    Location/Qualifiers
source                     1..11
                           mol_type = protein
                           organism = Homo sapiens
SEQUENCE: 1151
CQPTCCGSSC C                                                                      11

SEQ ID NO: 1152            moltype = AA   length = 11
FEATURE                    Location/Qualifiers
source                     1..11
                           mol_type = protein
                           organism = Homo sapiens
SEQUENCE: 1152
CQPTCCHPSC C                                                                      11

SEQ ID NO: 1153            moltype = AA   length = 11
FEATURE                    Location/Qualifiers
source                     1..11
                           mol_type = protein
                           organism = Homo sapiens
SEQUENCE: 1153
CQPTCCQPTC C                                                                      11

SEQ ID NO: 1154            moltype = AA   length = 11
FEATURE                    Location/Qualifiers
source                     1..11
                           mol_type = protein
                           organism = Homo sapiens
SEQUENCE: 1154
CQPTCCRPSC C                                                                      11

SEQ ID NO: 1155            moltype = AA   length = 11
FEATURE                    Location/Qualifiers
source                     1..11
                           mol_type = protein
                           organism = Homo sapiens
SEQUENCE: 1155
CQPTCCRPTC C                                                                      11

SEQ ID NO: 1156            moltype = AA   length = 11
```

-continued

| FEATURE | Location/Qualifiers |
| --- | --- |
| source | 1..11 |
| | mol_type = protein |
| | organism = Homo sapiens |

SEQUENCE: 1156
CQPTCCRTTC C								11

SEQ ID NO: 1157	moltype = AA  length = 11
FEATURE			Location/Qualifiers
source			1..11
				mol_type = protein
				organism = Homo sapiens

SEQUENCE: 1157
CQQACCMPVC C								11

SEQ ID NO: 1158	moltype = AA  length = 11
FEATURE			Location/Qualifiers
source			1..11
				mol_type = protein
				organism = Homo sapiens

SEQUENCE: 1158
CQQACCVPIC C								11

SEQ ID NO: 1159	moltype = AA  length = 11
FEATURE			Location/Qualifiers
source			1..11
				mol_type = protein
				organism = Homo sapiens

SEQUENCE: 1159
CQQACCVPVC C								11

SEQ ID NO: 1160	moltype = AA  length = 11
FEATURE			Location/Qualifiers
source			1..11
				mol_type = protein
				organism = Homo sapiens

SEQUENCE: 1160
CQQSCCVPVC C								11

SEQ ID NO: 1161	moltype = AA  length = 11
FEATURE			Location/Qualifiers
source			1..11
				mol_type = protein
				organism = Homo sapiens

SEQUENCE: 1161
CQSCCVSVC C								11

SEQ ID NO: 1162	moltype = AA  length = 11
FEATURE			Location/Qualifiers
source			1..11
				mol_type = protein
				organism = Homo sapiens

SEQUENCE: 1162
CQSNCCVPVC C								11

SEQ ID NO: 1163	moltype = AA  length = 11
FEATURE			Location/Qualifiers
source			1..11
				mol_type = protein
				organism = Homo sapiens

SEQUENCE: 1163
CQSSCCCPAS C								11

SEQ ID NO: 1164	moltype = AA  length = 11
FEATURE			Location/Qualifiers
source			1..11
				mol_type = protein
				organism = Homo sapiens

SEQUENCE: 1164
CQSSCCKPCC S								11

SEQ ID NO: 1165	moltype = AA  length = 11
FEATURE			Location/Qualifiers
source			1..11
				mol_type = protein
				organism = Homo sapiens

SEQUENCE: 1165
CQSSCCKPCS C								11

| | | |
|---|---|---|
| SEQ ID NO: 1166<br>FEATURE<br>source | moltype = AA   length = 11<br>Location/Qualifiers<br>1..11<br>mol_type = protein<br>organism = Homo sapiens | |
| SEQUENCE: 1166<br>CQSSCCKPYC C | | 11 |
| SEQ ID NO: 1167<br>FEATURE<br>source | moltype = AA   length = 11<br>Location/Qualifiers<br>1..11<br>mol_type = protein<br>organism = Homo sapiens | |
| SEQUENCE: 1167<br>CQSSCCNPCC S | | 11 |
| SEQ ID NO: 1168<br>FEATURE<br>source | moltype = AA   length = 11<br>Location/Qualifiers<br>1..11<br>mol_type = protein<br>organism = Homo sapiens | |
| SEQUENCE: 1168<br>CQSSCCQSSC C | | 11 |
| SEQ ID NO: 1169<br>FEATURE<br>source | moltype = AA   length = 11<br>Location/Qualifiers<br>1..11<br>mol_type = protein<br>organism = Homo sapiens | |
| SEQUENCE: 1169<br>CQSSCCVPVC C | | 11 |
| SEQ ID NO: 1170<br>FEATURE<br>source | moltype = AA   length = 11<br>Location/Qualifiers<br>1..11<br>mol_type = protein<br>organism = Homo sapiens | |
| SEQUENCE: 1170<br>CQSSCFKPCC C | | 11 |
| SEQ ID NO: 1171<br>FEATURE<br>source | moltype = AA   length = 11<br>Location/Qualifiers<br>1..11<br>mol_type = protein<br>organism = Homo sapiens | |
| SEQUENCE: 1171<br>CQSSCSKPCC C | | 11 |
| SEQ ID NO: 1172<br>FEATURE<br>source | moltype = AA   length = 11<br>Location/Qualifiers<br>1..11<br>mol_type = protein<br>organism = Homo sapiens | |
| SEQUENCE: 1172<br>CQSSCYKPCC C | | 11 |
| SEQ ID NO: 1173<br>FEATURE<br>source | moltype = AA   length = 11<br>Location/Qualifiers<br>1..11<br>mol_type = protein<br>organism = Homo sapiens | |
| SEQUENCE: 1173<br>CQSVCCQPTC C | | 11 |
| SEQ ID NO: 1174<br>FEATURE<br>source | moltype = AA   length = 11<br>Location/Qualifiers<br>1..11<br>mol_type = protein<br>organism = Homo sapiens | |
| SEQUENCE: 1174<br>CQTTCCCPSC V | | 11 |
| SEQ ID NO: 1175<br>FEATURE<br>source | moltype = AA   length = 11<br>Location/Qualifiers<br>1..11<br>mol_type = protein<br>organism = Homo sapiens | |
| SEQUENCE: 1175<br>CQTTCCRPSC C | | 11 |

| | | |
|---|---|---|
| SEQ ID NO: 1176<br>FEATURE<br>source | moltype = AA   length = 11<br>Location/Qualifiers<br>1..11<br>mol_type = protein<br>organism = Homo sapiens | |
| SEQUENCE: 1176<br>CQTTCCRTTC C | | 11 |
| SEQ ID NO: 1177<br>FEATURE<br>source | moltype = AA   length = 11<br>Location/Qualifiers<br>1..11<br>mol_type = protein<br>organism = Homo sapiens | |
| SEQUENCE: 1177<br>CRPACCETTC C | | 11 |
| SEQ ID NO: 1178<br>FEATURE<br>source | moltype = AA   length = 11<br>Location/Qualifiers<br>1..11<br>mol_type = protein<br>organism = Homo sapiens | |
| SEQUENCE: 1178<br>CRPACCQNTC C | | 11 |
| SEQ ID NO: 1179<br>FEATURE<br>source | moltype = AA   length = 11<br>Location/Qualifiers<br>1..11<br>mol_type = protein<br>organism = Homo sapiens | |
| SEQUENCE: 1179<br>CRPCCCLRPV C | | 11 |
| SEQ ID NO: 1180<br>FEATURE<br>source | moltype = AA   length = 11<br>Location/Qualifiers<br>1..11<br>mol_type = protein<br>organism = Homo sapiens | |
| SEQUENCE: 1180<br>CRPCCCVRPV C | | 11 |
| SEQ ID NO: 1181<br>FEATURE<br>source | moltype = AA   length = 11<br>Location/Qualifiers<br>1..11<br>mol_type = protein<br>organism = Homo sapiens | |
| SEQUENCE: 1181<br>CRPCCWATTC C | | 11 |
| SEQ ID NO: 1182<br>FEATURE<br>source | moltype = AA   length = 11<br>Location/Qualifiers<br>1..11<br>mol_type = protein<br>organism = Homo sapiens | |
| SEQUENCE: 1182<br>CRPLCCQTTC C | | 11 |
| SEQ ID NO: 1183<br>FEATURE<br>source | moltype = AA   length = 11<br>Location/Qualifiers<br>1..11<br>mol_type = protein<br>organism = Homo sapiens | |
| SEQUENCE: 1183<br>CRPQCCQSVC C | | 11 |
| SEQ ID NO: 1184<br>FEATURE<br>source | moltype = AA   length = 11<br>Location/Qualifiers<br>1..11<br>mol_type = protein<br>organism = Homo sapiens | |
| SEQUENCE: 1184<br>CRPQCCQTTC C | | 11 |
| SEQ ID NO: 1185<br>FEATURE<br>source | moltype = AA   length = 11<br>Location/Qualifiers<br>1..11<br>mol_type = protein<br>organism = Homo sapiens | |
| SEQUENCE: 1185 | | |

```
CRPRCCISSC C                                                                       11

SEQ ID NO: 1186           moltype = AA   length = 11
FEATURE                   Location/Qualifiers
source                    1..11
                          mol_type = protein
                          organism = Homo sapiens SEQUENCE: 1186
CRPSCCESSC C                                                                       11

SEQ ID NO: 1187           moltype = AA   length = 11
FEATURE                   Location/Qualifiers
source                    1..11
                          mol_type = protein
                          organism = Homo sapiens SEQUENCE: 1187
CRPSCCISSC C                                                                       11

SEQ ID NO: 1188           moltype = AA   length = 11
FEATURE                   Location/Qualifiers
source                    1..11
                          mol_type = protein
                          organism = Homo sapiens SEQUENCE: 1188
CRPSCCKPQC C                                                                       11

SEQ ID NO: 1189           moltype = AA   length = 11
FEATURE                   Location/Qualifiers
source                    1..11
                          mol_type = protein
                          organism = Homo sapiens SEQUENCE: 1189
CRPSCCPSCC Q                                                                       11

SEQ ID NO: 1190           moltype = AA   length = 11
FEATURE                   Location/Qualifiers
source                    1..11
                          mol_type = protein
                          organism = Homo sapiens SEQUENCE: 1190
CRPSCCQTTC C                                                                       11

SEQ ID NO: 1191           moltype = AA   length = 11
FEATURE                   Location/Qualifiers
source                    1..11
                          mol_type = protein
                          organism = Homo sapiens SEQUENCE: 1191
CRPSCCRPQC C                                                                       11

SEQ ID NO: 1192           moltype = AA   length = 11
FEATURE                   Location/Qualifiers
source                    1..11
                          mol_type = protein
                          organism = Homo sapiens SEQUENCE: 1192
CRPSCCVSRC C                                                                       11

SEQ ID NO: 1193           moltype = AA   length = 11
FEATURE                   Location/Qualifiers
source                    1..11
                          mol_type = protein
                          organism = Homo sapiens SEQUENCE: 1193
CRPSCCVSSC C                                                                       11

SEQ ID NO: 1194           moltype = AA   length = 11
FEATURE                   Location/Qualifiers
source                    1..11
                          mol_type = protein
                          organism = Homo sapiens SEQUENCE: 1194
CRPTCCQNTC C                                                                       11

SEQ ID NO: 1195           moltype = AA   length = 11
FEATURE                   Location/Qualifiers
source                    1..11
                          mol_type = protein
                          organism = Homo sapiens
```

```
SEQUENCE: 1195
CRPVCCCEPT C                                                                             11

SEQ ID NO: 1196        moltype = AA  length = 11
FEATURE                Location/Qualifiers
source                 1..11
                       mol_type = protein
                       organism = Homo sapiens
SEQUENCE: 1196
CRPVCCCYSC E                                                                             11

SEQ ID NO: 1197        moltype = AA  length = 11
FEATURE                Location/Qualifiers
source                 1..11
                       mol_type = protein
                       organism = Homo sapiens
SEQUENCE: 1197
CRTTCCHPSC C                                                                             11

SEQ ID NO: 1198        moltype = AA  length = 11
FEATURE                Location/Qualifiers
source                 1..11
                       mol_type = protein
                       organism = Homo sapiens
SEQUENCE: 1198
CRTTCCRPSC C                                                                             11

SEQ ID NO: 1199        moltype = AA  length = 11
FEATURE                Location/Qualifiers
source                 1..11
                       mol_type = protein
                       organism = Homo sapiens
SEQUENCE: 1199
CSCCKPYCSQ C                                                                             11

SEQ ID NO: 1200        moltype = AA  length = 11
FEATURE                Location/Qualifiers
source                 1..11
                       mol_type = protein
                       organism = Homo sapiens
SEQUENCE: 1200
CSKPCCCQSS C                                                                             11

SEQ ID NO: 1201        moltype = AA  length = 11
FEATURE                Location/Qualifiers
source                 1..11
                       mol_type = protein
                       organism = Homo sapiens
SEQUENCE: 1201
CSPCCQPTCC R                                                                             11

SEQ ID NO: 1202        moltype = AA  length = 11
FEATURE                Location/Qualifiers
source                 1..11
                       mol_type = protein
                       organism = Homo sapiens
SEQUENCE: 1202
CSPCCVSSCC Q                                                                             11

SEQ ID NO: 1203        moltype = AA  length = 11
FEATURE                Location/Qualifiers
source                 1..11
                       mol_type = protein
                       organism = Homo sapiens
SEQUENCE: 1203
CSQCSCCKPC Y                                                                             11

SEQ ID NO: 1204        moltype = AA  length = 11
FEATURE                Location/Qualifiers
source                 1..11
                       mol_type = protein
                       organism = Homo sapiens
SEQUENCE: 1204
CSQCSCYKPC C                                                                             11

SEQ ID NO: 1205        moltype = AA  length = 11
FEATURE                Location/Qualifiers
source                 1..11
                       mol_type = protein
```

```
SEQUENCE: 1205
CSQSNCCKPC C                                                                   11

SEQ ID NO: 1206         moltype = AA   length = 11
FEATURE                 Location/Qualifiers
source                  1..11
                        mol_type = protein
                        organism = Homo sapiens
SEQUENCE: 1206
CSQSSCCKPC C                                                                   11

SEQ ID NO: 1207         moltype = AA   length = 11
FEATURE                 Location/Qualifiers
source                  1..11
                        mol_type = protein
                        organism = Homo sapiens
SEQUENCE: 1207
CSSSCCQPSC C                                                                   11

SEQ ID NO: 1208         moltype = AA   length = 11
FEATURE                 Location/Qualifiers
source                  1..11
                        mol_type = protein
                        organism = Homo sapiens
SEQUENCE: 1208
CTPSCCQPAC C                                                                   11

SEQ ID NO: 1209         moltype = AA   length = 11
FEATURE                 Location/Qualifiers
source                  1..11
                        mol_type = protein
                        organism = Homo sapiens
SEQUENCE: 1209
CVASCCQPSC C                                                                   11

SEQ ID NO: 1210         moltype = AA   length = 11
FEATURE                 Location/Qualifiers
source                  1..11
                        mol_type = protein
                        organism = Homo sapiens
SEQUENCE: 1210
CVPICCCKPV C                                                                   11

SEQ ID NO: 1211         moltype = AA   length = 11
FEATURE                 Location/Qualifiers
source                  1..11
                        mol_type = protein
                        organism = Homo sapiens
SEQUENCE: 1211
CVPSCCQPCC H                                                                   11

SEQ ID NO: 1212         moltype = AA   length = 11
FEATURE                 Location/Qualifiers
source                  1..11
                        mol_type = protein
                        organism = Homo sapiens
SEQUENCE: 1212
CVPVCCCKPM C                                                                   11

SEQ ID NO: 1213         moltype = AA   length = 11
FEATURE                 Location/Qualifiers
source                  1..11
                        mol_type = protein
                        organism = Homo sapiens
SEQUENCE: 1213
CVPVCCCKPV C                                                                   11

SEQ ID NO: 1214         moltype = AA   length = 11
FEATURE                 Location/Qualifiers
source                  1..11
                        mol_type = protein
                        organism = Homo sapiens
SEQUENCE: 1214
CVPVCCKPVC C                                                                   11

SEQ ID NO: 1215         moltype = AA   length = 11
FEATURE                 Location/Qualifiers
source                  1..11
```

-continued

```
                        mol_type = protein
                        organism = Homo sapiens
SEQUENCE: 1215
CVSSCCKPQC C                                                        11

SEQ ID NO: 1216         moltype = AA  length = 11
FEATURE                 Location/Qualifiers
source                  1..11
                        mol_type = protein
                        organism = Homo sapiens
SEQUENCE: 1216
CVSSCCQHSC C                                                        11

SEQ ID NO: 1217         moltype = AA  length = 11
FEATURE                 Location/Qualifiers
source                  1..11
                        mol_type = protein
                        organism = Homo sapiens
SEQUENCE: 1217
CVSSCCQPCC H                                                        11

SEQ ID NO: 1218         moltype = AA  length = 11
FEATURE                 Location/Qualifiers
source                  1..11
                        mol_type = protein
                        organism = Homo sapiens
SEQUENCE: 1218
CVSSCCQPCC R                                                        11

SEQ ID NO: 1219         moltype = AA  length = 11
FEATURE                 Location/Qualifiers
source                  1..11
                        mol_type = protein
                        organism = Homo sapiens
SEQUENCE: 1219
CVSSCCQPFC C                                                        11

SEQ ID NO: 1220         moltype = AA  length = 11
FEATURE                 Location/Qualifiers
source                  1..11
                        mol_type = protein
                        organism = Homo sapiens
SEQUENCE: 1220
CVSSCCQPSC C                                                        11

SEQ ID NO: 1221         moltype = AA  length = 11
FEATURE                 Location/Qualifiers
source                  1..11
                        mol_type = protein
                        organism = Homo sapiens
SEQUENCE: 1221
CVSSCCRPQC C                                                        11

SEQ ID NO: 1222         moltype = AA  length = 11
FEATURE                 Location/Qualifiers
source                  1..11
                        mol_type = protein
                        organism = Homo sapiens
SEQUENCE: 1222
CVTRCCSTPC C                                                        11

SEQ ID NO: 1223         moltype = AA  length = 11
FEATURE                 Location/Qualifiers
source                  1..11
                        mol_type = protein
                        organism = Homo sapiens
SEQUENCE: 1223
CVTSCCQPAC C                                                        11

SEQ ID NO: 1224         moltype = AA  length = 11
FEATURE                 Location/Qualifiers
source                  1..11
                        mol_type = protein
                        organism = Homo sapiens
SEQUENCE: 1224
CVTSCCQPSC C                                                        11

SEQ ID NO: 1225         moltype = AA  length = 11
FEATURE                 Location/Qualifiers
```

```
source                     1..11
                           mol_type = protein
                           organism = Homo sapiens
SEQUENCE: 1225
CVYSCCQPFC C                                                              11

SEQ ID NO: 1226            moltype = AA   length = 11
FEATURE                    Location/Qualifiers
source                     1..11
                           mol_type = protein
                           organism = Homo sapiens
SEQUENCE: 1226
CVYSCCQPSC C                                                              11

SEQ ID NO: 1227            moltype = AA   length = 11
FEATURE                    Location/Qualifiers
source                     1..11
                           mol_type = protein
                           organism = Homo sapiens
SEQUENCE: 1227
CYCPACCVSS C                                                              11

SEQ ID NO: 1228            moltype = AA   length = 11
FEATURE                    Location/Qualifiers
source                     1..11
                           mol_type = protein
                           organism = Homo sapiens
SEQUENCE: 1228
CYKPCCCQSS C                                                              11

SEQ ID NO: 1229            moltype = AA   length = 11
FEATURE                    Location/Qualifiers
source                     1..11
                           mol_type = protein
                           organism = Homo sapiens
SEQUENCE: 1229
CYKPCCCSSG C                                                              11

SEQ ID NO: 1230            moltype = AA   length = 11
FEATURE                    Location/Qualifiers
source                     1..11
                           mol_type = protein
                           organism = Homo sapiens
SEQUENCE: 1230
MCCCVPACSC S                                                              11

SEQ ID NO: 1231            moltype = AA   length = 11
FEATURE                    Location/Qualifiers
source                     1..11
                           mol_type = protein
                           organism = Homo sapiens
SEQUENCE: 1231
NCCVPVCCQC K                                                              11

SEQ ID NO: 1232            moltype = AA   length = 11
FEATURE                    Location/Qualifiers
source                     1..11
                           mol_type = protein
                           organism = Homo sapiens
SEQUENCE: 1232
QCSCCKPCYC S                                                              11

SEQ ID NO: 1233            moltype = AA   length = 11
FEATURE                    Location/Qualifiers
source                     1..11
                           mol_type = protein
                           organism = Homo sapiens
SEQUENCE: 1233
QCSCYKPCCC S                                                              11

SEQ ID NO: 1234            moltype = AA   length = 11
FEATURE                    Location/Qualifiers
source                     1..11
                           mol_type = protein
                           organism = Homo sapiens
SEQUENCE: 1234
SCCVPICCQC K                                                              11

SEQ ID NO: 1235            moltype = AA   length = 11
```

```
FEATURE                 Location/Qualifiers
source                  1..11
                        mol_type = protein
                        organism = Homo sapiens
SEQUENCE: 1235
SCCVPVCCQC K                                                             11

SEQ ID NO: 1236         moltype = AA   length = 11
FEATURE                 Location/Qualifiers
source                  1..11
                        mol_type = protein
                        organism = Homo sapiens
SEQUENCE: 1236
SCGCSQCNCC K                                                             11

SEQ ID NO: 1237         moltype = AA   length = 11
FEATURE                 Location/Qualifiers
source                  1..11
                        mol_type = protein
                        organism = Homo sapiens
SEQUENCE: 1237
SCGCSQCSCC K                                                             11

SEQ ID NO: 1238         moltype = AA   length = 11
FEATURE                 Location/Qualifiers
source                  1..11
                        mol_type = protein
                        organism = Homo sapiens
SEQUENCE: 1238
VCCCVPACSC S                                                             11

SEQ ID NO: 1239         moltype = AA   length = 11
FEATURE                 Location/Qualifiers
source                  1..11
                        mol_type = protein
                        organism = Homo sapiens
SEQUENCE: 1239
VCCCVPACSC T                                                             11
```